United States Patent
Schlabach et al.

(10) Patent No.: US 12,188,045 B2
(45) Date of Patent: Jan. 7, 2025

(54) GUIDE RNA COMBINATIONS AND METHODS OF USE

(71) Applicant: KSQ Therapeutics, Inc., Lexington, MA (US)

(72) Inventors: Michael R. Schlabach, Lexington, MA (US); Anja Fides Hohmann, Lexington, MA (US)

(73) Assignee: KSQ Therapeutics, Inc., Lexington, MA (US)

( * ) Notice: Subject to any disclaimer, the term of this patent is extended or adjusted under 35 U.S.C. 154(b) by 75 days.

(21) Appl. No.: 17/930,447

(22) Filed: Sep. 8, 2022

(65) Prior Publication Data

US 2023/0119142 A1  Apr. 20, 2023

Related U.S. Application Data

(63) Continuation of application No. 16/894,089, filed on Jun. 5, 2020, now abandoned.

(60) Provisional application No. 62/858,689, filed on Jun. 7, 2019.

(51) Int. Cl.
| | | |
|---|---|---|
| *C12N 15/90* | (2006.01) | |
| *A61K 35/17* | (2015.01) | |
| *C12N 9/22* | (2006.01) | |
| *C12N 15/11* | (2006.01) | |

(52) U.S. Cl.
CPC ............ *C12N 15/907* (2013.01); *A61K 35/17* (2013.01); *C12N 9/22* (2013.01); *C12N 15/11* (2013.01); *C12N 2310/20* (2017.05); *C12N 2800/80* (2013.01)

(58) Field of Classification Search
CPC ........ C12N 15/907; C12N 9/22; C12N 15/11; C12N 2310/20; C12N 2800/80; C12N 15/113; C12N 15/1137; C12N 15/90; A61K 35/17; A61K 39/4611; A61K 39/4644; C12Y 301/03048
See application file for complete search history.

(56) References Cited

U.S. PATENT DOCUMENTS

| | | |
|---|---|---|
| 7,399,586 B2 | 7/2008 | Klinghoffer et al. |
| 11,261,428 B2 | 3/2022 | Benson et al. |
| 11,332,713 B2 | 5/2022 | Benson et al. |
| 11,459,544 B2 | 10/2022 | Benson et al. |
| 2004/0077574 A1 | 4/2004 | Klinghoffer et al. |
| 2015/0020223 A1 | 1/2015 | Zhang et al. |
| 2017/0175128 A1 | 6/2017 | Welstead et al. |
| 2017/0224731 A1 | 8/2017 | Tiganis et al. |
| 2019/0284529 A1 | 9/2019 | Benson et al. |
| 2022/0081691 A1 | 3/2022 | Haining et al. |
| 2022/0220442 A1 | 7/2022 | Benson et al. |
| 2023/0088186 A1 | 3/2023 | Benson et al. |
| 2023/0340411 A1 | 10/2023 | Benson et al. |

FOREIGN PATENT DOCUMENTS

| | | |
|---|---|---|
| WO | WO 2015/188228 A1 | 12/2015 |
| WO | WO 2017/120998 A1 | 7/2017 |
| WO | WO 2018/075664 A1 | 4/2018 |
| WO | WO 2019/178420 A1 | 9/2019 |
| WO | WO 2019/178422 A1 | 9/2019 |
| WO | WO 2020/072126 A2 | 4/2020 |

OTHER PUBLICATIONS

Starr et al. A family of cytokine-inducible inhibitors of signaling. Nature (1997), 387 (26): 917-921. (Year: 1997).*
Ishibashi et al. A simple method using CRISPR-Cas9 to knock-out genes in murine cancerous cell lines. Nature (2020), 10:22345. (Year: 2020).*
Warren Anderson, Modeling autoimmune associated genetics in primary human T cells using CRISPR/Cas9 gene editing. PhD Thesis, University of Washington, 2019. (Year: 2019).*
Hashimoto et al., Silencing of SOCS1 in macrophages suppresses tumor development by enhancing antitumor inflammation. Cancer Sci. Apr. 2009;100(4):730-6. doi: 10.1111/j.1349-7006.2009.01098.x.

* cited by examiner

*Primary Examiner* — Iqbal H Chowdhury

(74) *Attorney, Agent, or Firm* — Wolf, Greenfield & Sacks, P.C.

(57) ABSTRACT

The present disclosure provides gRNA compositions, CRISPR/Cas systems comprising the same, and methods of their use in the modification of immune effector cells. Methods of treating a cell proliferative disorder, such as a cancer, using the modified immune effector cells described herein are also provided.

18 Claims, 3 Drawing Sheets

Specification includes a Sequence Listing.

US 12,188,045 B2

GUIDE RNA COMBINATIONS AND METHODS OF USE

RELATED APPLICATION

This application is a continuation of U.S. application Ser. No. 16/894,089, filed Jun. 5, 2020, which claims priority to U.S. Provisional Patent Application No. 62/858,689, filed on Jun. 7, 2019, each of which is incorporated by reference herein in its entirety.

REFERENCE TO AN ELECTRONICALLY FILED SEQUENCE LISTING

The contents of the electronic sequence listing (K071370016US02-SEQ-HJD.xml; Size: 465,757 bytes; Date of Creation: Sep. 8, 2022) is herein incorporated by reference in its entirety.

FIELD

The disclosure relates to methods, compositions, and components for editing a target nucleic acid sequence, or modulating expression of a target nucleic acid sequence, and applications thereof in connection with immunotherapy, including use with receptor-engineered immune effector cells, such as e.g., T cells and tumor infiltrating lymphocytes (TILs), in the treatment of cell proliferative diseases, inflammatory diseases, and/or infectious diseases.

BACKGROUND

Adoptive cell transfer utilizing genetically modified T cells, in particular CAR-T cells has entered clinical testing as a therapeutic for solid and hematologic malignancies. Results to date have been mixed. In hematologic malignancies (especially lymphoma, CLL and ALL), the majority of patients in several Phase 1 and 2 trials exhibited at least a partial response, with some exhibiting complete responses (Kochenderfer et al., 2012 Blood 1 19, 2709-2720). In 2017, the FDA approved two CAR-T therapies, Kymriah™ and Yescarta™, both for the treatment of hematological cancers. However, improvements in adoptive T cell therapies are needed. Genetic modification of T cells (such as using CRISPR-based systems) can increase the effector functions of T cells when the right genes are targeted for editing in the right way. However, gene-editing efficacy is highly unpredictable especially when two or more genes are edited.

SUMMARY

The present disclosure provides CRISPR/Cas systems comprising SOCS1-targeting and PTPN2-targeting gRNA molecules, as well as modified immune effector cells comprising the same. The combinations of SOCS1-targeting and PTPN2-targeting gRNA molecules described herein result in an enhanced reduced expression and/or function of both SOCS1 and PTPN2 compared to previously described combinations of SOCS1-targeting and PTPN2-targeting gRNA molecules. Advantageously, in some embodiments the SOCS1-targeting gRNA and the PTPN2-targeting gRNA together demonstrate at least about 50%, at least about 60%, at least 70%, at least 80%, or at least 90%, or about the same efficacy compared to gene-editing with SOCS1-targeting gRNA or the PTPN2-targeting gRNA individually. The present disclosure further provides modified immune effector cells comprising these combinations of SOCS1-targeting and PTPN2-targeting gRNA molecules and methods of using the same in the treatment of various cancers.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence encoded by SEQ ID NO: 3; and a Cas endonuclease. In some embodiments, the PTPN2-targeting gRNA molecule comprises a targeting domain sequence encoded by one of SEQ ID NOs: 146-148 and 162-272.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence that binds to SEQ ID NO: 3; and a Cas endonuclease. In some embodiments, the PTPN2-targeting gRNA molecule comprises a targeting domain sequence that binds to one of SEQ ID NOs: 146-148 and 162-272.

In some embodiments, the present disclosure provides a CRISPR/Cas system comprising: a SOCS1-targeting gRNA molecule comprising a targeting domain sequence encoded by one of SEQ ID NOs: 1-3 and a PTPN2-targeting gRNA molecule comprising a targeting domain sequence encoded by one of SEQ ID NOs: 146-148; and a Cas endonuclease. In some embodiments, the SOCS1-targeting gRNA molecule comprises a targeting domain sequence encoded by SEQ ID NO: 1. In some embodiments, the SOCS1-targeting gRNA molecule comprises a targeting domain sequence encoded by SEQ ID NO: 2. In some embodiments, the SOCS1-targeting gRNA molecule comprises a targeting domain sequence encoded by SEQ ID NO: 3. In some embodiments, the PTPN2-targeting gRNA molecule comprises a targeting domain sequence encoded by SEQ ID NO: 146. In some embodiments, the PTPN2-targeting gRNA molecule comprises a targeting domain sequence encoded by SEQ ID NO: 147. In some embodiments, the PTPN2-targeting gRNA molecule comprises a targeting domain sequence encoded by SEQ ID NO: 148.

In some embodiments, the present disclosure provides a CRISPR/Cas system comprising: a SOCS1-targeting gRNA molecule comprising a targeting domain sequence that binds to one of SEQ ID NOs: 1-3 and a PTPN2-targeting gRNA molecule comprising a targeting domain sequence that binds to one of SEQ ID NOs: 146-148; and a Cas endonuclease. In some embodiments, the SOCS1-targeting gRNA molecule comprises a targeting domain sequence that binds to SEQ ID NO: 1. In some embodiments, the SOCS1-targeting gRNA molecule comprises a targeting domain sequence that binds to SEQ ID NO: 2. In some embodiments, the SOCS1-targeting gRNA molecule comprises a targeting domain sequence that binds to SEQ ID NO: 3. In some embodiments, the PTPN2-targeting gRNA molecule comprises a targeting domain sequence that binds to SEQ ID NO: 146. In some embodiments, the PTPN2-targeting gRNA molecule comprises a targeting domain sequence that binds to SEQ ID NO: 147. In some embodiments, the PTPN2-targeting gRNA molecule comprises a targeting domain sequence that binds to SEQ ID NO: 148.

In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 148. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 148. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 148.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence that is encoded by one of SEQ ID NOs: 1-3 and 17-145; and a Cas endonuclease. In some embodiments, the PTPN2-targeting gRNA molecule comprises a targeting domain sequence that is encoded by one of SEQ ID NOs: 146-148 and 162-272.

In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 148. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 148. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 148.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence that binds to one of SEQ ID NOs: 1-3 and 17-145; and a Cas endonuclease. In some embodiments, the PTPN2-targeting gRNA molecule comprises a targeting domain sequence that binds to one of SEQ ID NOs: 146-148 and 162-272.

In some embodiments, the Cas endonuclease is a Cas9 endonuclease. In some embodiments, the Cas endonuclease is a wild-type Cas endonuclease comprising two enzymatically active domains, and capable of inducing double stranded DNA breaks. In some embodiments, the Cas protein is a Cas nickase mutant comprising one enzymatically active domain and capable of inducing single stranded DNA breaks. In some embodiments, the Cas protein is a deactivated Cas protein (dCas) and is associated with a heterologous protein capable of modulating the expression of the one or more endogenous target genes. In some embodiments, the heterologous protein is selected from the group consisting of MAX-interacting protein 1 (MXI1), Krüppel-associated box (KRAB) domain, and four concatenated mSin3 domains (SID4X).

In some embodiments, the gRNAs are single gRNA (sgRNA) molecules. In some embodiments, the gRNAs are dual gRNA molecules. In some embodiments, the gRNA targeting domains are 16, 17, 18, 19, 20, 21, 22, 23, 24, 25, 26 or more nucleotides in length. In some embodiments, the gRNAs comprise a modification at or near the 5' end (e.g., within 1-10, 1-5, or 1-2 nucleotides of the 5' end) and/or a modification at or near the 3' end (e.g., within 1-10, 1-5, or 1-2 nucleotides of the 3' end). In some embodiments, the modified gRNAs exhibit increased resistance to nucleases when introduced into an immune effector cell. In some embodiments, the modified gRNAs do not induce an innate immune response when introduced into an immune effector cell or induce a decreased innate immune response compared to an unmodified gRNA when introduced into an immune effector cell. In some embodiments, the gRNA molecules and the Cas endonuclease are complexed as ribonucleoproteins (RNPs). In some embodiments, the gRNA molecules and the Cas endonuclease are not complexed as ribonucleoproteins (RNPs).

In some embodiments, the CRISPR/Cas system comprises a vector encoding the SOCS1-targeting gRNA molecule and the PTPN2-targeting gRNA molecule. In some embodiments, the CRISPR/Cas system comprises a first vector encoding the SOCS1-targeting gRNA molecule and a second vector encoding the PTPN2-targeting gRNA molecule. In some embodiments, the CRISPR/Cas system comprises a vector encoding the Cas endonuclease. In some embodiments, the CRISPR/Cas system comprises an mRNA polynucleotide encoding the Cas endonuclease.

In some embodiments, the present disclosure provides a vector comprising one or more polynucleotides encoding a SOCS1-targeting gRNA molecule and a PTPN2-targeting gRNA molecule, wherein the SOCS1-targeting gRNA molecule comprises a targeting domain sequence encoded by SEQ ID NO: 3. In some embodiments, the PTPN2-targeting gRNA molecule comprises a targeting domain sequence encoded by one of SEQ ID NOs: 146-148 and 162-272.

In some embodiments, the present disclosure provides a vector comprising one or more polynucleotides encoding a SOCS1-targeting gRNA molecule and a PTPN2-targeting gRNA molecule, wherein the SOCS1-targeting gRNA molecule comprises a targeting domain sequence that binds to SEQ ID NO: 3. In some embodiments, the PTPN2-targeting gRNA molecule comprises a targeting domain sequence that binds to one of SEQ ID NOs: 146-148 and 162-272.

In some embodiments, the present disclosure provides a vector comprising one or more polynucleotides encoding a SOCS1-targeting gRNA molecule comprising a targeting domain sequence encoded by one of SEQ ID NOs: 1-3 and a PTPN2-targeting gRNA molecule comprising a targeting domain sequence encoded by one of SEQ ID NOs: 146-148. In some embodiments, the SOCS1-targeting gRNA molecule comprises a targeting domain sequence encoded by SEQ ID NO: 1. In some embodiments, the SOCS1-targeting gRNA molecule comprises a targeting domain sequence encoded by SEQ ID NO: 2. In some embodiments, the SOCS1-targeting gRNA molecule comprises a targeting domain sequence encoded by SEQ ID NO: 3. In some embodiments, the PTPN2-targeting gRNA molecule comprises a targeting domain sequence encoded by SEQ ID NO: 146. In some embodiments, the PTPN2-targeting gRNA molecule comprises a targeting domain sequence encoded by SEQ ID NO: 147. In some embodiments, the PTPN2-targeting gRNA molecule comprises a targeting domain sequence encoded by SEQ ID NO: 148. In some embodiments, the vector further comprises a polynucleotide encoding a Cas endonuclease.

In some embodiments, the present disclosure provides a vector comprising one or more polynucleotides encoding a SOCS1-targeting gRNA molecule comprising a targeting domain sequence that binds to one of SEQ ID NOs: 1-3 and a PTPN2-targeting gRNA molecule comprising a targeting domain sequence that binds to one of SEQ ID NOs: 146-148. In some embodiments, the SOCS1-targeting gRNA molecule comprises a targeting domain sequence that binds to SEQ ID NO: 1. In some embodiments, the SOCS1-targeting gRNA molecule comprises a targeting domain sequence that binds to SEQ ID NO: 2. In some embodiments, the SOCS1-targeting gRNA molecule comprises a targeting domain sequence that binds to SEQ ID NO: 3. In some embodiments, the PTPN2-targeting gRNA molecule comprises a targeting domain sequence that binds to SEQ ID NO: 146. In some embodiments, the PTPN2-targeting gRNA molecule comprises a targeting domain sequence that binds to SEQ ID NO: 147. In some embodiments, the PTPN2-targeting gRNA molecule comprises a targeting domain sequence that binds to SEQ ID NO: 148. In some embodiments, the vector further comprises a polynucleotide encoding a Cas endonuclease.

In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 1 and the PTPN2-targeting gRNA molecule comprises a targeting domain sequence that is encoded by SEQ ID NO: 148. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 2 and the PTPN2-targeting gRNA molecule comprises a targeting domain sequence that is encoded by SEQ ID NO: 148. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 146. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 147. In some embodiments, the SOCS1-targeting gRNA molecule comprises a targeting domain sequence that is encoded by SEQ ID NO: 3 and the PTPN2-targeting gRNA molecule comprises a targeting domain sequence that is encoded by SEQ ID NO: 148.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence that is encoded by one of SEQ ID NOs: 1-3 and 17-145; and a Cas endonuclease. In some embodiments, the PTPN2-targeting gRNA molecule comprises a targeting domain sequence that is encoded by one of SEQ ID NOs: 146-148 and 162-272.

In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 1 and the PTPN2-targeting gRNA molecule comprises a targeting domain sequence that binds to SEQ ID NO: 148. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 2 and the PTPN2-targeting gRNA molecule comprises a targeting domain sequence that binds to SEQ ID NO: 148. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 146. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 147. In some embodiments, the SOCS1-targeting gRNA molecule comprises a targeting domain sequence that binds to SEQ ID NO: 3 and the PTPN2-targeting gRNA molecule comprises a targeting domain sequence that binds to SEQ ID NO: 148.

In some embodiments, the present disclosure provides a CRISPR/Cas system comprising: a SOCS1-targeting gRNA molecule and a PTPN2-targeting gRNA molecule, wherein the SOCS1-targeting gRNA molecule comprises a targeting domain sequence that binds to one of SEQ ID NOs: 1-3 and 17-145; and a Cas endonuclease. In some embodiments, the PTPN2-targeting gRNA molecule comprises a targeting domain sequence that binds to one of SEQ ID NOs: 146-148 and 162-272. In some embodiments, the present disclosure provides a pharmaceutical composition comprising a CRISPR/Cas system or a vector comprising the same described herein.

In some embodiments, the present disclosure provides a modified immune effector cell comprising a CRISPR/Cas system or a vector described herein. In some embodiments, the CRISPR/Cas system-mediated gene editing efficiency of both SOCS1 and PTPN2 is at least about 50%, at least about 60%, at least 70%, at least 80%, or at least 90% of the gene editing efficiency achieved with CRISPR/Cas systems comprising the SOCS1-targeting gRNA or the PTPN2-targeting gRNA individually. In some embodiments, the immune effector cell is a natural killer (NK) cell, an NKT cell, or a tumor infiltrating lymphocyte. In some embodiments, the present disclosure provides a pharmaceutical composition comprising a modified immune effector cell described herein.

In some embodiments, the present disclosure provides a method of producing a modified immune effector cell comprising introducing a CRISPR/Cas system or a vector comprising the same described herein into the immune effector cell, wherein the CRISPR/Cas system-mediated gene editing efficiency of SOCS1 and PTPN2 is at least about 50%, at least about 60%, at least 70%, at least 80%, or at least 90% of the gene editing efficiency achieved with CRISPR/Cas systems comprising the SOCS1-targeting gRNA or the PTPN2-targeting gRNA individually. In some embodiments, the CRISPR/Cas system is introduced into the immune effector cell by transfection, transduction, electroporation, or physical disruption of the cell membrane by a microfluidics device. In some embodiments, the immune effector cell is a natural killer (NK) cell, an NKT cell, or a tumor infiltrating lymphocyte.

In some embodiments, the present disclosure provides a modified immune effector cell produced by the methods described herein.

In some embodiments, the present disclosure provides a method of treating cancer in a subject in need thereof comprising administering to the subject an effective amount of a modified immune effector cell described herein. In some embodiments, the cancer is selected from a leukemia, a lymphoma, or a solid tumor. In some embodiments, the solid tumor is a melanoma, a pancreatic tumor, a bladder tumor, a head and neck tumor, or a lung tumor or metastases thereof. In some embodiments, the cancer is a PD1-inhibitor resistant or refractory cancer. In some embodiments, the subject has previously been treated with a PD1 inhibitor or a PDL1 inhibitor. In some embodiments, the modified immune effector cells are autologous to the subject. In some embodiments, the modified immune effector cells are allogeneic to the subject. In some embodiments, the subject has not undergone lymphodepletion treatment prior to administration of the modified immune effector cells. In some embodiments, administration of the modified immune effector cells to the subject is not accompanied by high dose IL-2 treatment. In some embodiments, the subject has not undergone lymphodepletion prior to administration of the modified immune effector cells and administration of the modified immune effector cells to the subject is not accompanied by high dose IL-2 treatment.

DETAILED DESCRIPTION

Figure 1:
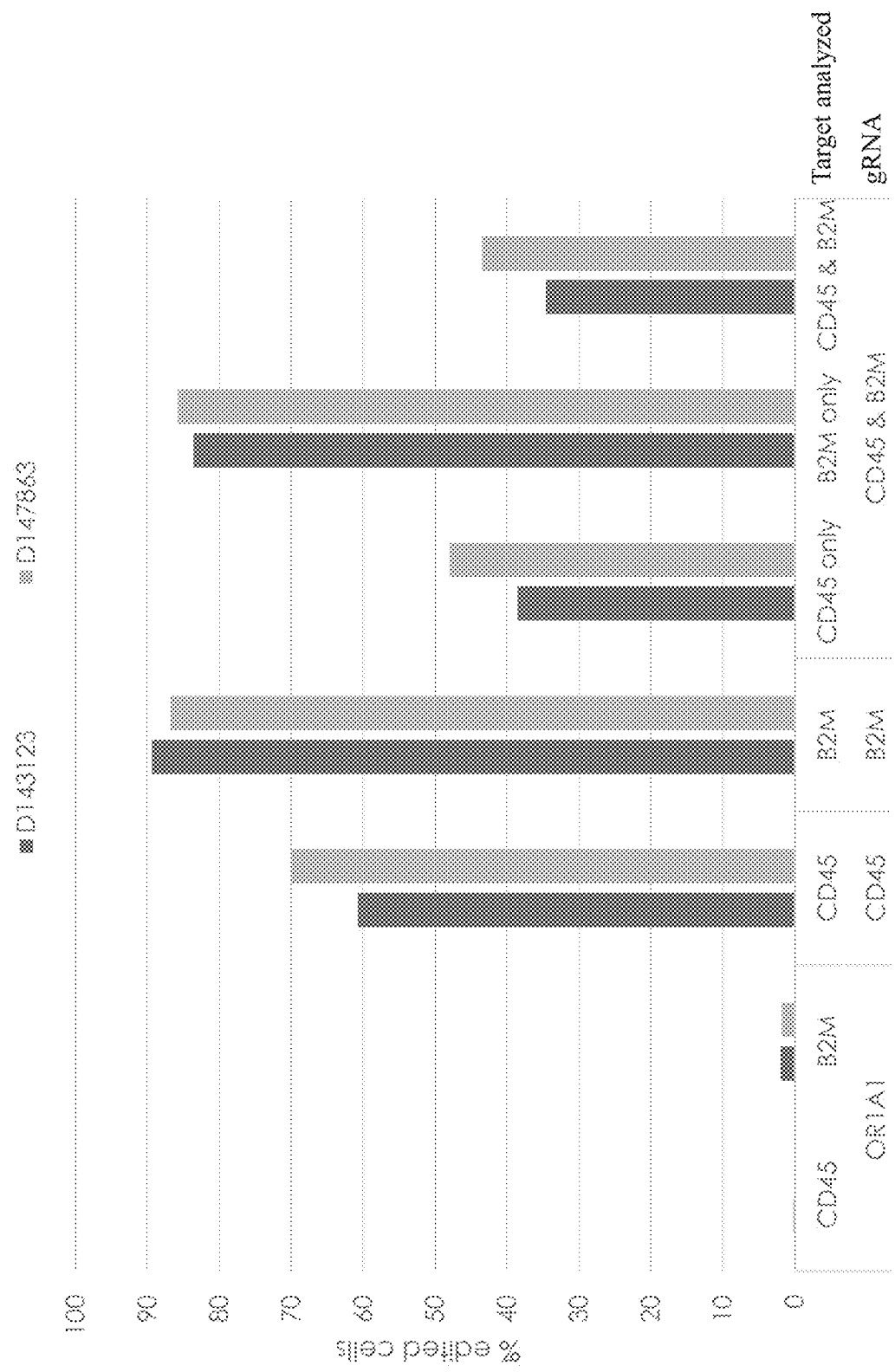
FIG. 1 shows the editing efficiency of RNPs with CD45 and B2M targeting gRNAs.

Genetic modification of T cells (such as using CRISPR-based systems) can increase the effector functions of T cells when the right genes are targeted for editing in the right way. However, gene-editing efficacy is highly unpredictable, especially when two or more genes are edited. Extensive experimentation has resulted in the identification of new gRNAs and/or selection of known gRNAs that have superior efficacy in gene editing. In particular, disclosed herein are, in some cases, gRNA combinations that demonstrate improved gene-editing of both SOCS1 and PTPN2. In some embodiments, the SOCS1-targeting gRNA and the PTPN2-targeting gRNA together demonstrate at least about 50%, at least about 60%, at least 70%, at least 80%, or at least 90%, or about the same efficacy compared to gene-editing with SOCS1-targeting gRNA or the PTPN2-targeting gRNA individually.

The present disclosure provides guide RNA (gRNA) combinations and methods of use in the modification of immune effector cells. In some embodiments, immune effector cells are modified by the methods of the present disclosure to reduce the expression and/or function of SOCS1 and PTPN2 such that one or more effector functions of the immune cells are enhanced. In some embodiments, the immune effector cells are further modified by introduction of transgenes conferring antigen specificity, such as introduction of T cell receptor (TCR) or chimeric antigen receptor (CAR) expression constructs. In some embodiments, the present disclosure provides methods of treating a cell proliferative disorder, such as a cancer, comprising administration of the modified immune effector cells described herein to a subject in need thereof.

Definitions

As used in this specification and the appended claims, the singular forms "a," "an" and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or 100% decrease as compared to a reference value. A decrease or reduction in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, a 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, 500%, or more increase as compared to a reference value. An increase in a particular value may also be represented as a fold-change in the value compared to a reference value, for example, at least a 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, increase as compared to the level of a reference value.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

"Fragment" refers to a portion of a polypeptide or polynucleotide molecule containing less than the entire polypeptide or polynucleotide sequence. In some embodiments, a fragment of a polypeptide or polynucleotide comprises at least 10%, 20%, 30%, 40%, 50%, 60%, 70%, 80%, 90%, 95%, 96%, 97%, 98%, or 99% of the entire length of the reference polypeptide or polynucleotide. In some embodiments, a polypeptide or polynucleotide fragment may contain 5, 10, 15, 20, 25, 30, 35, 40, 45, 50, 60, 70, 80, 90, 100, 200, 300, 400, 500, 600, 700, 800, 900, 1000, or more nucleotides or amino acids.

The term "sequence identity" refers to the percentage of bases or amino acids between two polynucleotide or polypeptide sequences that are the same, and in the same relative position. As such, one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

"Complementary" refers to the capacity for pairing, through base stacking and specific hydrogen bonding, between two sequences comprising naturally or non-naturally occurring bases or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

As referred to herein, a "complementary nucleic acid sequence" is a nucleic acid sequence comprising a sequence of nucleotides that enables it to non-covalently bind to another nucleic acid in a sequence-specific, antiparallel, manner (i.e., a nucleic acid specifically binds to a complementary nucleic acid) under the appropriate in vitro and/or in vivo conditions of temperature and solution ionic strength.

Methods of sequence alignment for comparison and determination of percent sequence identity and percent complementarity are well known in the art. Optimal alignment of sequences for comparison can be conducted, e.g., by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), by manual alignment and visual inspection (see, e.g., Brent et al., (2003) Current Protocols in Molecular Biology), by use of algorithms known in the art, including the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

Herein, the term "hybridize" refers to pairing between complementary nucleotide bases (e.g., adenine (A) forms a base pair with thymine (T) in a DNA molecule and with uracil (U) in an RNA molecule, and guanine (G) forms a base pair with cytosine (C) in both DNA and RNA molecules) to form a double-stranded nucleic acid molecule. (See, e.g., Wahl and Berger (1987) Methods Enzymol. 152:399; Kimmel, (1987) Methods Enzymol. 152:507). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary. It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted.

The term "modified" refers to a substance or compound (e.g., a cell, a polynucleotide sequence, and/or a polypeptide sequence) that has been altered or changed as compared to the corresponding unmodified substance or compound.

The term "naturally-occurring" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

"Isolated" refers to a material that is free to varying degrees from components which normally accompany it as found in its native state.

An "expression cassette" or "expression construct" refers to a DNA polynucleotide sequence operably linked to a promoter. "Operably linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

The term "recombinant vector" as used herein refers to a polynucleotide molecule capable of transferring or transporting another polynucleotide inserted into the vector. The inserted polynucleotide may be an expression cassette. In some embodiments, a recombinant vector may be a viral vector or a non-viral vector (e.g., a plasmid).

The term "sample" refers to a biological composition (e.g., a cell or a portion of a tissue) that is subjected to analysis and/or genetic modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts), subjects are rodents (e.g., mice, rats, hamsters), rabbits, primates, or swine such as inbred pigs and the like. The terms "subject" and "patient" are used interchangeably herein.

"Administration" refers herein to introducing an agent or composition into a subject.

"Treating" as used herein refers to delivering an agent or composition to a subject to affect a physiologic outcome.

As used herein, the term "effective amount" refers to the minimum amount of an agent or composition required to result in a particular physiological effect. The effective amount of a particular agent or composition may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent or composition may also be expressed as the half-maximal effective concentration ($EC_{50}$), which refers to the concentration of an agent that results in a magnitude of a particular physiological response that is half-way between a reference level and a maximum response level.

"Population" of cells refers to any number of cells greater than 1, but is preferably at least $1 \times 10^3$ cells, at least $1 \times 10^4$ cells, at least $1 \times 10^5$ cells, at least $1 \times 10^6$ cells, at least $1 \times 10^7$ cells, at least $1 \times 10^8$ cells, at least $1 \times 10^9$ cells, at least $1 \times 10^{10}$ cells, or more cells. A population of cells may refer to an in vitro population (e.g., a population of cells in culture) or an in vivo population (e.g., a population of cells residing in a particular tissue).

Herein, "gene editing efficiency" refers to the frequency of target-specific gene edits produced by a particular CRISPR/Cas system (i.e., a particular combination of gRNAs and/or Cas proteins). Gene editing efficiency can be measured by a variety of means known in the art, for example, by sequencing of the target nucleic acid sequence to identify modifications in the wild type sequence, Western blot analyses of the encoded protein, qPCR, functional assays to measure modifications to protein function, and/or flow cytometry analyses for surface or intracellular protein expression.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

CRISPR/Cas Systems

In some embodiments, the present disclosure provides CRISPR (Clustered Regularly Interspaced Short Palindromic Repeats)/Cas (CRISPR Associated) nuclease systems comprising a SOCS1-targeting gRNA and a PTPN2-targeting gRNA. Such systems described herein are suitable for use in the production of modified immune effector cells comprising reduced expression and/or function of SOCS1 and PTPN2. The combinations of SOCS1-targeting and PTPN2-targeting gRNAs of the CRISPR/Cas systems described herein are capable of reducing the expression and/or function of both SOCS1 and PTPN2 to levels similar to those achieved with CRISPR/Cas systems targeting either of the SOCS1 or PTPN2 genes alone. In such embodiments, the reduced expression or function of SOCS1 and PTPN2 enhances one or more effector functions of the immune cell.

The suppressors of cytokine signaling SOCS1 (SOCS1) gene encodes the SOCS1 protein, which comprises C-terminal SOCS box motifs, an SH2-domain, an ESS domain, and an N-terminal KIR domain. The 12 amino-acid residue called the kinase inhibitory region (KIR) has been found to be critical in the ability of SOCS1 to negatively regulate JAK1, TYK2 and JAK2 tyrosine kinase function.

The protein tyrosine phosphatase family (PTP) dephosphorylate phospho-tyrosine residues by their phosphatase catalytic domain. PTPN2 functions as a brake on both TCRs and cytokines, which signal through JAK/STAT signaling complexes, and thus serves as a checkpoint on both Signals 1 and 3. Following T cell engagement with antigen and activation of the TCR, positive signals are amplified downstream by the kinases Lck and Fyn by phosphorylation of tyrosine residues. PTPN2 serves to dephosphorylate both Lck and Fyn and thus attenuate TCR signaling. In addition, following T cell encounter with cytokines and signaling through common γ chain receptor complexes, which transmit positive signals though JAK/STAT signaling, PTPN2 also attenuates TCR signaling by dephosphorylation of STAT1 and STAT3. The sum functional impact of PTPN2 loss on T cell function is a lowering of the activation threshold needed for fulminant T cell activation through the TCR, and a hypersensitivity to growth and differentiation-enhancing cytokines.

In addition, in GEM models, deletion of Ptpn2 in the whole mouse increases cytokine levels, lymphocytic infiltration in nonlymphoid tissues and early signs of rheumatoid arthritis-like symptoms; these mice do not survive past 5 weeks of age. Thus, PTPN2 has been identified as critical for postnatal development in mice. Consistent with this autoimmune phenotype, deletion of Ptpn2 in the T cell lineage from birth also results in an increase in lymphocytic infiltration in non-lymphoid tissues. Importantly, an inducible knockout of Ptpn2 in adult mouse T cells did not result in any autoimmune manifestations. Outside of its role in autoimmunity, Ptpn2 deletion was identified to associate with a small percentage of T cell acute lymphoblastic leukemia in humans (ALL); and to enhance skin tumor development in a two-stage chemically-induced carcinogenicity mouse model. These data have led some to postulate that PTPN2 may be a tumor suppressor protein.

TABLE 1

| | Endogenous target genes | | | | |
|---|---|---|---|---|---|
| Gene Symbol | Gene Name | Human UniProt Ref. | Human NCBI Ref | Murine UniProt Ref. | Murine NCBI Ref |
| SOCS1 | suppressor of cytokine signaling 1 | O15524 | 8651 (SEQ ID NO: 312) | O35716 | 12703 (SEQ ID NO: 313) |
| PTPN2 | protein tyrosine phosphatase, non-receptor type 2 | P17706 | 5771 (SEQ ID NO: 314) | Q06180 | 19255 (SEQ ID NO: 315) |

In some embodiments, the CRISPR/Cas system is a Class 2 system. Class 2 CRISPR/Cas systems are divided into three types: Type II, Type V, and Type VI systems. In some embodiments, the CRISPR/Cas system is a Class 2 Type II system, utilizing the Cas9 protein. In such embodiments, the site-directed modifying polypeptide is a Cas9 DNA endonuclease (or variant thereof) and the nucleic acid guide molecule is a guide RNA (gRNA). In some embodiments, the CRISPR/Cas system is a Class 2 Type V system, utilizing the Cas12 proteins (e.g., Cas12a (also known as Cpf1), Cas12b (also known as C2c1), Cas12c (also known as C2c3), Cas12d (also known as CasY), and Cas12e (also known as CasX)). In such embodiments, the site-directed modifying polypeptide is a Cas12 DNA endonuclease (or variant thereof) and the nucleic acid guide molecule is a gRNA. In some embodiments, the CRISPR/Cas system is a Class 2 and Type VI system, utilizing the Cas13 proteins (e.g., Cas13a (also known as C2c2), Cas13b, and Cas13c). (See, Pyzocha et al., ACS Chemical Biology, 13(2), 347-356). In such embodiments, the site-directed modifying polypeptide is a Cas13 RNA riboendonuclease and the nucleic acid guide molecule is a gRNA.

A Cas polypeptide refers to a polypeptide that can interact with a gRNA molecule and, in concert with the gRNA molecule, home or localize to a target DNA. Cas polypeptides include naturally occurring Cas proteins and engineered, altered, or otherwise modified Cas proteins that differ by one or more amino acid residues from a naturally-occurring Cas sequence.

The gRNA mediates the target specificity of the CRIPSR/Cas systems by specifically hybridizing with a target nucleic acid sequence and interacting with a Cas protein to produce one or more modifications within or around the target nucleic acid sequence. Reference herein to a target gene encompasses the full-length DNA sequence for that particular gene which comprises a plurality of target genetic loci (i.e., portions of a particular target gene sequence (e.g., an exon or an intron)). Within each target genetic loci are shorter stretches of DNA sequences referred to herein as "target DNA sequences" that can be modified by the CRISPR/Cas systems described herein. Further, each target genetic loci comprises a "target modification site," which refers to the precise location of the modification induced by the CRISPR/Cas system (e.g., the location of an insertion, a deletion, or mutation, the location of a DNA break, or the location of an epigenetic modification). The CRISPR/Cas systems described herein comprise 2 or more nucleic acid guides (e.g., 2, 3, 4, 5, 6, 7, 8, 9, 10, or more nucleic acid guides).

The precise location of the target modification site is determined by both (i) base-pairing complementarity between the gRNA and the target nucleic acid sequence; and (ii) the location of a short motif, referred to as the protospacer adjacent motif (PAM), in the target DNA sequence (referred to as a protospacer flanking sequence (PFS) in target RNA sequences). PAM sequences facilitate the unwinding of the DNA double helix to allow DNA base-pairing with the sgRNA. The PAM/PFS sequence is required for Cas binding to the target nucleic acid sequence. A variety of PAM/PFS sequences are known in the art and are suitable for use with a particular Cas endonuclease (e.g., a Cas9 endonuclease) (See e.g., Nat Methods. 2013 November; 10(11): 1116-1121 and Sci Rep. 2014; 4: 5405). In some embodiments, the PAM sequence is located within 50 base pairs of the target modification site in a target DNA sequence. In some embodiments, the PAM sequence is located within 10 base pairs of the target modification site in a target DNA sequence. In some embodiments, the PAM sequence is located within 3 base pairs of the target modification site in a target DNA sequence. In some embodiments, the PAM sequence is located downstream of the target modification site in a target DNA sequence. In some embodiments, the PAM sequence is located within 3, 10 or 50 base pairs downstream of the target modification site in a target DNA sequence. The DNA sequences that can be targeted by this method are limited only by the relative distance of the PAM sequence to the target modification site and the presence of a unique 20 base pair sequence to mediate sequence-specific, gRNA-mediated Cas binding. In some embodiments, the PFS sequence is located at the 3' end of the target RNA sequence. In some embodiments, the target modification site is located at the 5' terminus of the target locus. In some embodiments, the target modification site is located at the 3' end of the target locus. In some embodiments, the target modification site is located within an intron or an exon of the target locus.

In some embodiments, the present disclosure provides one or more polynucleotides encoding a gRNA and/or a Cas protein. In some embodiments, a gRNA-encoding and/or a Cas protein-encoding nucleic acid is comprised in an expression vector, e.g., a recombinant expression vector.

Cas Proteins

Cas molecules of a variety of species can be used in the methods and compositions described herein, including Cas molecules derived from *S. pyogenes, S. aureus, N. meningitidis, S. thermophiles, Acidovorax avenae, Actinobacillus pleuropneumoniae, Actinobacillus succinogenes, Actinobacillus suis, Actinomyces* sp., *Cycliphilusdenitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gammaproteobacterium, Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae.*

Cas molecules also include those from phage-encoded CRISPR-Cas systems. Phages that encode such systems include ICP1 and other phages that use these systems to overcome phage inducible chromosomal island-like elements (PLEs). (McKitterick et al., Phil. Trans. R. Soc. B 374: 20180089 (2019), incorporated herein by reference in its entirety.)

In some embodiments, the Cas protein is a naturally-occurring Cas protein. In some embodiments, the Cas endonuclease is selected from the group consisting of C2C1, C2C3, Cpf1 (also referred to as Cas12a), Cas12b, Cas12c, Cas12d, Cas12e, Cas13a, Cas13b, Cas13c, Cas13d, Cas1, CaslB, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In some embodiments, the Cas protein is an endoribonuclease such as a Cas13 protein. In some embodiments, the Cas13 protein is a Cas13a (Abudayyeh et al., Nature 550 (2017), 280-284), Cas13b (Cox et al., Science (2017) 358: 6336, 1019-1027), Cas13c (Cox et al., Science (2017) 358:6336, 1019-1027), or Cas13d (Zhang et al., Cell 175 (2018), 212-223) protein.

In some embodiments, the Cas protein is a wild-type or naturally occurring Cas9 protein or a Cas9 ortholog. Wild-type Cas9 is a multi-domain enzyme that uses an HNH nuclease domain to cleave the target strand of DNA and a RuvC-like domain to cleave the non-target strand. Binding of WT Cas9 to DNA based on gRNA specificity results in double-stranded DNA breaks that can be repaired by non-homologous end joining (NHEJ) or homology-directed repair (HDR). Exemplary naturally occurring Cas9 molecules are described in Chylinski et al., RNA Biology 2013 10:5, 727-737 and additional Cas9 orthologs are described in International PCT Publication No. WO 2015/071474. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 1 1 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

In some embodiments, the naturally occurring Cas9 polypeptide is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, the Cas polypeptide comprises one or more of the following activities:
  (a) a nickase activity, i.e., the ability to cleave a single strand, e.g., the non-complementary strand or the complementary strand, of a nucleic acid molecule;
  (b) a double stranded nuclease activity, i.e., the ability to cleave both strands of a double stranded nucleic acid and create a double stranded break, which in an embodiment is the presence of two nickase activities;
  (c) an endonuclease activity;
  (d) an exonuclease activity; and/or
  (e) a helicase activity, i.e., the ability to unwind the helical structure of a double stranded nucleic acid.

In some embodiments, the Cas polypeptide is fused to heterologous proteins that recruit DNA-damage signaling proteins, exonucleases, or phosphatases to further increase the likelihood or the rate of repair of the target sequence by one repair mechanism or another. In some embodiments, a WT Cas polypeptide is co-expressed with a nucleic acid repair template to facilitate the incorporation of an exogenous nucleic acid sequence by homology-directed repair.

In some embodiments, different Cas proteins (i.e., Cas9 proteins from various species) may be advantageous to use in the various provided methods in order to capitalize on various enzymatic characteristics of the different Cas proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from S. pyogenes and recognizes the PAM sequence motif NGG, NAG, NGA (Mali et al, Science 2013; 339 (6121): 823-826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190(4): 1390-1400). In some embodiments, the Cas protein is a Cas9 protein derived from S. mutans and recognizes the PAM sequence motif NGG and/or NAAR (R=A or G) (See, e.g., Deveau et al, J BACTERIOL 2008; 190(4): 1390-1400). In some embodiments, the Cas protein is a Cas9 protein derived from S. aureus and recognizes the PAM sequence motif NNGRR (R=A or G). In some embodiments, the Cas protein is a Cas9 protein derived from S. aureus and recognizes the PAM sequence motif N GRRT (R=A or G). In some embodiments, the Cas protein is a Cas9 protein derived from S. aureus and recognizes the PAM sequence motif N GRRV (R=A or G). In some embodiments, the Cas protein is a Cas9 protein derived from N. meningitidis and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the Cas protein is a Cas13a protein derived from Leptotrichia shahii and recognizes the PFS sequence motif of a single 3' A, U, or C.

In some embodiments, a polynucleotide encoding a Cas protein is provided. In some embodiments, the polynucleotide encodes a Cas protein that is at least 90% identical to a Cas protein described in International PCT Publication No. WO 2015/071474 or Chylinski et al., RNA, Biology 2013 10:5, 727-737. In some embodiments, the polynucleotide encodes a Cas protein that is at least 95%, 96%, 97%, 98%, or 99% identical to a Cas protein described in International PCT Publication No. WO 2015/071474 or Chylinski et al., RNA Biology 2013 10:5, 727-737. In some embodiments, the polynucleotide encodes a Cas protein that is 100% identical to a Cas protein described in International PCT Publication No. WO 2015/071474 or Chylinski et al., RNA Biology 2013 10:5, 727-737.

Cas Mutants

In some embodiments, the Cas polypeptides are engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild-type Cas protein.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a deactivated Cas (dCas) mutant. In such embodiments, the Cas polypeptide does not comprise any intrinsic enzymatic activity and is unable to mediate target nucleic acid cleavage. In such embodiments, the dCas may be fused with a heterologous protein that is capable of modifying the target nucleic acid in a non-cleavage based manner. For example, in some embodiments, a dCas protein is fused to transcription activator or transcription repressor domains (e.g., the Kruppel associated box (KRAB or SKD); the Mad mSIN3 interaction domain (SID or SID4X); the ERF repressor domain (ERD); the MAX-interacting protein 1 (MXI1); methyl-CpG binding protein 2 (MECP2); etc.). In some such cases, the dCas fusion protein is targeted by the gRNA to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target DNA or modifies a polypeptide associated with the target DNA). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, the dCas is a dCas13 mutant (Konermann et al., Cell 173 (2018), 665-676). These dCas13 mutants can then be fused to enzymes that modify RNA, including adenosine deaminases (e.g., ADAR1 and ADAR2). Adenosine deaminases convert adenine to inosine, which the translational machinery treats like guanine, thereby creating a functional A→G change in the RNA sequence. In some embodiments, the dCas is a dCas9 mutant.

In some embodiments, the mutant Cas9 is a Cas9 nickase mutant. Cas9 nickase mutants comprise only one catalytically active domain (either the HNH domain or the RuvC domain). The Cas9 nickase mutants retain DNA binding based on gRNA specificity, but are capable of cutting only one strand of DNA resulting in a single-strand break (e.g. a "nick"). In some embodiments, two complementary Cas9 nickase mutants (e.g., one Cas9 nickase mutant with an inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

In some embodiments, the Cas polypeptides described herein can be engineered to alter the PAM/PFS specificity of the Cas polypeptide. In some embodiments, a mutant Cas polypeptide has a PAM/PFS specificity that is different from the PAM/PFS specificity of the parental Cas polypeptide. For example, a naturally occurring Cas protein can be modified to alter the PAM/PFS sequence that the mutant Cas polypeptide recognizes to decrease off target sites, improve specificity, or eliminate a PAM/PFS recognition requirement. In some embodiments, a Cas protein can be modified to increase the length of the PAM/PFS recognition sequence. In some embodiments, the length of the PAM recognition sequence is at least 4, 5, 6, 7, 8, 9, 10 or 15 amino acids in length. Cas polypeptides that recognize different PAM/PFS sequences and/or have reduced off-target activity can be generated using directed evolution. Exemplary methods and systems that can be used for directed evolution of Cas polypeptides are described, e.g., in Esvelt et al. Nature 2011, 472(7344): 499-503.

Exemplary Cas mutants are described in International PCT Publication No. WO 2015/161276 and Konermann et al., Cell 173 (2018), 665-676, which are incorporated herein by reference in their entireties.

gRNAs

The present disclosure provides guide RNAs (gRNAs) that direct Cas endonucleases to a specific target nucleic acid sequence. A gRNA comprises a "nucleic acid-targeting segment" or "targeting domain", also known as the crRNA, and protein-binding segment. The targeting domain may also be referred to as a "spacer" sequence and comprises a nucleotide sequence that is complementary to a target nucleic acid sequence. As such, the targeting domain of a gRNA interacts with a target nucleic acid in a sequence-specific manner via hybridization (i.e., base pairing), and determines the location within the target nucleic acid that the gRNA will bind. The targeting domain of a gRNA can be modified (e.g., by genetic engineering) to hybridize to any desired sequence within a target nucleic acid sequence. In some embodiments, the targeting domain sequence is between about 13 and about 22 nucleotides in length. In some embodiments, the targeting domain sequence is about 13, 14, 15, 16, 17, 18, 19, 20, 21, or 22 nucleotides in length. In some embodiments, the targeting domain sequence is about 20 nucleotides in length.

The protein-binding segment of a guide RNA comprises, in part, two complementary stretches of nucleotides that hybridize to one another to form a double stranded RNA duplex (dsRNA duplex), which facilitates binding to the Cas protein to form a ribonucleoprotein (RNP) complex. The guide RNA guides the bound Cas polypeptide to a specific nucleotide sequence within target nucleic acid via the above-described targeting domain. The protein-binding segment of a guide RNA comprises two stretches of nucleotides that are complementary to one another and which form a double stranded RNA duplex. The protein-binding segment of a gRNA may also be referred to as a "scaffold" segment or a "tracr RNA". In some embodiments, the tracr RNA sequence is between about 30 and about 180 nucleotides in length. In some embodiments, the tracr RNA sequence is between about 40 and about 90 nucleotides, about 50 and about 90 nucleotides, about 60 and about 90 nucleotides, about 65 and about 85 nucleotides, about 70 and about 80 nucleotides, about 65 and about 75 nucleotides, or about 75 and about 85 nucleotides in length. In some embodiments, the tracr RNA sequence is about 70, 71, 72, 73, 74, 75, 76, 77, 78, 79, 80, 81, 82, 83, 84, 85, 86, 87, 88, or about 90 nucleotides in length. In some embodiments, the tracr RNA comprises a nucleic acid sequence encoded by the DNA sequence of SEQ ID NO: 305 (See Mali et al., Science (2013) 339(6121):823-826), SEQ ID NOs: 306-307 (See PCT Publication No. WO 2016/106236), SEQ ID NOs: 309-310 (See Deltcheva et al., Nature. 2011 Mar. 31; 471 (7340): 602-607), or SEQ ID NO: 311 (See Chen et al., Cell 2013, 155(7); 1479-1491). Any of the foregoing tracr sequences are suitable for use in combination with any of the gRNA targeting domain embodiments described herein.

In some embodiments, a gRNA comprises two separate RNA molecules (i.e., a "dual gRNA"). A dual gRNA comprises two separate RNA molecules: a "crispr RNA" (or "crRNA") and a "tracr RNA". A crRNA molecule comprises a spacer sequence covalently linked to a "tracr mate"

sequence. The tracer mate sequence comprises a stretch of nucleotides that are complementary to a corresponding sequence in the tracr RNA molecule. The crRNA molecule and tracr RNA molecule hybridize to one another via the complementarity of the tracr and tracer mate sequences.

In some embodiments, a gRNA comprises a single RNA molecule (i.e. a "single guide RNA" or "sgRNA"). In such embodiments, the nucleic acid-targeting sequence and the protein-binding sequence are present in a single RNA molecule by fusion of the spacer sequence to the tracr RNA sequence. In some embodiments, the sgRNA is about 50 to about 200 nucleotides in length. In some embodiments, the sgRNA is about 75 to about 150 or about 100 to about 125 nucleotides in length. In some embodiments, the sgRNA is about 100 nucleotides in length. Herein, use of the term "guide RNA" or "gRNA" is inclusive of both dual gRNAs and sgRNAs.

In some embodiments, any of the nucleic acids described herein can have 1, 2, 3, 4 or 5 nucleotides differing from a base sequence. For example, in some embodiments, the CRISPR/Cas system comprises a SOCS1-targeting gRNA comprising a targeting domain sequence that is complementary to a nucleic acid sequence with 1, 2, 3, 4, or 5 nucleotides differing from a target DNA sequence of one of SEQ ID NOs: 1-3 and a PTPN2-targeting gRNA comprising a targeting domain sequence that is complementary to a nucleic acid sequence with 1, 2, 3, 4, or 5 nucleotides differing from a target DNA sequence of one of SEQ ID NOs: 146-148. In some embodiments, the CRISPR/Cas system comprises a SOCS1-targeting gRNA comprising a targeting domain sequence encoded by a nucleic acid sequence with 1, 2, 3, 4, or 5 nucleotides differing from one of SEQ ID NOs: 1-3 and a PTPN2-targeting gRNA comprising a targeting domain sequence encoded by a nucleic acid sequence with 1, 2, 3, 4, or 5 nucleotides differing from one of SEQ ID NOs: 146-148. This can also be expressed as percent identity as provided below.

In some embodiments, the CRISPR/Cas system comprises a SOCS1-targeting gRNA and a PTPN2-targeting gRNA, wherein the SOCS1-targeting gRNA comprises a targeting domain sequence that is complementary to a nucleic acid sequence at least 75%, 80%, 85%, 90%, 95%, or 100% identical to the target DNA sequence of SEQ ID NO: 3. In some embodiments, the CRISPR/Cas system comprises a SOCS1-targeting gRNA and a PTPN2-targeting gRNA, wherein the SOCS1-targeting gRNA comprises a targeting domain sequence encoded by a nucleic acid sequence that is at least 75%, 80%, 85%, 90%, 95%, or 100% identical to SEQ ID NO: 3. In some aspects of this embodiment, the PTPN2-targeting gRNA comprises a targeting domain sequence that is at least 75%, 80%, 85%, 90%, 95%, or 100% identical to a target DNA sequence selected from SEQ ID NOs: 146-148 or comprises a targeting domain sequence encoded by a nucleic acid sequence that is complementary to a nucleic acid sequence at least 75%, 80%, 85%, 90%, 95%, or 100% identical to a nucleic acid sequence selected from SEQ ID NOs: 146-148. In some aspects of this embodiment, the SOCS1-targeting gRNA comprises a targeting domain sequence encoded by a nucleic acid sequence that is at least 95%, 96%, 97%, 98%, 99%, or 100% identical to SEQ ID NO: 3 and the PTPN2-targeting gRNA comprises a targeting domain sequence encoded by a nucleic acid sequence that is at least 95%, 96%, 97%, 98%, 99%, or 100% identical to one of SEQ ID NOs: 146-148 and 162-272.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of one of SEQ ID NOs: 1-3 and a PTPN2-targeting gRNA comprising a targeting domain sequence that is complementary to a nucleic acid sequence at least 75%, 80%, 85%, 90%, 95%, or 100% identical to a target DNA sequence of one of SEQ ID NOs: 146-148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to one of SEQ ID NOs: 1-3 and a PTPN2-targeting gRNA comprising a targeting domain sequence encoded by a nucleic acid sequence that is at least 95%, 96%, 97%, 98%, 99%, or 100% identical to one of SEQ ID NOs: 146-148.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 1 and a PTPN2-targeting gRNA comprising a targeting domain sequence that is complementary to a nucleic acid sequence at least 75%, 80%, 85%, 90%, 95%, or 100% identical to a target DNA sequence of one of SEQ ID NOs: 146-148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 1 and a PTPN2-targeting gRNA comprising a targeting domain sequence encoded by a nucleic acid sequence that is at least 95%, 96%, 97%, 98%, 99%, or 100% identical to one of SEQ ID NOs: 146-148.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 2 and a PTPN2-targeting gRNA comprising a targeting domain sequence that is complementary to a nucleic acid sequence at least 75%, 80%, 85%, 90%, 95%, or 100% identical to a target DNA sequence of one of SEQ ID NOs: 146-148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 2 and a PTPN2-targeting gRNA comprising a targeting domain sequence encoded by a nucleic acid sequence that is at least 95%, 96%, 97%, 98%, 99%, or 100% identical to one of SEQ ID NOs: 146-148.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 3 and a PTPN2-targeting gRNA comprising a targeting domain sequence that is complementary to a nucleic acid sequence at least 75%, 80%, 85%, 90%, 95%, or 100% identical to a target DNA sequence of one of SEQ ID NOs: 146-148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 3 and a PTPN2-targeting gRNA comprising a targeting domain sequence encoded by a nucleic acid sequence that is at least 95%, 96%, 97%, 98%, 99%, or 100% identical to one of SEQ ID NOs: 146-148.

In some embodiments, the CRISPR/Cas system comprises a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 146 and a SOCS1-targeting gRNA comprising a targeting domain sequence that is complementary to a nucleic acid sequence at least 75%, 80%, 85%, 90%, 95%, or 100% identical to a target DNA sequence of one of SEQ ID NOs: 1-3. In some embodiments, the CRISPR/Cas system comprises a PTPN2-targeting gRNA comprising a targeting domain sequence encoded by a nucleic acid sequence that is at least 95%, 96%, 97%, 98%, 99%, or 100% identical to SEQ ID NO: 146 and a SOCS1-targeting gRNA comprising a targeting domain sequence encoded by a nucleic acid sequence that is at least 95%, 96%, 97%, 98%, 99%, or 100% identical to one of SEQ ID NOs: 1-3.

In some embodiments, the CRISPR/Cas system comprises a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 147 and a SOCS1-targeting gRNA comprising a targeting domain sequence that is complementary to a nucleic acid sequence at least 75%, 80%, 85%, 90%, 95%, or 100% identical to a target DNA sequence of one of SEQ ID NOs: 1-3. In some embodiments, the CRISPR/Cas system comprises a PTPN2-targeting gRNA comprising a targeting domain sequence encoded by a nucleic acid sequence that is at least 95%, 96%, 97%, 98%, 99%, or 100% identical to SEQ ID NO: 147 and a SOCS1-targeting gRNA comprising a targeting domain sequence encoded by a nucleic acid sequence that is at least 95%, 96%, 97%, 98%, 99%, or 100% identical to one of SEQ ID NOs: 1-3.

In some embodiments, the CRISPR/Cas system comprises a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 148 and a SOCS1-targeting gRNA comprising a targeting domain sequence that is complementary to a nucleic acid sequence at least 75%, 80%, 85%, 90%, 95%, or 100% identical to a target DNA sequence of one of SEQ ID NOs: 1-3. In some embodiments, the CRISPR/Cas system comprises a PTPN2-targeting gRNA comprising a targeting domain sequence encoded by a nucleic acid sequence that is at least 95%, 96%, 97%, 98%, 99%, or 100% identical to SEQ ID NO: 148 and a SOCS1-targeting gRNA comprising a targeting domain sequence encoded by a nucleic acid sequence that is at least 95%, 96%, 97%, 98%, 99%, or 100% identical to one of SEQ ID NOs: 1-3.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 1 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 146. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 146. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 1 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 147. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 1 and a PTPN2-targeting gRNA comprising a targeting domain sequence encoded by a nucleic acid sequence that is at least 95%, 96%, 97%, 98%, 99%, or 100% identical to SEQ ID NO: 147. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 1 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 1 and a PTPN2-targeting gRNA comprising a targeting domain sequence encoded by a nucleic acid sequence that is at least 95%, 96%, 97%, 98%, 99%, or 100% identical to SEQ ID NO: 148.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 2 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 146. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 2 and a PTPN2-targeting gRNA comprising a targeting domain sequence encoded by a nucleic acid sequence that is at least 95%, 96%, 97%, 98%, 99%, or 100% identical to SEQ ID NO: 146. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 2 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 147. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 2 and a PTPN2-targeting gRNA comprising a targeting domain sequence encoded by a nucleic acid sequence that is at least 95%, 96%, 97%, 98%, 99%, or 100% identical to SEQ ID NO: 147. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 2 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 2 and a PTPN2-targeting gRNA comprising a targeting domain sequence encoded by a nucleic acid sequence that is at least 95%, 96%, 97%, 98%, 99%, or 100% identical to SEQ ID NO: 148.

In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 3 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 146. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 3 and a PTPN2-targeting gRNA comprising a targeting domain sequence encoded by a nucleic acid sequence that is at least 95%, 96%, 97%, 98%, 99%, or 100% identical to SEQ ID NO: 146. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 3 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 147. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 3 and a PTPN2-targeting gRNA comprising a targeting domain sequence encoded by a nucleic acid sequence that is at least 95%, 96%, 97%, 98%, 99%, or 100% identical to SEQ ID NO: 147. In some embodiments, the CRISPR/Cas system comprises a SOCS1-targeting gRNA comprising a targeting domain sequence that is complementary to a nucleic acid sequence at least 75%, 80%, 85%, 90%, 95%, or 100% identical to a target DNA sequence of SEQ ID NO: 3 and a PTPN2-targeting gRNA comprising a targeting domain sequence that is complementary to a nucleic acid sequence at least 75%, 80%, 85%, 90%, 95%, or 100% identical to a target DNA sequence of SEQ ID NO: 148. In some embodiments, the CRISPR/Cas system comprises a SOCS1-targeting gRNA comprising a targeting domain sequence encoded by a nucleic acid sequence that is at least 95%, 96%, 97%, 98%, 99%, or 100% identical to SEQ ID NO: 3 and a PTPN2-targeting gRNA comprising a targeting domain sequence encoded by a nucleic acid sequence that is at least 95%, 96%, 97%, 98%, 99%, or 100% identical to SEQ ID NO: 148.

In some embodiments, the nucleic acid-binding segments of the gRNA sequences described herein are designed to minimize off-target binding using algorithms known in the art (e.g., Cas-OFF finder) to identify target sequences that are unique to a particular target locus or target gene.

In some embodiments, the gRNAs described herein can comprise one or more modified nucleosides or nucleotides which introduce stability toward nucleases. In such embodiments, these modified gRNAs may elicit a reduced innate immune response as compared to a non-modified gRNA. The term "innate immune response" includes a cellular response to exogenous nucleic acids, including single stranded nucleic acids, generally of viral or bacterial origin, which involves the induction of cytokine expression and release, particularly the interferons, and cell death.

In some embodiments, the gRNAs described herein are modified at or near the 5' end (e.g., within 1-10, 1-5, or 1-2 nucleotides of their 5' end). In some embodiments, the 5' end of a gRNA is modified by the inclusion of a eukaryotic mRNA cap structure or cap analog (e.g., a G(5')ppp(5')G cap analog, a m7G(5')ppp(5')G cap analog, or a 3'-0-Me-m7G (5')ppp(5')G anti reverse cap analog (ARCA)). In some embodiments, an in vitro transcribed gRNA is modified by treatment with a phosphatase (e.g., calf intestinal alkaline phosphatase) to remove the 5' triphosphate group. In some embodiments, a gRNA comprises a modification at or near its 3' end (e.g., within 1-10, 1-5, or 1-2 nucleotides of its 3' end). For example, in some embodiments, the 3' end of a gRNA is modified by the addition of one or more (e.g., 25-200) adenine (A) residues.

In some embodiments, modified nucleosides and modified nucleotides can be present in a gRNA. In some embodiments, modified nucleosides and nucleotides can include one or more of:

(a) alteration, e.g., replacement, of one or both of the non-linking phosphate oxygens and/or of one or more of the linking phosphate oxygens in the phosphodiester backbone linkage;

(b) alteration, e.g., replacement, of a constituent of the ribose sugar, e.g., of the 2' hydroxyl on the ribose sugar;

(c) wholesale replacement of the phosphate moiety with "dephospho" linkers;

(d) modification or replacement of a naturally occurring nucleobase;

(e) replacement or modification of the ribose-phosphate backbone;

(f) modification of the 3' end or 5' end of the oligonucleotide, e.g., removal, modification or replacement of a terminal phosphate group or conjugation of a moiety; and (g) modification of the sugar.

In some embodiments, the modifications listed above can be combined to provide modified nucleosides and nucleotides that can have two, three, four, or more modifications. For example, in some embodiments, a modified nucleoside or nucleotide can have a modified sugar and a modified nucleobase. In some embodiments, every base of a gRNA is modified. In some embodiments, each of the phosphate groups of a gRNA molecule are replaced with phosphorothioate groups. In some embodiments, one or more of the phosphate groups of the gRNA molecule is replaced with a phosphorothioate and a methyl is added to the 2' OH. This modification is also referred to as 2'-O-methyl 3'-phosphorothioate-RNA.

In some embodiments, a software tool can be used to optimize the choice of gRNA within a user's target sequence, e.g., to minimize total off-target activity across the genome. Off target activity may be other than cleavage. For example, for each possible gRNA choice using S. pyogenes Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then be ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool.

Modified Immune Effector Cells

In some embodiments, the present disclosure provides modified immune effector cells comprising the CRISPR/Cas systems comprising a SOCS1-targeting gRNA and a PTPN2-targeting gRNA described herein. Herein, the term "modified immune effector cells" encompasses immune effector cells comprising one or more genomic modifications resulting in the reduced expression and/or function of two or more endogenous target genes as well as immune effector cells comprising a CRISPR/Cas system capable of reducing the expression and/or function of two or more endogenous target genes. Herein, an "un-modified immune effector cell" or "control immune effector cell" refers to a cell or population of cells wherein the genomes have not been modified and that does not comprise a CRISPR/Cas system or comprises a control CRISPR/Cas system (e.g., an empty vector control, a non-targeting gRNA, a scrambled siRNA, etc.).

The term "immune effector cell" refers to cells involved in mounting innate and adaptive immune responses, including but not limited to lymphocytes (such as T-cells (including thymocytes) and B-cells), natural killer (NK) cells, NKT cells, macrophages, monocytes, eosinophils, basophils, neutrophils, dendritic cells, and mast cells. In some embodiments, the modified immune effector cell is a T cell, such as a CD4+ T cell, a CD8+ T cell (also referred to as a cytotoxic T cell or CTL), a regulatory T cell (Treg), a Th1 cell, a Th2 cell, or a Th17 cell.

In some embodiments, the modified immune effector cell is a T cell that has been isolated from a tumor sample (referred to herein as "tumor infiltrating lymphocytes" or "TILs"). Without wishing to be bound by theory, it is thought that TILs possess increased specificity to tumor antigens (Radvanyi et al., 2012 Clin Canc Res 18:6758-6770) and can therefore mediate tumor antigen-specific immune response (e.g., activation, proliferation, and cytotoxic activity against the cancer cell) leading to cancer cell destruction (Brudno et al., 2018 Nat Rev Clin Onc 15:31-46)) without the introduction of an exogenous engineered receptor. Therefore, in some embodiments, TILs are isolated from a tumor in a subject, expanded ex vivo, and re-infused into a subject. In some embodiments, TILs are modified to express one or more exogenous receptors specific for an autologous tumor antigen, expanded ex vivo, and re-infused into the subject. Such embodiments can be modeled using in vivo mouse models wherein mice have been transplanted with a cancer cell line expressing a cancer antigen (e.g., CD19) and are treated with modified T cells that express an exogenous receptor that is specific for the cancer antigen.

In some embodiments, the modified immune effector cell is an animal cell or is derived from an animal cell, including invertebrate animals and vertebrate animals (e.g., fish, amphibian, reptile, bird, or mammal). In some embodiments, the modified immune effector cell is a mammalian cell or is derived from a mammalian cell (e.g., a pig, a cow, a goat, a sheep, a rodent, a non-human primate, a human, etc.). In some embodiments, the modified immune effector cell is a rodent cell or is derived from a rodent cell (e.g., a rat or a mouse). In some embodiments, the modified immune effector cell is a human cell or is derived from a human cell.

In some embodiments, the modified immune effector cells comprise one or more modifications (e.g., insertions, deletions, or mutations of one or more nucleic acids) in the genomic DNA sequence of an endogenous target gene resulting in the reduced expression and/or function of the endogenous gene. In such embodiments, the modified immune effector cells comprise a "modified endogenous target gene." In some embodiments, the modifications in the genomic DNA sequence reduce or inhibit mRNA transcription, thereby reducing the expression level of the encoded mRNA transcript and protein. In some embodiments, the modifications in the genomic DNA sequence reduce or inhibit mRNA translation, thereby reducing the expression level of the encoded protein. In some embodiments, the modifications in the genomic DNA sequence encode a modified endogenous protein with reduced or altered function compared to the unmodified (i.e., wild-type) version of the endogenous protein (e.g., a dominant-negative mutant, described infra).

In some embodiments, the modified immune effector cells comprise one or more genomic modifications at a genomic location other than an endogenous target gene that result in the reduced expression and/or function of the endogenous target gene or that result in the expression of a modified version of an endogenous protein. For example, in some embodiments, a polynucleotide sequence encoding a CRISPR/Cas system is inserted into one or more locations in the genome, thereby reducing the expression and/or function of an endogenous target gene upon the expression of the CRISPR/Cas system. In some embodiments, a polynucleotide sequence encoding a modified version of an endogenous protein is inserted at one or more locations in the genome, wherein the function of the modified version of the protein is reduced compared to the un-modified or wild-type version of the protein (e.g., a dominant-negative mutant, described infra).

In some embodiments, the modified immune effector cells described herein comprise two or more modified endogenous target genes, wherein the one or more modifications result in a reduced expression and/or function of a gene product (i.e., an mRNA transcript or a protein) encoded by the endogenous target gene compared to an unmodified immune effector cell. For example, in some embodiments, a modified immune effector cell demonstrates reduced expression of an mRNA transcript and/or reduced expression of a protein. In some embodiments, the expression of the gene product in a modified immune effector cell is reduced by at least 5% compared to the expression of the gene product in an unmodified immune effector cell. In some embodiments, the expression of the gene product in a modified immune effector cell is reduced by at least 10%, 20%, 30%, 40%, 50%, 60%, 70%, 80%, 90%, or more compared to the expression of the gene product in an unmodified immune effector cell. In some embodiments, the modified immune effector cells described herein demonstrate reduced expression and/or function of gene products encoded by a plurality (e.g., two or more) of endogenous target genes compared to the expression of the gene products in an unmodified immune effector cell. For example, in some embodiments, a modified immune effector cell demonstrates reduced expression and/or function of gene products from 2, 3, 4, 5, 6, 7, 8, 9, 10, or more endogenous target genes compared to the expression of the gene products in an unmodified immune effector cell.

In some embodiments, the present disclosure provides a modified immune effector cell wherein two or more endogenous target genes, or a portion thereof, are deleted (i.e., "knocked-out") such that the modified immune effector cell does not express the mRNA transcript or protein. In some embodiments, a modified immune effector cell comprises deletion of a plurality of endogenous target genes, or portions thereof. In some embodiments, a modified immune effector cell comprises deletion of 2, 3, 4, 5, 6, 7, 8, 9, 10, or more endogenous target genes.

In some embodiments, the modified immune effector cells described herein comprise one or more modified endogenous target genes, wherein the one or more modifications to the target DNA sequence result in expression of a protein with reduced or altered function (e.g., a "modified endogenous protein") compared to the function of the corresponding protein expressed in an unmodified immune effector cell (e.g., a "unmodified endogenous protein"). In some embodiments, the modified immune effector cells described herein comprise 2, 3, 4, 5, 6, 7, 8, 9, 10, or more modified endogenous target genes encoding 2, 3, 4, 5, 6, 7, 8, 9, 10, or more modified endogenous proteins. In some embodiments, the modified endogenous protein demonstrates reduced or altered binding affinity for another protein expressed by the modified immune effector cell or expressed by another cell; reduced or altered signaling capacity; reduced or altered enzymatic activity; reduced or altered DNA-binding activity; or reduced or altered ability to function as a scaffolding protein.

In some embodiments, the modified endogenous target gene comprises one or more dominant negative mutations. As used herein, a "dominant-negative mutation" refers to a substitution, deletion, or insertion of one or more nucleotides of a target gene such that the encoded protein acts antagonistically to the protein encoded by the unmodified target gene. The mutation is dominant-negative because the negative phenotype confers genetic dominance over the positive phenotype of the corresponding unmodified gene. A gene comprising one or more dominant-negative mutations and the protein encoded thereby are referred to as a "dominant-negative mutants", e.g. dominant-negative genes and dominant-negative proteins.

In some embodiments, the modified immune effector cells described herein comprise a CRISPR/Cas system described herein and further comprise one or more exogenous transgenes inserted at one or more genomic loci (e.g., a genetic "knock-in"). In some embodiments, the one or more exogenous transgenes encode detectable tags, safety-switch systems, chimeric switch receptors, and/or engineered antigen-specific receptors.

In some embodiments, the modified immune effector cells described herein further comprise an exogenous transgene encoding a detectable tag. Examples of detectable tags include but are not limited to, FLAG tags, poly-histidine tags (e.g. 6×His), SNAP tags, Halo tags, cMyc tags, glutathione-S-transferase tags, avidin, enzymes, fluorescent proteins, luminescent proteins, chemiluminescent proteins, bioluminescent proteins, and phosphorescent proteins. In some embodiments the fluorescent protein is selected from the group consisting of blue/UV proteins (such as BFP, TagBFP, mTagBFP2, Azurite, EBFP2, mKalamal, Sirius, Sapphire, and T-Sapphire); cyan proteins (such as CFP, eCFP, Cerulean, SCFP3A, mTurquoise, mTurquoise2, monomeric Midoriishi-Cyan, TagCFP, and mTFP1); green proteins (such as: GFP, eGFP, meGFP (A208K mutation), Emerald, Superfolder GFP, Monomeric Azami Green, TagGFP2, mUKG, mWasabi, Clover, and mNeonGreen); yellow proteins (such as YFP, eYFP, Citrine, Venus, SYFP2, and TagYFP); orange proteins (such as Monomeric Kusabira-Orange, mKOκ, mKO2, mOrange, and mOrange2); red proteins (such as RFP, mRaspberry, mCherry, mStrawberry, mTangerine, tdTomato, TagRFP, TagRFP-T, mApple, mRuby, and mRuby2); far-red proteins (such as mPlum, HcRed-Tandem, mKate2, mNeptune, and NirFP); near-infrared proteins (such as TagRFP657, IFP1.4, and iRFP); long stokes shift proteins (such as mKeima Red, LSS-mKate1, LSS-mKate2, and mBeRFP); photoactivatible proteins (such as PA-GFP, PAmCherry1, and PATagRFP); photoconvertible proteins (such as Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, and PSmOrange); and photoswitchable proteins (such as Dronpa). In some embodiments, the detectable tag can be selected from AmCyan, AsRed, DsRed2, DsRed Express, E2-Crimson, HcRed, ZsGreen, ZsYellow, mCherry, mStrawberry, mOrange, mBanana, mPlum, mRasberry, tdTomato, DsRed Monomer, and/or AcGFP, all of which are available from Clontech.

In some embodiments, the modified immune effector cells described herein further comprise an exogenous transgene encoding a safety-switch system. Safety-switch systems (also referred to in the art as suicide gene systems) comprise exogenous transgenes encoding for one or more proteins that enable the elimination of a modified immune effector cell after the cell has been administered to a subject. Examples of safety-switch systems are known in the art. For example, safety-switch systems include genes encoding for proteins that convert non-toxic pro-drugs into toxic compounds such as the Herpes simplex thymidine kinase (Hsv-tk) and ganciclovir (GCV) system (Hsv-tk/GCV). Hsv-tk converts non-toxic GCV into a cytotoxic compound that leads to cellular apoptosis. As such, administration of GCV to a subject that has been treated with modified immune effector cells comprising a transgene encoding the Hsv-tk protein can selectively eliminate the modified immune effector cells while sparing endogenous immune effector cells. (See e.g., Bonini et al., Science, 1997, 276(5319):1719-1724; Ciceri et al., Blood, 2007, 109(11):1828-1836; Bondanza et al., Blood 2006, 107(5):1828-1836).

Additional safety-switch systems include genes encoding for cell-surface markers, enabling elimination of modified immune effector cells by administration of a monoclonal antibody specific for the cell-surface marker via ADCC. In some embodiments, the cell-surface marker is CD20 and the modified immune effector cells can be eliminated by administration of an anti-CD20 monoclonal antibody such as Rituximab (See e.g., Introna et al., Hum Gene Ther, 2000, 11(4):611-620; Serafini et al., Hum Gene Ther, 2004, 14, 63-76; van Meerten et al., Gene Ther, 2006, 13, 789-797). Similar systems using EGF-R and Cetuximab or Panitumumab are described in International PCT Publication No. WO 2018006880. Additional safety-switch systems include transgenes encoding pro-apoptotic molecules comprising one or more binding sites for a chemical inducer of dimerization (CID), enabling elimination of modified immune effector cells by administration of a CID which induces oligomerization of the pro-apoptotic molecules and activation of the apoptosis pathway. In some embodiments, the pro-apoptotic molecule is Fas (also known as CD95) (Thomis et al., Blood, 2001, 97(5), 1249-1257). In some embodiments, the pro-apoptotic molecule is caspase-9 (Straathof et al., Blood, 2005, 105(11), 4247-4254).

In some embodiments, the modified immune effector cells described herein further comprise an exogenous transgene encoding a chimeric switch receptor. Chimeric switch receptors are engineered cell-surface receptors comprising an extracellular domain from an endogenous cell-surface receptor and a heterologous intracellular signaling domain, such that ligand recognition by the extracellular domain results in activation of a different signaling cascade than that activated by the wild type form of the cell-surface receptor. In some embodiments, the chimeric switch receptor comprises the extracellular domain of an inhibitory cell-surface receptor fused to an intracellular domain that leads to the transmission of an activating signal rather than the inhibitory signal normally transduced by the inhibitory cell-surface receptor. In particular embodiments, extracellular domains derived from cell-surface receptors known to inhibit immune effector cell activation can be fused to activating intracellular domains. Engagement of the corresponding ligand will then activate signaling cascades that increase, rather than inhibit, the activation of the immune effector cell. For example, in some embodiments, the modified immune effector cells described herein comprise a transgene encoding a PD1-CD28 switch receptor, wherein the extracellular domain of PD1 is fused to the intracellular signaling domain of CD28 (See e.g., Liu et al., Cancer Res 76:6 (2016), 1578-1590 and Moon et al., Molecular Therapy 22 (2014), S201). In some embodiments, the modified immune effector cells described herein comprise a transgene encoding the extracellular domain of CD200R and the intracellular signaling domain of CD28 (See Oda et al., Blood 130:22 (2017), 2410-2419).

In some embodiments, the modified immune effector cells described herein further comprise an engineered antigen-specific receptor recognizing a protein target expressed by a target cell, such as a tumor cell or an antigen presenting cell (APC), referred to herein as "modified receptor-engineered cells" or "modified RE-cells". The term "engineered antigen receptor" refers to a non-naturally occurring antigen-specific receptor such as a chimeric antigen receptor (CAR) or a recombinant T cell receptor (TCR). In some embodiments, the engineered antigen receptor is a CAR comprising an extracellular antigen binding domain fused via hinge and transmembrane domains to a cytoplasmic domain comprising a signaling domain. In some embodiments, the CAR extracellular domain binds to an antigen expressed by a target cell in an MHC-independent manner leading to activation and proliferation of the RE cell. In some embodiments, the extracellular domain of a CAR recognizes a tag fused to an antibody or antigen-binding fragment thereof. In such embodiments, the antigen-specificity of the CAR is dependent on the antigen-specificity of the labeled antibody, such that a single CAR construct can be used to target multiple different antigens by substituting one antibody for another (See e.g., U.S. Pat. Nos. 9,233,125 and 9,624,279; US Patent Application Publication Nos. 20150238631 and 20180104354, incorporated by reference herein in their entireties). In some embodiments, the extracellular domain of a CAR may comprise an antigen binding fragment derived from an antibody. Antigen binding domains that are useful in the present disclosure include, for example, scFvs; antibodies; antigen binding regions of antibodies; variable regions of the heavy/light chains; and single chain antibodies.

In some embodiments, the intracellular signaling domain of a CAR may be derived from the TCR complex zeta chain (such as CD3ξ signaling domains), FcγRIII, FcεRI, or the T-lymphocyte activation domain. In some embodiments, the intracellular signaling domain of a CAR further comprises a costimulatory domain, for example a 4-1BB, CD28, CD40, MyD88, or CD70 domain. In some embodiments, the intracellular signaling domain of a CAR comprises two costimulatory domains, for example any two of 4-1BB, CD28, CD40, MyD88, or CD70 domains. Exemplary CAR structures and intracellular signaling domains are known in the art (See e.g., WO 2009/091826; US 20130287748; WO 2015/142675; WO 2014/055657; and WO 2015/090229, incorporated herein by reference in their entireties).

CARs specific for a variety of tumor antigens are known in the art, for example CD171-specific CARs (Park et al., Mol Ther (2007) 15(4):825-833), EGFRvIII-specific CARs (Morgan et al., Hum Gene Ther (2012) 23(10):1043-1053), EGF-R-specific CARs (Kobold et al., J Natl Cancer Inst (2014) 107(1):364), carbonic anhydrase K-specific CARs (Lamers et al., Biochem Soc Trans (2016) 44(3):951-959), FR-α-specific CARs (Kershaw et al., Clin Cancer Res (2006) 12(20):6106-6015), HER2-specific CARs (Ahmed et al., J Clin Oncol (2015) 33(15)1688-1696; Nakazawa et al., Mol Ther (2011) 19(12):2133-2143; Ahmed et al., Mol Ther (2009) 17(10):1779-1787; Luo et al., Cell Res (2016) 26(7): 850-853; Morgan et al., Mol Ther (2010) 18(4):843-851; Grada et al., Mol Ther Nucleic Acids (2013) 9(2):32), CEA-specific CARs (Katz et al., Clin Cancer Res (2015) 21(14):3149-3159), IL13Ra2-specific CARs (Brown et al., Clin Cancer Res (2015) 21(18):4062-4072), GD2-specific CARs (Louis et al., Blood (2011) 118(23):6050-6056; Caruana et al., Nat Med (2015) 21(5):524-529), ErbB2-specific CARs (Wilkie et al., J Clin Immunol (2012) 32(5): 1059-1070), VEGF-R-specific CARs (Chinnasamy et al., Cancer Res (2016) 22(2):436-447), FAP-specific CARs (Wang et al., Cancer Immunol Res (2014) 2(2):154-166), MSLN-specific CARs (Moon et al, Clin Cancer Res (2011) 17(14):4719-30), NKG2D-specific CARs (VanSeggelen et al., Mol Ther (2015) 23(10):1600-1610), CD19-specific CARs (Axicabtagene ciloleucel (Yescarta®) and Tisagenlecleucel (Kymriah®). See also, Li et al., J Hematol and Oncol (2018) 11(22), reviewing clinical trials of tumor-specific CARs. Each of the references in this paragraph is incorporated herein by reference in its entirety. Exemplary CARs suitable for use according to the present disclosure are described below in Table 2.

TABLE 2

Exemplary CAR constructs

| CAR Ref ID | Target | Ag-binding domain | Intracellular Domain | Transmembrane Domain | AA SEQ ID | NA SEQ ID |
|---|---|---|---|---|---|---|
| KSQCAR017 | human EGFR | Cetuximab H225 scFv | CD3 zeta | CD8a hinge | 299 | 300 |
| KSQCAR1909 | human CD19 | FMC63 scFv | CD3 zeta | CD8a hinge | 301 | 302 |

TABLE 2-continued

Exemplary CAR constructs

| CAR Ref ID | Target | Ag-binding domain | Intracellular Domain | Transmembrane Domain | AA SEQ ID | NA SEQ ID |
|---|---|---|---|---|---|---|
| KSQCAR010 | human HER2 | Herceptin scFv | CD3 zeta | CD8a hinge | 303 | 304 |

In some embodiments, the engineered antigen receptor is a recombinant TCR. Recombinant TCRs comprise TCRα and/or TCRβ chains that have been isolated and cloned from T cell populations recognizing a particular target antigen. For example, TCRα and/or TCRβ genes (i.e., TRAC and TRBC) can be cloned from T cell populations isolated from individuals with particular malignancies or T cell populations that have been isolated from humanized mice immunized with specific tumor antigens or tumor cells. Recombinant TCRs recognize antigen through the same mechanisms as their endogenous counterparts (e.g., by recognition of their cognate antigen presented in the context of major histocompatibility complex (MHC) proteins expressed on the surface of a target cell). This antigen engagement stimulates endogenous signal transduction pathways leading to activation and proliferation of the TCR-engineered cells.

Recombinant TCRs specific for tumor antigens are known in the art, for example WT1-specific TCRs (JTCR016, Juno Therapeutics; WT1-TCRc4, described in US Patent Application Publication No. 20160083449), MART-1 specific TCRs (including the DMF4T clone, described in Morgan et al., Science 314 (2006) 126-129); the DMF5T clone, described in Johnson et al., Blood 114 (2009) 535-546); and the ID3T clone, described in van den Berg et al., Mol. Ther. 23 (2015) 1541-1550), gp100-specific TCRs (Johnson et al., Blood 114 (2009) 535-546), CEA-specific TCRs (Parkhurst et al., Mol Ther. 19 (2011) 620-626), NY-ESO and LAGE-1 specific TCRs (1G4T clone, described in Robbins et al., J Clin Oncol 26 (2011) 917-924; Robbins et al., Clin Cancer Res 21 (2015) 1019-1027; and Rapoport et al., Nature Medicine 21 (2015) 914-921), and MAGE-A3-specific TCRs (Morgan et al., J Immunother 36 (2013) 133-151) and Linette et al., Blood 122 (2013) 227-242). (See also, Debets et al., Seminars in Immunology 23 (2016) 10-21). Each of the references in this paragraph are incorporated herein by reference in their entireties.

To generate the recombinant TCRs, the native TRAC (SEQ ID NO: 278) and TRBC (SEQ ID NOs: 277) protein sequences are fused to the C-terminal ends of TCR-α and TCR-β chain variable regions specific for a protein or peptide of interest. For example, the engineered TCR can recognize the NY-ESO peptide (SLLMWITQC, SEQ ID NO: 274), such as the 1G4 TCR or the 95:LY TCR (Robbins et al, Journal of Immunology 2008 180:6116-6131, incorporated herein by reference in its entirety). In such illustrative embodiments, the paired 1G4-TCR α/βchains comprise SEQ ID NOs: 284 and 283, respectively and the paired 95:LY-TCR α/βchains comprise SEQ ID NOs: 287 and 286, respectively. The recombinant TCR can recognize the MART-1 peptide (AAGIGILTV, SEQ ID NO: 275), such as the DMF4 and DMF5 TCRs (Robbins et al, Journal of Immunology 2008 180:6116-6131). In such illustrative embodiments, the paired DMF4-TCR α/βchains comprise SEQ ID NOs: 290 and 289, respectively and the paired DMF5-TCR α/βchains comprise SEQ ID NOs: 293 and 292, respectively. The recombinant TCR can recognize the WT-1 peptide (RMFPNAPYL, SEQ ID NO: 276), such as the DLT TCR (Robbins et al, Journal of Immunology 2008 180:6116-6131). In such illustrative embodiments, the paired high-affinity DLT-TCR α/βchains comprise SEQ ID NOs: 281 and 280, respectively.

Codon-optimized DNA sequences encoding the recombinant TCRα and TCRβ chain proteins can be generated such that expression of both TCR chains is driven off of a single promoter in a stoichiometric fashion. In such embodiment, the P2A sequence (SEQ ID NO: 273) can be inserted between the DNA sequences encoding the TCRβ and the TCRα chain, such that the expression cassettes encoding the recombinant TCR chains comprise the following format: TCRβ-P2A-TCRα. As an illustrative embodiment, the protein sequence of the 1G4 NY-ESO-specific TCR expressed from such a cassette would comprise SEQ ID NO: 285, the protein sequence of the 95:LY NY-ESO-specific TCR expressed from such a cassette would comprise SEQ ID NO: 288, the protein sequence of the DMF4 MART1-specific TCR expressed from such a cassette would comprise SEQ ID NO: 291, the protein sequence of the DMF5 MART1-specific TCR expressed from such a cassette would comprise SEQ ID NO: 294, and the protein sequence of the DLT WT1-specific TCR expressed from such a cassette would comprise SEQ ID NO: 282.

In some embodiments, the engineered antigen receptor is directed against a target antigen selected from a cluster of differentiation molecule, such as CD3, CD4, CD8, CD16, CD24, CD25, CD33, CD34, CD45, CD64, CD71, CD78, CD80 (also known as B7-1), CD86 (also known as B7-2), CD96, CD116, CD117, CD123, CD133, and CD138, CD371 (also known as CLL1); a tumor-associated surface antigen, such as 5T4, BCMA (also known as CD269 and TNFRSF17, UniProt #Q02223), carcinoembryonic antigen (CEA), carbonic anhydrase 9 (CAIX or MN/CAIX), CD19, CD20, CD22, CD30, CD40, disialogangliosides such as GD2, ELF2M, ductal-epithelial mucin, ephrin B2, epithelial cell adhesion molecule (EpCAM), ErbB2 (HER2/neu), FCRL5 (UniProt #Q68SN8), FKBP11 (UniProt #Q9NYL4), glioma-associated antigen, glycosphingolipids, gp36, GPRC5D (UniProt #Q9NZD1), mut hsp70-2, intestinal carboxyl esterase, IGF-I receptor, ITGA8 (UniProt #P53708), KAMP3, LAGE-1a, MAGE, mesothelin, neutrophil elastase, NKG2D, Nkp30, NY-ESO-1, PAP, prostase, prostate-carcinoma tumor antigen-1 (PCTA-1), prostate specific antigen (PSA), PSMA, prostein, RAGE-1, ROR1, RU1 (SFMBT1), RU2 (DCDC2), SLAMF7 (UniProt #Q9NQ25), survivin, TAG-72, and telomerase; a major histocompatibility complex (MHC) molecule presenting a tumor-specific peptide epitope; tumor stromal antigens, such as the extra domain A (EDA) and extra domain B (EDB) of fibronectin; the A1 domain of tenascin-C (TnC A1) and fibroblast associated protein (FAP); cytokine receptors, such as epidermal growth factor receptor (EGFR), EGFR variant III (EGFRvIII), TFGβ-R or components thereof such as endoglin; a major histocompatibility complex (MHC) molecule; a virus-specific surface antigen such as an HIV-specific antigen (such as HIV gp120); an EBV-specific antigen, a CMV-specific antigen, a HPV-specific antigen, a Lassa virus-specific antigen, an Influenza virus-specific antigen as well as any derivate or variant of these surface antigens.

Effector Functions

In some embodiments, the modified immune effector cells described herein comprise a CRISPR/Cas comprising a SOCS1-targeting gRNA and a PTPN2-targeting gRNA, wherein the reduced expression and/or function of SOCS1 and PTPN2 enhances an effector function of the modified immune effector cell. Herein, the term "effector function" refers to functions of an immune cell related to the generation, maintenance, and/or enhancement of an immune response against a target cell or target antigen. In some embodiments, the modified immune effector cells described herein demonstrate one or more of the following characteristics compared to an unmodified immune effector cell: increased infiltration or migration in to a tumor, increased proliferation, increased or prolonged cell viability, increased resistance to inhibitory factors in the surrounding microenvironment such that the activation state of the cell is prolonged or increased, increased production of pro-inflammatory immune factors (e.g., pro-inflammatory cytokines, chemokines, and/or enzymes), increased cytotoxicity, and/or increased resistance to exhaustion.

In some embodiments, the modified immune effector cells described herein demonstrate increased infiltration into a tumor compared to an unmodified immune effector cell. In some embodiments, increased tumor infiltration by modified immune effector cells refers to an increase the number of modified immune effector cells infiltrating into a tumor during a given period of time compared to the number of unmodified immune effector cells that infiltrate into a tumor during the same period of time. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in tumor filtration compared to an unmodified immune cell. Tumor infiltration can be measured by isolating one or more tumors from a subject and assessing the number of modified immune cells in the sample by flow cytometry, immunohistochemistry, and/or immunofluorescence.

In some embodiments, the modified immune effector cells described herein demonstrate an increase in cell proliferation compared to an unmodified immune effector cell. In these embodiments, the result is an increase in the number of modified immune effector cells present compared to unmodified immune effector cells after a given period of time. For example, in some embodiments, modified immune effector cells demonstrate increased rates of proliferation compared to unmodified immune effector cells, wherein the modified immune effector cells divide at a more rapid rate than unmodified immune effector cells. In some embodiments, the modified immune effector cells demonstrate a 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more fold increase in the rate of proliferation compared to an unmodified immune cell. In some embodiments, modified immune effector cells demonstrate prolonged periods of proliferation compared to unmodified immune effector cells, wherein the modified immune effector cells and unmodified immune effector cells divide at similar rates, but wherein the modified immune effector cells maintain the proliferative state for a longer period of time. In some embodiments, the modified immune effector cells maintain a proliferative state for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased or prolonged cell viability compared to an unmodified immune effector cell. In such embodiments, the result is an increase in the number of modified immune effector cells or present compared to unmodified immune effector cells after a given period of time. For example, in some embodiments, modified immune effector cells described herein remain viable and persist for 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 25, 30, 35, 40, 45, 50, 60, 70, 80, 90, 100, or more times longer than an unmodified immune cell.

In some embodiments, the modified immune effector cells described herein demonstrate increased resistance to inhibitory factors compared to an unmodified immune effector cell. Exemplary inhibitory factors include signaling by immune checkpoint molecules (e.g., PD1, PDL1, CTLA4, LAG3, IDO) and/or inhibitory cytokines (e.g., IL-10, TGFβ).

In some embodiments, the modified T cells described herein demonstrate increased resistance to T cell exhaustion compared to an unmodified T cell. T cell exhaustion is a state of antigen-specific T cell dysfunction characterized by decreased effector function and leading to subsequent deletion of the antigen-specific T cells. In some embodiments, exhausted T cells lack the ability to proliferate in response to antigen, demonstrate decreased cytokine production, and/or demonstrate decreased cytotoxicity against target cells such as tumor cells. In some embodiments, exhausted T cells are identified by altered expression of cell surface markers and transcription factors, such as decreased cell surface expression of CD122 and CD127; increased expression of inhibitory cell surface markers such as PD1, LAG3, CD244, CD160, TIM3, and/or CTLA4; and/or increased expression of transcription factors such as Blimp1, NFAT, and/or BATF. In some embodiments, exhausted T cells demonstrate altered sensitivity cytokine signaling, such as increased sensitivity to TGFβ signaling and/or decreased sensitivity to IL-7 and IL-15 signaling. T cell exhaustion can be determined, for example, by co-culturing the T cells with a population of target cells and measuring T cell proliferation, cytokine production, and/or lysis of the target cells. In some embodiments, the modified immune effector cells described herein are co-cultured with a population of target cells (e.g., autologous tumor cells or cell lines that have been engineered to express a target tumor antigen) and effector cell proliferation, cytokine production, and/or target cell lysis is measured. These results are then compared to the results obtained from co-culture of target cells with a control population of immune cells (such as unmodified immune effector cells or immune effector cells that have a control modification).

In some embodiments, resistance to T cell exhaustion is demonstrated by increased production of one or more cytokines (e.g., IFNγ, TNFα, or IL-2) from the modified immune effector cells compared to the cytokine production observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in cytokine production from the modified immune effector cells compared to the cytokine production from the control population of immune cells is indicative of an increased resistance to T cell exhaustion. In some embodiments, resistance to T cell exhaustion is demonstrated by increased proliferation of the modified immune effector cells compared to the proliferation observed from the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in proliferation of the modified immune effector cells compared to the proliferation of the control population of immune cells is indicative of an increased resistance to T cell exhaustion. In some embodiments, resistance to T cell exhaustion is demonstrated by increased target cell lysis by the modified immune effector cells compared to the target cell lysis observed by the control population of immune cells. In some embodiments, a 1.1, 1.2, 1.3, 1.4, 1.5, 1.6, 1.7, 1.8, 1.9, 2.0, 2.5, 3.0, 3.5, 4.0, 4.5, 5, 6, 7, 8, 9, 10, 15, 20, 30, 35, 40, 45, 50, 60, 70, 80, 90, 100 or more fold increase in target cell lysis by the modified immune effector cells compared to the target cell lysis by the control population of immune cells is indicative of an increased resistance to T cell exhaustion.

In some embodiments, exhaustion of the modified immune effector cells compared to control populations of immune cells is measured during the in vitro or ex vivo manufacturing process. For example, in some embodiments, TILs isolated from tumor fragments are modified according to the methods described herein and then expanded in one or more rounds of expansion to produce a population of modified TILs. In such embodiments, the exhaustion of the modified TILs can be determined immediately after harvest and prior to a first round of expansion, after the first round of expansion but prior to a second round of expansion, and/or after the first and the second round of expansion. In some embodiments, exhaustion of the modified immune effector cells compared to control populations of immune cells is measured at one or more time points after transfer of the modified immune effector cells into a subject. For example, in some embodiments, the modified cells are produced according to the methods described herein and administered to a subject. Samples can then be taken from the subject at various time points after the transfer to determine exhaustion of the modified immune effector cells in vivo over time.

In some embodiments, the modified immune effector cells described herein demonstrate increased expression or production of pro-inflammatory immune factors compared to an unmodified immune effector cell. Examples of pro-inflammatory immune factors include cytolytic factors, such as granzyme B, perforin, and granulysin; and pro-inflammatory cytokines such as interferons (IFNα, IFNβ, IFNγ), TNFα, IL-1β, IL-12, IL-2, IL-17, CXCL8, and/or IL-6.

In some embodiments, the modified immune effector cells described herein demonstrate increased cytotoxicity against a target cell compared to an unmodified immune effector cell. In some embodiments, the modified immune effector cells demonstrate a 1, 2, 3, 4, 5, 6, 7, 8, 9, 10, 20, 30, 40, 50, 60, 70, 80, 90, 100, or more fold increase in cytotoxicity against a target cell compared to an unmodified immune cell.

Assays for measuring immune effector function are known in the art. For example, tumor infiltration can be measured by isolating tumors from a subject and determining the total number and/or phenotype of the lymphocytes present in the tumor by flow cytometry, immunohistochemistry, and/or immunofluorescence. Cell-surface receptor expression can be determined by flow cytometry, immunohistochemistry, immunofluorescence, Western blot, and/or qPCR. Cytokine and chemokine expression and production can be measured by flow cytometry, immunohistochemistry, immunofluorescence, Western blot, ELISA, and/or qPCR. Responsiveness or sensitivity to extracellular stimuli (e.g., cytokines, inhibitory ligands, or antigen) can be measured by assaying cellular proliferation and/or activation of downstream signaling pathways (e.g., phosphorylation of downstream signaling intermediates) in response to the stimuli. Cytotoxicity can be measured by target-cell lysis assays known in the art, including in vitro or ex vivo co-culture of the modified immune effector cells with target cells and in vivo murine tumor models, such as those described throughout the Examples.

Methods of Producing Modified Immune Effector Cells

In some embodiments, the present disclosure provides methods for producing modified immune effector cells. In some embodiments, the methods comprise introducing a CRISPR/Cas system comprising a SOCS1-targeting gRNA and a PTPN2-targeting gRNA into a population of immune effector cells, thereby reducing expression and/or function of SOCS1 and PTPN2.

The components of the CRISPR/Cas systems described herein can be introduced into target cells in a variety of forms using a variety of delivery methods and formulations. In some embodiments, a polynucleotide encoding one or more components of the system is delivered by a recombinant vector (e.g., a viral vector or plasmid). In some embodiments, where the system comprises more than a single component, a vector may comprise a plurality of polynucleotides, each encoding a component of the system. In some embodiments, where the system comprises more than a single component, a plurality of vectors may be used, wherein each vector comprises a polynucleotide encoding a particular component of the system. In some embodiments, a vector may also comprise a sequence encoding a signal peptide (e.g., for nuclear localization, nucleolar localization, mitochondrial localization), fused to the polynucleotide encoding the one or more components of the system. For example, a vector may comprise a nuclear localization sequence (e.g., from SV40) fused to the polynucleotide encoding the one or more components of the system. In some embodiments, the CRISPR/Cas system is delivered as a ribonucleoprotein (RNP) complex comprising complexes SOCS1-targeting gRNAs and a PTPN2-targeting gRNAs and the Cas proteins. In some embodiments, the introduction of the CRISPR/Cas system to the cell occurs in vitro. In some embodiments, the introduction of the CRISPR/Cas system to the cell occurs in vivo. In some embodiments, the introduction of the CRISPR/Cas system to the cell occurs ex vivo. In some embodiments, one or more components of the CRISPR/Cas system are introduced to the cell by transfection, transduction, electroporation, or physical disruption of the cell membrane by a microfluidics device. In some embodiments, one or more components of the CRISPR/Cas system are introduced to the cell by electroporation. In some embodiments, the SOCS1-targeting gRNA, the PTPN2-targeting gRNA, and the Cas protein are simultaneously introduced to the cell by electroporation.

In some embodiments, the recombinant vector comprising a polynucleotide encoding one or more components of a CRISPR/Cas system described herein is a viral vector. Suitable viral vectors include, but are not limited to, viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., U.S. Pat. No.

7,078,387; Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166: 154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

In some embodiments, the recombinant vector comprising a polynucleotide encoding one or more components of a CRISPR/Cas system described herein is a plasmid. Numerous suitable plasmid expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other plasmid vector may be used so long as it is compatible with the host cell. Depending on the cell type and CRISPR/Cas system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

In some embodiments, a polynucleotide sequence encoding one or more components of a CRISPR/Cas system described herein is operably linked to a control element, e.g., a transcriptional control element, such as a promoter. The transcriptional control element may be functional in either a eukaryotic cell (e.g., a mammalian cell) or a prokaryotic cell (e.g., bacterial or archaeal cell). In some embodiments, a polynucleotide sequence encoding one or more components of a CRISPR/Cas system described herein is operably linked to multiple control elements that allow expression of the polynucleotide in both prokaryotic and eukaryotic cells. Depending on the cell type and CRISPR/Cas system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-1. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to the site-directed modifying polypeptide, thus resulting in a chimeric polypeptide.

In some embodiments, a polynucleotide sequence encoding one or more components of a CRISPR/Cas system described herein is operably linked to an inducible promoter. In some embodiments, a polynucleotide sequence encoding one or more components of a CRISPR/Cas system described herein is operably linked to a constitutive promoter.

Methods of introducing polynucleotides and recombinant vectors into a host cell are known in the art, and any known method can be used to introduce components of a CRISPR/Cas system into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pii: 50169-409X(12)00283-9), microfluidics delivery methods (See e.g., International PCT Publication No. WO 2013/059343), and the like. In some embodiments, delivery via electroporation comprises mixing the cells with the components of a CRISPR/Cas system in a cartridge, chamber, or cuvette and applying one or more electrical impulses of defined duration and amplitude. In some embodiments, cells are mixed with components of a CRISPR/Cas system in a vessel connected to a device (e.g., a pump) which feeds the mixture into a cartridge, chamber, or cuvette wherein one or more electrical impulses of defined duration and amplitude are applied, after which the cells are delivered to a second vessel.

In some embodiments, one or more components of a CRISPR/Cas system, or polynucleotide sequence encoding one or more components of a CRISPR/Cas system described herein are introduced to a cell in a non-viral delivery vehicle, such as a transposon, a nanoparticle (e.g., a lipid nanoparticle), a liposome, an exosome, an attenuated bacterium, or a virus-like particle. In some embodiments, the vehicle is an attenuated bacterium (e.g., naturally or artificially engineered to be invasive but attenuated to prevent pathogenesis including *Listeria monocytogenes*, certain *Salmonella* strains, *Bifidobacterium longum*, and modified *Escherichia coli*), bacteria having nutritional and tissue-specific tropism to target specific cells, and bacteria having modified surface proteins to alter target cell specificity. In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In some embodiments, the vehicle is a biological liposome. For example, the biological liposome is a phospholipid-based particle derived from human cells (e.g., erythrocyte ghosts, which are red blood cells broken down into spherical structures derived from the subject and wherein tissue targeting can be achieved by attachment of various tissue or cell-specific ligands), secretory exosomes, or subject derived membrane-bound nanovescicles (30-100 nm) of endocytic origin (e.g., can be produced from various cell types and can therefore be taken up by cells without the need for targeting ligands).

In some embodiments, the methods of modified immune effector cells described herein comprise obtaining a population of immune effector cells from a sample. In some embodiments, a sample comprises a tissue sample, a fluid sample, a cell sample, a protein sample, or a DNA or RNA sample. In some embodiments, a tissue sample may be derived from any tissue type including, but not limited to skin, hair (including roots), bone marrow, bone, muscle, salivary gland, esophagus, stomach, small intestine (e.g., tissue from the duodenum, jejunum, or ileum), large intestine, liver, gallbladder, pancreas, lung, kidney, bladder, uterus, ovary, vagina, placenta, testes, thyroid, adrenal gland, cardiac tissue, thymus, spleen, lymph node, spinal cord, brain, eye, ear, tongue, cartilage, white adipose tissue, or brown adipose tissue. In some embodiments, a tissue sample may be derived from a cancerous, pre-cancerous, or non-cancerous tumor. In some embodiments, a fluid sample comprises buccal swabs, blood, plasma, oral mucous, vaginal mucous, peripheral blood, cord blood, saliva, semen, urine, ascites fluid, pleural fluid, spinal fluid, pulmonary lavage, tears, sweat, semen, seminal fluid, seminal plasma, prostatic fluid, pre-ejaculatory fluid (Cowper's fluid), excreta, cerebrospinal fluid, lymph, cell culture media comprising one or more populations of cells, buffered solutions comprising one or more populations of cells, and the like.

In some embodiments, the sample is processed to enrich or isolate a particular cell type, such as an immune effector cell, from the remainder of the sample. In certain embodiments, the sample is a peripheral blood sample which is then subject to leukapheresis to separate the red blood cells and platelets and to isolate lymphocytes. In some embodiments, the sample is a leukopak from which immune effector cells can be isolated or enriched. In some embodiments, the sample is a tumor sample that is further processed to isolate lymphocytes present in the tumor (i.e., to isolate tumor infiltrating lymphocytes).

In some embodiments, the isolated immune effector cells are expanded in culture to produce an expanded population of immune effector cells. One or more activating or growth factors may be added to the culture system during the expansion process. For example, in some embodiments, one or more cytokines (such as IL-2, IL-15, and/or IL-7) can be added to the culture system to enhance or promote cell proliferation and expansion. In some embodiments, introduction of the CRISPR/Cas systems described herein reduces the amounts of exogenous cytokines required to promote cell proliferation and expansion. In some embodiments, one or more activating antibodies, such as an anti-CD3 antibody (e.g., OKT3, G19-4, BC3, CRIS-7 and 64.1), may be added to the culture system to enhance or promote cell proliferation and expansion. In some embodiments, one or more costimulatory ligands may be added to the culture system, such as CD7, B7-1 (CD80), B7-2 (CD86), 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, ILT3, ILT4, an agonist or antibody that binds Toll ligand receptor, and a ligand that specifically binds with B7-H3. In some embodiments, the immune effector cells may be co-cultured with feeder cells during the expansion process. In some embodiments, the methods provided herein comprise one or more expansion phases. For example, in some embodiments, the immune effector cells can be expanded after isolation from a sample, allowed to rest, and then expanded again. In some embodiments, the immune effector cells can be expanded in one set of expansion conditions followed by a second round of expansion in a second, different, set of expansion conditions. Methods for ex vivo expansion of immune cells are known in the art, for example, as described in US Patent Application Publication Nos. 20180282694 and 20170152478 and U.S. Pat. Nos. 8,383,099 and 8,034,334.

At any point during the culture and expansion process, the CRISPR/Cas systems described herein can be introduced to the immune effector cells to produce a population of modified immune effector cells. In some embodiments, the CRISPR/Cas system is introduced to the population of immune effector cells immediately after enrichment from a sample. In some embodiments, the CRISPR/Cas system is introduced to the population of immune effector cells before, during, or after the one or more expansion process. In some embodiments, the CRISPR/Cas system is introduced to the population of immune effector cells immediately after enrichment from a sample or harvest from a subject, and prior to any expansion rounds. In some embodiments, the CRISPR/Cas system is introduced to the population of immune effector cells after a first round of expansion and prior to a second round of expansion. In some embodiments, the CRISPR/Cas system is introduced to the population of immune effector cells after a first and a second round of expansion.

In some embodiments, the modified immune effector cells produced by the methods described herein may be used immediately. Alternatively, the cells may be frozen at liquid nitrogen temperatures and stored for long periods of time, being thawed and capable of being reused. In such cases, the cells will usually be frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

In some embodiments, the modified immune effector cells may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

In some embodiments, a method of producing a modified immune effector cell involves contacting a target DNA sequence with a complex comprising a gRNA and a Cas polypeptide. As discussed above, a gRNA and Cas polypeptide form a complex, wherein the DNA-binding domain of the gRNA targets the complex to a target DNA sequence and wherein the Cas protein (or heterologous protein fused to an enzymatically inactive Cas protein) modifies the target DNA sequence. In some embodiments, this complex is formed intracellularly after introduction of the gRNA and Cas protein (or polynucleotides encoding the gRNA and Cas proteins) to a cell.

In some embodiments, the nucleic acid encoding the Cas protein is a DNA nucleic acid and is introduced to the cell by transduction. In some embodiments, the Cas9 and gRNA components of a CRISPR/Cas gene editing system are encoded by a single polynucleotide molecule. In some embodiments, the polynucleotide encoding the Cas protein and gRNA component are comprised in a viral vector and introduced to the cell by viral transduction. In some embodiments, the Cas9 and gRNA components of a CRISPR/Cas gene editing system are encoded by different polynucleotide molecules. In some embodiments, the polynucleotide encoding the Cas protein is comprised in a first viral vector and the polynucleotide encoding the gRNA is comprised in a second viral vector. In some aspects of this embodiment, the first viral vector is introduced to a cell prior to the second viral vector. In some aspects of this embodiment, the second viral vector is introduced to a cell prior to the first viral vector. In such embodiments, integration of the vectors results in sustained expression of the Cas9 and gRNA components. However, sustained expression of Cas9 may lead to increased off-target mutations and cutting in some cell types. Therefore, in some embodiments, an mRNA nucleic acid sequence encoding the Cas protein may be introduced to the population of cells by transfection. In such embodiments, the expression of Cas9 will decrease over time, and may reduce the number of off target mutations or cutting sites.

In some embodiments, this complex is formed in a cell-free system by mixing the gRNA molecules and Cas proteins together and incubating for a period of time sufficient to allow complex formation. This pre-formed complex comprising the gRNA and Cas protein, and referred to herein as a CRISPR-ribonucleoprotein (CRISPR-RNP), can then be introduced to a cell in order to modify a target DNA sequence. In some embodiments, the RNP complexes are introduced by electroporation. In some embodiments, the gRNAs and Cas proteins are individually introduced by electroporation.

Compositions and Kits

The term "composition" as used herein refers to a formulation of a CRISPR/Cas system or a modified immune effector cell described herein that is capable of being administered or delivered to a subject or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of a CRISPR/Cas system or a modified immune effector cell capable of being administered to a subject for the treatment of a particular disease or disorder or contacted with a cell for modification of one or more endogenous target genes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

"Pharmaceutically acceptable salt" includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

In some embodiments, the present disclosure provides kits for carrying out a method described herein. In some embodiments, a kit can include one or more SOCS1-targeting gRNAs and one or more PTPN2-targeting gRNAs. In some embodiments, such kits may further comprise one or more Cas proteins or a polynucleotide encoding the same. In some embodiments, a kit can include one or more polynucleotides encoding one or more SOCS1-targeting gRNAs and one or more PTPN2-targeting gRNAs. In some embodiments, such kits may further comprise one or more Cas proteins or a polynucleotide encoding the same. In some embodiments, a kit can include a modified immune effector cell described herein.

In some embodiments, the kits described herein further comprise one or more immune checkpoint inhibitors. Several immune checkpoint inhibitors are known in the art and have received FDA approval for the treatment of one or more cancers. For example, FDA-approved PD-L1 inhibitors include Atezolizumab (Tecentriq®, Genentech), Avelumab (Bavencio®, Pfizer), and Durvalumab (Imfinzi®, AstraZeneca); FDA-approved PD-1 inhibitors include Pembrolizumab (Keytruda®, Merck) and Nivolumab (Opdivo®, Bristol-Myers Squibb); and FDA-approved CTLA4 inhibitors include Ipilimumab (Yervoy®, Bristol-Myers Squibb). Additional inhibitory immune checkpoint molecules that may be the target of future therapeutics include A2AR, B7-H3, B7-H4, BTLA, IDO, LAGS (e.g., BMS-986016, under development by BSM), KIR (e.g., Lirilumab, under development by BSM), TIM3, TIGIT, and VISTA.

In some embodiments, the kits described herein comprise one or more components of a CRISPR/Cas system (or one or more polynucleotides encoding the one or more components) and one or more immune checkpoint inhibitors known in the art (e.g., a PD1 inhibitor, a CTLA4 inhibitor, a PDL1 inhibitor, etc.). In some embodiments, the kits described herein comprise one or more components of a CRISPR/Cas system (or one or more polynucleotides encoding the one or more components) and an anti-PD1 antibody (e.g., Pembrolizumab or Nivolumab). In some embodiments, the kits described herein comprise a modified immune effector cell described herein (or population thereof) and one or more immune checkpoint inhibitors known in the art (e.g., a PD1 inhibitor, a CTLA4 inhibitor, a PDL1 inhibitor, etc.). In some embodiments, the kits described herein comprise a modified immune effector cell described herein (or population thereof) and an anti-PD1 antibody (e.g., Pembrolizumab or Nivolumab).

In some embodiments, the kit comprises one or more components of a CRISPR/Cas system (or one or more polynucleotides encoding the one or more components) and a reagent for reconstituting and/or diluting the components.

In some embodiments, a kit comprising one or more components of a CRISPR/Cas system (or one or more polynucleotides encoding the one or more components) and further comprises one or more additional reagents, where such additional reagents can be selected from: a buffer for introducing the CRISPR/Cas system into a cell; a wash buffer; a control reagent; a control expression vector or RNA polynucleotide; a reagent for in vitro production of the CRISPR/Cas system from DNA, and the like. Components of a kit can be in separate containers or can be combined in a single container.

In addition to above-mentioned components, in some embodiments a kit further comprises instructions for using the components of the kit to practice the methods of the present disclosure. The instructions for practicing the methods are generally recorded on a suitable recording medium. For example, the instructions may be printed on a substrate, such as paper or plastic, etc. As such, the instructions may be present in the kits as a package insert or in the labeling of the container of the kit or components thereof (i.e., associated with the packaging or sub-packaging). In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Therapeutic Methods and Applications

In some embodiments, the modified immune effector cells and CRISPR/Cas systems described herein may be used in a variety of therapeutic applications. For example, in some embodiments the modified immune effector cells and/or CRISPR/Cas systems described herein may be administered to a subject for purposes such as gene therapy, e.g. to treat a disease, for use as an antiviral, for use as an antipathogenic, for use as an anti-cancer therapeutic, or for biological research.

In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

Administration of the modified immune effector cells described herein, populations thereof, and compositions thereof can occur by injection, irrigation, inhalation, consumption, electro-osmosis, hemodialysis, iontophoresis, and other methods known in the art. In some embodiments, administration route is local or systemic. In some embodiments, administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, or intrauterine.

In some embodiments, the administration route is by infusion (e.g., continuous or bolus). Examples of methods for local administration, that is, delivery to the site of injury or disease, include through an Ommaya reservoir, e.g. for intrathecal delivery (See e.g., U.S. Pat. Nos. 5,222,982 and 5,385,582, incorporated herein by reference); by bolus injection, e.g. by a syringe, e.g. into a joint; by continuous infusion, e.g. by cannulation, such as with convection (See e.g., US Patent Application Publication No. 2007-0254842, incorporated herein by reference); or by implanting a device upon which the cells have been reversibly affixed (see e.g. US Patent Application Publication Nos. 2008-0081064 and 2009-0196903, incorporated herein by reference). In some embodiments, the administration route is by topical administration or direct injection. In some embodiments, the modified immune effector cells described herein may be provided to the subject alone or with a suitable substrate or matrix, e.g. to support their growth and/or organization in the tissue to which they are being transplanted.

In some embodiments, at least $1\times10^3$ cells are administered to a subject. In some embodiments, at least $5\times10^3$ cells, $1\times10^4$ cells, $5\times10^4$ cells, $1\times10^5$ cells, $5\times10^5$ cells, $1\times10^6$, $2\times10^6$, $3\times10^6$, $4\times10^6$, $5\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more cells are administered to a subject. In some embodiments, between about $1\times10^7$ and about $1\times10^{12}$ cells are administered to a subject. In some embodiments, between about $1\times10^8$ and about $1\times10^{12}$ cells are administered to a subject. In some embodiments, between about $1\times10^9$ and about $1\times10^{12}$ cells are administered to a subject. In some embodiments, between about $1\times10^{10}$ and about $1\times10^{12}$ cells are administered to a subject. In some embodiments, between about $1\times10^{11}$ and about $1\times10^{12}$ cells are administered to a subject. In some embodiments, between about $1\times10^7$ and about $1\times10^{11}$ cells are administered to a subject. In some embodiments, between about $1\times10^7$ and about $1\times10^{10}$ cells are administered to a subject. In some embodiments, between about $1\times10^7$ and about $1\times10^9$ cells are administered to a subject. In some embodiments, between about $1\times10^7$ and about $1\times10^8$ cells are administered to a subject. The number of administrations of treatment to a subject may vary. In some embodiments, introducing the modified immune effector cells into the subject may be a one-time event. In some embodiments, such treatment may require an on-going series of repeated treatments. In some embodiments, multiple administrations of the modified immune effector cells may be required before an effect is observed. The exact protocols depend upon the disease or condition, the stage of the disease and parameters of the individual subject being treated.

In some embodiments, the CRISPR/Cas systems described herein are employed to modify cellular DNA or RNA in vivo, such as for gene therapy or for biological research. In such embodiments, a CRISPR/Cas system may be administered directly to the subject, such as by the methods described supra. In some embodiments, the CRISPR/Cas systems described herein are employed for the ex vivo or in vitro modification of a population of immune effector cells. In such embodiments, the CRISPR/Cas systems described herein are administered to a sample comprising immune effector cells.

In some embodiments, the modified immune effector cells described herein are administered to a subject. In some embodiments, the modified immune effector cells described herein administered to a subject are autologous immune effector cells. The term "autologous" in this context refers to cells that have been derived from the same subject to which they are administered. For example, immune effector cells may be obtained from a subject, modified ex vivo according to the methods described herein, and then administered to the same subject in order to treat a disease. In such embodiments, the cells administered to the subject are autologous immune effector cells. In some embodiments, the modified immune effector cells, or compositions thereof, administered to a subject are allogeneic immune effector cells. The term "allogeneic" in this context refers to cells that have been derived from one subject and are administered to another subject. For example, immune effector cells may be obtained from a first subject, modified ex vivo according to the methods described herein and then administered to a second subject in order to treat a disease. In such embodiments, the cells administered to the subject are allogeneic immune effector cells.

In some embodiments, the modified immune effector cells described herein are administered to a subject in order to treat a disease. In some embodiments, treatment comprises delivering an effective amount of a population of cells (e.g., a population of modified immune effector cells) or composition thereof to a subject in need thereof. In some embodiments, treating refers to the treatment of a disease in a mammal, e.g., in a human, including (a) inhibiting the disease, i.e., arresting disease development or preventing disease progression; (b) relieving the disease, i.e., causing regression of the disease state or relieving one or more symptoms of the disease; and (c) curing the disease, i.e., remission of one or more disease symptoms. In some embodiments, treatment may refer to a short-term (e.g., temporary and/or acute) and/or a long-term (e.g., sustained) reduction in one or more disease symptoms. In some embodiments, treatment results in an improvement or remediation of the symptoms of the disease. The improvement is an observable or measurable improvement, or may be an improvement in the general feeling of well-being of the subject.

The effective amount of a modified immune effector cell administered to a particular subject will depend on a variety of factors, several of which will differ from patient to patient including the disorder being treated and the severity of the disorder; activity of the specific agent(s) employed; the age, body weight, general health, sex and diet of the patient; the timing of administration, route of administration; the duration of the treatment; drugs used in combination; the judgment of the prescribing physician; and like factors known in the medical arts.

In some embodiments, the effective amount of a modified immune effector cell may be the number of cells required to result in at least 1, 2, 3, 4, 5, 6, 7, 8, 9, 10, 20, 30, 40, 50, 60, 70, 80, 90, 100, or more fold decrease in tumor mass or volume, decrease in the number of tumor cells, or decrease in the number of metastases. In some embodiments, the effective amount of a modified immune effector cell may be the number of cells required to achieve an increase in life expectancy, an increase in progression-free or disease-free survival, or amelioration of various physiological symptoms associated with the disease being treated. In some embodiments, an effective amount of modified immune effector cells will be at least $1\times10^3$ cells, for example $5\times10^3$ cells, $1\times10^4$ cells, $5\times10^4$ cells, $1\times10^5$ cells, $5\times10^5$ cells, $1\times10^6$, $2\times10^6$, $3\times10^6$, $4\times10^6$, $5\times10^6$, $1\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more cells.

In some embodiments, the modified immune effector cells and CRISPR/Cas systems described herein may be used in the treatment of a cell-proliferative disorder, such as a cancer. Cancers that may be treated using the compositions and methods disclosed herein include cancers of the blood and solid tumors. For example, cancers that may be treated using the compositions and methods disclosed herein include, but are not limited to, adenoma, carcinoma, sarcoma, leukemia or lymphoma. In some embodiments, the cancer is chronic lymphocytic leukemia (CLL), B cell acute lymphocytic leukemia (B-ALL), acute lymphoblastic leukemia (ALL), acute myeloid leukemia (AML), non-Hodgkin's lymphoma (NHL), diffuse large cell lymphoma (DLCL), diffuse large B cell lymphoma (DLBCL), Hodgkin's lymphoma, multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma, and liver cancer. In some embodiments, the cancer is selected from melanoma, head and neck cancer, cervical cancer, bladder cancer and lung cancer.

As described above, several immune checkpoint inhibitors are currently approved for use in a variety of oncologic indications (e.g., PD-L1 inhibitors such as Atezolizumab (Tecentriq®, Genentech), Avelumab (Bavencio®, Pfizer), and Durvalumab (Imfinzi®, AstraZeneca); FDA-approved PD-1 inhibitors such as Pembrolizumab (Keytruda®, Merck) and Nivolumab (Opdivo®, Bristol-Myers Squibb); and FDA-approved CTLA4 inhibitors such as Ipilimumab (Yervoy®, Bristol-Myers Squibb). Additional inhibitory immune checkpoint molecules that may be the target of future therapeutics include A2AR, B7-H3, B7-H4, BTLA, IDO, LAGS (e.g., BMS-986016, under development by BSM), KIR (e.g., Lirilumab, under development by BSM), TIM3, TIGIT, and VISTA In some embodiments, administration of a modified immune effector cell comprising reduced expression and/or function of an endogenous target gene described herein results in an enhanced therapeutic effect (e.g., a more significant reduction in tumor growth, an increase in tumor infiltration by lymphocytes, an increase in the length of progression free survival, etc.) than is observed after treatment with an immune checkpoint inhibitor.

Further, some oncologic indications are non-responsive (i.e., are insensitive) to treatment with immune checkpoint inhibitors. Further still, some oncologic indications that are initially responsive (i.e., sensitive) to treatment with immune checkpoint inhibitors develop an inhibitor-resistant phenotype during the course of treatment. Therefore, in some embodiments, the modified immune effector cells described herein, or compositions thereof, are administered to treat a cancer that is the cancer is resistant (or partially resistant), refractory (or partially refractory), or insensitive (or partially insensitive) to treatment with one or more immune checkpoint inhibitors. In some embodiments, administration of the modified immune effector cells or compositions thereof to a subject suffering from a cancer is resistant (or partially resistant), refractory (or partially refractory), or insensitive (or partially insensitive) to treatment with one or more immune checkpoint inhibitors results in treatment of the cancer (e.g., reduction in tumor growth, an increase in the length of progression free survival, etc.). In some embodiments, the cancer is resistant (or partially resistant), refractory (or partially refractory), or insensitive (or partially insensitive) to treatment with a PD1 inhibitor.

In some embodiments, the modified immune effector cells or compositions thereof are administered in combination with an immune checkpoint inhibitor. In some embodiments, administration of the modified immune effector cells in combination with the immune checkpoint inhibitor results in an enhanced therapeutic effect in a cancer that is resistant, refractory, or insensitive to treatment by an immune checkpoint inhibitor than is observed by treatment with either the modified immune effector cells or the immune checkpoint inhibitor alone. In some embodiments, administration of the modified immune effector cells in combination with the immune checkpoint inhibitor results in an enhanced therapeutic effect in a cancer that is partially resistant, partially refractory, or partially insensitive to treatment by an immune checkpoint inhibitor than is observed by treatment with either the modified immune effector cells or the immune checkpoint inhibitor alone. In some embodiments, the cancer is resistant (or partially resistant), refractory (or partially refractory), or insensitive (or partially insensitive) to treatment with a PD1 inhibitor.

In some embodiments, administration of a modified immune effector cell described herein, or composition thereof, in combination with an anti-PD1 antibody results in an enhanced therapeutic effect in a cancer that is resistant or insensitive to treatment by the anti-PD1 antibody alone. In some embodiments, administration of a modified immune effector cell described herein or composition thereof in combination with an anti-PD1 antibody results in an enhanced therapeutic effect in a cancer that is partially resistant or partially insensitive to treatment by the anti-PD1 antibody alone.

Cancers that demonstrate resistance or sensitivity to immune checkpoint inhibition are known in the art and can be tested in a variety of in vivo and in vitro models. For example, some melanomas are sensitive to treatment with an immune checkpoint inhibitor such as an anti-PD1 antibody and can be modeled in an in vivo B16-Ova tumor model. Further, some colorectal cancers are known to be resistant to treatment with an immune checkpoint inhibitor such as an anti-PD1 antibody and can be modeled in a PMEL/MC38-gp100 model. Further still, some lymphomas are known to be insensitive to treatment with an immune checkpoint inhibitor such as an anti-PD1 antibody and can be modeled in various models by adoptive transfer or subcutaneous administration of lymphoma cell lines, such as Raji cells.

Current adoptive cell therapy, including TIL therapy, includes lymphodepletion seven (7) days prior to TIL infusion using Cy/Flu based treatment. The lymphodepletion is believed necessary to deplete the endogenous Treg population, to boost endogenous IL-7 and IL-15 production and to create physical space for the TIL infusion. This lymphodepletion is associated with severe grade 3, 4, and sometimes 5 adverse events and can significantly impact patient outcome. In addition, current therapy includes an infusion of high dose IL-2 5 days prior to TIL infusion in order to boost function and survival of the transferred TILs. However, the high dose IL-2 infusion is associated with severe grade 3 and 4 adverse events, including capillary leak syndrome. In some embodiments, the modified immune effector cells described herein are transferred to a recipient host that has not undergone lymphodepletion treatment and/or are transferred to a recipient host in the absence of high dose IL-2 treatment. Without wishing to be bound by theory, it is possible that the modified immune effector cells described herein (e.g., modified TILs) demonstrate increased sensitivity to IL-7, IL-15 and/or IL-2, therefore allowing for increased steps enhanced competitive fitness, survival, and/or persistence of the modified cells such that lymphodepletion and/or high dose IL-2 is not required.

In some embodiments, the modified immune effector cells and CRISPR/Cas systems described herein may be used in the treatment of a viral infection. In some embodiments, the virus is selected from one of adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus, or retroviruses.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

EXAMPLES

Example 1: Materials and Methods

The experiments described herein utilize the CRISPR/Cas9 system to reduce expression of SOCS1 and PTPN2 in T cell populations.

gRNA-Cas9 RNPs: Unless otherwise indicated, the following experiments use dual gRNA molecules formed by duplexing 200 μM tracrRNA (IDT Cat #1072534) with 200 μM of target-specific crRNA (IDT) in nuclease free duplex buffer (IDT Cat #11-01-03-01) for 5 min at 95° C., to form 100 μM of tracrRNA:crRNA duplex, where the tracrRNA and crRNA are present at a 1:1 ratio. Unless otherwise indicated, the Cas9 protein derived from S. pyogenes (IDT Cat #1074182) was used in the following experiments. gRNA-Cas9 ribonucleoproteins (RNPs) were formed by combining 1.2 μL of 100 μM tracrRNA:crRNA duplex with 1.7 μL of 60 μM Cas9 protein and 2.1 μL of PBS. gRNAs used in the following experiments are provided below in Table 3.

TABLE 3 gRNA Sequences

| gRNA ID | Target sequence | SEQ ID |
|---|---|---|
| SOCS1-A | GACGCCTGCGGATTCTACTG | 1 |
| SOCS1-B | TGGACGCCTGCGGATTCTAC | 2 |
| SOCS1-C | AGTGCTCCAGCAGCTCGAAG | 3 |
| PTPN2-D | CGAGCGGGAGTTCGAAGAGT | 146 |
| PTPN2-F | GCCCAATGCCTGCACTACAG | 147 |
| PTPN2-E | GGAAACTTGGCCACTCTATG | 148 |

Human T cell Isolation and Activation: Total human PBMCs were isolated from fresh leukopacks by Ficoll gradient centrifugation. CD8+ T-cells were then purified from total PBMCs using a CD8+ T-cell isolation kit (Stemcell Technologies Cat #17953). For T cell activation, CD8+ T cells were plated at $2\times10^6$ cells/mL in X-VIVO 15 T Cell Expansion Medium (Lonza, Cat #04-418Q) in a T175 flask, with 6.25 μL/mL of ImmunoCult T-cell activators (anti-CD3/CD28/CD2, StemCell Technologies, Vancouver BC, Canada) and 10 ng/mL human IL2. T-cells were activated for 18 hours prior to RNP transfection.

Human TIL Isolation and Activation: Tumor infiltrating lymphocytes can also be modified by the methods described herein. In such cases, tumors are surgically resected from human patients and diced with scalpel blades into 1 $mm^3$ pieces, with a single piece of tumor placed into each well of a 24 plate. Alternatively, a digestion protocol can be used (See e.g., Lee and Margolin Curr Oncol Rep 2012 Oct. 14(5) 468-474). 2 mL of complete TIL media (RPMI+10% heat inactivated human male AB serum, 1 mM pyruvate, 20 μg/mL gentamycin, 1× glutamax) supplemented with 6000 U/mL of recombinant human IL-2 is added to each well of isolated TILs. 1 mL of media is removed from the well and replaced with fresh media and IL-2 up to 3 times a week as needed. As wells reach confluence, they are split 1:1 in new media+IL-2. After 4-5 weeks of culture, the cells are harvested for rapid expansion.

TIL Rapid Expansion: TILs are rapidly expanded by activating 500,000 TILs with $26\times10^6$ allogeneic, irradiated (5000cGy) PBMC feeder cells in 20 mL TIL media+20 mL of Aim-V media (Invitrogen)+30 ng/mL OKT3 mAb. 48 hours later (Day 2), 6000 U/mL IL-2 is added to the cultures. On day 5, 20 mL of media is removed, and 20 mL fresh media (+30 ng/ml OKT3) is added. On Day 7, cells are counted, and reseeded at $60\times10^6$ cells/L in G-Rex6M well plates (Wilson Wolf, Cat #80660M) or G-Rex100M (Wilson Wolf, Cat #81100S), depending on the number of cells available. 6000 U/mL fresh IL-2 is added on Day 9 and 3000 U/mL fresh IL-2 is added on Day 12. TILs are harvested on Day 14. Expanded cells are then slow-frozen in Cryostor CS-10 (Stemcell Technologies Cat #07930) using Coolcell Freezing containers (Corning) and stored long term in liquid nitrogen.

Electroporation of human T cells: Primary human Pan T cells were isolated from healthy donor PBMCs, and activated using IL-2 (10 ng/mL) and anti-CD3/28/2 (6.25 μL/mL) activators. One day post isolation, cells were resuspended at 1 M cells/mL. Two days post isolation cells were harvested, and resuspended in nucleofection buffer (18% supplement 1, 82% P3 buffer from the Amaxa P3 primary cell 4D-Nuclefector X kit S) at a concentration of $100\times10^6$ cells/mL. 20 μL of cell suspension were combined with 5 μL of sgRNA/Cas9 RNP complexes (containing a total of 120 pmol of sgRNA and 104 pmol of Cas9 nuclease; in cases where two sgRNAs were combined, 60 pmol of sgRNA 1 and 60 pmol of sgRNA 2 were used). 24 μL of the cell/RNP mix was then added to each electroporation well in a 16-well electroporation strip. Cells were electroporated using the Lonza electroporator using the "Nucleofection of activated CD8 T-cells" program. After electroporation, 75 μL of warm X-VIVO 15 media with IL-2 (10 ng/mL) was added to each well and cells were transferred to a G-Rex6M well plates. 10 ng/mL of fresh recombinant human IL-2 was added to the cultures every two days.

Example 2: Effects of SOCS1 and PTPN2 GRNA Combinations on Editing Efficiency

To evaluate the effect that pairing two guides in one RNP mix with Cas9 would have on DNA editing efficiencies of both guides, three SOCS1 and three PTPN2 guides were evaluated in a 3×3 combination matrix. The editing efficiency of each guide in a single guide RNP (Cas9:gRNA-1) was compared to the editing efficiencies observed when using this guide in a dual guide RNP mixture (Cas9:gRNA-1 and Cas9:gRNA-2) with either of the three selected guides against the respective other gene.

Specifically, primary human pan T cells were isolated as described in Example 1 and electroporated in arrayed fashion with Cas9:gRNA-1 or Cas9:gRNA-1:gRNA-2 RNPs. Details of the RNP reactions are provided below:

|  | Guide (μL) | Cas9 (μL) | PBS (μL) |
|---|---|---|---|
| Single | 1.2 | 1.7 | 2.1 |
| Double | 0.6 gRNA-1 + 0.6 gRNA-2 | 1.7 | 2.1 |

Cells were cultured for 5 days, at which point pellets were harvested. DNA was extracted and amplicons spanning the genomic target loci for the various sgRNAs were amplified by polymerase chain reaction (PCR) using guide-specific primer sets and sequenced by next-generation sequencing (NGS). Sequencing reads were aligned to the predicted guide cut sites, and the percentage of reads displaying an edited DNA sequence was determined for both genes.

Figure 2:
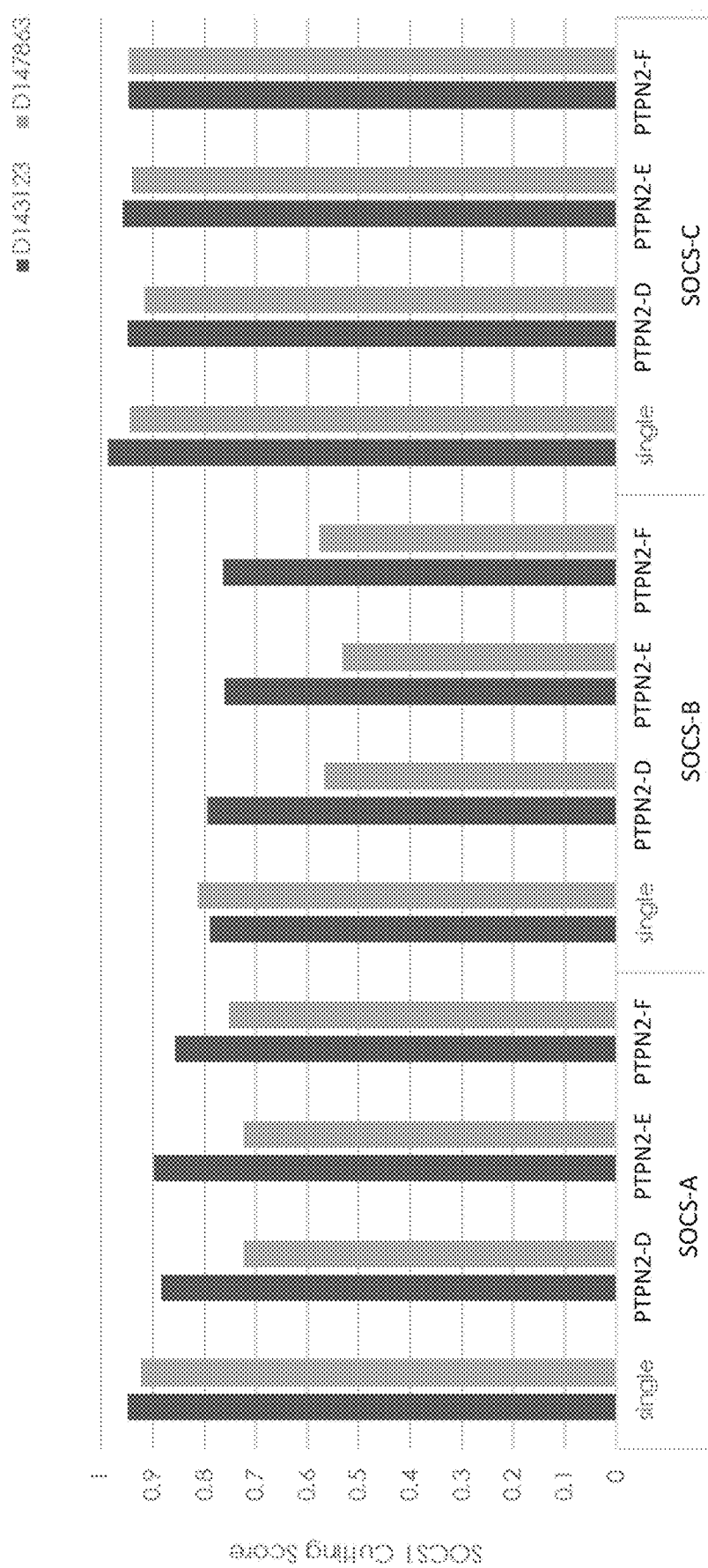
FIG. 2 shows the SOCS1-editing efficiency of SOCS1 gRNAs when used in combination with PTPN2-targeting gRNAs.
Figure 3:
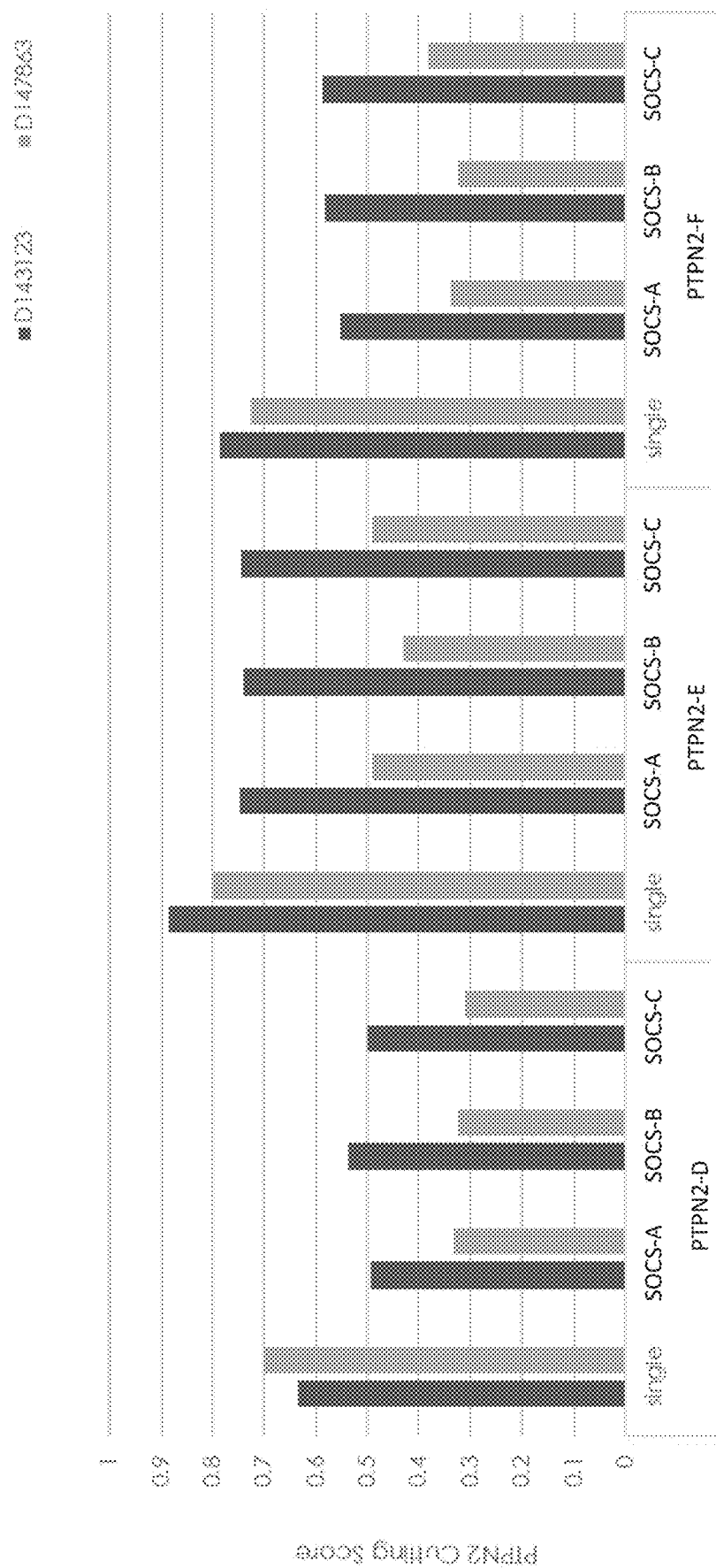
FIG. 3 shows the PTPN2-editing efficiency of PTPN2 gRNAs when used in combination with SOCS1-targeting gRNAs.

As shown in FIG. 1, combining two guides in one RNP mixture can reduce the editing efficiencies observed for each of the two target genes compared to those observed with a single guide RNP mixture. The percentage of CD45-edited cells decreased when RNPs including one CD45 gRNA and one B2M gRNA were used. FIG. 2 shows that particular SOCS1-targeting gRNAs can achieve high levels of SOCS1-editing even when used in combination with another gRNA (See SOCS1-C gRNA cutting score). FIG. 3 shows the unpredictability of identifying gRNAs that can achieve the high levels of gene editing when used in combination, as all of the PTPN2-targeting gRNAs tested showed decreased PTPN2 editing when used in combination.

Listing of gRNA Target Sequences:

| gRNA | Sequence | SEQ ID |
|---|---|---|
| hSOCS1_gRNA_6 | GACGCCTGCGGATTCTACTG | 1 |
| hSOCS1_gRNA_5 | TGGACGCCTGCGGATTCTAC | 2 |
| hSOCS1_gRNA_7 | AGTGCTCCAGCAGCTCGAAG | 3 |
| mSocs1_gRNA_1 | GAAGTGCACGCGGATGCTCG | 4 |
| mSocs1_gRNA_2 | AGTGCTCCAGCAGCTCGAAA | 5 |
| mSocs1_gRNA_3 | GCCGGCCGCTTCCACTTGGA | 6 |
| mSocs1_gRNA_4 | GCTGTGTCGCCAGCGCATCG | 7 |
| mSocs1_gRNA_5 | GCGACTGTCGCGCACCAAGA | 8 |
| mSocs1_gRNA_6 | GCGTGCACGGGGCGCACGAG | 9 |
| mSocs1_gRNA_7 | TCACGGAGTACCGGGTTAAG | 10 |
| mSocs1_gRNA_8 | GGACGCCTGCGGCTTCTATT | 11 |
| mSocs1_gRNA_9 | GCGCGAAGAAGCAGTTCCGT | 12 |
| mSocs1_gRNA_10 | GCTCAGCGTGAAGATGGCTT | 13 |
| mSocs1_gRNA_11 | CGAGCCCGTGGGCACCTTCT | 14 |
| mSocs1_gRNA_12 | ATCCGCGTGCACTTCCAGGC | 15 |
| mSocs1_gRNA_13 | CGCCAGGTTCTCGCGACCCA | 16 |
| hSOCS1_gRNA_1 | GCGGCTGCGCGCCGAGCCCG | 17 |
| hSOCS1_gRNA_2 | GGACGCCTGCGGATTCTACT | 18 |
| hSOCS1_gRNA_3 | GGCTGCCATCCAGGTGAAAG | 19 |
| hSOCS1_gRNA_4 | GCGGCTGTCGCGCACCAGGA | 20 |
| hSOCS1_gRNA_8 | GCCGGCCGCTTTCACCTGGA | 21 |
| hSOCS1_gRNA_9 | AGTAGAATCCGCAGGCGTCC | 22 |
| hSOCS1_gRNA_10 | CGCACCAGGAAGGTGCCCAC | 23 |
| hSOCS1_gRNA_11 | GGCCGGCCTGAAAGTGCACG | 24 |
| hSOCS1_gRNA_12 | TCCGTTCGCACGCCGATTAC | 25 |
| hSOCS1_gRNA_13 | AGCGCGCTCCTGGACGCCTG | 26 |
| hSOCS1_gRNA_14 | CGGCTGCGCGCCGAGCCCGT | 27 |
| hSOCS1_gRNA_15 | ACGCCTGCGGATTCTACTGG | 28 |
| hSOCS1_gRNA_16 | CGAGGCCATCTTCACGCTAA | 29 |
| hSOCS1_gRNA_17 | TCAGGCCGGCCGCTTTCACC | 30 |
| hSOCS1_gRNA_18 | CTTAGCGTGAAGATGGCCTC | 31 |
| hSOCS1_gRNA_19 | GCCGGTAATCGGCGTGCGAA | 32 |
| hSOCS1_gRNA_20 | CTGCATTGTCGGCTGCCACC | 33 |
| hSOCS1_gRNA_21 | GTGCGCCCCGTGCACGCTCA | 34 |
| hSOCS1_gRNA_22 | GCTGTGCCGCCAGCGCATCG | 35 |
| hSOCS1_gRNA_23 | CACGCGGCGCTGGCGCAGCG | 36 |
| hSOCS1_gRNA_24 | GCTCCTGCAGCGGCCGCACG | 37 |
| hSOCS1_gRNA_25 | AGCTCTCGCGGCTGCCATCC | 38 |
| hSOCS1_gRNA_26 | TGGTGCGCGACAGCCGCCAG | 39 |
| hSOCS1_gRNA_27 | GATGGTAGCACACAACCAGG | 40 |
| hSOCS1_gRNA_28 | AGAGGCAGTCGAAGCTCTCG | 41 |
| hSOCS1_gRNA_29 | GCTGGCGGCTGTCGCGCACC | 42 |
| hSOCS1_gRNA_30 | CCGAGGCCATCTTCACGCTA | 43 |
| hSOCS1_gRNA_31 | GGGGCCCCAGCATGCGGCG | 44 |
| hSOCS1_gRNA_32 | GCTGCTGGAGCACTACGTGG | 45 |
| hSOCS1_gRNA_33 | CGAGCTGCTGGAGCACTACG | 46 |
| hSOCS1_gRNA_34 | CGAAAAAGCAGTTCCGCTGG | 47 |
| hSOCS1_gRNA_35 | GCAGGCGTCCAGGAGCGCGC | 48 |
| hSOCS1_gRNA_36 | GGGGCCCCTGAGCGTGCACG | 49 |
| hSOCS1_gRNA_37 | GCGGCGCCGCGCCGCATGCT | 50 |
| hSOCS1_gRNA_38 | GCACGCGGCGCTGGCGCAGC | 51 |
| hSOCS1_gRNA_39 | TGGGGGCCCCTGAGCGTGCA | 52 |
| hSOCS1_gRNA_40 | CAGGAAGGTGCCCACGGGCT | 53 |
| hSOCS1_gRNA_41 | TGCGCCCCGTGCACGCTCAG | 54 |
| hSOCS1_gRNA_42 | GCCATCCAGGTGAAAGCGGC | 55 |
| hSOCS1_gRNA_43 | CACGCGCGCCAGCGCGCTCC | 56 |

Listing of gRNA Target Sequences:

| gRNA | Sequence | SEQ ID |
|---|---|---|
| hSOCS1_gRNA_44 | GGGCCCCCAGTAGAATCCGC | 57 |
| hSOCS1_gRNA_45 | ATCCGCGTGCACTTTCAGGC | 58 |
| hSOCS1_gRNA_46 | CGAGCCCGTGGGCACCTTCC | 59 |
| hSOCS1_gRNA_47 | CCACAGCAGCAGAGCCCCGA | 60 |
| hSOCS1_gRNA_48 | AGCCAGGTTCTCGCGGCCCA | 61 |
| hSOCS1_gRNA_49 | AAAGTGCACGCGGATGCTCG | 62 |
| hSOCS1_gRNA_50 | CTCTTCCTCCTCCTCGCCCG | 63 |
| hSOCS1_gRNA_51 | GCGTGCACGGGCGCACGAG | 64 |
| hSOCS1_gRNA_52 | AAGTGCACGCGGATGCTCGT | 65 |
| hSOCS1_gRNA_53 | CGTGCGCCCCGTGCACGCTC | 66 |
| hSOCS1_gRNA_54 | GCAGCGGCCGCACGCGGCGC | 67 |
| hSOCS1_gRNA_55 | CCTTAGCGTGAAGATGGCCT | 68 |
| hSOCS1_gRNA_56 | CAGGTTCTCGCGGCCCACGG | 69 |
| hSOCS1_gRNA_57 | GCGCACCAGGAAGGTGCCCA | 70 |
| hSOCS1_gRNA_58 | GCTGCCGGTCAAATCTGGAA | 71 |
| hSOCS1_gRNA_59 | CGGCGTGCGAACGGAATGTG | 72 |
| hSOCS1_gRNA_60 | CAGCAGCAGAGCCCCGACGG | 73 |
| hSOCS1_gRNA_61 | GGGCGAAAAGCAGTTCCGC | 74 |
| hSOCS1_gRNA_62 | CGCACGCGGCGCTGGCGCAG | 75 |
| hSOCS1_gRNA_63 | GGATGCGAGCCAGGTTCTCG | 76 |
| hSOCS1_gRNA_64 | TGGCGGCACAGCTCCTGCAG | 77 |
| hSOCS1_gRNA_65 | GCGCCCGCGGCCGTGCCCCG | 78 |
| hSOCS1_gRNA_66 | GGCGCCGCGCCGCATGCTGG | 79 |
| hSOCS1_gRNA_67 | CGGTGGCCACGATGCGCTGG | 80 |
| hSOCS1_gRNA_68 | TGCTGTGGAGACTGCATTGT | 81 |
| hSOCS1_gRNA_69 | TAGGATGGTAGCACACAACC | 82 |
| hSOCS1_gRNA_70 | GCGGCCGTGCCCCGCGGTCC | 83 |
| hSOCS1_gRNA_71 | GAGCATCCGCGTGCACTTTC | 84 |
| hSOCS1_gRNA_72 | CGCTGCCGGTCAAATCTGGA | 85 |
| hSOCS1_gRNA_73 | CAGCGCATCGTGGCCACCGT | 86 |
| hSOCS1_gRNA_74 | GCGGATGCTCGTGGGTCCCG | 87 |
| hSOCS1_gRNA_75 | CGGCGCCGCGCCGCATGCTG | 88 |
| hSOCS1_gRNA_76 | CGGTCAAATCTGGAAGGGGA | 89 |
| hSOCS1_gRNA_77 | AGGAAGGTTCTGGCCGCCGT | 90 |
| hSOCS1_gRNA_78 | CCACGGTGGCCACGATGCGC | 91 |
| hSOCS1_gRNA_79 | CGCTGCGCCAGCGCCGCGTG | 92 |
| hSOCS1_gRNA_80 | AGGAGCTCAGGTAGTCGCGG | 93 |
| hSOCS1_gRNA_81 | GCAGCGGGGCCCCCAGCATG | 94 |
| hSOCS1_gRNA_82 | GGAAGGAGCTCAGGTAGTCG | 95 |
| hSOCS1_gRNA_83 | TCGCGGAGGACGGGGTTGAG | 96 |
| hSOCS1_gRNA_84 | CGACTGCCTCTTCGAGCTGC | 97 |
| hSOCS1_gRNA_85 | GCGCCGCGTGCGGCCGCTGC | 98 |
| hSOCS1_gRNA_86 | CACCGTGGGCCGCGAGAACC | 99 |
| hSOCS1_gRNA_87 | GTGCCCCGCGGTCCCGGCCC | 100 |
| hSOCS1_gRNA_88 | CTGCCGGTCAAATCTGGAAG | 101 |
| hSOCS1_gRNA_89 | CTTCCCCTTCCAGATTTGAC | 102 |
| hSOCS1_gRNA_90 | CTCAGGTAGTCGCGGAGGAC | 103 |
| hSOCS1_gRNA_91 | CGGGCGCTGCCGGTCAAATC | 104 |
| hSOCS1_gRNA_92 | GGAAGGTTCTGGCCGCCGTC | 105 |
| hSOCS1_gRNA_93 | GCTCAGGTAGTCGCGGAGGA | 106 |
| hSOCS1_gRNA_94 | GCGGAAGTGCGTGTCGCCGG | 107 |
| hSOCS1_gRNA_95 | GGACCGCGGGGCACGGCCGC | 108 |
| hSOCS1_gRNA_96 | GGGACCGCGGGGCACGGCCG | 109 |
| hSOCS1_gRNA_97 | GCGCGTGATGCGCCGGTAAT | 110 |
| hSOCS1_gRNA_98 | TCAGGTAGTCGCGGAGGACG | 111 |
| hSOCS1_gRNA_99 | TGCGGAAGTGCGTGTCGCCG | 112 |
| hSOCS1_gRNA_100 | GGGGCCGGGACCGCGGGCA | 113 |
| hSOCS1_gRNA_101 | CCGTCGGGGCTCTGCTGCTG | 114 |
| hSOCS1_gRNA_102 | GAAGGTTCTGGCCGCCGTCG | 115 |
| hSOCS1_gRNA_103 | GTGTGCTACCATCCTACAGA | 116 |
| hSOCS1_gRNA_104 | GTCGCGGAGGACGGGGTTGA | 117 |
| hSOCS1_gRNA_105 | CGCTGGCGCGCGTGATGCGC | 118 |
| hSOCS1_gRNA_106 | GCGTGCACGGCGGGCGCTGC | 119 |
| hSOCS1_gRNA_107 | TCTGGAAGGGGAAGGAGCTC | 120 |
| hSOCS1_gRNA_108 | GTGCGTGTCGCCGGGGCCG | 121 |
| hSOCS1_gRNA_109 | GGGCACGGCCGCGGGCGCGC | 122 |
| hSOCS1_gRNA_110 | GTTAATGCTGCGTGCACGGC | 123 |
| hSOCS1_gRNA_111 | GCACGGCCGCGGGCGCGCGG | 124 |
| hSOCS1_gRNA_112 | GGGGCACGGCCGCGGGCGCG | 125 |
| hSOCS1_gRNA_113 | GTGCGGAAGTGCGTGTCGCC | 126 |
| hSOCS1_gRNA_114 | GAGGAAGAGGAGGAAGGTTC | 127 |
| hSOCS1_gRNA_115 | GGCTGGCCCCTTCTGTAGGA | 128 |
| hSOCS1_gRNA_116 | GGGGCCGGGCCGGGACCGC | 129 |
| hSOCS1_gRNA_117 | CGCGGAGGACGGGGTTGAGG | 130 |

-continued

Listing of gRNA Target Sequences:

| gRNA | Sequence | SEQ ID |
|---|---|---|
| hSOCS1_gRNA_118 | TTTCGCCCTTAGCGTGAAGA | 131 |
| hSOCS1_gRNA_119 | GGCACGGCCGCGGGCGCGCG | 132 |
| hSOCS1_gRNA_120 | AGTCGCGGAGGACGGGGTTG | 133 |
| hSOCS1_gRNA_121 | GGGCCGGGGCCGGGACCGCG | 134 |
| hSOCS1_gRNA_122 | AAGTGCGTGTCGCCGGGGGC | 135 |
| hSOCS1_gRNA_123 | CTCCGGCTGGCCCCTTCTGT | 136 |
| hSOCS1_gRNA_124 | GGCGGCGCCGCGCCGCATGC | 137 |
| hSOCS1_gRNA_125 | AGTGCGTGTCGCGGGGGCC | 138 |
| hSOCS1_gRNA_126 | TGTGCGGAAGTGCGTGTCGC | 139 |
| hSOCS1_gRNA_127 | GTGTCGCGGGGGCCGGGGC | 140 |
| hSOCS1_gRNA_128 | TGTCGCCGGGGCCGGGGCC | 141 |
| hSOCS1_gRNA_129 | GCGGTCCCGGCCCCGGCCCC | 142 |
| hSOCS1_gRNA_130 | CGCGGGGGCCGCGGGCGAGG | 143 |
| hSOCS1_gRNA_131 | CGCGGGCGAGGAGGAGGAAG | 144 |
| hSOCS1_gRNA_132 | GGGCGAGGAGGAGGAAGAGG | 145 |
| hPTPN2_gRNA_32 | CGAGCGGGAGTTCGAAGAGT | 146 |
| hPTPN2_gRNA_31 | GCCCAATGCCTGCACTACAG | 147 |
| hPTPN2_gRNA_40 | GGAAACTTGGCCACTCTATG | 148 |
| mPTPN2_gRNA_1 | AATCTGGCCAGGTGGTATAA | 149 |
| mPTPN2_gRNA_2 | AATATGAGAAAGTATCGAAT | 150 |
| mPTPN2_gRNA_3 | ATCACTGCAGGTCCATGGTC | 151 |
| mPTPN2_gRNA_4 | ATGTGCACAGTACTGGCCAA | 152 |
| mPTPN2_gRNA_5 | GGCAGCATGTGTTCGGAAGT | 153 |
| mPTPN2_gRNA_6 | AAGAAGTTTAGAAATGAAGC | 154 |
| mPTPN2_gRNA_7 | GCCACACCATGAGCCAGAAA | 155 |
| mPTPN2_gRNA_8 | CCTTTCTTGCAGATGGAAAA | 156 |
| mPTPN2_gRNA_9 | GTACTTTGCTCCTTCTATTA | 157 |
| mPTPN2_gRNA_10 | AGAAATGAAGCTGGTGACTC | 158 |
| mPTPN2_gRNA_11 | GTTTAGCATGACAACTGCTT | 159 |
| mPTPN2_gRNA_12 | GCCCGATGCCCGCACTGCAA | 160 |
| mPTPN2_gRNA_13 | TGACAGAGAAATGGTGTTTA | 161 |
| hPTPN2_gRNA_1 | CCATGCCCACCACCATCGAG | 162 |
| hPTPN2_gRNA_2 | TCTACGGAAACGTATTCGAG | 163 |
| hPTPN2_gRNA_3 | TTTAGTATATTGAGAACTTG | 164 |
| hPTPN2_gRNA_4 | GCACTACAGTGGATCACCGC | 165 |
| hPTPN2_gRNA_5 | TGTCATGCTGAACCGCATTG | 166 |
| hPTPN2_gRNA_6 | GGAAACTTGGCCACTCTATG | 167 |

-continued

Listing of gRNA Target Sequences:

| gRNA | Sequence | SEQ ID |
|---|---|---|
| hPTPN2_gRNA_7 | GTATTTGAAATTATTAATGC | 168 |
| hPTPN2_gRNA_8 | CAGTTTAGTTGACATAGAAG | 169 |
| hPTPN2_gRNA_9 | GGGTCTGAATAAGACCCATT | 170 |
| hPTPN2_gRNA_10 | CCATGACTATCCTCATAGAG | 171 |
| hPTPN2_gRNA_11 | CCATGACTATCCTCATAGAG | 172 |
| hPTPN2_gRNA_12 | CTCTTCGAACTCCCGCTCGA | 173 |
| hPTPN2_gRNA_13 | GAACCCTGACCATGGGCCTG | 174 |
| hPTPN2_gRNA_14 | GCTCCTTGAACCCTGACCAT | 175 |
| hPTPN2_gRNA_15 | AGTTGGATACTCAGCGTCGC | 176 |
| hPTPN2_gRNA_16 | CCGCTCGATGGTGGTGGGCA | 177 |
| hPTPN2_gRNA_17 | CAGAAATGGCAGCATGTGTT | 178 |
| hPTPN2_gRNA_18 | GCACTACAGTGGATCACCGC | 179 |
| hPTPN2_gRNA_19 | GGTAGACACTTGTCTTGTTT | 180 |
| hPTPN2_gRNA_20 | TGGCAGCATGTGTTAGGAAG | 181 |
| hPTPN2_gRNA_21 | AGGCCCATGGTCAGGGTTCA | 182 |
| hPTPN2_gRNA_22 | GTTCAGCATGACAACTGCTT | 183 |
| hPTPN2_gRNA_23 | CAATGGAGGAGAACAGTGAG | 184 |
| hPTPN2_gRNA_24 | CTCTTCTATGTCAACTAAAC | 185 |
| hPTPN2_gRNA_25 | AGTGGATCACCGCAGGCCCA | 186 |
| hPTPN2_gRNA_26 | CTGACAGGTGACCGATGTAC | 187 |
| hPTPN2_gRNA_27 | AACTCCCGCTCGATGGTGGT | 188 |
| hPTPN2_gRNA_28 | GTCTCCCTGATCCATCCAGT | 189 |
| hPTPN2_gRNA_29 | TAGAGGAAAGTCCTGTACAT | 190 |
| hPTPN2_gRNA_30 | ATGTATGGAAAGGATGGTAA | 191 |
| hPTPN2_gRNA_33 | TCACCGCAGGCCCATGGTCA | 192 |
| hPTPN2_gRNA_34 | CAGTTTAGTTGACATAGAAG | 193 |
| hPTPN2_gRNA_35 | CCATGCCCACCACCATCGAG | 194 |
| hPTPN2_gRNA_36 | GCCAAACCATAAGCCAGAAA | 195 |
| hPTPN2_gRNA_37 | CCGATTCTTTCTCCACAATG | 196 |
| hPTPN2_gRNA_38 | TTCGAACTCCCGCTCGATGG | 197 |
| hPTPN2_gRNA_39 | AGTGCAGGCATTGGGCGCTC | 198 |
| hPTPN2_gRNA_41 | ATCCACTGTAGTGCAGGCAT | 199 |
| hPTPN2_gRNA_42 | CACTCTATGAGGATAGTCAT | 200 |
| hPTPN2_gRNA_43 | CCACTCTATGAGGATAGTCA | 201 |
| hPTPN2_gRNA_44 | TCCACTGTAGTGCAGGCATT | 202 |
| hPTPN2_gRNA_45 | AAGTTCTTTCCATCGTTTCT | 203 |
| hPTPN2_gRNA_46 | TCGCTGGCAGCCGCTGTACT | 204 |

Listing of gRNA Target Sequences:

| gRNA | Sequence | SEQ ID |
|---|---|---|
| hPTPN2_gRNA_47 | GAACTCCCGCTCGATGGTGG | 205 |
| hPTPN2_gRNA_48 | AGGATGGTAAAGGCACCAAC | 206 |
| hPTPN2_gRNA_49 | AAAGGGAGATTCTAGTATAC | 207 |
| hPTPN2_gRNA_50 | AGAATTTAGGATGTATGGAA | 208 |
| hPTPN2_gRNA_51 | GGGTCTGAATAAGACCCATT | 209 |
| hPTPN2_gRNA_52 | GGCACCAACTGGATGGATCA | 210 |
| hPTPN2_gRNA_53 | CTCTAAAATGCAAGATACAA | 211 |
| hPTPN2_gRNA_54 | GTATTTGAAATTATTAATGC | 212 |
| hPTPN2_gRNA_55 | CCTTTCTTGCAGATGGAAAA | 213 |
| hPTPN2_gRNA_56 | CTGCACCTTCTGAGCTGTGG | 214 |
| hPTPN2_gRNA_57 | ATGCTGCCATTTCTGGCTTA | 215 |
| hPTPN2_gRNA_58 | TTTCTTTAAACAGCATCTCT | 216 |
| hPTPN2_gRNA_59 | AGACATGGAATGCAGAATGC | 217 |
| hPTPN2_gRNA_60 | AGGCACCAACTGGATGGATC | 218 |
| hPTPN2_gRNA_61 | TAATGACTGAAAATACAAT | 219 |
| hPTPN2_gRNA_62 | GAATGCAGAATGCAGGAAAT | 220 |
| hPTPN2_gRNA_63 | TTTAGGATGTATGGAAGGA | 221 |
| hPTPN2_gRNA_64 | CTAACACATGCTGCCATTTC | 222 |
| hPTPN2_gRNA_65 | TCATACATGGCTATAATAGA | 223 |
| hPTPN2_gRNA_66 | ACGATGGAAAGAACTTTCTA | 224 |
| hPTPN2_gRNA_67 | ACGTATTCGAGAGGACAGAA | 225 |
| hPTPN2_gRNA_68 | GCGGTGATCCACTGTAGTGC | 226 |
| hPTPN2_gRNA_69 | TATTAATGCTGGATGTTAAA | 227 |
| hPTPN2_gRNA_70 | GAGATGCTGTTTAAAGAAAC | 228 |
| hPTPN2_gRNA_71 | CAGCAAGAATTTAGGATGTA | 229 |
| hPTPN2_gRNA_72 | TTGACATAGAAGAGGCACAA | 230 |
| hPTPN2_gRNA_73 | GATTCAGGGACTCCAAAATC | 231 |
| hPTPN2_gRNA_74 | CTCACTTTCATTATACTACC | 232 |
| hPTPN2_gRNA_75 | TTTAGTATATTGAGAACTTG | 233 |
| hPTPN2_gRNA_76 | AGGGACTCCAAAATCTGGCC | 234 |
| hPTPN2_gRNA_77 | AGGTTAAATGTGCACAGTAC | 235 |
| hPTPN2_gRNA_78 | ATCACCGCAGGCCCATGGTC | 236 |
| hPTPN2_gRNA_79 | AGCATCTCTTGGTCATCTGT | 237 |
| hPTPN2_gRNA_80 | GAAGGAGCAAAATGTATAAA | 238 |
| hPTPN2_gRNA_81 | GCCATTTCTGGCTTATGGTT | 239 |
| hPTPN2_gRNA_82 | CTGGATGGATCAGGGAGACA | 240 |
| hPTPN2_gRNA_83 | AAATACAATGGGAACAGAAT | 241 |
| hPTPN2_gRNA_84 | ATAATGACTGAAAATACAA | 242 |
| hPTPN2_gRNA_85 | CATGCCCACCACCATCGAGC | 243 |
| hPTPN2_gRNA_86 | AACATGAGAAAATACCGAAT | 244 |
| hPTPN2_gRNA_87 | AGAAATGAAGCTGGTGATTC | 245 |
| hPTPN2_gRNA_88 | CCGCATTGTGGAGAAAGAAT | 246 |
| hPTPN2_gRNA_89 | GAAATGAAGCTGGTGATTCA | 247 |
| hPTPN2_gRNA_90 | TTGTTTAAAGTGAGAGAATC | 248 |
| hPTPN2_gRNA_91 | CCGCGACTCACCAAGTACAG | 249 |
| hPTPN2_gRNA_92 | GAACATGAGAAAATACCGAA | 250 |
| hPTPN2_gRNA_93 | TATACTACCTGGCCAGATTT | 251 |
| hPTPN2_gRNA_94 | TATGAGAATCTCAGTTGATC | 252 |
| hPTPN2_gRNA_95 | TCAACTGAGATTCTCATACA | 253 |
| hPTPN2_gRNA_96 | TGAGAATCTCAGTTGATCTG | 254 |
| hPTPN2_gRNA_97 | ATGAGAATCTCAGTTGATCT | 255 |
| hPTPN2_gRNA_98 | TGGTAAAGGCACCAACTGGA | 256 |
| hPTPN2_gRNA_99 | TGTCATGCTGAACCGCATTG | 257 |
| hPTPN2_gRNA_100 | TTTGGTGAATGATCAAAGGC | 258 |
| hPTPN2_gRNA_101 | ATGAAAGTGAGATATTGTTC | 259 |
| hPTPN2_gRNA_102 | TATTTCCTCATAGTGCTCTA | 260 |
| hPTPN2_gRNA_103 | AGAAGGAGCAAAATGTATAA | 261 |
| hPTPN2_gRNA_104 | TTTGTTTGGTGAATGATCAA | 262 |
| hPTPN2_gRNA_105 | TCTACGGAAACGTATTCGAG | 263 |
| hPTPN2_gRNA_106 | AAAGGCCACCACAGCTCAGA | 264 |
| hPTPN2_gRNA_107 | AGGTGCAGCAGATGAAACAG | 265 |
| hPTPN2_gRNA_108 | GGCTCCTTGAACCCTGACCA | 266 |
| hPTPN2_gRNA_109 | AAGGAGTTACATCTTAACAC | 267 |
| hPTPN2_gRNA_110 | TAAAATGCAAGATACAATGG | 268 |
| hPTPN2_gRNA_111 | ACAAGTGTCTACCAGAGAGA | 269 |
| hPTPN2_gRNA_112 | GCGCTCTGGCACCTTCTCTC | 270 |
| hPTPN2_gRNA_113 | CTGCTGCACCTTCTGAGCTG | 271 |
| hPTPN2_gRNA_114 | TCTTCCCTACCTAGAAACGA | 272 |

The invention claimed is:

1. A modified immune effector cell comprising:
   a SOCS1-targeting gRNA molecule and a PTPN2-targeting gRNA molecule, wherein the SOCS1-targeting gRNA molecule comprises a targeting domain sequence encoded by any one of SEQ ID NOs: 1-3; and a Cas endonuclease.

2. The modified immune effector cell of claim 1, wherein the PTPN2-targeting gRNA molecule comprises a targeting domain sequence encoded by one of SEQ ID NOs: 146-148.

3. The modified immune effector cell of claim 1, wherein the Cas endonuclease is a Cas9 endonuclease.

4. The modified immune effector cell of claim 1, wherein the Cas endonuclease is a wild-type Cas endonuclease comprising two enzymatically active domains, and capable of inducing double stranded DNA breaks.

5. The modified immune effector cell of claim 1, wherein the Cas endonuclease is a Cas nickase mutant comprising one enzymatically active domain and capable of inducing single stranded DNA breaks.

6. The modified immune effector cell of claim 1, wherein the Cas endonuclease is a deactivated Cas protein (dCas) and is associated with a heterologous protein capable of modulating expression of one or more endogenous target genes.

7. The modified immune effector cell of claim 6, wherein the heterologous protein is selected from the group consisting of MAX-interacting protein 1 (MXI1), Krüppel-associated box (KRAB) domain, and four concatenated mSin3 domains (SID4X).

8. The modified immune effector cell of claim 1, wherein the SOCS1-targeting gRNA molecule and a PTPN2-targeting gRNA molecule are single gRNA (sgRNA) molecules.

9. The modified immune effector cell of claim 1, wherein the SOCS1-targeting gRNA molecule and the PTPN2-targeting gRNA molecule are dual gRNA molecules.

10. The modified immune effector cell of claim 1, wherein each of the SOCS1-targeting gRNA molecule and the PTPN2-targeting gRNA molecule comprises a modification at or near the 5' end and/or a modification at or near the 3' end.

11. The modified immune effector cell of claim 1, wherein the SOCS1-targeting gRNA molecule and the PTPN2-targeting gRNA molecule are complexed with the Cas endonuclease as ribonucleoproteins (RNPs).

12. The modified immune effector cell of claim 1, comprising a vector encoding the SOCS1-targeting gRNA molecule and the PTPN2-targeting gRNA molecule.

13. The modified immune effector cell of claim 1, comprising a first vector encoding the SOCS1-targeting gRNA molecule and a second vector encoding the PTPN2-targeting gRNA molecule.

14. The modified immune effector cell of claim 1, comprising a vector encoding the Cas endonuclease or an mRNA polynucleotide encoding the Cas endonuclease.

15. The modified immune effector cell of claim 1, wherein the modified immune effector cell is a human tumor-infiltrating lymphocyte.

16. The modified immune effector cell of claim 1, wherein modified immune effector cell is a human T cell.

17. The modified immune effector cell of claim 16, wherein the human T cell comprises an engineered T cell receptor.

18. The modified immune effector cell of claim 16, wherein the human T cell comprises an engineered chimeric antigen receptor.

\* \* \* \* \*

SEQUENCE LISTING

```
Sequence total quantity: 315
SEQ ID NO: 1                moltype = DNA   length = 20
FEATURE                     Location/Qualifiers
source                      1..20
                            mol_type = genomic DNA
                            organism = Homo sapiens
SEQUENCE: 1
gacgcctgcg gattctactg                                                        20

SEQ ID NO: 2                moltype = DNA   length = 20
FEATURE                     Location/Qualifiers
source                      1..20
                            mol_type = genomic DNA
                            organism = Mus musculus
SEQUENCE: 2
tggacgcctg cggattctac                                                        20

SEQ ID NO: 3                moltype = DNA   length = 20
FEATURE                     Location/Qualifiers
source                      1..20
                            mol_type = genomic DNA
                            organism = Mus musculus
SEQUENCE: 3
agtgctccag cagctcgaag                                                        20

SEQ ID NO: 4                moltype = DNA   length = 20
FEATURE                     Location/Qualifiers
source                      1..20
                            mol_type = genomic DNA
                            organism = Mus musculus
SEQUENCE: 4
gaagtgcacg cggatgctcg                                                        20

SEQ ID NO: 5                moltype = DNA   length = 20
FEATURE                     Location/Qualifiers
source                      1..20
                            mol_type = genomic DNA
                            organism = Mus musculus
SEQUENCE: 5
agtgctccag cagctcgaaa                                                        20

SEQ ID NO: 6                moltype = DNA   length = 20
FEATURE                     Location/Qualifiers
source                      1..20
                            mol_type = genomic DNA
                            organism = Mus musculus
SEQUENCE: 6
gccggccgct tccacttgga                                                        20

SEQ ID NO: 7                moltype = DNA   length = 20
FEATURE                     Location/Qualifiers
source                      1..20
                            mol_type = genomic DNA
                            organism = Mus musculus
SEQUENCE: 7
gctgtgtcgc cagcgcatcg                                                        20

SEQ ID NO: 8                moltype = DNA   length = 20
FEATURE                     Location/Qualifiers
source                      1..20
                            mol_type = genomic DNA
                            organism = Mus musculus
SEQUENCE: 8
gcgactgtcg cgcaccaaga                                                        20

SEQ ID NO: 9                moltype = DNA   length = 20
FEATURE                     Location/Qualifiers
source                      1..20
                            mol_type = genomic DNA
                            organism = Mus musculus
SEQUENCE: 9
gcgtgcacgg ggcgcacgag                                                        20

SEQ ID NO: 10               moltype = DNA   length = 20
FEATURE                     Location/Qualifiers
source                      1..20
                            mol_type = genomic DNA
                            organism = Mus musculus
```

```
SEQUENCE: 10
tcacggagta ccgggttaag                                                   20

SEQ ID NO: 11          moltype = DNA   length = 20
FEATURE                Location/Qualifiers
source                 1..20
                       mol_type = genomic DNA
                       organism = Mus musculus
SEQUENCE: 11
ggacgcctgc ggcttctatt                                                   20

SEQ ID NO: 12          moltype = DNA   length = 20
FEATURE                Location/Qualifiers
source                 1..20
                       mol_type = genomic DNA
                       organism = Mus musculus
SEQUENCE: 12
gcgcgaagaa gcagttccgt                                                   20

SEQ ID NO: 13          moltype = DNA   length = 20
FEATURE                Location/Qualifiers
source                 1..20
                       mol_type = genomic DNA
                       organism = Mus musculus
SEQUENCE: 13
gctcagcgtg aagatggctt                                                   20

SEQ ID NO: 14          moltype = DNA   length = 20
FEATURE                Location/Qualifiers
source                 1..20
                       mol_type = genomic DNA
                       organism = Mus musculus
SEQUENCE: 14
cgagcccgtg ggcaccttct                                                   20

SEQ ID NO: 15          moltype = DNA   length = 20
FEATURE                Location/Qualifiers
source                 1..20
                       mol_type = genomic DNA
                       organism = Mus musculus
SEQUENCE: 15
atccgcgtgc acttccaggc                                                   20

SEQ ID NO: 16          moltype = DNA   length = 20
FEATURE                Location/Qualifiers
source                 1..20
                       mol_type = genomic DNA
                       organism = Mus musculus
SEQUENCE: 16
cgccaggttc tcgcgaccca                                                   20

SEQ ID NO: 17          moltype = DNA   length = 20
FEATURE                Location/Qualifiers
source                 1..20
                       mol_type = genomic DNA
                       organism = Homo sapiens
SEQUENCE: 17
gcggctgcgc gccgagcccg                                                   20

SEQ ID NO: 18          moltype = DNA   length = 20
FEATURE                Location/Qualifiers
source                 1..20
                       mol_type = genomic DNA
                       organism = Homo sapiens
SEQUENCE: 18
ggacgcctgc ggattctact                                                   20

SEQ ID NO: 19          moltype = DNA   length = 20
FEATURE                Location/Qualifiers
source                 1..20
                       mol_type = genomic DNA
                       organism = Homo sapiens
SEQUENCE: 19
ggctgccatc caggtgaaag                                                   20

SEQ ID NO: 20          moltype = DNA   length = 20
FEATURE                Location/Qualifiers
source                 1..20
                       mol_type = genomic DNA
```

```
                                    organism = Homo sapiens
SEQUENCE: 20
gcggctgtcg cgcaccagga                                                          20

SEQ ID NO: 21          moltype = DNA  length = 20
FEATURE                Location/Qualifiers
source                 1..20
                       mol_type = genomic DNA
                       organism = Homo sapiens
SEQUENCE: 21
gccggccgct ttcacctgga                                                          20

SEQ ID NO: 22          moltype = DNA  length = 20
FEATURE                Location/Qualifiers
source                 1..20
                       mol_type = genomic DNA
                       organism = Homo sapiens
SEQUENCE: 22
agtagaatcc gcaggcgtcc                                                          20

SEQ ID NO: 23          moltype = DNA  length = 20
FEATURE                Location/Qualifiers
source                 1..20
                       mol_type = genomic DNA
                       organism = Homo sapiens
SEQUENCE: 23
cgcaccagga aggtgcccac                                                          20

SEQ ID NO: 24          moltype = DNA  length = 20
FEATURE                Location/Qualifiers
source                 1..20
                       mol_type = genomic DNA
                       organism = Homo sapiens
SEQUENCE: 24
ggccggcctg aaagtgcacg                                                          20

SEQ ID NO: 25          moltype = DNA  length = 20
FEATURE                Location/Qualifiers
source                 1..20
                       mol_type = genomic DNA
                       organism = Homo sapiens
SEQUENCE: 25
tccgttcgca cgccgattac                                                          20

SEQ ID NO: 26          moltype = DNA  length = 20
FEATURE                Location/Qualifiers
source                 1..20
                       mol_type = genomic DNA
                       organism = Homo sapiens
SEQUENCE: 26
agcgcgctcc tggacgcctg                                                          20

SEQ ID NO: 27          moltype = DNA  length = 20
FEATURE                Location/Qualifiers
source                 1..20
                       mol_type = genomic DNA
                       organism = Homo sapiens
SEQUENCE: 27
cggctgcgcg ccgagcccgt                                                          20

SEQ ID NO: 28          moltype = DNA  length = 20
FEATURE                Location/Qualifiers
source                 1..20
                       mol_type = genomic DNA
                       organism = Homo sapiens
SEQUENCE: 28
acgcctgcgg attctactgg                                                          20

SEQ ID NO: 29          moltype = DNA  length = 20
FEATURE                Location/Qualifiers
source                 1..20
                       mol_type = genomic DNA
                       organism = Homo sapiens
SEQUENCE: 29
cgaggccatc ttcacgctaa                                                          20

SEQ ID NO: 30          moltype = DNA  length = 20
FEATURE                Location/Qualifiers
source                 1..20
```

```
                        mol_type = genomic DNA
                        organism = Homo sapiens
SEQUENCE: 30
tcaggccggc cgctttcacc                                           20

SEQ ID NO: 31           moltype = DNA  length = 20
FEATURE                 Location/Qualifiers
source                  1..20
                        mol_type = genomic DNA
                        organism = Homo sapiens
SEQUENCE: 31
cttagcgtga agatggcctc                                           20

SEQ ID NO: 32           moltype = DNA  length = 20
FEATURE                 Location/Qualifiers
source                  1..20
                        mol_type = genomic DNA
                        organism = Homo sapiens
SEQUENCE: 32
gccggtaatc ggcgtgcgaa                                           20

SEQ ID NO: 33           moltype = DNA  length = 20
FEATURE                 Location/Qualifiers
source                  1..20
                        mol_type = genomic DNA
                        organism = Homo sapiens
SEQUENCE: 33
ctgcattgtc ggctgccacc                                           20

SEQ ID NO: 34           moltype = DNA  length = 20
FEATURE                 Location/Qualifiers
source                  1..20
                        mol_type = genomic DNA
                        organism = Homo sapiens
SEQUENCE: 34
gtgcgccccg tgcacgctca                                           20

SEQ ID NO: 35           moltype = DNA  length = 20
FEATURE                 Location/Qualifiers
source                  1..20
                        mol_type = genomic DNA
                        organism = Homo sapiens
SEQUENCE: 35
gctgtgccgc cagcgcatcg                                           20

SEQ ID NO: 36           moltype = DNA  length = 20
FEATURE                 Location/Qualifiers
source                  1..20
                        mol_type = genomic DNA
                        organism = Homo sapiens
SEQUENCE: 36
cacgcggcgc tggcgcagcg                                           20

SEQ ID NO: 37           moltype = DNA  length = 20
FEATURE                 Location/Qualifiers
source                  1..20
                        mol_type = genomic DNA
                        organism = Homo sapiens
SEQUENCE: 37
gctcctgcag cggccgcacg                                           20

SEQ ID NO: 38           moltype = DNA  length = 20
FEATURE                 Location/Qualifiers
source                  1..20
                        mol_type = genomic DNA
                        organism = Homo sapiens
SEQUENCE: 38
agctctcgcg gctgccatcc                                           20

SEQ ID NO: 39           moltype = DNA  length = 20
FEATURE                 Location/Qualifiers
source                  1..20
                        mol_type = genomic DNA
                        organism = Homo sapiens
SEQUENCE: 39
tggtgcgcga cagccgccag                                           20

SEQ ID NO: 40           moltype = DNA  length = 20
FEATURE                 Location/Qualifiers
```

```
source                   1..20
                         mol_type = genomic DNA
                         organism = Homo sapiens
SEQUENCE: 40
gatggtagca cacaaccagg                                                    20

SEQ ID NO: 41            moltype = DNA   length = 20
FEATURE                  Location/Qualifiers
source                   1..20
                         mol_type = genomic DNA
                         organism = Homo sapiens
SEQUENCE: 41
agaggcagtc gaagctctcg                                                    20

SEQ ID NO: 42            moltype = DNA   length = 20
FEATURE                  Location/Qualifiers
source                   1..20
                         mol_type = genomic DNA
                         organism = Homo sapiens
SEQUENCE: 42
gctggcggct gtcgcgcacc                                                    20

SEQ ID NO: 43            moltype = DNA   length = 20
FEATURE                  Location/Qualifiers
source                   1..20
                         mol_type = genomic DNA
                         organism = Homo sapiens
SEQUENCE: 43
ccgaggccat cttcacgcta                                                    20

SEQ ID NO: 44            moltype = DNA   length = 20
FEATURE                  Location/Qualifiers
source                   1..20
                         mol_type = genomic DNA
                         organism = Homo sapiens
SEQUENCE: 44
ggggccccca gcatgcggcg                                                    20

SEQ ID NO: 45            moltype = DNA   length = 20
FEATURE                  Location/Qualifiers
source                   1..20
                         mol_type = genomic DNA
                         organism = Homo sapiens
SEQUENCE: 45
gctgctggag cactacgtgg                                                    20

SEQ ID NO: 46            moltype = DNA   length = 20
FEATURE                  Location/Qualifiers
source                   1..20
                         mol_type = genomic DNA
                         organism = Homo sapiens
SEQUENCE: 46
cgagctgctg gagcactacg                                                    20

SEQ ID NO: 47            moltype = DNA   length = 20
FEATURE                  Location/Qualifiers
source                   1..20
                         mol_type = genomic DNA
                         organism = Homo sapiens
SEQUENCE: 47
cgaaaaagca gttccgctgg                                                    20

SEQ ID NO: 48            moltype = DNA   length = 20
FEATURE                  Location/Qualifiers
source                   1..20
                         mol_type = genomic DNA
                         organism = Homo sapiens
SEQUENCE: 48
gcaggcgtcc aggagcgcgc                                                    20

SEQ ID NO: 49            moltype = DNA   length = 20
FEATURE                  Location/Qualifiers
source                   1..20
                         mol_type = genomic DNA
                         organism = Homo sapiens
SEQUENCE: 49
ggggcccctg agcgtgcacg                                                    20

SEQ ID NO: 50            moltype = DNA   length = 20
```

```
FEATURE                 Location/Qualifiers
source                  1..20
                        mol_type = genomic DNA
                        organism = Homo sapiens
SEQUENCE: 50
gcggcgccgc gccgcatgct                                           20

SEQ ID NO: 51           moltype = DNA  length = 20
FEATURE                 Location/Qualifiers
source                  1..20
                        mol_type = genomic DNA
                        organism = Homo sapiens
SEQUENCE: 51
gcacgcggcg ctggcgcagc                                           20

SEQ ID NO: 52           moltype = DNA  length = 20
FEATURE                 Location/Qualifiers
source                  1..20
                        mol_type = genomic DNA
                        organism = Homo sapiens
SEQUENCE: 52
tgggggcccc tgagcgtgca                                           20

SEQ ID NO: 53           moltype = DNA  length = 20
FEATURE                 Location/Qualifiers
source                  1..20
                        mol_type = genomic DNA
                        organism = Homo sapiens
SEQUENCE: 53
caggaaggtg cccacgggct                                           20

SEQ ID NO: 54           moltype = DNA  length = 20
FEATURE                 Location/Qualifiers
source                  1..20
                        mol_type = genomic DNA
                        organism = Homo sapiens
SEQUENCE: 54
tgcgcccgt gcacgctcag                                            20

SEQ ID NO: 55           moltype = DNA  length = 20
FEATURE                 Location/Qualifiers
source                  1..20
                        mol_type = genomic DNA
                        organism = Homo sapiens
SEQUENCE: 55
gccatccagg tgaaagcggc                                           20

SEQ ID NO: 56           moltype = DNA  length = 20
FEATURE                 Location/Qualifiers
source                  1..20
                        mol_type = genomic DNA
                        organism = Homo sapiens
SEQUENCE: 56
cacgcgcgcc agcgcgctcc                                           20

SEQ ID NO: 57           moltype = DNA  length = 20
FEATURE                 Location/Qualifiers
source                  1..20
                        mol_type = genomic DNA
                        organism = Homo sapiens
SEQUENCE: 57
gggcccccag tagaatccgc                                           20

SEQ ID NO: 58           moltype = DNA  length = 20
FEATURE                 Location/Qualifiers
source                  1..20
                        mol_type = genomic DNA
                        organism = Homo sapiens
SEQUENCE: 58
atccgcgtgc actttcaggc                                           20

SEQ ID NO: 59           moltype = DNA  length = 20
FEATURE                 Location/Qualifiers
source                  1..20
                        mol_type = genomic DNA
                        organism = Homo sapiens
SEQUENCE: 59
cgagcccgtg ggcaccttcc                                           20
```

| | | |
|---|---|---|
| SEQ ID NO: 60<br>FEATURE<br>source<br><br>SEQUENCE: 60<br>ccacagcagc agagcccga | moltype = DNA   length = 20<br>Location/Qualifiers<br>1..20<br>mol_type = genomic DNA<br>organism = Homo sapiens | <br><br><br><br><br>20 |
| SEQ ID NO: 61<br>FEATURE<br>source<br><br>SEQUENCE: 61<br>agccaggttc tcgcggccca | moltype = DNA   length = 20<br>Location/Qualifiers<br>1..20<br>mol_type = genomic DNA<br>organism = Homo sapiens | <br><br><br><br><br>20 |
| SEQ ID NO: 62<br>FEATURE<br>source<br><br>SEQUENCE: 62<br>aaagtgcacg cggatgctcg | moltype = DNA   length = 20<br>Location/Qualifiers<br>1..20<br>mol_type = genomic DNA<br>organism = Homo sapiens | <br><br><br><br><br>20 |
| SEQ ID NO: 63<br>FEATURE<br>source<br><br>SEQUENCE: 63<br>ctcttcctcc tcctcgcccg | moltype = DNA   length = 20<br>Location/Qualifiers<br>1..20<br>mol_type = genomic DNA<br>organism = Homo sapiens | <br><br><br><br><br>20 |
| SEQ ID NO: 64<br>FEATURE<br>source<br><br>SEQUENCE: 64<br>gcgtgcacgg ggcgcacgag | moltype = DNA   length = 20<br>Location/Qualifiers<br>1..20<br>mol_type = genomic DNA<br>organism = Homo sapiens | <br><br><br><br><br>20 |
| SEQ ID NO: 65<br>FEATURE<br>source<br><br>SEQUENCE: 65<br>aagtgcacgc ggatgctcgt | moltype = DNA   length = 20<br>Location/Qualifiers<br>1..20<br>mol_type = genomic DNA<br>organism = Homo sapiens | <br><br><br><br><br>20 |
| SEQ ID NO: 66<br>FEATURE<br>source<br><br>SEQUENCE: 66<br>cgtgcgcccc gtgcacgctc | moltype = DNA   length = 20<br>Location/Qualifiers<br>1..20<br>mol_type = genomic DNA<br>organism = Homo sapiens | <br><br><br><br><br>20 |
| SEQ ID NO: 67<br>FEATURE<br>source<br><br>SEQUENCE: 67<br>gcagcggccg cacgcggcgc | moltype = DNA   length = 20<br>Location/Qualifiers<br>1..20<br>mol_type = genomic DNA<br>organism = Homo sapiens | <br><br><br><br><br>20 |
| SEQ ID NO: 68<br>FEATURE<br>source<br><br>SEQUENCE: 68<br>ccttagcgtg aagatggcct | moltype = DNA   length = 20<br>Location/Qualifiers<br>1..20<br>mol_type = genomic DNA<br>organism = Homo sapiens | <br><br><br><br><br>20 |
| SEQ ID NO: 69<br>FEATURE<br>source<br><br>SEQUENCE: 69<br>caggttctcg cggcccacgg | moltype = DNA   length = 20<br>Location/Qualifiers<br>1..20<br>mol_type = genomic DNA<br>organism = Homo sapiens | <br><br><br><br><br>20 |

| | | |
|---|---|---|
| SEQ ID NO: 70<br>FEATURE<br>source | moltype = DNA   length = 20<br>Location/Qualifiers<br>1..20<br>mol_type = genomic DNA<br>organism = Homo sapiens | |
| SEQUENCE: 70<br>gcgcaccagg aaggtgccca | | 20 |
| SEQ ID NO: 71<br>FEATURE<br>source | moltype = DNA   length = 20<br>Location/Qualifiers<br>1..20<br>mol_type = genomic DNA<br>organism = Homo sapiens | |
| SEQUENCE: 71<br>gctgccggtc aaatctggaa | | 20 |
| SEQ ID NO: 72<br>FEATURE<br>source | moltype = DNA   length = 20<br>Location/Qualifiers<br>1..20<br>mol_type = genomic DNA<br>organism = Homo sapiens | |
| SEQUENCE: 72<br>cggcgtgcga acggaatgtg | | 20 |
| SEQ ID NO: 73<br>FEATURE<br>source | moltype = DNA   length = 20<br>Location/Qualifiers<br>1..20<br>mol_type = genomic DNA<br>organism = Homo sapiens | |
| SEQUENCE: 73<br>cagcagcaga gccccgacgg | | 20 |
| SEQ ID NO: 74<br>FEATURE<br>source | moltype = DNA   length = 20<br>Location/Qualifiers<br>1..20<br>mol_type = genomic DNA<br>organism = Homo sapiens | |
| SEQUENCE: 74<br>gggcgaaaaa gcagttccgc | | 20 |
| SEQ ID NO: 75<br>FEATURE<br>source | moltype = DNA   length = 20<br>Location/Qualifiers<br>1..20<br>mol_type = genomic DNA<br>organism = Homo sapiens | |
| SEQUENCE: 75<br>cgcacgcggc gctggcgcag | | 20 |
| SEQ ID NO: 76<br>FEATURE<br>source | moltype = DNA   length = 20<br>Location/Qualifiers<br>1..20<br>mol_type = genomic DNA<br>organism = Homo sapiens | |
| SEQUENCE: 76<br>ggatgcgagc caggttctcg | | 20 |
| SEQ ID NO: 77<br>FEATURE<br>source | moltype = DNA   length = 20<br>Location/Qualifiers<br>1..20<br>mol_type = genomic DNA<br>organism = Homo sapiens | |
| SEQUENCE: 77<br>tggcggcaca gctcctgcag | | 20 |
| SEQ ID NO: 78<br>FEATURE<br>source | moltype = DNA   length = 20<br>Location/Qualifiers<br>1..20<br>mol_type = genomic DNA<br>organism = Homo sapiens | |
| SEQUENCE: 78<br>gcgcccgcgg ccgtgccccg | | 20 |
| SEQ ID NO: 79<br>FEATURE<br>source | moltype = DNA   length = 20<br>Location/Qualifiers<br>1..20<br>mol_type = genomic DNA<br>organism = Homo sapiens | |
| SEQUENCE: 79 | | |

```
ggcgccgcgc cgcatgctgg                                               20

SEQ ID NO: 80         moltype = DNA   length = 20
FEATURE               Location/Qualifiers
source                1..20
                      mol_type = genomic DNA
                      organism = Homo sapiens
SEQUENCE: 80
cggtggccac gatgcgctgg                                               20

SEQ ID NO: 81         moltype = DNA   length = 20
FEATURE               Location/Qualifiers
source                1..20
                      mol_type = genomic DNA
                      organism = Homo sapiens
SEQUENCE: 81
tgctgtggag actgcattgt                                               20

SEQ ID NO: 82         moltype = DNA   length = 20
FEATURE               Location/Qualifiers
source                1..20
                      mol_type = genomic DNA
                      organism = Homo sapiens
SEQUENCE: 82
taggatggta gcacacaacc                                               20

SEQ ID NO: 83         moltype = DNA   length = 20
FEATURE               Location/Qualifiers
source                1..20
                      mol_type = genomic DNA
                      organism = Homo sapiens
SEQUENCE: 83
gcggccgtgc cccgcggtcc                                               20

SEQ ID NO: 84         moltype = DNA   length = 20
FEATURE               Location/Qualifiers
source                1..20
                      mol_type = genomic DNA
                      organism = Homo sapiens
SEQUENCE: 84
gagcatccgc gtgcactttc                                               20

SEQ ID NO: 85         moltype = DNA   length = 20
FEATURE               Location/Qualifiers
source                1..20
                      mol_type = genomic DNA
                      organism = Homo sapiens
SEQUENCE: 85
cgctgccggt caaatctgga                                               20

SEQ ID NO: 86         moltype = DNA   length = 20
FEATURE               Location/Qualifiers
source                1..20
                      mol_type = genomic DNA
                      organism = Homo sapiens
SEQUENCE: 86
cagcgcatcg tggccaccgt                                               20

SEQ ID NO: 87         moltype = DNA   length = 20
FEATURE               Location/Qualifiers
source                1..20
                      mol_type = genomic DNA
                      organism = Homo sapiens
SEQUENCE: 87
gcggatgctc gtgggtcccg                                               20

SEQ ID NO: 88         moltype = DNA   length = 20
FEATURE               Location/Qualifiers
source                1..20
                      mol_type = genomic DNA
                      organism = Homo sapiens
SEQUENCE: 88
cggcgccgcg ccgcatgctg                                               20

SEQ ID NO: 89         moltype = DNA   length = 20
FEATURE               Location/Qualifiers
source                1..20
                      mol_type = genomic DNA
                      organism = Homo sapiens
```

```
SEQUENCE: 89
cggtcaaatc tggaagggga                                                    20

SEQ ID NO: 90           moltype = DNA   length = 20
FEATURE                 Location/Qualifiers
source                  1..20
                        mol_type = genomic DNA
                        organism = Homo sapiens
SEQUENCE: 90
aggaaggttc tggccgccgt                                                    20

SEQ ID NO: 91           moltype = DNA   length = 20
FEATURE                 Location/Qualifiers
source                  1..20
                        mol_type = genomic DNA
                        organism = Homo sapiens
SEQUENCE: 91
ccacggtggc cacgatgcgc                                                    20

SEQ ID NO: 92           moltype = DNA   length = 20
FEATURE                 Location/Qualifiers
source                  1..20
                        mol_type = genomic DNA
                        organism = Homo sapiens
SEQUENCE: 92
cgctgcgcca gcgccgcgtg                                                    20

SEQ ID NO: 93           moltype = DNA   length = 20
FEATURE                 Location/Qualifiers
source                  1..20
                        mol_type = genomic DNA
                        organism = Homo sapiens
SEQUENCE: 93
aggagctcag gtagtcgcgg                                                    20

SEQ ID NO: 94           moltype = DNA   length = 20
FEATURE                 Location/Qualifiers
source                  1..20
                        mol_type = genomic DNA
                        organism = Homo sapiens
SEQUENCE: 94
gcagcggggc ccccagcatg                                                    20

SEQ ID NO: 95           moltype = DNA   length = 20
FEATURE                 Location/Qualifiers
source                  1..20
                        mol_type = genomic DNA
                        organism = Homo sapiens
SEQUENCE: 95
ggaaggagct caggtagtcg                                                    20

SEQ ID NO: 96           moltype = DNA   length = 20
FEATURE                 Location/Qualifiers
source                  1..20
                        mol_type = genomic DNA
                        organism = Homo sapiens
SEQUENCE: 96
tcgcggagga cggggttgag                                                    20

SEQ ID NO: 97           moltype = DNA   length = 20
FEATURE                 Location/Qualifiers
source                  1..20
                        mol_type = genomic DNA
                        organism = Homo sapiens
SEQUENCE: 97
cgactgcctc ttcgagctgc                                                    20

SEQ ID NO: 98           moltype = DNA   length = 20
FEATURE                 Location/Qualifiers
source                  1..20
                        mol_type = genomic DNA
                        organism = Homo sapiens
SEQUENCE: 98
gcgccgcgtg cggccgctgc                                                    20

SEQ ID NO: 99           moltype = DNA   length = 20
FEATURE                 Location/Qualifiers
source                  1..20
                        mol_type = genomic DNA
```

```
                                       organism = Homo sapiens
SEQUENCE: 99
caccgtgggc cgcgagaacc                                                           20

SEQ ID NO: 100           moltype = DNA  length = 20
FEATURE                  Location/Qualifiers
source                   1..20
                         mol_type = genomic DNA
                         organism = Homo sapiens
SEQUENCE: 100
gtgccccgcg gtcccggccc                                                           20

SEQ ID NO: 101           moltype = DNA  length = 20
FEATURE                  Location/Qualifiers
source                   1..20
                         mol_type = genomic DNA
                         organism = Homo sapiens
SEQUENCE: 101
ctgccggtca aatctggaag                                                           20

SEQ ID NO: 102           moltype = DNA  length = 20
FEATURE                  Location/Qualifiers
source                   1..20
                         mol_type = genomic DNA
                         organism = Homo sapiens
SEQUENCE: 102
cttccccttc cagatttgac                                                           20

SEQ ID NO: 103           moltype = DNA  length = 20
FEATURE                  Location/Qualifiers
source                   1..20
                         mol_type = genomic DNA
                         organism = Homo sapiens
SEQUENCE: 103
ctcaggtagt cgcggaggac                                                           20

SEQ ID NO: 104           moltype = DNA  length = 20
FEATURE                  Location/Qualifiers
source                   1..20
                         mol_type = genomic DNA
                         organism = Homo sapiens
SEQUENCE: 104
cgggcgctgc cggtcaaatc                                                           20

SEQ ID NO: 105           moltype = DNA  length = 20
FEATURE                  Location/Qualifiers
source                   1..20
                         mol_type = genomic DNA
                         organism = Homo sapiens
SEQUENCE: 105
ggaaggttct ggccgccgtc                                                           20

SEQ ID NO: 106           moltype = DNA  length = 20
FEATURE                  Location/Qualifiers
source                   1..20
                         mol_type = genomic DNA
                         organism = Homo sapiens
SEQUENCE: 106
gctcaggtag tcgcggagga                                                           20

SEQ ID NO: 107           moltype = DNA  length = 20
FEATURE                  Location/Qualifiers
source                   1..20
                         mol_type = genomic DNA
                         organism = Homo sapiens
SEQUENCE: 107
gcggaagtgc gtgtcgccgg                                                           20

SEQ ID NO: 108           moltype = DNA  length = 20
FEATURE                  Location/Qualifiers
source                   1..20
                         mol_type = genomic DNA
                         organism = Homo sapiens
SEQUENCE: 108
ggaccgcggg gcacggccgc                                                           20

SEQ ID NO: 109           moltype = DNA  length = 20
FEATURE                  Location/Qualifiers
source                   1..20
```

```
                        mol_type = genomic DNA
                        organism = Homo sapiens
SEQUENCE: 109
gggaccgcgg ggcacggccg                                                   20

SEQ ID NO: 110          moltype = DNA   length = 20
FEATURE                 Location/Qualifiers
source                  1..20
                        mol_type = genomic DNA
                        organism = Homo sapiens
SEQUENCE: 110
gcgcgtgatg cgccggtaat                                                   20

SEQ ID NO: 111          moltype = DNA   length = 20
FEATURE                 Location/Qualifiers
source                  1..20
                        mol_type = genomic DNA
                        organism = Homo sapiens
SEQUENCE: 111
tcaggtagtc gcggaggacg                                                   20

SEQ ID NO: 112          moltype = DNA   length = 20
FEATURE                 Location/Qualifiers
source                  1..20
                        mol_type = genomic DNA
                        organism = Homo sapiens
SEQUENCE: 112
tgcggaagtg cgtgtcgccg                                                   20

SEQ ID NO: 113          moltype = DNA   length = 20
FEATURE                 Location/Qualifiers
source                  1..20
                        mol_type = genomic DNA
                        organism = Homo sapiens
SEQUENCE: 113
ggggccggga ccgcggggca                                                   20

SEQ ID NO: 114          moltype = DNA   length = 20
FEATURE                 Location/Qualifiers
source                  1..20
                        mol_type = genomic DNA
                        organism = Homo sapiens
SEQUENCE: 114
ccgtcgggc tctgctgctg                                                    20

SEQ ID NO: 115          moltype = DNA   length = 20
FEATURE                 Location/Qualifiers
source                  1..20
                        mol_type = genomic DNA
                        organism = Homo sapiens
SEQUENCE: 115
gaaggttctg gccgccgtcg                                                   20

SEQ ID NO: 116          moltype = DNA   length = 20
FEATURE                 Location/Qualifiers
source                  1..20
                        mol_type = genomic DNA
                        organism = Homo sapiens
SEQUENCE: 116
gtgtgctacc atcctacaga                                                   20

SEQ ID NO: 117          moltype = DNA   length = 20
FEATURE                 Location/Qualifiers
source                  1..20
                        mol_type = genomic DNA
                        organism = Homo sapiens
SEQUENCE: 117
gtcgcggagg acggggttga                                                   20

SEQ ID NO: 118          moltype = DNA   length = 20
FEATURE                 Location/Qualifiers
source                  1..20
                        mol_type = genomic DNA
                        organism = Homo sapiens
SEQUENCE: 118
cgctggcgcg cgtgatgcgc                                                   20

SEQ ID NO: 119          moltype = DNA   length = 20
FEATURE                 Location/Qualifiers
```

```
source                          1..20
                                mol_type = genomic DNA
                                organism = Homo sapiens
SEQUENCE: 119
gcgtgcacgg cgggcgctgc                                                    20

SEQ ID NO: 120                  moltype = DNA   length = 20
FEATURE                         Location/Qualifiers
source                          1..20
                                mol_type = genomic DNA
                                organism = Homo sapiens
SEQUENCE: 120
tctggaaggg gaaggagctc                                                    20

SEQ ID NO: 121                  moltype = DNA   length = 20
FEATURE                         Location/Qualifiers
source                          1..20
                                mol_type = genomic DNA
                                organism = Homo sapiens
SEQUENCE: 121
gtgcgtgtcg ccgggggccg                                                    20

SEQ ID NO: 122                  moltype = DNA   length = 20
FEATURE                         Location/Qualifiers
source                          1..20
                                mol_type = genomic DNA
                                organism = Homo sapiens
SEQUENCE: 122
gggcacggcc gcgggcgcgc                                                    20

SEQ ID NO: 123                  moltype = DNA   length = 20
FEATURE                         Location/Qualifiers
source                          1..20
                                mol_type = genomic DNA
                                organism = Homo sapiens
SEQUENCE: 123
gttaatgctg cgtgcacggc                                                    20

SEQ ID NO: 124                  moltype = DNA   length = 20
FEATURE                         Location/Qualifiers
source                          1..20
                                mol_type = genomic DNA
                                organism = Homo sapiens
SEQUENCE: 124
gcacggccgc gggcgcgcgg                                                    20

SEQ ID NO: 125                  moltype = DNA   length = 20
FEATURE                         Location/Qualifiers
source                          1..20
                                mol_type = genomic DNA
                                organism = Homo sapiens
SEQUENCE: 125
ggggcacggc cgcgggcgcg                                                    20

SEQ ID NO: 126                  moltype = DNA   length = 20
FEATURE                         Location/Qualifiers
source                          1..20
                                mol_type = genomic DNA
                                organism = Homo sapiens
SEQUENCE: 126
gtgcggaagt gcgtgtcgcc                                                    20

SEQ ID NO: 127                  moltype = DNA   length = 20
FEATURE                         Location/Qualifiers
source                          1..20
                                mol_type = genomic DNA
                                organism = Homo sapiens
SEQUENCE: 127
gaggaagagg aggaaggttc                                                    20

SEQ ID NO: 128                  moltype = DNA   length = 20
FEATURE                         Location/Qualifiers
source                          1..20
                                mol_type = genomic DNA
                                organism = Homo sapiens
SEQUENCE: 128
ggctggcccc ttctgtagga                                                    20

SEQ ID NO: 129                  moltype = DNA   length = 20
```

```
FEATURE            Location/Qualifiers
source             1..20
                   mol_type = genomic DNA
                   organism = Homo sapiens
SEQUENCE: 129
ggggccgggg ccgggaccgc                                               20

SEQ ID NO: 130     moltype = DNA   length = 20
FEATURE            Location/Qualifiers
source             1..20
                   mol_type = genomic DNA
                   organism = Homo sapiens
SEQUENCE: 130
cgcggaggac ggggttgagg                                               20

SEQ ID NO: 131     moltype = DNA   length = 20
FEATURE            Location/Qualifiers
source             1..20
                   mol_type = genomic DNA
                   organism = Homo sapiens
SEQUENCE: 131
tttcgccctt agcgtgaaga                                               20

SEQ ID NO: 132     moltype = DNA   length = 20
FEATURE            Location/Qualifiers
source             1..20
                   mol_type = genomic DNA
                   organism = Homo sapiens
SEQUENCE: 132
ggcacggccg cgggcgcgcg                                               20

SEQ ID NO: 133     moltype = DNA   length = 20
FEATURE            Location/Qualifiers
source             1..20
                   mol_type = genomic DNA
                   organism = Homo sapiens
SEQUENCE: 133
agtcgcggag gacggggttg                                               20

SEQ ID NO: 134     moltype = DNA   length = 20
FEATURE            Location/Qualifiers
source             1..20
                   mol_type = genomic DNA
                   organism = Homo sapiens
SEQUENCE: 134
gggccggggc cgggaccgcg                                               20

SEQ ID NO: 135     moltype = DNA   length = 20
FEATURE            Location/Qualifiers
source             1..20
                   mol_type = genomic DNA
                   organism = Homo sapiens
SEQUENCE: 135
aagtgcgtgt cgccgggggc                                               20

SEQ ID NO: 136     moltype = DNA   length = 20
FEATURE            Location/Qualifiers
source             1..20
                   mol_type = genomic DNA
                   organism = Homo sapiens
SEQUENCE: 136
ctccggctgg cccttctgt                                                20

SEQ ID NO: 137     moltype = DNA   length = 20
FEATURE            Location/Qualifiers
source             1..20
                   mol_type = genomic DNA
                   organism = Homo sapiens
SEQUENCE: 137
ggcggcgccg cgccgcatgc                                               20

SEQ ID NO: 138     moltype = DNA   length = 20
FEATURE            Location/Qualifiers
source             1..20
                   mol_type = genomic DNA
                   organism = Homo sapiens
SEQUENCE: 138
agtgcgtgtc gccgggggcc                                               20
```

```
SEQ ID NO: 139          moltype = DNA  length = 20
FEATURE                 Location/Qualifiers
source                  1..20
                        mol_type = genomic DNA
                        organism = Homo sapiens
SEQUENCE: 139
tgtgcggaag tgcgtgtcgc                                                    20

SEQ ID NO: 140          moltype = DNA  length = 20
FEATURE                 Location/Qualifiers
source                  1..20
                        mol_type = genomic DNA
                        organism = Homo sapiens
SEQUENCE: 140
gtgtcgccgg gggccggggc                                                    20

SEQ ID NO: 141          moltype = DNA  length = 20
FEATURE                 Location/Qualifiers
source                  1..20
                        mol_type = genomic DNA
                        organism = Homo sapiens
SEQUENCE: 141
tgtcgccggg ggccggggcc                                                    20

SEQ ID NO: 142          moltype = DNA  length = 20
FEATURE                 Location/Qualifiers
source                  1..20
                        mol_type = genomic DNA
                        organism = Homo sapiens
SEQUENCE: 142
gcggtcccgg ccccggcccc                                                    20

SEQ ID NO: 143          moltype = DNA  length = 20
FEATURE                 Location/Qualifiers
source                  1..20
                        mol_type = genomic DNA
                        organism = Homo sapiens
SEQUENCE: 143
cgcgggggcc gcgggcgagg                                                    20

SEQ ID NO: 144          moltype = DNA  length = 20
FEATURE                 Location/Qualifiers
source                  1..20
                        mol_type = genomic DNA
                        organism = Homo sapiens
SEQUENCE: 144
cgcgggcgag gaggaggaag                                                    20

SEQ ID NO: 145          moltype = DNA  length = 20
FEATURE                 Location/Qualifiers
source                  1..20
                        mol_type = genomic DNA
                        organism = Homo sapiens
SEQUENCE: 145
gggcgaggag gaggaagagg                                                    20

SEQ ID NO: 146          moltype = DNA  length = 20
FEATURE                 Location/Qualifiers
source                  1..20
                        mol_type = genomic DNA
                        organism = Homo sapiens
SEQUENCE: 146
cgagcgggag ttcgaagagt                                                    20

SEQ ID NO: 147          moltype = DNA  length = 20
FEATURE                 Location/Qualifiers
source                  1..20
                        mol_type = genomic DNA
                        organism = Homo sapiens
SEQUENCE: 147
gcccaatgcc tgcactacag                                                    20

SEQ ID NO: 148          moltype = DNA  length = 20
FEATURE                 Location/Qualifiers
source                  1..20
                        mol_type = genomic DNA
                        organism = Homo sapiens
SEQUENCE: 148
ggaaacttgg ccactctatg                                                    20
```

```
SEQ ID NO: 149          moltype = DNA   length = 20
FEATURE                 Location/Qualifiers
source                  1..20
                        mol_type = genomic DNA
                        organism = Mus musculus
SEQUENCE: 149
aatctggcca ggtggtataa                                                 20

SEQ ID NO: 150          moltype = DNA   length = 20
FEATURE                 Location/Qualifiers
source                  1..20
                        mol_type = genomic DNA
                        organism = Mus musculus
SEQUENCE: 150
aatatgagaa agtatcgaat                                                 20

SEQ ID NO: 151          moltype = DNA   length = 20
FEATURE                 Location/Qualifiers
source                  1..20
                        mol_type = genomic DNA
                        organism = Mus musculus
SEQUENCE: 151
atcactgcag gtccatggtc                                                 20

SEQ ID NO: 152          moltype = DNA   length = 20
FEATURE                 Location/Qualifiers
source                  1..20
                        mol_type = genomic DNA
                        organism = Mus musculus
SEQUENCE: 152
atgtgcacag tactggccaa                                                 20

SEQ ID NO: 153          moltype = DNA   length = 20
FEATURE                 Location/Qualifiers
source                  1..20
                        mol_type = genomic DNA
                        organism = Mus musculus
SEQUENCE: 153
ggcagcatgt gttcggaagt                                                 20

SEQ ID NO: 154          moltype = DNA   length = 20
FEATURE                 Location/Qualifiers
source                  1..20
                        mol_type = genomic DNA
                        organism = Mus musculus
SEQUENCE: 154
aagaagttta gaaatgaagc                                                 20

SEQ ID NO: 155          moltype = DNA   length = 20
FEATURE                 Location/Qualifiers
source                  1..20
                        mol_type = genomic DNA
                        organism = Mus musculus
SEQUENCE: 155
gccacaccat gagccagaaa                                                 20

SEQ ID NO: 156          moltype = DNA   length = 20
FEATURE                 Location/Qualifiers
source                  1..20
                        mol_type = genomic DNA
                        organism = Mus musculus
SEQUENCE: 156
cctttcttgc agatggaaaa                                                 20

SEQ ID NO: 157          moltype = DNA   length = 20
FEATURE                 Location/Qualifiers
source                  1..20
                        mol_type = genomic DNA
                        organism = Mus musculus
SEQUENCE: 157
gtactttgct ccttctatta                                                 20

SEQ ID NO: 158          moltype = DNA   length = 20
FEATURE                 Location/Qualifiers
source                  1..20
                        mol_type = genomic DNA
                        organism = Mus musculus
SEQUENCE: 158
```
agaaatgaag ctggtgactc                                                  20

SEQ ID NO: 159          moltype = DNA   length = 20
FEATURE                 Location/Qualifiers
source                  1..20
                        mol_type = genomic DNA
                        organism = Mus musculus
SEQUENCE: 159
gtttagcatg acaactgctt                                                  20

SEQ ID NO: 160          moltype = DNA   length = 20
FEATURE                 Location/Qualifiers
source                  1..20
                        mol_type = genomic DNA
                        organism = Mus musculus
SEQUENCE: 160
gcccgatgcc cgcactgcaa                                                  20

SEQ ID NO: 161          moltype = DNA   length = 20
FEATURE                 Location/Qualifiers
source                  1..20
                        mol_type = genomic DNA
                        organism = Mus musculus
SEQUENCE: 161
tgacagagaa atggtgttta                                                  20

SEQ ID NO: 162          moltype = DNA   length = 20
FEATURE                 Location/Qualifiers
source                  1..20
                        mol_type = genomic DNA
                        organism = Homo sapiens
SEQUENCE: 162
ccatgcccac caccatcgag                                                  20

SEQ ID NO: 163          moltype = DNA   length = 20
FEATURE                 Location/Qualifiers
source                  1..20
                        mol_type = genomic DNA
                        organism = Homo sapiens
SEQUENCE: 163
tctacggaaa cgtattcgag                                                  20

SEQ ID NO: 164          moltype = DNA   length = 20
FEATURE                 Location/Qualifiers
source                  1..20
                        mol_type = genomic DNA
                        organism = Homo sapiens
SEQUENCE: 164
tttagtatat tgagaacttg                                                  20

SEQ ID NO: 165          moltype = DNA   length = 20
FEATURE                 Location/Qualifiers
source                  1..20
                        mol_type = genomic DNA
                        organism = Homo sapiens
SEQUENCE: 165
gcactacagt ggatcaccgc                                                  20

SEQ ID NO: 166          moltype = DNA   length = 20
FEATURE                 Location/Qualifiers
source                  1..20
                        mol_type = genomic DNA
                        organism = Homo sapiens
SEQUENCE: 166
tgtcatgctg aaccgcattg                                                  20

SEQ ID NO: 167          moltype = DNA   length = 20
FEATURE                 Location/Qualifiers
source                  1..20
                        mol_type = genomic DNA
                        organism = Homo sapiens
SEQUENCE: 167
ggaaacttgg ccactctatg                                                  20

SEQ ID NO: 168          moltype = DNA   length = 20
FEATURE                 Location/Qualifiers
source                  1..20
                        mol_type = genomic DNA
                        organism = Homo sapiens

| | | |
|---|---|---|
| SEQUENCE: 168 gtatttgaaa ttattaatgc | | 20 |
| SEQ ID NO: 169 FEATURE source | moltype = DNA length = 20 Location/Qualifiers 1..20 mol_type = genomic DNA organism = Homo sapiens | |
| SEQUENCE: 169 cagtttagtt gacatagaag | | 20 |
| SEQ ID NO: 170 FEATURE source | moltype = DNA length = 20 Location/Qualifiers 1..20 mol_type = genomic DNA organism = Homo sapiens | |
| SEQUENCE: 170 gggtctgaat aagacccatt | | 20 |
| SEQ ID NO: 171 FEATURE source | moltype = DNA length = 20 Location/Qualifiers 1..20 mol_type = genomic DNA organism = Homo sapiens | |
| SEQUENCE: 171 ccatgactat cctcatagag | | 20 |
| SEQ ID NO: 172 FEATURE source | moltype = DNA length = 20 Location/Qualifiers 1..20 mol_type = genomic DNA organism = Homo sapiens | |
| SEQUENCE: 172 ccatgactat cctcatagag | | 20 |
| SEQ ID NO: 173 FEATURE source | moltype = DNA length = 20 Location/Qualifiers 1..20 mol_type = genomic DNA organism = Homo sapiens | |
| SEQUENCE: 173 ctcttcgaac tcccgctcga | | 20 |
| SEQ ID NO: 174 FEATURE source | moltype = DNA length = 20 Location/Qualifiers 1..20 mol_type = genomic DNA organism = Homo sapiens | |
| SEQUENCE: 174 gaaccctgac catgggcctg | | 20 |
| SEQ ID NO: 175 FEATURE source | moltype = DNA length = 20 Location/Qualifiers 1..20 mol_type = genomic DNA organism = Homo sapiens | |
| SEQUENCE: 175 gctccttgaa ccctgaccat | | 20 |
| SEQ ID NO: 176 FEATURE source | moltype = DNA length = 20 Location/Qualifiers 1..20 mol_type = genomic DNA organism = Homo sapiens | |
| SEQUENCE: 176 agttggatac tcagcgtcgc | | 20 |
| SEQ ID NO: 177 FEATURE source | moltype = DNA length = 20 Location/Qualifiers 1..20 mol_type = genomic DNA organism = Homo sapiens | |
| SEQUENCE: 177 ccgctcgatg gtggtgggca | | 20 |
| SEQ ID NO: 178 FEATURE source | moltype = DNA length = 20 Location/Qualifiers 1..20 mol_type = genomic DNA | |

```
                              organism = Homo sapiens
SEQUENCE: 178
cagaaatggc agcatgtgtt                                                    20

SEQ ID NO: 179          moltype = DNA  length = 20
FEATURE                 Location/Qualifiers
source                  1..20
                        mol_type = genomic DNA
                        organism = Homo sapiens
SEQUENCE: 179
gcactacagt ggatcaccgc                                                    20

SEQ ID NO: 180          moltype = DNA  length = 20
FEATURE                 Location/Qualifiers
source                  1..20
                        mol_type = genomic DNA
                        organism = Homo sapiens
SEQUENCE: 180
ggtagacact tgtcttgttt                                                    20

SEQ ID NO: 181          moltype = DNA  length = 20
FEATURE                 Location/Qualifiers
source                  1..20
                        mol_type = genomic DNA
                        organism = Homo sapiens
SEQUENCE: 181
tggcagcatg tgttaggaag                                                    20

SEQ ID NO: 182          moltype = DNA  length = 20
FEATURE                 Location/Qualifiers
source                  1..20
                        mol_type = genomic DNA
                        organism = Homo sapiens
SEQUENCE: 182
aggcccatgg tcagggttca                                                    20

SEQ ID NO: 183          moltype = DNA  length = 20
FEATURE                 Location/Qualifiers
source                  1..20
                        mol_type = genomic DNA
                        organism = Homo sapiens
SEQUENCE: 183
gttcagcatg acaactgctt                                                    20

SEQ ID NO: 184          moltype = DNA  length = 20
FEATURE                 Location/Qualifiers
source                  1..20
                        mol_type = genomic DNA
                        organism = Homo sapiens
SEQUENCE: 184
caatggagga gaacagtgag                                                    20

SEQ ID NO: 185          moltype = DNA  length = 20
FEATURE                 Location/Qualifiers
source                  1..20
                        mol_type = genomic DNA
                        organism = Homo sapiens
SEQUENCE: 185
ctcttctatg tcaactaaac                                                    20

SEQ ID NO: 186          moltype = DNA  length = 20
FEATURE                 Location/Qualifiers
source                  1..20
                        mol_type = genomic DNA
                        organism = Homo sapiens
SEQUENCE: 186
agtggatcac cgcaggccca                                                    20

SEQ ID NO: 187          moltype = DNA  length = 20
FEATURE                 Location/Qualifiers
source                  1..20
                        mol_type = genomic DNA
                        organism = Homo sapiens
SEQUENCE: 187
ctgacaggtg accgatgtac                                                    20

SEQ ID NO: 188          moltype = DNA  length = 20
FEATURE                 Location/Qualifiers
source                  1..20
```

```
                            mol_type = genomic DNA
                            organism = Homo sapiens
SEQUENCE: 188
aactcccgct cgatggtggt                                              20

SEQ ID NO: 189              moltype = DNA  length = 20
FEATURE                     Location/Qualifiers
source                      1..20
                            mol_type = genomic DNA
                            organism = Homo sapiens
SEQUENCE: 189
gtctccctga tccatccagt                                              20

SEQ ID NO: 190              moltype = DNA  length = 20
FEATURE                     Location/Qualifiers
source                      1..20
                            mol_type = genomic DNA
                            organism = Homo sapiens
SEQUENCE: 190
tagaggaaag tcctgtacat                                              20

SEQ ID NO: 191              moltype = DNA  length = 20
FEATURE                     Location/Qualifiers
source                      1..20
                            mol_type = genomic DNA
                            organism = Homo sapiens
SEQUENCE: 191
atgtatggaa aggatggtaa                                              20

SEQ ID NO: 192              moltype = DNA  length = 20
FEATURE                     Location/Qualifiers
source                      1..20
                            mol_type = genomic DNA
                            organism = Homo sapiens
SEQUENCE: 192
tcaccgcagg cccatggtca                                              20

SEQ ID NO: 193              moltype = DNA  length = 20
FEATURE                     Location/Qualifiers
source                      1..20
                            mol_type = genomic DNA
                            organism = Homo sapiens
SEQUENCE: 193
cagtttagtt gacatagaag                                              20

SEQ ID NO: 194              moltype = DNA  length = 20
FEATURE                     Location/Qualifiers
source                      1..20
                            mol_type = genomic DNA
                            organism = Homo sapiens
SEQUENCE: 194
ccatgcccac caccatcgag                                              20

SEQ ID NO: 195              moltype = DNA  length = 20
FEATURE                     Location/Qualifiers
source                      1..20
                            mol_type = genomic DNA
                            organism = Homo sapiens
SEQUENCE: 195
gccaaaccat aagccagaaa                                              20

SEQ ID NO: 196              moltype = DNA  length = 20
FEATURE                     Location/Qualifiers
source                      1..20
                            mol_type = genomic DNA
                            organism = Homo sapiens
SEQUENCE: 196
ccgattcttt ctccacaatg                                              20

SEQ ID NO: 197              moltype = DNA  length = 20
FEATURE                     Location/Qualifiers
source                      1..20
                            mol_type = genomic DNA
                            organism = Homo sapiens
SEQUENCE: 197
ttcgaactcc cgctcgatgg                                              20

SEQ ID NO: 198              moltype = DNA  length = 20
FEATURE                     Location/Qualifiers
```

```
source                     1..20
                           mol_type = genomic DNA
                           organism = Homo sapiens
SEQUENCE: 198
agtgcaggca ttgggcgctc                                                    20

SEQ ID NO: 199             moltype = DNA   length = 20
FEATURE                    Location/Qualifiers
source                     1..20
                           mol_type = genomic DNA
                           organism = Homo sapiens
SEQUENCE: 199
atccactgta gtgcaggcat                                                    20

SEQ ID NO: 200             moltype = DNA   length = 20
FEATURE                    Location/Qualifiers
source                     1..20
                           mol_type = genomic DNA
                           organism = Homo sapiens
SEQUENCE: 200
cactctatga ggatagtcat                                                    20

SEQ ID NO: 201             moltype = DNA   length = 20
FEATURE                    Location/Qualifiers
source                     1..20
                           mol_type = genomic DNA
                           organism = Homo sapiens
SEQUENCE: 201
ccactctatg aggatagtca                                                    20

SEQ ID NO: 202             moltype = DNA   length = 20
FEATURE                    Location/Qualifiers
source                     1..20
                           mol_type = genomic DNA
                           organism = Homo sapiens
SEQUENCE: 202
tccactgtag tgcaggcatt                                                    20

SEQ ID NO: 203             moltype = DNA   length = 20
FEATURE                    Location/Qualifiers
source                     1..20
                           mol_type = genomic DNA
                           organism = Homo sapiens
SEQUENCE: 203
aagttctttc catcgtttct                                                    20

SEQ ID NO: 204             moltype = DNA   length = 20
FEATURE                    Location/Qualifiers
source                     1..20
                           mol_type = genomic DNA
                           organism = Homo sapiens
SEQUENCE: 204
tcgctggcag ccgctgtact                                                    20

SEQ ID NO: 205             moltype = DNA   length = 20
FEATURE                    Location/Qualifiers
source                     1..20
                           mol_type = genomic DNA
                           organism = Homo sapiens
SEQUENCE: 205
gaactcccgc tcgatggtgg                                                    20

SEQ ID NO: 206             moltype = DNA   length = 20
FEATURE                    Location/Qualifiers
source                     1..20
                           mol_type = genomic DNA
                           organism = Homo sapiens
SEQUENCE: 206
aggatggtaa aggcaccaac                                                    20

SEQ ID NO: 207             moltype = DNA   length = 20
FEATURE                    Location/Qualifiers
source                     1..20
                           mol_type = genomic DNA
                           organism = Homo sapiens
SEQUENCE: 207
aaagggagat tctagtatac                                                    20

SEQ ID NO: 208             moltype = DNA   length = 20
```

```
FEATURE                 Location/Qualifiers
source                  1..20
                        mol_type = genomic DNA
                        organism = Homo sapiens
SEQUENCE: 208
agaatttagg atgtatggaa                                                          20

SEQ ID NO: 209          moltype = DNA   length = 20
FEATURE                 Location/Qualifiers
source                  1..20
                        mol_type = genomic DNA
                        organism = Homo sapiens
SEQUENCE: 209
gggtctgaat aagacccatt                                                          20

SEQ ID NO: 210          moltype = DNA   length = 20
FEATURE                 Location/Qualifiers
source                  1..20
                        mol_type = genomic DNA
                        organism = Homo sapiens
SEQUENCE: 210
ggcaccaact ggatggatca                                                          20

SEQ ID NO: 211          moltype = DNA   length = 20
FEATURE                 Location/Qualifiers
source                  1..20
                        mol_type = genomic DNA
                        organism = Homo sapiens
SEQUENCE: 211
ctctaaaatg caagatacaa                                                          20

SEQ ID NO: 212          moltype = DNA   length = 20
FEATURE                 Location/Qualifiers
source                  1..20
                        mol_type = genomic DNA
                        organism = Homo sapiens
SEQUENCE: 212
gtatttgaaa ttattaatgc                                                          20

SEQ ID NO: 213          moltype = DNA   length = 20
FEATURE                 Location/Qualifiers
source                  1..20
                        mol_type = genomic DNA
                        organism = Homo sapiens
SEQUENCE: 213
cctttcttgc agatggaaaa                                                          20

SEQ ID NO: 214          moltype = DNA   length = 20
FEATURE                 Location/Qualifiers
source                  1..20
                        mol_type = genomic DNA
                        organism = Homo sapiens
SEQUENCE: 214
ctgcaccttc tgagctgtgg                                                          20

SEQ ID NO: 215          moltype = DNA   length = 20
FEATURE                 Location/Qualifiers
source                  1..20
                        mol_type = genomic DNA
                        organism = Homo sapiens
SEQUENCE: 215
atgctgccat ttctggctta                                                          20

SEQ ID NO: 216          moltype = DNA   length = 20
FEATURE                 Location/Qualifiers
source                  1..20
                        mol_type = genomic DNA
                        organism = Homo sapiens
SEQUENCE: 216
tttctttaaa cagcatctct                                                          20

SEQ ID NO: 217          moltype = DNA   length = 20
FEATURE                 Location/Qualifiers
source                  1..20
                        mol_type = genomic DNA
                        organism = Homo sapiens
SEQUENCE: 217
agacatggaa tgcagaatgc                                                          20
```

```
SEQ ID NO: 218          moltype = DNA   length = 20
FEATURE                 Location/Qualifiers
source                  1..20
                        mol_type = genomic DNA
                        organism = Homo sapiens
SEQUENCE: 218
aggcaccaac tggatggatc                                                    20

SEQ ID NO: 219          moltype = DNA   length = 20
FEATURE                 Location/Qualifiers
source                  1..20
                        mol_type = genomic DNA
                        organism = Homo sapiens
SEQUENCE: 219
taatgactga aaaatacaat                                                    20

SEQ ID NO: 220          moltype = DNA   length = 20
FEATURE                 Location/Qualifiers
source                  1..20
                        mol_type = genomic DNA
                        organism = Homo sapiens
SEQUENCE: 220
gaatgcagaa tgcaggaaat                                                    20

SEQ ID NO: 221          moltype = DNA   length = 20
FEATURE                 Location/Qualifiers
source                  1..20
                        mol_type = genomic DNA
                        organism = Homo sapiens
SEQUENCE: 221
tttaggatgt atggaaagga                                                    20

SEQ ID NO: 222          moltype = DNA   length = 20
FEATURE                 Location/Qualifiers
source                  1..20
                        mol_type = genomic DNA
                        organism = Homo sapiens
SEQUENCE: 222
ctaacacatg ctgccatttc                                                    20

SEQ ID NO: 223          moltype = DNA   length = 20
FEATURE                 Location/Qualifiers
source                  1..20
                        mol_type = genomic DNA
                        organism = Homo sapiens
SEQUENCE: 223
tcatacatgg ctataataga                                                    20

SEQ ID NO: 224          moltype = DNA   length = 20
FEATURE                 Location/Qualifiers
source                  1..20
                        mol_type = genomic DNA
                        organism = Homo sapiens
SEQUENCE: 224
acgatggaaa gaactttcta                                                    20

SEQ ID NO: 225          moltype = DNA   length = 20
FEATURE                 Location/Qualifiers
source                  1..20
                        mol_type = genomic DNA
                        organism = Homo sapiens
SEQUENCE: 225
acgtattcga gaggacagaa                                                    20

SEQ ID NO: 226          moltype = DNA   length = 20
FEATURE                 Location/Qualifiers
source                  1..20
                        mol_type = genomic DNA
                        organism = Homo sapiens
SEQUENCE: 226
gcggtgatcc actgtagtgc                                                    20

SEQ ID NO: 227          moltype = DNA   length = 20
FEATURE                 Location/Qualifiers
source                  1..20
                        mol_type = genomic DNA
                        organism = Homo sapiens
SEQUENCE: 227
tattaatgct ggatgttaaa                                                    20
```

```
SEQ ID NO: 228           moltype = DNA   length = 20
FEATURE                  Location/Qualifiers
source                   1..20
                         mol_type = genomic DNA
                         organism = Homo sapiens
SEQUENCE: 228
gagatgctgt ttaaagaaac                                                     20

SEQ ID NO: 229           moltype = DNA   length = 20
FEATURE                  Location/Qualifiers
source                   1..20
                         mol_type = genomic DNA
                         organism = Homo sapiens
SEQUENCE: 229
cagcaagaat ttaggatgta                                                     20

SEQ ID NO: 230           moltype = DNA   length = 20
FEATURE                  Location/Qualifiers
source                   1..20
                         mol_type = genomic DNA
                         organism = Homo sapiens
SEQUENCE: 230
ttgacataga agaggcacaa                                                     20

SEQ ID NO: 231           moltype = DNA   length = 20
FEATURE                  Location/Qualifiers
source                   1..20
                         mol_type = genomic DNA
                         organism = Homo sapiens
SEQUENCE: 231
gattcaggga ctccaaaatc                                                     20

SEQ ID NO: 232           moltype = DNA   length = 20
FEATURE                  Location/Qualifiers
source                   1..20
                         mol_type = genomic DNA
                         organism = Homo sapiens
SEQUENCE: 232
ctcactttca ttatactacc                                                     20

SEQ ID NO: 233           moltype = DNA   length = 20
FEATURE                  Location/Qualifiers
source                   1..20
                         mol_type = genomic DNA
                         organism = Homo sapiens
SEQUENCE: 233
tttagtatat tgagaacttg                                                     20

SEQ ID NO: 234           moltype = DNA   length = 20
FEATURE                  Location/Qualifiers
source                   1..20
                         mol_type = genomic DNA
                         organism = Homo sapiens
SEQUENCE: 234
agggactcca aaatctggcc                                                     20

SEQ ID NO: 235           moltype = DNA   length = 20
FEATURE                  Location/Qualifiers
source                   1..20
                         mol_type = genomic DNA
                         organism = Homo sapiens
SEQUENCE: 235
aggttaaatg tgcacagtac                                                     20

SEQ ID NO: 236           moltype = DNA   length = 20
FEATURE                  Location/Qualifiers
source                   1..20
                         mol_type = genomic DNA
                         organism = Homo sapiens
SEQUENCE: 236
atcaccgcag gcccatggtc                                                     20

SEQ ID NO: 237           moltype = DNA   length = 20
FEATURE                  Location/Qualifiers
source                   1..20
                         mol_type = genomic DNA
                         organism = Homo sapiens
SEQUENCE: 237
```
agcatctctt ggtcatctgt                                                      20

SEQ ID NO: 238         moltype = DNA   length = 20
FEATURE                Location/Qualifiers
source                 1..20
                       mol_type = genomic DNA
                       organism = Homo sapiens SEQUENCE: 238
gaaggagcaa aatgtataaa                                                      20

SEQ ID NO: 239         moltype = DNA   length = 20
FEATURE                Location/Qualifiers
source                 1..20
                       mol_type = genomic DNA
                       organism = Homo sapiens SEQUENCE: 239
gccatttctg gcttatggtt                                                      20

SEQ ID NO: 240         moltype = DNA   length = 20
FEATURE                Location/Qualifiers
source                 1..20
                       mol_type = genomic DNA
                       organism = Homo sapiens SEQUENCE: 240
ctggatggat cagggagaca                                                      20

SEQ ID NO: 241         moltype = DNA   length = 20
FEATURE                Location/Qualifiers
source                 1..20
                       mol_type = genomic DNA
                       organism = Homo sapiens SEQUENCE: 241
aaatacaatg ggaacagaat                                                      20

SEQ ID NO: 242         moltype = DNA   length = 20
FEATURE                Location/Qualifiers
source                 1..20
                       mol_type = genomic DNA
                       organism = Homo sapiens SEQUENCE: 242
ataatgactg aaaaatacaa                                                      20

SEQ ID NO: 243         moltype = DNA   length = 20
FEATURE                Location/Qualifiers
source                 1..20
                       mol_type = genomic DNA
                       organism = Homo sapiens SEQUENCE: 243
catgcccacc accatcgagc                                                      20

SEQ ID NO: 244         moltype = DNA   length = 20
FEATURE                Location/Qualifiers
source                 1..20
                       mol_type = genomic DNA
                       organism = Homo sapiens SEQUENCE: 244
aacatgagaa aataccgaat                                                      20

SEQ ID NO: 245         moltype = DNA   length = 20
FEATURE                Location/Qualifiers
source                 1..20
                       mol_type = genomic DNA
                       organism = Homo sapiens SEQUENCE: 245
agaaatgaag ctggtgattc                                                      20

SEQ ID NO: 246         moltype = DNA   length = 20
FEATURE                Location/Qualifiers
source                 1..20
                       mol_type = genomic DNA
                       organism = Homo sapiens SEQUENCE: 246
ccgcattgtg gagaaagaat                                                      20

SEQ ID NO: 247         moltype = DNA   length = 20
FEATURE                Location/Qualifiers
source                 1..20
                       mol_type = genomic DNA
                       organism = Homo sapiens

| | | |
|---|---|---|
| SEQUENCE: 247 gaaatgaagc tggtgattca | | 20 |
| SEQ ID NO: 248 FEATURE source | moltype = DNA length = 20 Location/Qualifiers 1..20 mol_type = genomic DNA organism = Homo sapiens | |
| SEQUENCE: 248 ttgtttaaag tgagagaatc | | 20 |
| SEQ ID NO: 249 FEATURE source | moltype = DNA length = 20 Location/Qualifiers 1..20 mol_type = genomic DNA organism = Homo sapiens | |
| SEQUENCE: 249 ccgcgactca ccaagtacag | | 20 |
| SEQ ID NO: 250 FEATURE source | moltype = DNA length = 20 Location/Qualifiers 1..20 mol_type = genomic DNA organism = Homo sapiens | |
| SEQUENCE: 250 gaacatgaga aaataccgaa | | 20 |
| SEQ ID NO: 251 FEATURE source | moltype = DNA length = 20 Location/Qualifiers 1..20 mol_type = genomic DNA organism = Homo sapiens | |
| SEQUENCE: 251 tatactacct ggccagattt | | 20 |
| SEQ ID NO: 252 FEATURE source | moltype = DNA length = 20 Location/Qualifiers 1..20 mol_type = genomic DNA organism = Homo sapiens | |
| SEQUENCE: 252 tatgagaatc tcagttgatc | | 20 |
| SEQ ID NO: 253 FEATURE source | moltype = DNA length = 20 Location/Qualifiers 1..20 mol_type = genomic DNA organism = Homo sapiens | |
| SEQUENCE: 253 tcaactgaga ttctcataca | | 20 |
| SEQ ID NO: 254 FEATURE source | moltype = DNA length = 20 Location/Qualifiers 1..20 mol_type = genomic DNA organism = Homo sapiens | |
| SEQUENCE: 254 tgagaatctc agttgatctg | | 20 |
| SEQ ID NO: 255 FEATURE source | moltype = DNA length = 20 Location/Qualifiers 1..20 mol_type = genomic DNA organism = Homo sapiens | |
| SEQUENCE: 255 atgagaatct cagttgatct | | 20 |
| SEQ ID NO: 256 FEATURE source | moltype = DNA length = 20 Location/Qualifiers 1..20 mol_type = genomic DNA organism = Homo sapiens | |
| SEQUENCE: 256 tggtaaaggc accaactgga | | 20 |
| SEQ ID NO: 257 FEATURE source | moltype = DNA length = 20 Location/Qualifiers 1..20 mol_type = genomic DNA | |

```
                              organism = Homo sapiens
SEQUENCE: 257
tgtcatgctg aaccgcattg                                                  20

SEQ ID NO: 258          moltype = DNA  length = 20
FEATURE                 Location/Qualifiers
source                  1..20
                        mol_type = genomic DNA
                        organism = Homo sapiens
SEQUENCE: 258
tttggtgaat gatcaaaggc                                                  20

SEQ ID NO: 259          moltype = DNA  length = 20
FEATURE                 Location/Qualifiers
source                  1..20
                        mol_type = genomic DNA
                        organism = Homo sapiens
SEQUENCE: 259
atgaaagtga gatattgttc                                                  20

SEQ ID NO: 260          moltype = DNA  length = 20
FEATURE                 Location/Qualifiers
source                  1..20
                        mol_type = genomic DNA
                        organism = Homo sapiens
SEQUENCE: 260
tatttcctca tagtgctcta                                                  20

SEQ ID NO: 261          moltype = DNA  length = 20
FEATURE                 Location/Qualifiers
source                  1..20
                        mol_type = genomic DNA
                        organism = Homo sapiens
SEQUENCE: 261
agaaggagca aaatgtataa                                                  20

SEQ ID NO: 262          moltype = DNA  length = 20
FEATURE                 Location/Qualifiers
source                  1..20
                        mol_type = genomic DNA
                        organism = Homo sapiens
SEQUENCE: 262
tttgtttggt gaatgatcaa                                                  20

SEQ ID NO: 263          moltype = DNA  length = 20
FEATURE                 Location/Qualifiers
source                  1..20
                        mol_type = genomic DNA
                        organism = Homo sapiens
SEQUENCE: 263
tctacggaaa cgtattcgag                                                  20

SEQ ID NO: 264          moltype = DNA  length = 20
FEATURE                 Location/Qualifiers
source                  1..20
                        mol_type = genomic DNA
                        organism = Homo sapiens
SEQUENCE: 264
aaaggccacc acagctcaga                                                  20

SEQ ID NO: 265          moltype = DNA  length = 20
FEATURE                 Location/Qualifiers
source                  1..20
                        mol_type = genomic DNA
                        organism = Homo sapiens
SEQUENCE: 265
aggtgcagca gatgaaacag                                                  20

SEQ ID NO: 266          moltype = DNA  length = 20
FEATURE                 Location/Qualifiers
source                  1..20
                        mol_type = genomic DNA
                        organism = Homo sapiens
SEQUENCE: 266
ggctccttga accctgacca                                                  20

SEQ ID NO: 267          moltype = DNA  length = 20
FEATURE                 Location/Qualifiers
source                  1..20
```

```
                            mol_type = genomic DNA
                            organism = Homo sapiens
SEQUENCE: 267
aaggagttac atcttaacac                                                         20

SEQ ID NO: 268              moltype = DNA   length = 20
FEATURE                     Location/Qualifiers
source                      1..20
                            mol_type = genomic DNA
                            organism = Homo sapiens
SEQUENCE: 268
taaaatgcaa gatacaatgg                                                         20

SEQ ID NO: 269              moltype = DNA   length = 20
FEATURE                     Location/Qualifiers
source                      1..20
                            mol_type = genomic DNA
                            organism = Homo sapiens
SEQUENCE: 269
acaagtgtct accagagaga                                                         20

SEQ ID NO: 270              moltype = DNA   length = 20
FEATURE                     Location/Qualifiers
source                      1..20
                            mol_type = genomic DNA
                            organism = Homo sapiens
SEQUENCE: 270
gcgctctggc accttctctc                                                         20

SEQ ID NO: 271              moltype = DNA   length = 20
FEATURE                     Location/Qualifiers
source                      1..20
                            mol_type = genomic DNA
                            organism = Homo sapiens
SEQUENCE: 271
ctgctgcacc ttctgagctg                                                         20

SEQ ID NO: 272              moltype = DNA   length = 20
FEATURE                     Location/Qualifiers
source                      1..20
                            mol_type = genomic DNA
                            organism = Homo sapiens
SEQUENCE: 272
tcttccctac ctagaaacga                                                         20

SEQ ID NO: 273              moltype = AA   length = 22
FEATURE                     Location/Qualifiers
REGION                      1..22
                            note = P2A linker
source                      1..22
                            mol_type = protein
                            organism = synthetic construct
SEQUENCE: 273
GSGATNFSLL KQAGDVEENP GP                                                      22

SEQ ID NO: 274              moltype = AA   length = 8
FEATURE                     Location/Qualifiers
REGION                      1..8
                            note = NyESO peptide
source                      1..8
                            mol_type = protein
                            organism = synthetic construct
SEQUENCE: 274
SLLMWITQ                                                                       8

SEQ ID NO: 275              moltype = AA   length = 9
FEATURE                     Location/Qualifiers
REGION                      1..9
                            note = MART1 peptide
source                      1..9
                            mol_type = protein
                            organism = synthetic construct
SEQUENCE: 275
AAGIGILTV                                                                      9

SEQ ID NO: 276              moltype = AA   length = 9
FEATURE                     Location/Qualifiers
REGION                      1..9
                            note = WT1 peptide
```

```
source                      1..9
                            mol_type = protein
                            organism = synthetic construct
SEQUENCE: 276
RMFPNAPYL                                                                   9

SEQ ID NO: 277              moltype = AA  length = 310
FEATURE                     Location/Qualifiers
REGION                      1..310
                            note = Native WT1 TCRb
source                      1..310
                            mol_type = protein
                            organism = synthetic construct
SEQUENCE: 277
MSNQVLCCVV LCFLGANTVD GGITQSPKYL FRKEGQNVTL SCEQNLNHDA MYWYRQDPGQ          60
GLRLIYYSQI VNDFQKGDIA EGYSVSREKK ESFPLTVTSA QKNPTAFYLC ASSPGALYEQ         120
YFGPGTRLTV TEDLKNVFPP EVAVFEPSEA EISHTQKATL VCLATGFYPD HVELSWWVNG         180
KEVHSGVCTD PQPLKEQPAL NDSRYCLSSR LRVSATFWQN PRNHFRCQVQ FYGLSENDEW         240
TQDRAKPVTQ IVSAEAWGRA DCGFTSESYQ QGVLSATILY EILLGKATLY AVLVSALVLM         300
AMVKRKDSRG                                                                310

SEQ ID NO: 278              moltype = AA  length = 270
FEATURE                     Location/Qualifiers
REGION                      1..270
                            note = Native WT1 TCRa
source                      1..270
                            mol_type = protein
                            organism = synthetic construct
SEQUENCE: 278
MTSIRAVFIF LWLQLDLVNG ENVEQHPSTL SVQEGDSAVI KCTYSDSASN YFPWYKQELG          60
KRPQLIIDIR SNVGEKKDQR IAVTLNKTAK HFSLHITETQ PEDSAVYFCA ATEDYQLIWG         120
AGTKLIIKPD IQNPDPAVYQ LRDSKSSDKS VCLFTDFDSQ TNVSQSKDSD VYITDKCVLD         180
MRSMDFKSNS AVAWSNKSDF ACANAFNNSI IPEDTFFPSP ESSCDVKLVE KSFETDTNLN         240
FQNLSVIGFR ILLLKVAGFN LLMTLRLWSS                                          270

SEQ ID NO: 279              moltype = AA  length = 602
FEATURE                     Location/Qualifiers
REGION                      1..602
                            note = Native WT1 TCRa TCRb
source                      1..602
                            mol_type = protein
                            organism = synthetic construct
SEQUENCE: 279
MSNQVLCCVV LCFLGANTVD GGITQSPKYL FRKEGQNVTL SCEQNLNHDA MYWYRQDPGQ          60
GLRLIYYSQI VNDFQKGDIA EGYSVSREKK ESFPLTVTSA QKNPTAFYLC ASSPGALYEQ         120
YFGPGTRLTV TEDLKNVFPP EVAVFEPSEA EISHTQKATL VCLATGFYPD HVELSWWVNG         180
KEVHSGVCTD PQPLKEQPAL NDSRYCLSSR LRVSATFWQN PRNHFRCQVQ FYGLSENDEW         240
TQDRAKPVTQ IVSAEAWGRA DCGFTSESYQ QGVLSATILY EILLGKATLY AVLVSALVLM         300
AMVKRKDSRG GSGATNFSLL KQAGDVEENP GPMTSIRAVF IFLWLQLDLV NGENVEQHPS         360
TLSVQEGDSA VIKCTYSDSA SNYFPWYKQE LGKRPQLIID IRSNVGEKKD QRIAVTLNKT         420
AKHFSLHITE TQPEDSAVYF CAATEDYQLI WGAGTKLIIK PDIQNPDPAV YQLRDSKSSD         480
KSVCLFTDFD SQTNVSQSKD SDVYITDKCV LDMRSMDFKS NSAVAWSNKS DFACANAFNN         540
SIIPEDTFFP SPESSCDVKL VEKSFETDTN LNFQNLSVIG FRILLLKVAG FNLLMTLRLW         600
SS                                                                        602

SEQ ID NO: 280              moltype = AA  length = 310
FEATURE                     Location/Qualifiers
REGION                      1..310
                            note = DLT WT1 TCRb
source                      1..310
                            mol_type = protein
                            organism = synthetic construct
SEQUENCE: 280
MSNQVLCCVV LCFLGANTVD GGITQSPKYL FRKEGQNVTL SCEQNLNHDA MYWYRQDPGQ          60
GLRLIYYSQI VNDFQKGDIA EGYSVSREKK ESFPLTVTSA QKNPTAFYLC ASSPGALYEQ         120
YFGPGTRLTV TEDLKNVFPP EVAVFEPSEA EISHTQKATL VCLATGFYPD HVELSWWVNG         180
KEVHSGVCTD PQPLKEQPAL NDSRYCLSSR LRVSATFWQN PRNHFRCQVQ FYGLSENDEW         240
TQDRAKPVTQ IVSAEAWGRA DCGFTSESYQ QGVLSATILY EILLGKATLY AVLVSALVLM         300
AMVKRKDSRG                                                                310

SEQ ID NO: 281              moltype = AA  length = 270
FEATURE                     Location/Qualifiers
REGION                      1..270
                            note = DLT WT1 TCRa
source                      1..270
                            mol_type = protein
                            organism = synthetic construct
SEQUENCE: 281
MTSIRAVFIF LWLQLDLVNG ENVEQHPSTL SVQEGDSAVI KCTYSDSASN YFPWYKQELG          60
```

```
KRPQLIIDIR SNVGEKKDQR IAVTLNKTAK HFSLHITETQ PEDSAVYFCA ATEDLTLIWG      120
AGTKLIIKPD IQNPDPAVYQ LRDSKSSDKS VCLFTDFDSQ TNVSQSKDSD VYITDKCVLD     180
MRSMDFKSNS AVAWSNKSDF ACANAFNNSI IPEDTFFPSP ESSCDVKLVE KSFETDTNLN     240
FQNLSVIGFR ILLLKVAGFN LLMTLRLWSS                                     270

SEQ ID NO: 282          moltype = AA  length = 602
FEATURE                 Location/Qualifiers
REGION                  1..602
                        note = DLT WT1 TCRa TCRb
source                  1..602
                        mol_type = protein
                        organism = synthetic construct
SEQUENCE: 282
MSNQVLCCVV LCFLGANTVD GGITQSPKYL FRKEGQNVTL SCEQNLNHDA MYWYRQDPGQ      60
GLRLIYYSQI VNDFQKGDIA EGYSVSREKK ESFPLTVTSA QKNPTAFYLC ASSPGALYEQ     120
YFGPGTRLTV TEDLKNVFPP EVAVFEPSEA EISHTQKATL VCLATGFYPD HVELSWWVNG     180
KEVHSGVCTD PQPLKEQPAL NDSRYCLSSR LRVSATFWQN PRNHFRCQVQ FYGLSENDEW     240
TQDRAKPVTQ IVSAEAWGRA DCGFTSESYQ QGVLSATILY EILLGKATLY AVLVSALVLM     300
AMVKRKDSRG GSGATNFSLL KQAGDVEENP GPMTSIRAVF IFLWLQLDLV NGENVEQHPS     360
TLSVQEGDSA VIKCTYSDSA SNYFPWYKQE LGKRPQLIID IRSNVGEKKD QRIAVTLNKT     420
AKHFSLHITE TQPEDSAVYF CAATEDLTLI WGAGTKLIIK PDIQNPDPAV YQLRDSKSSD     480
KSVCLFTDFD SQTNVSQSKD SDVYITDKCV LDMRSMDFKS NSAVAWSNKS DFACANAFNN     540
SIIPEDTFFP SPESSCDVKL VEKSFETDTN LNFQNLSVIG FRILLLKVAG FNLLMTLRLW     600
SS                                                                   602

SEQ ID NO: 283          moltype = AA  length = 311
FEATURE                 Location/Qualifiers
REGION                  1..311
                        note = IG4 NyESO TCRb
source                  1..311
                        mol_type = protein
                        organism = synthetic construct
SEQUENCE: 283
MSIGLLCCAA LSLLWAGPVN AGVTQTPKFQ VLKTGQSMTL QCAQDMNHEY MSWYRQDPGM      60
GLRLIHYSVG AGITDQGEVP NGYNVSRSTT EDFPLRLLSA APSQTSVYFC ASSYVGNTGE     120
LFFGEGSRLT VLEDLKNVFP PEVAVFEPSE AEISHTQKAT LVCLATGFYP DHVELSWWVN     180
GKEVHSGVCT DPQPLKEQPA LNDSRYCLSS RLRVSATFWQ NPRNHFRCQV QFYGLSENDE     240
WTQDRAKPVT QIVSAEAWGR ADCGFTSESY QQGVLSATIL YEILLGKATL YAVLVSALVL     300
MAMVKRKDSR G                                                         311

SEQ ID NO: 284          moltype = AA  length = 274
FEATURE                 Location/Qualifiers
REGION                  1..274
                        note = IG4 NyESO TCRa
source                  1..274
                        mol_type = protein
                        organism = synthetic construct
SEQUENCE: 284
METLLGLLIL WLQLQWVSSK QEVTQIPAAL SVPEGENLVL NCSFTDSAIY NLQWFRQDPG      60
KGLTSLLLIQ SSQREQTSGR LNASLDKSSG RSTLYIAASQ PGDSATYLCA VRPTSGGSYI     120
PTFGRGTSLI VHPYIQNPDP AVYQLRDSKS SDKSVCLFTD FDSQTNVSQS KDSDVYITDK     180
CVLDMRSMDF KSNSAVAWSN KSDFACANAF NNSIIPEDTF FPSPESSCDV KLVEKSFETD     240
TNLNFQNLSV IGFRILLLKV AGFNLLMTLR LWSS                                274

SEQ ID NO: 285          moltype = AA  length = 607
FEATURE                 Location/Qualifiers
REGION                  1..607
                        note = IG4 NyESO TCRa TCRb
source                  1..607
                        mol_type = protein
                        organism = synthetic construct
SEQUENCE: 285
MSIGLLCCAA LSLLWAGPVN AGVTQTPKFQ VLKTGQSMTL QCAQDMNHEY MSWYRQDPGM      60
GLRLIHYSVG AGITDQGEVP NGYNVSRSTT EDFPLRLLSA APSQTSVYFC ASSYVGNTGE     120
LFFGEGSRLT VLEDLKNVFP PEVAVFEPSE AEISHTQKAT LVCLATGFYP DHVELSWWVN     180
GKEVHSGVCT DPQPLKEQPA LNDSRYCLSS RLRVSATFWQ NPRNHFRCQV QFYGLSENDE     240
WTQDRAKPVT QIVSAEAWGR ADCGFTSESY QQGVLSATIL YEILLGKATL YAVLVSALVL     300
MAMVKRKDSR GGSGATNFSL LKQAGDVEEN PGPMETLLGL LILWLQLQWV SSKQEVTQIP     360
AALSVPEGEN LVLNCSFTDS AIYNLQWFRQ DPGKGLTSLL LIQSSQREQT SGRLNASLDK     420
SSGRSTLYIA ASQPGDSATY LCAVRPTSGG SYIPTFGRGT SLIVHPYIQN PDPAVYQLRD     480
SKSSDKSVCL FTDFDSQTNV SQSKDSDVYI TDKCVLDMRS MDFKSNSAVA WSNKSDFACA     540
NAFNNSIIPE DTFFPSPESS CDVKLVEKSF ETDTNLNFQN LSVIGFRILL LKVAGFNLLM     600
TLRLWSS                                                              607

SEQ ID NO: 286          moltype = AA  length = 311
FEATURE                 Location/Qualifiers
REGION                  1..311
                        note = 95LY NyESO TCRb
source                  1..311
```

```
                        mol_type = protein
                        organism = synthetic construct
SEQUENCE: 286
MSIGLLCCAA LSLLWAGPVN AGVTQTPKFQ VLKTGQSMTL QCAQDMNHEY MSWYRQDPGM    60
GLRLIHYSVG AGITDQGEVP NGYNVSRSTT EDFPLRLLSA APSQTSVYFC ASSYVGNTGE   120
LFFGEGSRLT VLEDLKNVFP PEVAVFEPSE AEISHTQKAT LVCLATGFYP DHVELSWWVN   180
GKEVHSGVCT DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR G                                                        311

SEQ ID NO: 287          moltype = AA  length = 274
FEATURE                 Location/Qualifiers
REGION                  1..274
                        note = 95LY NyESO TCRa
source                  1..274
                        mol_type = protein
                        organism = synthetic construct
SEQUENCE: 287
METLLGLLIL WLQLQWVSSK QEVTQIPAAL SVPEGENLVL NCSFTDSAIY NLQWFRQDPG    60
KGLTSLLLIQ SSQREQTSGR LNASLDKSSG RSTLYIAASQ PGDSATYLCA VRPLYGGSYI   120
PTFGRGTSLI VHPYIQNPDP AVYQLRDSKS SDKSVCLFTD FDSQTNVSQS KDSDVYITDK   180
CVLDMRSMDF KSNSAVAWSN KSDFACANAF NNSIIPEDTF FPSPESSCDV KLVEKSFETD   240
TNLNFQNLSV IGFRILLLKV AGFNLLMTLR LWSS                               274

SEQ ID NO: 288          moltype = AA  length = 607
FEATURE                 Location/Qualifiers
REGION                  1..607
                        note = 95LY NyESO TCRa TCRb
source                  1..607
                        mol_type = protein
                        organism = synthetic construct
SEQUENCE: 288
MSIGLLCCAA LSLLWAGPVN AGVTQTPKFQ VLKTGQSMTL QCAQDMNHEY MSWYRQDPGM    60
GLRLIHYSVG AGITDQGEVP NGYNVSRSTT EDFPLRLLSA APSQTSVYFC ASSYVGNTGE   120
LFFGEGSRLT VLEDLKNVFP PEVAVFEPSE AEISHTQKAT LVCLATGFYP DHVELSWWVN   180
GKEVHSGVCT DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR GGSGATNFSL LKQAGDVEEN PGPMETLLGL LILWLQLQWV SSKQEVTQIP   360
AALSVPEGEN LVLNCSFTDS AIYNLQWFRQ DPGKGLTSLL LIQSSQREQT SGRLNASLDK   420
SSGRSTLYIA ASQPGDSATY LCAVRPLYGG SYIPTFGRGT SLIVHPYIQN PDPAVYQLRD   480
SKSSDKSVCL FTDFDSQTNV SQSKDSDVYI TDKCVLDMRS MDFKSNSAVA WSNKSDFACA   540
NAFNNSIIPE DTFFPSPESS CDVKLVEKSF ETDTNLNFQN LSVIGFRILL LKVAGFNLLM   600
TLRLWSS                                                             607

SEQ ID NO: 289          moltype = AA  length = 311
FEATURE                 Location/Qualifiers
REGION                  1..311
                        note = DMF4 MART TCRb
source                  1..311
                        mol_type = protein
                        organism = synthetic construct
SEQUENCE: 289
MGTRLFFYVA LCLLWTGHMD AGITQSPRHK VTETGTPVTL RCHQTENHRY MYWYRQDPGH    60
GLRLIHYSYG VKDTDKGEVS DGYSVSRSKT EDFLLTLESA TSSQTSVYFC AISEVGVGQP   120
QHFGDGTRLS ILEDLKNVFP PEVAVFEPSE AEISHTQKAT LVCLATGFYP DHVELSWWVN   180
GKEVHSGVCT DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR G                                                        311

SEQ ID NO: 290          moltype = AA  length = 268
FEATURE                 Location/Qualifiers
REGION                  1..268
                        note = DMF4 MART TCRa
source                  1..268
                        mol_type = protein
                        organism = synthetic construct
SEQUENCE: 290
MLLEHLLIIL WMQLTWVSGQ QLNQSPQSMF IQEGEDVSMN CTSSSIFNTW LWYKQEPGEG    60
PVLLIALYKA GELTSNGRLT AQFGITRKDS FLNISASIPS DVGIYFCAGG TGNQFYFGTG   120
TSLTVIPNIQ NPDPAVYQLR DSKSSDKSVC LFTDFDSQTN VSQSKDSDVY ITDKCVLDMR   180
SMDFKSNSAV AWSNKSDFAC ANAFNNSIIP EDTFFPSPES SCDVKLVEKS FETDTNLNFQ   240
NLSVIGFRIL LLKVAGFNLL MTLRLWSS                                      268

SEQ ID NO: 291          moltype = AA  length = 601
FEATURE                 Location/Qualifiers
REGION                  1..601
                        note = DMF4 MART TCRa TCRb
source                  1..601
                        mol_type = protein
```

```
                              organism = synthetic construct
SEQUENCE: 291
MGTRLFFYVA LCLLWTGHMD AGITQSPRHK VTETGTPVTL RCHQTENHRY MYWYRQDPGH    60
GLRLIHYSYG VKDTDKGEVS DGYSVSRSKT EDFLLTLESA TSSQTSVYFC AISEVGVGQP   120
QHFGDGTRLS ILEDLKNVFP PEVAVFEPSE AEISHTQKAT LVCLATGFYP DHVELSWWVN   180
GKEVHSGVCT DPQPLKEQPA LNDSRYCLSS RLRVSATFWQ NPRNHFRCQV QFYGLSENDE   240
WTQDRAKPVT QIVSAEAWGR ADCGFTSESY QQGVLSATIL YEILLGKATL YAVLVSALVL   300
MAMVKRKDSR GGSGATNFSL LKQAGDVEEN PGPMLLEHLL IILWMQLTWV SGQQLNQSPQ   360
SMFIQEGEDV SMNCTSSSIF NTWLWYKQEP GEGPVLLIAL YKAGELTSNG RLTAQFGITR   420
KDSFLNISAS IPSDVGIYFC AGGTGNQFYF GTGTSLTVIP NIQNPDPAVY QLRDSKSSDK   480
SVCLFTDFDS QTNVSQSKDS DVYITDKCVL DMRSMDFKSN SAVAWSNKSD FACANAFNNS   540
IIPEDTFFPS PESSCDVKLV EKSFETDTNL NFQNLSVIGF RILLLKVAGF NLLMTLRLWS   600
S                                                                   601

SEQ ID NO: 292             moltype = AA length = 310
FEATURE                    Location/Qualifiers
REGION                     1..310
                           note = DMF5 MART TCRb
source                     1..310
                           mol_type = protein
                           organism = synthetic construct
SEQUENCE: 292
MRIRLLCCVA FSLLWAGPVI AGITQAPTSQ ILAAGRRMTL RCTQDMRHNA MYWYRQDLGL    60
GLRLIHYSNT AGTTGKGEVP DGYSVSRANT DDFPLTLASA VPSQTSVYFC ASSLSFGTEA   120
FFGQGTRLTV VEDLKNVFPP EVAVFEPSEA EISHTQKATL VCLATGFYPD HVELSWWVNG   180
KEVHSGVCTD PQPLKEQPAL NDSRYCLSSR LRVSATFWQN PRNHFRCQVQ FYGLSENDEW   240
TQDRAKPVTQ IVSAEAWGRA DCGFTSESYQ QGVLSATILY EILLGKATLY AVLVSALVLM   300
AMVKRKDSRG                                                          310

SEQ ID NO: 293             moltype = AA length = 272
FEATURE                    Location/Qualifiers
REGION                     1..272
                           note = DMF5 MART TCRa
source                     1..272
                           mol_type = protein
                           organism = synthetic construct
SEQUENCE: 293
MKSLRVLLVI LWLQLSWVWS QQKEVEQNSG PLSVPEGAIA SLNCTYSDRG SQSFFWYRQY    60
SGKSPELIMF IYSNGDKEDG RFTAQLNKAS QYVSLLIRDS QPSDSATYLC AVNFGGGKLI   120
FGQGTELSVK PNIQNPDPAV YQLRDSKSSD KSVCLFTDFD SQTNVSQSKD SDVYITDKCV   180
LDMRSMDFKS NSAVAWSNKS DFACANAFNN SIIPEDTFFP SPESSCDVKL VEKSFETDTN   240
LNFQNLSVIG FRILLLKVAG FNLLMTLRLW SS                                 272

SEQ ID NO: 294             moltype = AA length = 604
FEATURE                    Location/Qualifiers
REGION                     1..604
                           note = DMF5 MART TCRa TCRb
source                     1..604
                           mol_type = protein
                           organism = synthetic construct
SEQUENCE: 294
MRIRLLCCVA FSLLWAGPVI AGITQAPTSQ ILAAGRRMTL RCTQDMRHNA MYWYRQDLGL    60
GLRLIHYSNT AGTTGKGEVP DGYSVSRANT DDFPLTLASA VPSQTSVYFC ASSLSFGTEA   120
FFGQGTRLTV VEDLKNVFPP EVAVFEPSEA EISHTQKATL VCLATGFYPD HVELSWWVNG   180
KEVHSGVCTD PQPLKEQPAL NDSRYCLSSR LRVSATFWQN PRNHFRCQVQ FYGLSENDEW   240
TQDRAKPVTQ IVSAEAWGRA DCGFTSESYQ QGVLSATILY EILLGKATLY AVLVSALVLM   300
AMVKRKDSRG GSGATNFSLL KQAGDVEENP GPMKSLRVLL VILWLQLSWV WSQQKEVEQN   360
SGPLSVPEGA IASLNCTYSD RGSQSFFWYR QYSGKSPELI MFIYSNGDKE DGRFTAQLNK   420
ASQYVSLLIR DSQPSDSATY LCAVNFGGGK LIFGQGTELS VKPNIQNPDP AVYQLRDSKS   480
SDKSVCLFTD FDSQTNVSQS KDSDVYITDK CVLDMRSMDF KSNSAVAWSN KSDFACANAF   540
NNSIIPEDTF FPSPESSCDV KLVEKSFETD TNLNFQNLSV IGFRILLLKV AGFNLLMTLR   600
LWSS                                                                604

SEQ ID NO: 295             moltype = AA length = 142
FEATURE                    Location/Qualifiers
source                     1..142
                           mol_type = protein
                           organism = Homo sapiens
SEQUENCE: 295
PNIQNPDPAV YQLRDSKSSD KSVCLFTDFD SQTNVSQSKD SDVYITDKTV LDMRSMDFKS    60
NSAVAWSNKS DFACANAFNN SIIPEDTFFP SPESSCDVKL VEKSFETDTN LNFQNLSVIG   120
FRILLLKVAG FNLLMTLRLW SS                                            142

SEQ ID NO: 296             moltype = AA length = 142
FEATURE                    Location/Qualifiers
REGION                     1..142
                           note = TCR alpha sequence
source                     1..142
                           mol_type = protein
```

```
                         organism = synthetic construct
SEQUENCE: 296
PNIQNPDPAV YQLRDSKSSD KSVCLFTDFD SQTNVSQSKD SDVYITDKCV LDMRSMDFKS    60
NSAVAWSNKS DFACANAFNN SIIPEDTFFP SPESSCDVKL VEKSFETDTN LNFQNLSVIG   120
FRILLLKVAG FNLLMTLRLW SS                                           142

SEQ ID NO: 297           moltype = AA  length = 178
FEATURE                  Location/Qualifiers
source                   1..178
                         mol_type = protein
                         organism = Homo sapiens
SEQUENCE: 297
DLKNVFPPEV AVFEPSEAEI SHTQKATLVC LATGFYPDHV ELSWWVNGKE VHSGVSTDPQ    60
PLKEQPALND SRYCLSSRLR VSATFWQNPR NHFRCQVQFY GLSENDEWTQ DRAKPVTQIV   120
SAEAWGRADC GFTSESYQQG VLSATILYEI LLGKATLYAV LVSALVLMAM VKRKDSRG     178

SEQ ID NO: 298           moltype = AA  length = 178
FEATURE                  Location/Qualifiers
REGION                   1..178
                         note = TCR alpha sequence
source                   1..178
                         mol_type = protein
                         organism = synthetic construct
SEQUENCE: 298
DLKNVFPPEV AVFEPSEAEI SHTQKATLVC LATGFYPDHV ELSWWVNGKE VHSGVCTDPQ    60
PLKEQPALND SRYCLSSRLR VSATFWQNPR NHFRCQVQFY GLSENDEWTQ DRAKPVTQIV   120
SAEAWGRADC GFTSESYQQG VLSATILYEI LLGKATLYAV LVSALVLMAM VKRKDSRG     178

SEQ ID NO: 299           moltype = AA  length = 444
FEATURE                  Location/Qualifiers
REGION                   1..444
                         note = KSQCAR017 CAR Sequence
source                   1..444
                         mol_type = protein
                         organism = synthetic construct
SEQUENCE: 299
MLLLVTSLLL CELPHPAFLL IPDILLTQSP VILSVSPGER VSFSCRASQS IGTNIHWYQQ    60
RTNGSPRLLI KYASESISGI PSRFSGSGSG TDFTLSINSV ESEDIADYYC QQNNNWPTTF   120
GAGTKLELKG GGGSGGGGSG GGGSQVQLKQ SGPGLVQPSQ SLSITCTVSG FSLTNYGVHW   180
VRQSPGKGLE WLGVIWSGGN TDYNTPFTSR LSINKDNSKS QVFFKMNSLQ SNDTAIYYCA   240
RALTYYDYEF AYWGQGTLVT VSATTTPAPR PPTPAPTIAS QPLSLRPEAC RPAAGGAVHT   300
RGLDFACDIY IWAPLAGTCG VLLLSLVITL YCRVKFSRSA DAPAYQQGQN QLYNELNLGR   360
REEYDVLDKR RGRDPEMGGK PRRKNPQEGL YNELQKDKMA EAYSEIGMKG ERRRGKGHDG   420
LYQGLSTATK DTYDALHMQA LPPR                                         444

SEQ ID NO: 300           moltype = DNA  length = 1328
FEATURE                  Location/Qualifiers
misc_feature             1..1328
                         note = KSQCAR017 CAR Sequence
source                   1..1328
                         mol_type = other DNA
                         organism = synthetic construct
SEQUENCE: 300
atgctcctcc tggttactag cttgcttttg tgcgaactgc cgcatcctgc cttccttctc    60
atcccagata tacttctgac acaatctccg gtaatcctcc ccgtctcacc ggggagcga   120
gtgtcatttt catgccgggc gagtcaatcc atcgggacga atattcactg gtatcagcaa   180
aggactaacg gctcaccacg ccttctcatc aagtatgcca gtgagtccat aagtggcatt   240
ccctctagat tctcaggatc aggcagtggc acggacttca cattgtcaat taatagcgta   300
gaaagtgagg acatagcaga ttattattgc caacaaaaca ataactggcc taccacattc   360
ggtgcaggca ccaagcttga gttgaagggg ggtggtggtt ctggaggcgg tgggagcggt   420
ggtggtgggt cacaagtgca gcttaagcaa agcggaccag tcctggtcca acctagccag   480
tcactgtcaa tcacatgtac ggtatccggc tttagtctga caaattatgg cgtccactgg   540
gtaaggcaat cccctggaaa gggcctcgag tggttggggg tgatttggag cggaggaaac   600
accgactata atacccttt cacctccaga ctgtccataa acaaggacaa ctctaaaagt   660
caggtattct tcaaaatgaa cagtctgcaa agtaatgaca cagcgatata ttattgcgcg   720
agagcccta catactacga ttcgagttc gctattggg gacaaggaac gttggtgacg   780
gtgtctgcca caaccactcc tgctcccagg ccaccaacac cggcgcctac catagcgtca   840
cagccgctta gtctcaggcc ggaagcgtgt cgccccgcag ccggtggggc ggtccacaca   900
cgcggggctgg atttcgcatg cgatatatac atctgggcac ccttgccggg gacctgcggt   960
gttttgctct tgtctctcgt aatcacgctg tactgtcggg ttaagttttc aagatctcga  1020
gatgccccgg cataccaaca agggcagaat cagttgtaca acgaactgaa cttgggcaga  1080
cgcgaggagt atgatgtctt ggacaagagg cggggggcgcg acccgaaaat gggtggcaaa  1140
ccacggcgca agaaccccca agaggggctt tacaacgaat gcagaaagga caagatggcc  1200
gaggcataca gcgagattgg catgaaagga gagaggagga gggggaaggg gcatgatggc  1260
ctttatcagg gccttctac tgccaccaag gacacatacg acgcactgca catgcaggca  1320
ttgccacc                                                           1328

SEQ ID NO: 301           moltype = AA  length = 446
FEATURE                  Location/Qualifiers
```

| | | |
|---|---|---|
| REGION | 1..446 | |
| | note = KSQCAR1909 CAR Sequence | |
| source | 1..446 | |
| | mol_type = protein | |
| | organism = synthetic construct | |

SEQUENCE: 301

```
MLLLVTSLLL CELPHPAFLL IPDIQMTQTT SSLSASLGDR VTISCRASQD ISKYLNWYQQ    60
KPDGTVKLLI YHTSRLHSGV PSRFSGSGSG TDYSLTISNL EQEDIATYFC QQGNTLPYTF   120
GGGTKLEITG GGGSGGGGSG GGGSEVKLQE SGPGLVAPSQ SLSVTCTVSG VSLPDYGVSW   180
IRQPPRKGLE WLGVIWGSET TYYNSALKSR LTIIKDNSKS QVFLKMNSLQ TDDTAIYYCA   240
KHYYYGGSYA MDYWGQGTSV TVSSTTTPAP RPPTPAPTIA SQPLSLRPEA CRPAAGGAVH   300
TRGLDFACDI YIWAPLAGTC GVLLLSLVIT LYCLRVKFSR SADAPAYQQG QNQLYNELNL   360
GRREEYDVLD KRRGRDPEMG GKPRRKNPQE GLYNELQKDK MAEAYSEIGM KGERRRGKGH   420
DGLYQGLSTA TKDTYDALHM QALPPR                                       446
```

| | | |
|---|---|---|
| SEQ ID NO: 302 | moltype = DNA   length = 1338 | |
| FEATURE | Location/Qualifiers | |
| misc_feature | 1..1338 | |
| | note = KSQCAR1909 CAR Sequence | |
| source | 1..1338 | |
| | mol_type = other DNA | |
| | organism = synthetic construct | |

SEQUENCE: 302

```
atgctccttc ttgtgacgtc actcctgctt tgtgagctgc cgcacccggc ctttctgctc     60
ataccccgac atacaaatga cacagacgac agttcccttt ccgcctcctt gggcgaccga    120
gtgacaatca gttgccgagc ttcccaggac atatctaaat atttgaattg gtatcagcaa    180
aagccagatg gtacggttaa acttcttatc taccacacct ccaggctcca ttctggggtt    240
ccgagccgat tctctggatc tggctcaggg accgattatt ctttgactat ttccaatttg    300
gagcaggaag acatcgcaac ctatttctgc caacaaggaa atacgctgcc atacaccttc    360
ggcgggggca ccaaactcga gattactggg ggtggggga gtgggaggag gggttccggt    420
ggaggtgggt cagaagtcaa gctgcaagag agtgggcccg gttggttgc tcctagccaa    480
tccttgagtg taacatgcac cgttagcgga gtttcacttc ctgactacgg tgttagctgg    540
ataagacagc cccgaggaa gggtctgaa tggctggggg tcatttgggg cagtgagacg    600
acatattaca acagtgcctt gaaatctcgg cttacgatca taaaagacaa tagtaaaagc    660
caagtgttcc tcaagatgaa ctctcttcag accgacgaca cagccatcta ctattgcgca    720
aaacattatt attatggagg tagttacgct atggactatt ggggccaggg gacttcagtg    780
acggtgagta gtaccacgac tccggcaccg agaccaccaa caccagcccc aacaattgcc    840
tcacagccct tgagccttag acccgaggcc tgtaggcccg ccgcaggagg ggcagttcat    900
acgcgaggat tggactttgc atgtgacatc tatatctggg ccccacttgc gggaacttgc    960
ggtgtccttt tgctctcatt ggtcattacc ctctattgtt tgagagtaaa attttcccgc   1020
tccgctgatg cgcctgcata ccagcaaggt cagaaccaac tctacaatga gcttaacctc   1080
ggtagaagag aggaatatga cgtcttggat aagaggagag gccgagaccc agaaatgggg   1140
ggaaagccgc gccgcaagaa tccacaagaa ggtctttaca tgaactgca aggacaaa   1200
atggccgaag cgtatagcga gataggaatg aaaggcgaac ggagacgggg caaggggcat   1260
gacgggcttt accaaggact tagcacagcg acgaaggata catacgacgc actgcatatg   1320
caagcgctgc caccgcgc                                                1338
```

| | | |
|---|---|---|
| SEQ ID NO: 303 | moltype = AA   length = 496 | |
| FEATURE | Location/Qualifiers | |
| REGION | 1..496 | |
| | note = KSQCAR010 CAR Sequence | |
| source | 1..496 | |
| | mol_type = protein | |
| | organism = synthetic construct | |

SEQUENCE: 303

```
MDFQVQIFSF LLISASVIMS RGATGGATTT TCAGGTGCAG ATTTTCAGCT TCCTGCTAAT    60
CAGTGCCTCA DIQMTQSPSS LSASVGDRVT ITCRASQDVN TAVAWYQQKP GKAPKLLIYS   120
ASFLYSGVPS RFSGSRSGTD FTLTISSLQP EDFATYYCQQ HYTTPPTFGQ GTKVEIKRTG   180
STSGSGKPGS GEGSEVQLVE SGGGLVQPGG SLRLSCAASG FNIKDTYIHW VRQAPGKGLE   240
WVARIYPTNG YTRYADSVKG RFTISADTSK NTAYLQMNSL RAEDTAVYYC SRWGGDGFYA   300
MDVWGQGTLV TVSSTTTPAP RPPTPAPTIA SQPLSLRPEA CRPAAGGAVH TRGLDFACDI   360
YIWAPLAGTC GVLLLSLVIT LYCLRVKFSR SADAPAYQQG QNQLYNELNL GRREEYDVLD   420
KRRGRDPEMG GKPRRKNPQE GLYNELQKDK MAEAYSEIGM KGERRRGKGH DGLYQGLSTA   480
TKDTYDALHM QALPPR                                                  496
```

| | | |
|---|---|---|
| SEQ ID NO: 304 | moltype = DNA   length = 1488 | |
| FEATURE | Location/Qualifiers | |
| misc_feature | 1..1488 | |
| | note = KSQCAR010 CAR Sequence | |
| source | 1..1488 | |
| | mol_type = other DNA | |
| | organism = synthetic construct | |

SEQUENCE: 304

```
atggactttc aggtgcagat cttctcattc ctccttatca gtgcgagtgt aattatgtca    60
agaggtgcta caggcggtgc taccacgacg acatgcgcag ggggtaccgg ttgtgcagga   120
gcgaccacga ctacctgcgc aggttgtacc acctgttgta ctggatgtac tgctgcgaca   180
tgtgcgggga cggttgttg cacttgtgcg gacatacaaa tgacgcaaag cccgtccagc   240
ctgtctgcat cagttgggga tagagtgacg attacatgta gagcaagcca ggatgttaac   300
accgcctagc gtggtaccaa acaaaaacca ggtaagcccg aagctgct catatactcc   360
```

```
gccagctttc tgtattcagg cgttcccagt cggttcagcg gcagcagatc agggacggat    420
tttacgctca ctatctcttc ccttcagcct gaagattttg ctacctatta ttgtcagcag    480
cattacacga ctcccccaac ttttggtcag gggactaaag ttgaaatcaa acgaacgggc    540
tccacctcag gtagcggtaa gccaggcagc ggagaagggt ctgaagtcca gttggttgag    600
agtggaggcg gtcttgtgca acccggtggc agcttgcgac tgagctgtgc agcgtctgga    660
ttcaacataa aagatactta tattcattgg gtaagacagg ctcctggtaa agggctggaa    720
tgggtggcac gaatatatcc gactaacggt tataccagat acgccgattc tgttaagggc    780
aggttcacaa taagcgccga cacaagtaag aatacggcgt atctgcagat gaattcactt    840
cgagctgaag acacagcggt atactactga tccaggtggg gtggggatgg ttttttatgcg    900
atggacgttt ggggtcaagg aacactggta actgttagtt ctaccacgac acctgctcct    960
aggccccccca caccgcacc tacgatcgct tcccagccgc ttagcctccg cccggaggca    1020
tgccggcccg ctgcgggggg agcggtacat actcgcgggt tggacttcgc ttgcgacatc    1080
tacatttggg caccactggc aggcacatgt ggcgttctgt tgcttagtct ggttattaca    1140
ctgtattgcc tgcgagttaa attctcccgc agcgctgatg cgcccgccta tcagcaaggt    1200
caaaaccagc tgtataatga gcttaatttg gacgccgag aagagtatga cgtccttgac    1260
aagaggcgcg ggcgcgatcc ggagatgggg ggtaaaccgc gccggaaaaa cccccaggaa    1320
ggcctttaca atgagctcca aaaagataaa atggcagagg catactctga aataggaatg    1380
aagggcgaga gacgccgggg taagggacac gatggcctttt atcaagggct tagtacagcc    1440
acgaaggata cgtatgacgc tctgcacatg caggctcttc ccccgaga                1488

SEQ ID NO: 305           moltype = DNA  length = 83
FEATURE                  Location/Qualifiers
misc_feature             1..83
                         note = tracr RNA 1
source                   1..83
                         mol_type = other DNA
                         organism = synthetic construct
SEQUENCE: 305
gttttagagc tagaaatagc aagttaaaat aaggctagtc cgttatcaac ttgaaaaagt    60
ggcaccgagt cggtgctttt ttt                                           83

SEQ ID NO: 306           moltype = DNA  length = 65
FEATURE                  Location/Qualifiers
misc_feature             1..65
                         note = tracr RNA 2
source                   1..65
                         mol_type = other DNA
                         organism = synthetic construct
SEQUENCE: 306
gggcttcatg ccgaaatcaa caccctgtca ttttatggca gggtgttttc gttatttaat    60
ttttt                                                                65

SEQ ID NO: 307           moltype = DNA  length = 39
FEATURE                  Location/Qualifiers
misc_feature             1..39
                         note = tracr RNA 3
source                   1..39
                         mol_type = other DNA
                         organism = synthetic construct
SEQUENCE: 307
aaatcaacac cctgtcattt tatggcaggg tgttttttt                           39

SEQ ID NO: 308           moltype = DNA  length = 170
FEATURE                  Location/Qualifiers
misc_feature             1..170
                         note = tracr RNA 4
source                   1..170
                         mol_type = other DNA
                         organism = synthetic construct
SEQUENCE: 308
gtattaagta ttgtttttatg gctgataaat ttctttgaat ttctccttga ttatttgtta    60
taaaagttat aaaataatct tgttggaacc attcaaaaca gcatagcaag ttaaaataag   120
gctagtccgt tatcaacttg aaaaagtggc accgagtcgg tgcttttttt             170

SEQ ID NO: 309           moltype = DNA  length = 89
FEATURE                  Location/Qualifiers
misc_feature             1..89
                         note = tracr RNA 5
source                   1..89
                         mol_type = other DNA
                         organism = synthetic construct
SEQUENCE: 309
gttggaacca ttcaaaacag catagcaagt taaaataagg ctagtccgtt atcaacttga    60
aaaagtggca ccgagtcggt gcttttttt                                     89

SEQ ID NO: 310           moltype = DNA  length = 76
FEATURE                  Location/Qualifiers
misc_feature             1..76
                         note = tracr RNA 6
```

```
source                  1..76
                        mol_type = other DNA
                        organism = synthetic construct
SEQUENCE: 310
aaaacagcat agcaagttaa aataaggcta gtccgttatc aacttgaaaa agtggcaccg    60
agtcggtgct tttttt                                                   76

SEQ ID NO: 311          moltype = DNA  length = 93
FEATURE                 Location/Qualifiers
misc_feature            1..93
                        note = tracr RNA 7
source                  1..93
                        mol_type = other DNA
                        organism = synthetic construct
SEQUENCE: 311
gtttaagagc tatgctggaa acagcatagc aagtttaaat aaggctagtc cgttatcaac    60
ttgaaaaagt ggcaccgagt cggtgctttt ttt                                 93

SEQ ID NO: 312          moltype = DNA  length = 1766
FEATURE                 Location/Qualifiers
source                  1..1766
                        mol_type = genomic DNA
                        organism = Homo sapiens
SEQUENCE: 312
ggcagctgca cggctcctgg ccccggagca tgcgcgagag ccgccccgga gcgcccggga    60
gccccccgcc gtcccgcccg cggcgtcccg cccccccggg ccaggtgagc cgggcctgg   120
gcgaggaggc gggagggagg agggagggga gtccagggca gccaggagtc gggcgagcct   180
cggggggctgc agaatgggt cgcggccgcg atgcccctga ccctcgcgg ccccaccag     240
gccgcccccc gcgcgcgggg ctcccgcagc acagcctttc tccggcccta gcccaaatcg   300
cccagaccag gcgcggatcc cagcctggcc agcaggcggg cggcgagccg                360
gggccggacg gctggagcca gaaccggctg ctctccacgc cccctctcg gtgctgcccg   420
gaggccggac tccgcctcca ccgagcccc acccgccggg aagagctccg cggagtacag   480
agcccatttt ctagctgtgt ccactgaggc tgaacggatc cgcgcggact tggtgctccg   540
tgctcgcccc ctagggccgg gtccgccggg agcgccgcc tccggagttg tccggccggc    600
gcacacctgc ccggccccgc agcgcccag ctcacctctt tgtctctccc gcagcgcacc   660
cccgacgct atgcccacc cctccggctg gccccttctg taggatggta gcacacaacc     720
aggtggcagc cgacaatgca gtctccacag cagcagagcc ccgacggcgg ccagaacctt   780
cctcctcttc ctcctcctcg cccgcggccc ccgcgcgccc gcgccgtgc cccgcggtcc    840
cggcccggcc cccgccggac acgcacttcc gcacattccg ttcgcacgcc gattaccggc   900
gcatcacgcg cgccagcgcg ctcctggacg cctgcggatt ctactgggggg cccctgagcg   960
tgcacggggc gcacgagcgg ctgcgcgccg agcccgtggg caccttcctg gtgcgcgaca  1020
gccgccagcg gaactgcttt ttcgcccctta gcgtgaagat ggcctcggga cccacgagca  1080
tccgcgtgca ctttcaggcc ggccgctttc acctggatgg cagccgcgag agcttcgact  1140
gcctcttcga gctgctggag cactacgtgg cggcgccgcg ccgcatgctg ggggcccgc   1200
tgcgccagcc ccgcgtgcgg ccgctgcagg agctgtgccg ccagcgcatc gtggccaccg  1260
tgggccgcga gaacctggct cgcatccccc tcaaccccgt cctccgcgac tacctgagct  1320
ccttccctt ccagatttga ccggcagcgc ccgccgtgca gcagcatta actgggatgc  1380
cgtgttattt tgttattact tgcctggaac catgtgggta ccctcccgg cctgggttgg   1440
agggagcgga tgggtgtagg ggcgaggcgc ctcccgccct cggctggaga cgaggccgca  1500
gaccccttct cacctcttga gggggtcctc ccctcctgg tgctccctct gggtcccct    1560
ggttgttgta gcagcttaac tgtatctgga gccaggacct gaactcgcac ctcctacctc  1620
ttcatgtta catataccca gtatctttgc acaaaccagg ggttggggga gggtctctgg  1680
ctttattttt ctgctgtgca gaatcctatt ttatattttt taaagtcagt ttaggtaata  1740
aactttatta tgaaagtttt tttttt                                     1766

SEQ ID NO: 313          moltype = DNA  length = 1729
FEATURE                 Location/Qualifiers
source                  1..1729
                        mol_type = genomic DNA
                        organism = Mus musculus
SEQUENCE: 313
agcagagaga actgcggccg tggcagcggc acggctccca gccccggagc atgcgcgaca    60
gccgccccgg agccccagcc cgcggctccc cgcgtcctgc cgccaggtga gccaaggcag   120
ctgcgaggga gcaggcggga gggatggga ggtgatggga gcagagcccg gcaggactaa   180
cctcgcagac tgtatggcag ggtcgaggat gccacgcctc tggcgccccc cacccccgc   240
cccggctccc ccaggaggcc cctcgctcga gcggggcgcc gtcagccct cctctccggc   300
cctgagccct gatcctccgc ccgggttcca gtccccggcg tggccagtag gcggcagccg   360
cgaggcgact agcaccagc ggggacggcc gggagtcggg cccctctcca cgccccttc     420
tccacgcgcg cggggaggca gggctccacc gccagtcgg aagggttccg catacaggaa   480
cggcctactt cgcagatgag cccaccgagg ctcaagctcc gggcggattc tgcgtggcgc   540
tctcgctcct tgggggtctgt tggccggcct gtgccaccg gacgcccggc tcactgcctc   600
tgtctccccc atcagcgcag cccggacg tatgggcccac ccctcagct ggcccctcga   660
gtaggatggt agcacgcaac caggtggcag ccgacaatgc gatctccccg gcagcagagc   720
ccgacgcgg tcctcgtcct cgtcttcgtc ctcgccagcg gcccgtgaa                780
gtccccggcc ctgccggcg gtccagccc cagcccctgg cgacactcac ttccgcacct    840
tccgctccca ctccgattac cggcgcatca cgcgaccag cgcgctcctg gacgcctgcg   900
gcttctattg ggggaccctg agcgtgcacg gggcgcacga gcggctgcgt gccgagcccg   960
tgggcacctt ccttggtgcgc gacagtcgcc aacggaactg cttcttcgcg ctcagcgtga  1020
agatggcttc gggccccacg agcatccgcg tgcacttcca ggcggccgc ttccacttgg   1080
```

```
acggcagccg cgagaccttc gactgccttt tcgagctgct ggagcactac gtggcggcgc  1140
cgcgccgcat gttgggggcc ccgctgcgcc agcgccgcgt gcggccgctg caggagctgt  1200
gtcgccagcg catcgtggcc gccgtgggtc gcgagaacct ggcgcgcatc cctcttaacc  1260
cggtactccg tgactacctg agttccttcc ccttccagat ctgaccggct gccgctgtgc  1320
cgcagcatta agtgggggcg ccttattatt tcttattatt aattattatt attttttctgg  1380
aaccacgtgg gagccctccc cgcctggtc ggagggagtg gttgtggagg gtgagatgcc  1440
tcccacttct ggctggagac ctcatcccac ctctcagggg tggggtgct ccctcctgg  1500
tgctccctcc gggtccccc tggttgtagc agcttgtgtc tggggccagg acctgaattc  1560
cactcctacc tctccatgtt tacatattcc cagtatcttt gcacaaacca ggggtcgggg  1620
agggtctctg gcttcatttt tctgctgtgc agaatatcct attttatatt tttacagcca  1680
gtttaggtaa taaactttat tatgaaagtt tttttttaaa agaaacaaa              1729

SEQ ID NO: 314          moltype = DNA  length = 98858
FEATURE                 Location/Qualifiers
source                  1..98858
                        mol_type = genomic DNA
                        organism = Homo sapiens
SEQUENCE: 314
gctcgggcgc cgagtctgcg cgctgacgtc cgacgctcca ggtactttcc ccacggccga  60
cagggcttgg cgtgggggcg gggcgcggcg cgcagcgcgc atgcgccgca gcgccagcgc  120
tctccccgga tcgtgcgggg cctgagcctc tccgccggcg caggctctgc tcgcgccagc  180
tcgctcccgc agccatgccc accaccatcg agcgggagtt gcaagagttg gatactcagc  240
gtcgctggca gccgctgtac ttggtgagtc gcggacccac gcggcagtcg ccgacctcct  300
ccgagacccg gactcgtgcc ctgtccgcag ggtcctccc gcctccccg cctctcgcct  360
ctagcctctc gctcggggcg gaagtggcgg cgcggtccgc gtcaggggcg cgcctgcgct  420
gaccgctctc ttgctccttt tggtttaaaa aaaaaaaaa aaaagcata cttgagctga  480
gcagctcatg gttagcgcaa gcgcagttag ttctggaggg cggtgccaca gcggcttctt  540
ggggagcgcg tggatgcgcc accagcgttg cgcggcccgg gtctggggt ccttgggaaa  600
gccgtgggg cgctcgggcg cgcgccccg ggccgcagct tcgccgtagc tcccacgccg  660
ctgtgcttgg ttcttgctcg cggacagctc tttctctgtc cgggtgtttt gtggccgggt  720
gggcagctgg cgtcccccgg agcggtgagg gcggggcgg gcgagccggg ccgcggcgtc  780
cgggtccagc tggcgccgc gcaggacctg tgggagcagg ccgctctggg cgccgggccg  840
gccgccgcag ccctctgcga ggcgaagctc gctctcctgg cggagccgcg gtggttgggg  900
gtggctcgtg gcctctggcg agggcagcgc tctcgggacc ctccgtcttc attttccccc  960
gtggcccagc agcgcccagc gtgggttcgg ccccataga accttccggg aacgaaagag  1020
gctttgcttg tgttcgtcca gtgatagcgt gtcattctct ttatagtttt ccttactgag  1080
gtatactttc cctacagtga aacgcagctt tcatgtgtgc tcccagacgg gtgtcacaaa  1140
tgaatcccct cttgcaagcc cctcaaatc aaaatagcct ttccttgccc tgagaaagtg  1200
ccctcatccc ctccccgggg gcacgtgtt ccgatgccta tcgccctaat cgtgcctgtt  1260
cagctcacat agatgcaata tgtagtataa acacctgtga ttcgctttt ttatgtcaac  1320
tagactacct tttaattcaa acaaaacttt atctcttta aaatgatgta actgcttcc  1380
ccttcgttta atccttgtcg tattattccc aagattgaat ttggtgacgg ttaagttaat  1440
gctgcttctg atgtttggtt ctctctgtgt aaagtaaaag acgggctttc tcgtaaatgg  1500
atgatcctgg gttttccccc tttccattta attagatggc agtgaaaat gtgttcagaa  1560
agtaacgttt tcttcttgaa cacattagtg gaagtataa atattctgat tcccatgata  1620
cagagtatgt tagaataggg atctaagttt taaagaatgc tggtaaggac tcttccaatt  1680
atagacaatc tgaaacgcaa atttctggtag gaatcttcat gtgagagagc ctgccagctg  1740
catcttctcc agttacattt gttttagcag aggctgctgt ctctctaagg gataggttat  1800
atatcgaaat agatttgaaa agagaaaagt gaatataact taattcagct taacattttg  1860
gtttaagaaa tttaattttc tttggtatca ttaatatcct tgaaaattca atgagaattg  1920
tgattcctct ttcagaaaa atgaacttaa ctcgcatcca ctggagattt cacatgcatt  1980
ttcaaaaaga taaggaaatc cttctataga ttcttaccga ggaatcctgt agtttccttg  2040
gttggtcaat gctcatatta ttttttccta gttgaaaaca agaccattag tttggtcagt  2100
agaaaccatg gcatgcacac tggtgttaca gtaaagtag gtcacaaacc aagaaagtta  2160
gtaatggaaa gcaagtcagg aagtttgagc tatgtgttct cctgtggcct tagaaacatcc  2220
attcagccat tccacaaata tgcccggacc cccagtggaa ttgcagcttt tgctcctggc  2280
cttggggatt cagcagagaa tgctcctggc aagtttccta ccctcgaggt gctcactcta  2340
gggcttattc ttttgggcc tcattgtagt tccatatttt cattcattcg ttcataacat  2400
gcttgttatg tgctagtgtt agacactgag gattcttgtt aaaagacagg agtcccagtt  2460
tttaaggatg cagccctgta aataggtaag ctgatgaaaa cgttaaagtg atacatgtaa  2520
agctagcttg aagcacaggg tcttgtggag ttgagttacc taggagtcct gtatttccca  2580
aaaagggta cacatgggag ttctggtgaa gcttctcgag ggagggagga cctcacctaa  2640
gtcttgaaag acattggcca ggggaagagg acaagggagg tgaagagaat tactgttcca  2700
gcaaggaggg agtgcacaaa ggcactgagg gaatgctgag agaaccaccc acagtttagc  2760
ctggagactg tgtgaagtt gagatgctgc agagtaaggc agagcctaga tcagactaag  2820
gaatttgagc tgtttaatag gaactcattg tggaattgta agtctggaaa taccatgatc  2880
atatttgctt cttttttttt tgacagagtc ccgctctgtc gcccaggctg gagtgcagtg  2940
gtgcgacgtc agctcactgc aacctctgcc tcctgggttc aagtgattca cttacctcag  3000
cctcctgcgt agttgaaatt acaggcacac accaccatgc ccggttgatt tttttgtact  3060
tttagtagag acagggtttc gacatgttgg ccaggctggt ctcgaactcc tgacctcagg  3120
tgatccgcct gcctcggcct ctcaaagtgc tgggattaca gcatgagcc actgctctgg  3180
gctgatcata tttacttgtt agcaagatcg ttctgactgc tagcagactg gatgaggaaa  3240
gtgtaggcac gcagcacagg gcagtagtcg gttggagtaa acctgaagag acatgatgag  3300
cttctgttag gcagtggcag gagggatgga ggggagatac agatttgaaa tgaaatgga  3360
aaggggtata cgttatgtac aagtttggtt ttgaaacttt aattctgttt gaggtaccta  3420
cgagacactg aaatgaagct agttgaatgt ataaatttgg agttcgggag agagggtctg  3480
agtaaatgtg attttggaaa tcatgaacac atgggtgata tttgaggtct tagacattga  3540
tgagatcatc tagggaagat acagagcgtt tggaaatatc aaaggccaag acagaatct  3600
tgacagacaa catttaaaag gatgggtgga gaaagaggaa cttgcaaaaa agactggtga  3660
```

```
ggaacaacca cagaagtggg gaggaaagca gtggagggag ttgagggtga gcagggccac   3720
ctgacaggta agggccagcc tgagagggcc atgacattga gcagctagat taacagatac   3780
cttaaaggga gttgtgtcag cggactacac aagacagata cctggagttc aggagagaag   3840
gtaggaggaa atgcaaacta ccaagtgtac actgctcttt ttagaagccc aacttgaaga   3900
agtggggaga ggtagctaaa atgaagcaag atttgtgtgac ttctcactta aacccttgaa   3960
cggctttccg ttgctcacag tgtaaattca gcccctcctc cggctcacaa gacctcatgg   4020
cctgtgtctc ttgcttgatt tcccctatca cttttcctcc tcttttccac tgtgttgtat   4080
tcttggaagt gtgtgtgtcc attctcccct tagggcgttt gtaaatgttg ttctctttgc   4140
cttggcacaa ctttccccccc ttctcttttcc tttcttgctt aaactgcctc ctactcatcc   4200
ctgaagtctc acttccttgg caggccttct tgacctgccc atgctgggta tgagcccctg   4260
ttgcgtactt ctttagcatc ccaagacttc ccctttcata gcgggaattg gatgtcatac   4320
agcagcaaat gatttcggga acacaatttg cattaagcaa accactatct tgaaagtaac   4380
acagcttgag taggaaaaaa gtgtttaagg tggctttctg ctttgtttag cacagcagtg   4440
ggtgatgttt ctgataatgt ttttgaagag ttgtgcttttt tttggtaatg ctcatggagc   4500
tgggaaaaga aaggctttgc tcttgagcaa aaactgagta caactaaaag ctggacttgc   4560
ttagtggtag gagaacttga taccttgttg aaattctagc gggaaaaatg aatttagtat   4620
tttgagtctg gaactctggt cccttattcc tttttgctcc ttttgaaaag tgtcttttat   4680
ttcatgagtt tgataatagg aggtttctta gaaatgaatt attgggttgg agcagaacag   4740
actctgttaa tctgagttta tattttttat tacttcttca gagtttcatg aaggcactga   4800
cagtgctttg cacagtatca ggtgcttagt aagcacttga aaatatgtgc tgaatgaatg   4860
actttttacg aggaaagggc aacttgatat atttatgtga ttgcagggat gaacctaaag   4920
agagaggtgg aggttgaaat agaagggatg attgttggag ccagaaatct tagaaagcaa   4980
gagtcaatgg gaccaagagc acacaggtgg aagaattgat cgtgaaagag tgctggccag   5040
gcggtggctc atccctgtaa tcccagcgct tgggaggct gaggtgggag gatcacttga   5100
ggtcaggagg ttagggctgc agtgagccat aattgtgcca ctgcactaca gactaggtga   5160
cagagtgaga tcctgtctct aaaacaagaa cagcaaaaca aagggtgcag ttggaaaagt   5220
ttaatttggt ctgattgtgt gaggttaatt ctgactttttt gagtaatgtt catgatccct   5280
ttttggcttt tccttttgtc actgctgatt gctgtcttca tcaggctgag ctttgagaaa   5340
ggcagagaga aggaatggag tctgtgtgcc tactgaggaa aagactaaaa ctggggaatc   5400
gcaaaagcta tgttatgggt tgtttctaag aagtgatggc tcagaaggaa tttggcttat   5460
ttattttttaa attcctttct tttttaaaga gttctcactc tgttgcccag tctggagtac   5520
aagtgcagtg gtgcaatcat agctcactgc aaccttaaac tcctgggctc aggtgagcct   5580
ctcacctcag cctcttggaa attggttgat taattagggt ttataaacaa tggaactcct   5640
gactgacttc attttttcttt ttttgaaacc aagtcttgct ctgtcccca ggctggagtg   5700
cagtagtgtg atctcagctc actgcaacct ctgctccccc caggttcaag cagttctact   5760
gcctcagcct cccgagtagc tgggattaca ggtgcccacc agcacgccca gctaattttt   5820
gtattttag tagaaacggg gtttcaccat gtttgtcagg ctggtcttga actcctgacc   5880
tcaggtgatc cacctgcctc ggcctcccaa agtgctgctg ggattacagg tgtgagccac   5940
cacgcccagc cacattttc tttttcttc tttttttcct ttttctttct ttttttttct   6000
tttttcttttct tttcttttg agactgggtc tcacttgtc acccagtctg gagtgcagtg   6060
gcgtgatctc agctcactgc agtctcgacc tctgggctt tagacatcct cctgcctcag   6120
tccccacgt agctgggcct ggctaatttt tttgtattt ttgtagagac agggtttaac   6180
tatttgccc aggctggtct tcaactcctg agttcaagca atctgtccac ctcagcctc   6240
caaaggctta ggattacaag catgagccac tgtgcctggc catttttctt ttttcttttt   6300
cttttttga gacagtcttg ctctgttgcc caggctggag tgcagtggcg tcatctcggc   6360
tcgctgcaag ctctgcctcc caggttcacg ccattctcct gcctcagcct tctgagtagc   6420
tgggactaca ggcgcccgcc aacactacag gcgcccgacc ccacgccagg ctaattttt   6480
gtattttag tagagacggg gtttgaccgt gttagccagg atggtcttga tctcctgact   6540
ttgtgatcca cctgcctcgg cctcccaaag tgctgggatt ataggcatga gccactgcgc   6600
ctggccgcca tttttcttta ttagaaattt gtagttcaaa tattgctaga gaacaatttt   6660
taccatttgt gagtcagcta attttttagaa gtcagatatc aagtgcacac tgttcttctc   6720
atacttacag cggggcagcc agttaggcag gtgaatcaaa gctgtcttat tctaaaacac   6780
ttcccttgcc tactagttac acattctcct gcctgctgtc taatctcagt gcttttacat   6840
ggttgcacaa actctgaatt cccttgaaga ttggctactc tctcacacct tggagtcttc   6900
atgtgttgga tatactccat gcctaccata tctatttggg aaacatcttc aagactagac   6960
cgtagtctcc ttgggcaaag ttaaatgctc cccttctct catttcttag ttctctatat   7020
tcttttatta gaatatgaac cacattgttt tgtaactgtc tacttgtctg ttctgtgtag   7080
ctccttgagg gtggtctttt ttttttcttg ttttcccacc acctacctac gggacctgaa   7140
acatgttaga tgctcagtaa atattcagta aacacaggaa aactgttccc tttaaatg   7200
tcagcacctt agtttattcc aaaccccctca tttatggctg aggaaacact gggccaatac   7260
agtgttgtga cttatctgat gttacaatat ctgctagtgt cataactggg actcaaatcc   7320
agtccttctg attctcgttt cagcactgcc ctaatttacc catgtgacta cctgtagtgc   7380
tttcttctta tgatctattt gagatcagtg gcacagaggg aatcgtctta attttgatgg   7440
ctaggaggga gtgatgtgt tataataggt agggtcattt tgggacttga ggcctttaaa   7500
acagtgtctg ggatccaggg atcagacttg aaaggtattt gcaaatctcc tgaaactgct   7560
aaattttatg tacgtgtgtt cccaggtatt tcgtttctag gtgattctgt agcttttgtc   7620
agtttcttag tggatttgtc tgtgatccct caaaaggtaa agaccactgc ttgaagggaa   7680
agcagccttg ggatgggtgc cccaatgggg aatgtatacc tagaaatcat attgctttgc   7740
ctttgacatg tgtttataga ttactgatat ctataattac ggaaatccag atagttgcgt   7800
ttgtctccta gcttttctag ttgcctcttt tttgatttct tgattttaac cagaatcttc   7860
ttttttttctt gagaagggt ctcattccgt cacccaggct ggagtgcagt ggcacgatcg   7920
taggtcactg cagactcaaa actcctggct caagtggtcc tttgcctcag cctcccgaga   7980
agctgggact acaggcacac accaccacgc ctgacaaatt tcttcttctt cttcttcttt   8040
ttgttgttgt tcttgttggc caggtggtct tggtcttgaa ctcccggcct caagtggtct   8100
gctcaccttg gcttcccgaa gtggcgagat tacaggcatg agccaccatg cccagccctt   8160
aaccagaatt ttgttttgtt ttgttttttg agacagggtc tcactctgtc acccagactg   8220
gagtgcagtg atgagatcac ggctcactgc acagatgcac gccaccatgc ttggctaatt   8280
ttttatgttt tgtagagaca ggttctcacc atgttgccca gactggtctc gaactcccgg   8340
gctaaagcga tcttccggct tcacccttcc ataatgctgg ggagccacag tgcttggcca   8400
```

```
accagaatct taaaagcccct ttttactttt tccagatagt tactctgcag agaatttctg   8460
attcccagtt ggagaactgt tacagctctc tcagtcccct gctgttcttt tagctacctt   8520
gtctttgtcc tcttacctgt ccactctcta ctccccttct tcccttttggt ctccaaatag  8580
tccagataaa ccagagagat ggacagataa ggtctgggta cgcgaaatta aaattaacat   8640
agtgtgctct tcactttctt gaataaacgt tacgtatgat ttgtttccct tggaaatcct   8700
catctagatt ctctactctc tattccttaa cttaatgccc cattaaggta gttttttctt   8760
aatgaaagc tgttgagagt cagaggatat ttaaaccaac taataaactg aacttttaat    8820
aataccaccc ttactttgga taagagtgat tagccatata ctaaatcctc aatcagttta   8880
gcatgtaaaa tttaagacat agcagctgat aactgaggaa gagatacatt tccacaggct   8940
aactttaaag aatataagct ctcactttcc tgagtagaag aaaactaaac ttttctgttc   9000
tatgcttttt ttttttttaa ttttttatttt tattgatcat tcttgggtgt ttctcacaga  9060
gagggatttg gcagggtcat aggacaatag tgaaggaag gtcagcagat aaacaagtga    9120
acaaaggtct ctggttttcc taggcagagg accctgaggc cttccgcagt gtttgtgtcc   9180
ctgggtactt gagattaggg agtggtgatg actgttaacg agcatgctgc cttcaagcat   9240
ctgtttaaca aagcacatct tgcactgccc ttaatccatt taaccctgag tggacacagc   9300
acatgtttca gagagcacag ggttgggggg taaggtcaca gatcaacagg atcccaaggc   9360
agaagaattt ttcttagtac agaacaaaat gaaaagtctc ccatgtctac ttcttttccac  9420
acagacacgg caaccatccg atttctcaat cttttcccca cctttccctg cttttctattc  9480
cacaaaacca ccattgtcat catgccctgt tctcaatgag ctgttgggca cacctcccag   9540
acagggtggt ggccgggcag aggggctcct cacttcccag taggggcggc cgggcagagg   9600
cgcccctcac ctcccgggtg gggcggctgg ccggcgagg ggttgacccc cccacctccc    9660
tcccggacgg ggccggctggc cgggcgggg gctgacccc ccacctcccc ccggacggg     9720
gcggctggcc gggcgggggg ctgaaccccc cacctccctc ccggacgggg cggctggccg   9780
ggcgggagc tgaccccccc ccaccttcct cccggacggg gcggctggcc gggcagaggg    9840
gctcctcact tcccagtagg ggcggccggg cagaggcgcc cctcacctcc cggacgaggc   9900
ggcaggccgg gcggggctg atccccccac ctccctccg gaagggctc ctcacttccc      9960
agtaggggcg gccgggcaga ggcgcccctc acctcccaga cggggcggct ggccaagcgg  10020
ggggctgacc ccccaccctc cctcccggac ggggcggctg gccgggcggg gggctgaacc  10080
ccccacctcc ctcccggacg gggcggctgg ccggcgggg ggctgacccc caacctccc   10140
tcccagatgg ggcggctcgc ctggcggggg ctgacccccca cctccctcct ggacggggcg  10200
gctgccaggt ggagacgctc ctcacttccc agacagggtg gctgccgggc ggaggggctc  10260
ctcacttctc agacggggcg gctgccgggc ggagggtctc ctcacttctc agacggggcg  10320
gttgccaggt ggagggtctc ctcccttctc agatggggcg gctgggcaga gacgctcctc  10380
acctcccaga cggggtcgcg accgggcaga ggcgctcctc acatcccaga cggggcggcg  10440
gggcaaaggc actcccccaca tctcagacga tgggcagccg ggcagagacg ctcctcactt  10500
cctagatggg atggcggccg ggcagagatg ctcatcactt tccagactgg gcagccaggc  10560
agaggggctc ctaacatccc agacgatggg tggccaggca gagacgctcc tcacttccta  10620
gacggggtgg cggccaggca gaggctgcac tctgggcact ttgggaggcc aaggcaggcg  10680
gctggaggcg ggaggttgta gcgagccgag atcacgccac tgcactccag cctgggcacc  10740
attgagcact gagtgaacca gacaccgtct gcaatcccgg cacctccgga ggccgaggct  10800
ggcggatcac tcgcggttag gagctggagg ccagcccggc caacacagcg aaaccccgtc  10860
tccccaaaa aaatacgaaa accagtcagg catggcggcg cgcacctgca ctcgcaggca   10920
ctctgcagge tgaggcagga aatcaggca gggaggttgc agtgagccga gatggcagca   10980
gtacagtcca gcttcggctc ggcatcagag ggagactgtg gaaagagagg gagagggaga  11040
ccgtggggag acgagaccg tggggagagg gagaggaggc agagggagag ggagaggctt   11100
tttttttttt tcttgagac ggagtcttac tctgtcaacc aggctgggagt gcagtggcac   11160
gatcttggct cactgcaacc tccacctccc tggttcaagt gattctcctg cctcagcctc   11220
ccaagtagca gggactacag gcatgcgcca ccacacccag ctaattttg tattttagt     11280
agagatgggg tttcgctgtg ttggctgggc cagtcttgaa ctcctgacct caggtgatcc   11340
acccaccttg gcctcccaaa ttgctgggat tacaggcgtg agccaccgcg tccagcctgt   11400
tacattctta attgaaatag cattgcccct cagtgccatt atctgaaata gcttttaaga  11460
atgaatgtaa tgccatttta aatgtattta aatgttgtgc cgatttaatg ttctatgtac   11520
ggtacagtac tactaatggt tcaagaagtt gttttgactt aacagtgaaa tccttgcttt   11580
taaagatcat agatacctt agacaccttt aagatgaaac atgtttatga gaggaaatgt    11640
ccgcacaaat acaatcccccc gcaaacttag catgtggttt tagtaggttc ataggcccac   11700
ctggtgatcc ctaggataag aaattgtggt caagaaactg atttcagggg ccgggctggt   11760
ggcttacacc tgtaatccca gcactgtttg tctcaaaaca aagaaactgg ctcaaggttg   11820
gatactttc aaacgagagg aatggaggaa gggaatgcaa tgaataactt ttcaaatcca    11880
gtatgtctga tttaatatgc cgtttgctct gtcagtttca tttggttcgt gtcactgatc   11940
atttataacc tttttttcaaa ctgctttcat tccctaaagg aaaatctgat actgaattat  12000
tttatttctt ctttcactat atttgaacgg ttttatagtc tgaaagctat caatttctca   12060
ttacagttta cttcatagta cttctaggaa ttcttcctgt ggtttgaggt aaggctacag   12120
gattcctaga gtttgtaccc ctcagtcccc agtaaaggac ctggtacatc aatcagggta   12180
gccctagaaa gttggagtaa cttcgtaaca gtgggaactg cttctgttct atgttttttg   12240
tgggtttttt atttgttttt gttttttttgt ttttttgttt ttttttgag acagagtctt   12300
gctctgtggc cccaggctgg aatgctacgg cacgatctcg gcttactgca acctctgcat   12360
gctgagttca agcgattctc ctgcctcagc ctcctcagta gctgggatta caggcgtgca   12420
ccaccacgcc cagctaattg ttgtattttt agtagagaca gggtttcccc atgttggcca  12480
ggctgtcctt gaactcctga cttcaagtga tcagccacc tctcagagag ctgggattat    12540
acatgtgagc caacatgcct gccctgcctc attctttata ctacagtaaa gtcccggttg   12600
ggcaataatc taaacataaa agaaatgaaa ccataaaatt atataagaaa acaatggaga   12660
aaattttttg taatcaacag agtgaaaaag gatttttttaa tgccatgtca cagaaaccta  12720
gagaaaaaag gtttaagttt gatttcataa aatttaaat ttttgacata aataccataa    12780
aggtaaaaag ataaaaaatt ttaaatattt tcaatatata acaaaaacta aacttttctta  12840
atatgtaaag aactacatat caaaagaga gcgaaatac agatggcttt taaaaacagg     12900
taaagctgtt caccttcaca ataataacaa tttcaaatta tgactataat aataccattt   12960
ttcacctatc agacaaagat gaaaagttc attaatataa ttgtgtaggt gaagctcagg    13020
cactttctta tattattggt gacagtatac attgatatag cttctttgaa aggttattca   13080
tagcagcatt atttataaca gctaaaacct agaaataacc tatgtgtccc attatagatg   13140
```

```
actggctaag tgatgaatac tattaaattg ttaaaaagaa ctcattatct atatggaagt   13200
acttttaata tatactaagt gaaaaatcaa agtgcaaaac agtatgctaa tatctgtttt   13260
gtgagggtgg gatggatact tggatggagg aagacagaca ggcagtctgg cttatatatg   13320
gatagaatgt ctcggaaaat atacaaggca ctggttacag ttatcaccta agggaaagga   13380
ttgagggaga ggagaatgtg acttaacttt ttcactatat acccttttgt acggtttaat   13440
ttttgccaag tccatgtaat ccatgtatac atagggagca tatgtatata aatatatgta   13500
aatataagta aaaaaatatg tatgtgctgc cgggcgcggt ggctcactcc tgtaatctca   13560
gcactttggg aggccgaggt gggcggatca tgaggtcagg agatcgagac catcctggct   13620
aacacggtga aaccccgtct ctactaaaaa cacaaaaaaa atagccgggc gtggttgcgg   13680
gcgcctgtag tcccagctgc tcgggaggct gaggcaggag aatggtgtaa acctgggagg   13740
tggagcttgc agtaagccaa gatcgcgcca ctgcactcca gcctgggcaa cagagtgaaa   13800
ctctgtctca aaaaaaaaa aaaaacaaca cgcttttctc tctctctctc tctctctctc   13860
tctctctctc tctatatata tatatatata tacacacata tatatatacg tatatatata   13920
catatatata cgtgtatata tacatatata cgtatatata tgtatatata cacatatata   13980
tacacatata tatgtatata tatacatata tatacacata tatatgtata tatacacata   14040
tatatgtata tgtatatata tacatatata tatatatgct aaagttaagt actggattcc   14100
tatctgtatc tgctacctaa ctgcagtata aatcttggaa gttgagtctg tttcctcatt   14160
tgtaaccacc tcttagataa cacacataaa agcacatagc acatgcctga cacacagtag   14220
ggttcagtga cagtgagctg ttttagtctc taaactctct tcctcaaaga gagcttctca   14280
aagaaaaaaa aatgtagtga agaaaagaac ttactccacc agggatcttc tctcccccagc   14340
cagtggcagg catattaagg gctataagta agtggttatt ttaccatcct aaagtaatgg   14400
tgtttcaaag tatgcaagat tcttcatact tcactgtgtc cttttctgag catctttgta   14460
gagagtatat gcacaaacat ctgactaaca aagggaacac ttttcatcat ataatttagg   14520
attcacttag agacctaaag tataaagaaa gaaacttagg tatgttagcc cataaggaga   14580
aactcattat caatttggga ttatcttaag gtcctacctt ataaaattaa aatttaacag   14640
aagattattc tttttcaatt tcctaagttc ttattgctta ctacatcgta gcagttcgag   14700
ggagaatttg gtctaacgat gtaatgtttt ctgtatgcca tacatagaac aaagctatgt   14760
acgaaatact aaaaatatta tttgacatta tttaataaaa tattataact atttcaccccc   14820
gataatgatg gaaattaagt tgcagtaata tagatttta aaataaaaac ttcaaaacca   14880
ggcgccatgg ctcacgcctg tgataccagc gctttggaag gccgaggcag gcagattgct   14940
tgagaccagg agtttgagac cagtctaagc aacatagcaa ataaaaataa aaaattagcc   15000
aggcatggtg gtgtgcctgc agtcccacct acttgggagg ctgaggtggg gggatcactt   15060
gagcccctga agtcaaagct gcagtgagct gtgatcacac cactgcattc cagcctgagt   15120
gacaaggcaa gactttgtct caaaaatata agtaaaataa aattaaattt ttacttgttt   15180
atttttttga gacggcgtct ctcttttttcc caggctgggg tgtagtggtg tgttctcggc   15240
tcaccgtaac ctctgcctcc ggagttcaag cgattctcct gcctcagcct cccgagtagc   15300
tgggattaca ggtacgtgcc actatgccca gctagttttt gtactttttag tagagacagg   15360
gttttgccat gttggcaagg ctggtctcaa actcctaatg tcaagtgatc cgcctgcctg   15420
ggccccgcaa agtgttggga ttacaggcgt gagccaccgc acccagcctt aaaactttaa   15480
aattcagaat atgagccttt gtttttatagc ttcacttgtt aaaacaaatc aggagctggg   15540
tgtggtagct cacgcctgta atcccagcac ttggggaggc tgaagcgggc agatcacctg   15600
gtctcaatct ccctgaactc gtgatccgcc cgcctcagcc tcccaaagtg ctggaattac   15660
aaacgtgagc caccacgccc ggcctgaagt ttgaagtttt taaaaagaaa gagttgttag   15720
gcataattgt gtaaatagag gtaaaaattg acagcaagaa aggcagtaga aaactatgac   15780
aaatgaaggt gatggctcac gcctgtaatc ccagcacttt gggaggccaa ggcgggcgga   15840
tcacctgagg tcagtagttc aagacaagcc tggctaacat ggtgagaccc tgtctctact   15900
aaaaaataca aaaattagcc aggcatggtg atgtgcacct gttatcccag tcacttggga   15960
ggctgaggca ggagaattca cttgaacccg ggaggcggag gttacagtga gctgagatgc   16020
cgccacttca ctccagtctc tccagtcagt ccagacagag tgagactcaa tctcaaaaaa   16080
aaacaaaaaa caaaaacaa caactatgac aaataagtgt aatttcccag gactattaag   16140
gtcttgtaat cccatgcact ggaagctttt gttgttgttt tctgatttat cattgaagtg   16200
accaaagcgc agtggtaaga acaagccttt gtgattactt cacactagag aagggtcttt   16260
cccacatatt tgagacttaa ggagttgata gtgaacagtg taagcggcca cacaggtgtg   16320
ggttaagaac tgatgtgtgt attcactttc tgtaaagatg accaaacata tgttgttaga   16380
caaacgaaaa attcacccca agatcattga gggcatgcaa aatagtatga ggtagaggca   16440
gctgtaattc aggtgtccaa atacaagagc aggtggagaa aagaaaagaa actgagaaca   16500
gtaaagagtt tttaaagtta taacacacaa ttgttaaaat agaatgttca gtaccaagta   16560
gcagagtaga taatgcagaa cactgaggtg gcttgagaaa aatctctcag aactcaggaa   16620
agaggtgtgc gaaatgagcg ttaggagaga gcacttcccc aagtctgtga tagaaattcc   16680
tgaaagggaa cagaggagac tgaagcgaaa ctctattaag cgacaaggaa gactcaaatg   16740
gagaagctaa cccagttccg atgaagactt ggcacatatc tataatgtat tttttttgaa   16800
gtcagccaaa agaaagttta aatttgaggt acatctgaaa gagtaagcaa tacagaaaaa   16860
tcttgacaac atctgaggac aaaaaaaaaa gtactgatac tgttgagtgt gaggcaaaac   16920
ctcactttca gtctttcttg agaaatattg gcaaaatatt ccccttaatac aggagttcca   16980
tttttatttc atttatttat ttatttattt atttattgag acaggttctc actttgtcac   17040
ccaggctgga gtgcagtggt acagtcactg ctcactgcag ccttgacctc ctgggctcaa   17100
gtgatcctcc cagctttgcc tcccaagtag ctgggactgc aggcacgcat cactacgctt   17160
ggcttttattt ttatttttta tgtgtttatt tttattttta ttttttgtag atacgtggtt   17220
tcaccatgtt gcccaggctg gtcttgaact cctggcctca aatgactcc ctgccttgcc   17280
ccagagtgtt tttgtttttt tttttgttt gtttgttttt tgttttttgg agacaatctt   17340
gctctgtcac ccaggctgga atgcagtgag tggcgcgatc tcggctcact gcaaccaccg   17400
ccttctgggt tcaagcaatt ctcctgcctc agtgtcccga gtagctggga ctacaggtgc   17460
ccaccaccat ggccagctaa tttttgtat ttttagtag atggagtt tcaccatgtt   17520
agccaggatg gtctcgatct cctgaccctg tgatttcct cggcctccca aagtgctggg   17580
attacaggca tgagccacca cgcccggccg agatatattt cacataccat aaaattcacc   17640
taaaaggtac agtttagtgg ttttagtat attcacagct gtggaactaa atcttaattt   17700
cagaatattt tcaacaccc aaggagagac tgggtacata cagttattct ccattctcac   17760
ccacatccca accctgaca accactaatc tactttctgt ctccagattt ccctgtcctg   17820
gtctcatacc atgtgtagtc ttttgtatct gttttttgt tttgttttgt tttgtttgt   17880
```

```
tttgttttgt tttgtttttg agaggagtct ggctctgtcg cctaggctgg agtgcagtgg   17940
tgcaatcttg gctcactgca agccccgcct cctgggttca cgccattctc ctgcctcagc   18000
ctccccagta gctgggacta caggcgcccg ccaccacacc cggctaattt tttgtatttt   18060
tagtagagat ggggtttcac tgtgttagcc aggatggtct cgatctcctg acctcgtgat   18120
ccacctgcct cggcctccca aagtgctagg gttacaggcg tgagccaccg cgcccggctg   18180
gtttctttaa cttagcataa tgttttaaag tttcatctgt gttgtatgta tcattctttt   18240
gtttcttctt ctaagttagt aagattccat tatatagata tataccatttt tgtttatcca   18300
ttcaccagtt gatggacaaa tgattgtttt agctattatt aaaagtgcta ccatgaacat   18360
atgtgtccaa gtttttgtgt gaatgtatgt attcgttttct cttgggtatg tgccttggag   18420
tagaatagct agttcatatg ttaactcttt gttcagcatt tgttttcta aagtggctac   18480
atcattttaa cctttagttt tttgttttt ggtttttttt ttgggagtgg ggtggggctg   18540
gagtgcagtg gcgttatctc ggctcactgc aacctccgcc tcctgggttc aagcaattct   18600
cgttcctcag ccttccgagt agctgggact acagacacat gccatgacgc ccagctcact   18660
ctttttgccc agctcactct tttttattta gtagagacag ggtttcacca tgttgcccag   18720
gctggtctca aactcctgag ctcaggcaat ctgcccacct cagcagggtt tcaccgtgtt   18780
gaccaggctg gtctcaaact cttgacctca ggcgatccac ccacctcagc cttccaaagt   18840
gctaggatta caggcatgag ccactgtgcc ccgcctctct ctttttttttt tttttttaat   18900
aaagacagag tcttgctctg ttgtccaggc tggcatgcag tggcgtgatc acggcttact   18960
gcagctttga cctcctgagc tcaagtgatc ctcccacttc tgcctcccaa gtagctggga   19020
ccacagatgt gtaccaccat gccttgctaa ttttaaaatt ttttaataga gatgggggtc   19080
tgtctgtgtt gcccagactg gtctcaagtg attctcccac ctcagcctcc caagtattg   19140
ggattgcagg catgactcac agcgcctggc ctcagttttct ttcaagacca tcctataaca   19200
ccaagttagt ttgaggattc tatgaatgtc tgcttaaaga tatccttctg aattctgtga   19260
ttctcttgaa aggcttgttg caatgaaaaa caaagtataa tgatgacttt atgtgaagta   19320
tacttttgga atttcttaag cagaagtcct gagactttg agagtccctg tatttaaaca   19380
gtaccattta ggcacagtta ctgcttatga aatgaagagt agctagatga atataaaaaa   19440
tcttactctt acatttcaac ccagcattat ttgaacccag caaaattatt tctatagtag   19500
aatcaattta gttcctatt ttaagccatg catatatatc tcaaagcaaa tttcaagagg   19560
gattaaatgt tattatgtga aaatattagg aggtgaaata ataggagaaa gtaaacacat   19620
tgaaagtagg tatgttcagg ccaggcgcgg tggctttatgc ctgtaatccc agcacttgg   19680
gaggctgagg cggcagatc acgaggtcag gagatcgaga ccatcctggc taacacggtg   19740
aaacccgtc tctactaaaa atacaaaaaa aaattagccg ggcgtggtgg cgggcatttg   19800
tggtcccagc tactcgggag gctgaggcag gagaatcgat taaccctgg aggctgaggt   19860
tgcagtgagc cgagattgca ccactgcacc ctagcctggc aacagagcaa gactctgtct   19920
caaaaaaaaa aaaggaaagt ggtatgtttt acaatttaaa atctttgggc atggagataa   19980
gctataaggc cattgatcag aatgaccat ttcataatgt tccaaaaatt agactacttt   20040
ggaaaaaggt ggtgtgtggt cttaatgtag gcaatgcaca tgtgtgttta agtttcaaat   20100
acagctaagg agctaagtgg aattttttt tttttttttt accaaatagc gtgtattaat   20160
aatagctcag ttccatttac tgatttgttt ttcctttgtt tatgtcatat attatctttc   20220
caagagattg tgagtttatg ctactgccaa tttggtatga gggcctgttt ttaaaagagc   20280
tgcatgatat tcacttggat gtaccacgat ttattcaacc agtctttct ttgtcattag   20340
acatttagtt tatttaaagc cttttcaacat tataagtaac tgtgaaagat atctttgtgc   20400
tatgagttgc ctacattttg gatcattgcc actaagaaga aaattaacta gtgactcaat   20460
tattccttgc tttttttgag caaaaatcat attaaaaata attagattta aaattttgg   20520
ttaaattata ctttaaagca aagatccttg ccatttagat ctagtttggt attaaatgag   20580
aacgtggtt ctctactgtg ttggtggggg atatgttcat gatggatttt gctgtggaag   20640
gacatttgc aatgcctgga gagagttttg gttgttacag atgcagggag gggtgccaact   20700
gacatctaat gggtagaggc cagggatgct gctgctaaac atcctgcaat acacaagaca   20760
gtccccactt gccccccccc cccaaaaaa aattagctag cctaaaatgt cagtagtgct   20820
gaggctgaga aaccttggat taacaggttt cactgctgat gggaaacttt ttttttttta   20880
acagggcctt actctgttgc ccaggctaga gtgcagtagc aggatgctag ctcactgcag   20940
tcttgaactc ctgagttcaa gcaatcctcc tgtctctgcc tcccaagaag ctggaactac   21000
acatgcacac caccatcccc agctaattaa aaaaatttt tggcagagct ggtgtcttac   21060
tgtgttgccc aggctggtct caaactccta ccctcaagtg atccttccag ctgggcctcc   21120
caaagcacca ggattgcagg tgtgagccac tgtgcccaga ggaaacattc ggaatctgtg   21180
atagaagggg aaggttttag ctccagaaca caagtagagc tggctttgcc ttatgtgata   21240
gacctagtga atagctcagc tgtctgcttt cctaatgcca tttagacaga tactgtatat   21300
tttattgctt atgcaatgtg cttataaaat tgttttatttt tgtgtcttgg gtattcctga   21360
aaatgcctca tcagtgtcag atctagtttgc tgttgagatt tggttttgct gcgtatatta   21420
cagacctgat ttagctacat gggaaagaaa attaatcaat agctgattta acaaccagga   21480
gtttatgttt ctcatgtgat atgaattctg gagagagact taagggctgt tactgtggct   21540
tcttgatgtc acccatgact caatgctggt atttctgctt acctttctta ggaatgtgca   21600
ttttaccttg ctgtcacagg atggctcctg cctgttccca ccctcaccc ccggcagcaa   21660
aacctatgtt ccaaggcagc agcagtgagg acaaaggtac tcctcttgt   21720
cagcgttttc ctgcagcccc aacccagtgg tttctgctta ttccattgg ccagactgtc   21780
acaggacctt agaggctggg acaaatagtt ttcagctggg ctcattgtgg tctgaaaaca   21840
aaagcagtta cctttagtaa gaaagaaagg atattgggc tgggtgcagt ggctcacgcc   21900
tgtaattcca gcactttggg aggctgaggc gggcggatca cttaaggtca ggaattcaag   21960
accagcctgg ccaacatagt gaaactccgt ccctactaga aatacaaaaa ttagccaggc   22020
atggtggcgc atgcctgtaa tcccagctac tcaagaggct gagacaggag aatctcttga   22080
acccgggagg tggaggttgc agtgagctga gattgcacca ctgcactcca gcctgggcaa   22140
cagagtaaga ctctgcctca aaaacaaaa aaaaaaag aaagaaaag aggatattgg   22200
aataaacgct aatatgcacc tttgggagct gcttttttgaa atattggttc ttgtaagttc   22260
actgaaattt tttttataaa gtagaacaat atggagatt tgaaagaatg gactcaatgc   22320
aagagatctt attagctgag aaaatgtatt tatgttatga atgtatttct taaccccaag   22380
aacttggctg ttgtattgtg ttttgtaaat tttaaatctc cctactacta tactgggggc   22440
cttaccctct tttgtatagt gcacacaaag aagtgtgttt ctctgggcta aaaatagaaa   22500
tctgcacctg acagatggcc ttaagtgtgg aaaatgggtg tgtgtgtatc acagaagtgg   22560
aagaagtgga gggagtcctg ctctgcctgt tgttttaagc ctccccctccc tgcaaatcta   22620
```

```
tatctttcct atacactagt aatggtcaat aggttttgt tgttgttgtt gttttaatcc   22680
catttacagt agcgacaaaa cttatcaggt atctaagaat aaacctttat tatacattta   22740
tgctaacctt tagcatacct ttatgaagaa aactacaaaa ttaattaaaa tatcatgaac   22800
ggcaatgcaa atgggagaa taaatagggg acaacttgcc ttccagatgc attgattaca    22860
aagctgtagt aactaaaatt tgatactgtc tcaagggcaa gcaaatgctt ctgtgaagta   22920
gaatgaggat ctagaaacag actcctgcgt gtgctgaaac ttggtttatg atagagcagg   22980
tgttactgat aaatgcagaa accaataaat ggtattaagt caattaactt tccatttgga   23040
agggataaaa ttaaatttct cttccacgtg caggctaata acagtgtctt atatcttgca   23100
aaagtactta ccagtccatt cacttccaga aaaatggaga agtttcatat tagaaatttg   23160
tgcatcatgt ttcataaata aaaacttcag atactcggct gatggtgttg gctcaaacct   23220
gtaatcctag cactttggga ggctgaggca ggtagatgac ttgagcccag gtgttcgaga   23280
acagcctggg caaaaagtga gacccctatgt ctataaaaac aaataaacaa aatggcacct  23340
aacttttaaa atgcttttc ttacatgtaa taatgtgagc aaaagcataa tttaattttt    23400
cctattaaaa tgctttttt ttggtttctg ttacatttct gtatttactt gaattcttag    23460
aacactgttt cctgggagat caaacctggc cattctggat acatcagtag tgagagctta   23520
gtgcggacat agccttacag aatgtcttct atgttgaaat gcagagaacc cgaaggcgcc   23580
taggatgagc ctcaggcctg ctggttgttg cagtggcgca atctcagctc actgcagcct   23640
ccgcctcctg ggtttaagcg attctcatgc ctcagcctcc tgagtagctg ggattacagg   23700
cgctcgtcac caggcttggc taattttgt tttgttttgc ttttccgcc tcactctgtc     23760
acccaggcta gagtacagtg gtacgacctc ggctcactgc aacctcagcc acccggtttc   23820
aagcgattct cctgcctcag cctcccgagt agctgggatt acaggtgcct gccatcgcgc   23880
ctggctaatt tttgtagttt cagtagagac gagtttcac catcctggcc aggctggtct   23940
tgaactcctg acctcgtgat ccacccacct cggcctccca aagtgctggg attacaggca   24000
tgagccaccg cgcacagcct aattttgta tttttttggg gttttttttt atagagtctc    24060
actctgtcgc ccagactgga gtgcaatggc acgatcttgg ctcactgtaa cctccacctc   24120
ccgggttcaa gcaattcttc tgcctcagcc tcccgagtag ctggattac aggcacccat    24180
caccacgcct agctgatttt ttgtatattt agtagagacg ggtttcgct tgttggcca     24240
ggttggtctc aaactcctga cctcaggtga ttccccgcct cggcctccca aagcgctggt   24300
attacaggtg tgagccacca cacctggcca aattttgta tttttaatag agctgggttt    24360
tcacaatgtt ggccaggctc gtctcaaact cctgacctca gggaatccgc ctgcctcggc   24420
ctcccaaagt gttgggatta caggcgttag ccactgcgcc aggcttgttg ctgaacattt   24480
atggctctag aaataattt ttttttaagg agaagtaatg acaaacatga tagaaataaa    24540
atttgaggat atttctgggt tcaaaataaa gtaacagtta aatagcgtga acatgaagaa   24600
ataaatattt tcaggtagaa actccaaaat ttaggtagat gctgtgagtt ttagtcagaa   24660
tttgaatatg atgtggctga ccatagatac ctccattgca ttaattctgc ttcataaagt   24720
gtttgatgct tgcttgtagg tgttaatag agcctaatta gcagtaagta aacagatcta    24780
gagcacagac tttggcatct gaaggaccttt ggttcaatgc tgggactgcc acttactagc  24840
tatgggatct ttggtggatt tttaacctttt gaaagccttt catccctcac agatataatg  24900
gggaagaaaa tcgtttccat tagtattgtg aggattaaat gattaattga tgtaaacaat   24960
gtgcttttcca tagtacttgg catatcataa gtgcttcatg ttatttttacg ctggctggga  25020
agataagttt tgctgtggag aatttaagag ggatattaaa atatatttttt gttatttttaa 25080
ggaaattcga aatgagtccc atgactatcc tcatagagtg gccaagtttc cagaaaaacag  25140
aaatcgaaac agatacagag atgtaagccc atgtaagtac ttgtgggttt gtgtgcatgt   25200
gtatttttttg gttttgtttta ggaggcagga tgtagtgaaa aggagggctt ggggtcagtg 25260
ttgataaata cagtaatttt tttcctattt acgtaagaca cgttcttaa gaatttaaag    25320
gtgtagaata gtggaaggaa aataattac ccataattat ttcatccttc aaacataggc    25380
accattattt tggtgtattt cccacaacct gttttcctta tgcacagttt tccttttttt    25440
aaaataattg taattataga tgtctatata atatccatat gtatttccctt ttcatatcat  25500
tccatcccct ttgtaagttt tgcttaaaat agttattggt gtagtttggt ttttttcctt   25560
ccccaagtta taagagtagt atgtactcgc tgtagaaaac ttagaaaaca gagaagagta   25620
taaggaacaa acttattaa aaataaataa taacttggtt ttatattctt tggagttttt    25680
aaaaataaac atgtacttta aacgaaaat tagaatcttg ccacatactc atttgtagct    25740
cttttcttag cagtacattg taaactttt tttattataa acaatttta attgctttga    25800
cagtggcttt ggatatacca ctcttttgca taagttccct gttgttggac atttagatta   25860
tgatgtatac acacacagac gcacacaatt gtgtgaacaa ttataatact agagttcttt   25920
ggtgtattca tcatcatgcg gtgattttat tttttgttct gattcatgca gcttattcag   25980
atattaaatt gggcctcctt cgtgcttcag catatttccc tatgtttgac tttagtgggc   26040
taaacatagg ttttctcttt agggctccct gttggtaggg acttgaaaaa cagtatcaga   26100
ttgatcacat tctggttttt gcttgttact gattgttcgc ctgttgacta gggtatggtg   26160
ctgcctgcta agatcctg tgtaggttga acctttttgca tgttcaagga cacagactgt    26220
ataccttttat atacattgta gtcattggtt atagataaga tatttagggt ctggatgtac   26280
cactgaaaaa tccatcagtt actggaaaaa aatcctatt ttattctta catgaataga    26340
atgttttttct tatgttgacc aaatacattt ccaagaaggg tgtattggct gattttgggc   26400
aaatcaaatg agaagcagtc tctgaaatc tttcatgttt gttataaatt actattaaat    26460
actatgtttc tcttaatgct ttttttctta ctaccagtta gaagtgttct taaagacaag   26520
tagctagaag agtggttttc cattttcttc agttgcagca cacttgaaga tttgacccac   26580
ttcctctgaa acaggtggct catcacggtg gcagttccag tgtgggtgtg cgttcaggga   26640
atagcgggtg tgggcagtaa ttctgatact taggtgccct tccccgtcct ccaaatctct   26700
gattgagaat cactgagcta cagagaataa ttctcatgaa ttaccatgag ttttgaagac   26760
agtatttttcc agttgtacac cttgctttga tgcctttaat tttttaaaaa cttttgattt   26820
tgaaattgt agatttggat gcagttgaga aataatacag aaagatcgag tatcccctc     26880
acctagtttc ccccagtggt aacatcttgc ataactacag tccaatatca cacctgggaa   26940
cctgaaacaa tacagtccat ccaggtttca ccagttttac atgcactcat ttgtgtgtgc   27000
gtgtagttc tgtcagttt tatcacgtgt agattcctgg aatcaccacc acagtctaga    27060
tgcaaaccag tggagcattc ccatcacagg gtcacttgca ctgcctttct ggggccacag   27120
tctccttgct tggatcctcc ttccctaacc tggtgttgcc tttaatttt atatatttgt    27180
tgtaattgca attattggat gcactacact acatttgagt cccctaatta gttttatcga   27240
attgatctaa atgggatttt ttttttttt ttttgagat ggtgtctcac tctgttaccc     27300
aggctggagt gcagtggcgt gatcttggct tactgcaaac ccctgcctcc tggattcaag   27360
```

```
cgattctcct gcctcagcct cccaagtagc tgggattaca ggtgtgcacc accatgcccg   27420
gcttatttt gtatttttag tagagatgga gttgcaccat gttggccagg ctggtcttga    27480
actccttacc tcaagtgatc cgcctgcttc agtctcccaa agtgctggga ttacagtcat   27540
gagccaccat gcccagctga taattttatt ttaactggaa ttgagatgtt ttattttaaa   27600
gtaaaaacat ttgcaactta agttatcctc aagtatatac atcaataaaa cttatgattt   27660
ttctcctcag cttttagact tatgttgtat acctgcagtt gaaggctgca gggagactct   27720
ttaaaatatg cgttatcagg cctccctcca tcatcattgg gaccaggctc ttcctgtatg   27780
ccttctcatt gaaaagcact tagccttgag agaaccaagc ttccctcctg cggaccatgc   27840
agtggttgtc ctctggagct gtgctctgct gggagcagcc cccagtgcat gttctcctta   27900
ctcttcttct tctttgcccc ctcccctccc acacatgcct ccctagtaag ccatgttctc   27960
ctgatctctc agaaagagac tgctcattct tgcttctcac gtagccacag gattttctag   28020
tctgagccaa tatgcttcag cctgcaaatg gaaatgatct cttccaaggc ttgtgctggc   28080
cagcacatcc ccacaccgcc ttggcacctc tcctctcctg acttcagtca ttcactgtct   28140
ttctccttac cctctccttc ccaccttcct catcctgggt gacttcatgt ctctgggaaa   28200
gaactacggc tcattgcgct agagttccta gacctgttca gctccgctga cattgacctt   28260
tagtcatctt cacctctgaa atctgaaact ctgctgcctt gagggctact ttctgtcatt   28320
ccagctttca cttgcttact cccactgtac ctgctctttg acttcagcag gatctttagt   28380
tgactttttc atgtattgtg aagttggaaa tgtattgaat tgaaatttcg attaaaaaat   28440
gtagtgaagc atattacttt gtcctctaac ctaactatta ataactttct tgttgttttt   28500
atatttaaaa aataactctg gatttttaa ttccaccatt ttgtgaagct ccaacttagg    28560
aaaaatcagt cattcatcct ctctgcactt tgggcaaatg agcgtgtgcc ttgggtggac   28620
tccagtgtta ggtgggcttg gggttgcctt gctgtcctca tgccctcgtc tgccccactg   28680
ccaccgtgtt ccagctctgc accgagtaaa ttatctctca gagctcctca ccatgctcag   28740
gatatcgtcc tgctttcaat tctacagata aaaattgtaa aaatcaggaa acaccacctt   28800
agcttcatgt tctatcacct ggaaactcac tttcttttgc ccctatcctt ccctaaagtc   28860
ccaggagaga agcctccctc ccctctgtcc tagccgaatc cttcgtcccc atcctcctca   28920
tgggccctgc tcttcatcat cactgctttt tgtgtgtttt cagcctcttt ctatctcata   28980
acttcttctc ttttgtataa atatggttcg ctctctttg tctcaaccct tatatcctac    29040
cccagccccc acttcctttc ttacctacat ggatggacat ttcttacctg tacacaggct   29100
taaaagaatc aatgtgccat ttgtctctcc accctcccca ccatgcacac ttcagcccat   29160
gcttcttctc cagcctcccc actgaaactt attctaaaag cactgtagct gtagttgtca   29220
aatgcaatga gagactttcc actggtttcc ttctctgtga cttttgacat tattctcctg   29280
cttcagcctc ccgagtagct gggattacag gcacgagcca tgacgcctgg ctaattttg    29340
taattttagt agaaacaggg tttcaccatg ttggctgggc tggtctcgaa ctcctgatct   29400
caagtgattg gcccacctcg gcctctcaaa gtactaggat tacaagtgtg agccactgtg   29460
cccagccgac cgtgcctttt ttcctaaccc cgtaattttt ctgattttcc tctttggccc   29520
ctccccatt ttcagggtgt ctcctcctca ctttgccttt atttcttcag gagtctgttt    29580
ctctctcctt ctcactgtaa cacttggatg aatgatctca tctgctgtgg gcctagttc    29640
catctcgct tataacccca aatctcatct gcagtcgtgg acttttctgt ctacaggtct    29700
gtgtatccaa gtcatcatct ctgtctgggt gtcctgtagc cacctcagac tcagtataca   29760
ctgagtgagt gttcctccct gacacacttc actggcctta gccccacacc tgccttttct   29820
cctttccccc atgtttataa gtggtgccgt tatttacaca ttttctgaag ccagaaacag   29880
attcttccct cattcattc ccacgtcact aatactaatt tccatttcca tcatgtattc    29940
ctatttctt ttcttttttc tttttttttt ttttcaaga cagggtctgg ctctgtcact     30000
caggctggag tgcagtggca ccgtctcggc tcactgcaac ctccgcctcc caggctcagg   30060
tgatcctccc acctcagcct cctgagtagc tgggactaca ggtgcatgcc accatgctga   30120
gctagttttt tagatttttt gtagagatgg ggtttcgtca tgttgccag gctggtctca    30180
aactcctgga ctcatgtagt ccacctgcct cgacctcctg atgtgttggg attacaggtg   30240
tgaggcaccg tgctcagcct ccgtaatgta tttcaaatct gttttcttct ctgttcacat   30300
tggcttggtt caggccctac tacgcttttc ctcgtcatta cagtagcctc caaacccatc   30360
tccttgtttc ccttctgttc ccacttcagt ccatttttcat ggtatctgga gtaatcttta  30420
tataatgcaa gtgtgttttc cactctcctc tctaatagtg ctgcacaatt tttatgaaaa   30480
agttaaactt ctttagcatt atcatactgg gcttttttgga gattgacccc tttacacacc  30540
tctctaaatc ttttctaccc atttttcctag aaattattca tttcagtaaa actgaatcac  30600
ttggagttct tctagcgtga ctggtttta atacctcagt ggcttcaaat atgtcattcc    30660
cttttgaaa tattcttccc ctcctctctc tgacccatct caatcaaagt tctccttctg    30720
caaataccag ctcaacaacc tctttcccgt gagtggtatt tcatccagt ggaggtggtg    30780
gttctcgttc actaagtcca gaggggctca ggaatgtgta ttttttaaaa gctgggatgg   30840
tgttgctgta ccttttccaa ctgatagtca ttatgtaatt taaaaatgtag tttctggctg   30900
ggtgctgtgg ctcatgctta taatcccaac actttggaaa gctgaggtag gaggattgct   30960
taaggccagg agtttgagac cagcctgggc aacatctcta cacagaactt tttttttaatt  31020
agctgggacg tggtgatgca tgcctgtagt cccagctatt tgggaggctg gggcaggagg   31080
atcacttgag accactaatt caaagctgca gtgagttgca atggcaccag tgcactccag   31140
cttgggtgac agagcaagac tgtctctaaa aaattttta aatgcatttc tatacatagt    31200
acttgacagt tgctgatttg gttcagaaaa catttgttga aaaccagcta catgtttgat   31260
actatgctat gtatcgaata atttatggta tacttgagga gattaacaca taagcatgtt   31320
acagatattg taagatatga cagtgcattg atggagctga aagaggctc tgcccaagga    31380
ggcagggatg gcttttaaga aaaagaatgg tagcctgaac taggtaaata aagggaaatg   31440
gaaaaagaat tttttaaaaa ttcagagtcc cagatctttc ttttctagat ttggattcag   31500
ccggtctgga aatgtttatt tttaaacaat cttaacatga ttctttaca ctcactatgg    31560
caccactcct cagactgaca tatggaaact acatttggag ttctgaatac gagaaacata   31620
aaggaaaaag gatatttaa attaggaaga atttgggctg ggtgcagcag ctcatgattg    31680
tagtcccaac gctttgggag gccgaggagg gaggatcgct tgagcccagg aatttgagac   31740
tacagtgagc tgtgattgtg ccactgcact ccagcctgac caatgtgaga ccttgtctga   31800
aaaaaggaag aaaattgaaa ggatttgaag aggtccataa tctgctacaa cctagagatg   31860
cctcagttgt ctcagttaac tgtgagacat tgtagaagag atggacaaga acttcgttgt   31920
ttgaaaagag agtagcttgt aatggttact ttgggaaacg tctttatact attagagact   31980
accaccaaat tttgagatct tcctatttgc agtacaggta gaaatcccag tttactattt   32040
ggtctaaaag ggagtgccag caattgagtc aactgtcatg tcttttcact ggccatgaaa   32100
```

```
caatctgtgt gtgtgtgtgt gtgtgtgtgt gtgtgtgtgt gtgttaaaaa cccataccat   32160
aaatttcttg taggtgtata ttaacagtat tgttaactgt atgcacattg ttgtacaata   32220
gatttctgga acttttccat cttgtataac tgaaactcta aatccattga aaaactccct   32280
atcttcctct tcccccagcc cctggcagcc agcattctgc tttctgtttc tatgagtttg   32340
attactttag acactaaata tatgtgtaat catgcagtat ttgtctttct gcgactggtt   32400
tatttcattt gacatactgt cttcaaggtt catccatgtg aaacagtcag attttaaagg   32460
aaattaacac agagactcat gattctggta gtgtcaggtt acatagtcca tggtttgttg   32520
ctctacaaaa caaaaagatt ctcaaataaa catactttt aaatgagtta ctagaggggg   32580
aagaaggaag ggaaaacttc tatgctttcg gcacgctccc tgcatgatct tagcaaatgg   32640
cataactact ttgaatgcag atgtcagtat cagctctgag atttgtatgc agctaataag   32700
gtagcccccaa gatgtattaa gcaaaaatga atagaatttt ggggagaaat tgacaaatcc   32760
atgttcatgg gcttcttaat aagacaagat atttgtaaag aaatagattt atataatatt   32820
attctttttt cttttttttt tttttttttt gagacgagt ctcgctctgt cgcccaggcc   32880
ggactgcgga ctgcagtggc gcaatctcgg ctcactgcaa gctccgcctc ccgggttcac   32940
gccattctcc tgcctcagcc tcccgagtag ctgggactac aggcgcccgc caccgcgccc   33000
ggctaatttt ttgtattttt agtagagacg gggtttcacc ttgttagcca ggatggtctc   33060
gatctcctga cctcatgatc cacccgcctc ggcctcccaa agtgctggga ttacaggcgt   33120
gagccaccgc gcccggccta tataatatta ttaaccttaa tataagaaga aaaatacata   33180
gaacccctata tccagcaatt agaaaatgca cattttccta ggactgacat ggtctatttg   33240
taaaaaatgg accattgact aggctgtcaa gtaaatctta aaatttaaga atgcctggct   33300
gggcgctgtg gctcacgcct gtaatcccag cactttggga ggcctaggtg ggtggatcac   33360
ctgaggtcgg gagtttgaga ccagcctgac caacatggag aaaccctgtc tctactaaaa   33420
atacaaagat tagccaggca tagtggtgca tgcctgtaat ctcagctact caggaggctg   33480
aggcaggaga attgcttgaa tccgggaggc agaggttgcg gtgagccaag attgtgccac   33540
tgcactccag cctgggcaac gagagcgaaa ctctgtctca aaaaaaaaaa attcctatct   33600
tatagctcat aatttttat cttaatgcaa taaaatata ggttattaat aaaaagataa   33660
acatttccat aaatttgaa gttttaacat ttctaaatcg tgggtcaaga caaaattata   33720
atggaaactt aaaatataaac aatatataaa atactgctta tcaaaacttg tgtaaaggag   33780
ctaaaacagt actgcaatga aaatatattg tcttaaatat ttatattata ttttatttat   33840
tattttttag atggagtctt gctctgttgc ctaggctgga gtgcagggt gtgatctcag   33900
ctcactgcag cctctgcctc tcgagttcaa gcaattctcc tgcctcagcc cctcgagtag   33960
ctgggagtac aggcacgtgc caccaggcct ggctaatttt gtgttttta gtagagacag   34020
tttcactgtg ttggccaggc tggtctcaaa ctcctgacct taagtgatct gcctgcctcg   34080
gccttccaaa gtgctaggat tacaggcatg agccactgtg cctactgtg tattttaaga   34140
tgaaagttaa aattaatgtg ctgtctaacc taattagag taaaaataag agaatgagaa   34200
aaaaaaagca gaaagaagta acaacaacaa aggagcagaa atagaaatca cagttacagc   34260
acaagggacc aactaaacta aatgttagcc tcggtaagac tgatcaactc tgtcaagatc   34320
gagcacgatc aatcaaacaa gaaagaaaga aggtgcatat aaacaatatc aggagaaaga   34380
gtgggcacat aaatacaggt atacaaagaa agcgtgaatt gaatactgcc aacaattta   34440
tggcagtaaa tatgattttt tagaaaaaat ggaacagatt cctagaaaaa cataaattac   34500
caaaactgac tcaagcagaa gtagagtctg aagagtccac ttaaagacat taataaacaa   34560
aatccacaaa gaaaacactg gccagctgg ttttaccggt atgtttcata ataatgcaag   34620
tgaatataga tgtagaaatc ctaacaaagg attagcaaa tgaatatagc aatgtattaa   34680
aaagataata cattatgttc acattaagtt tatttcagga atgtaagggt agctaacatt   34740
agaatacctt ttttatttt tatttattta ttttttgaga cagggttcg ctcttgttgc   34800
ttaggctgga gtgcggtggc acgatcttgg ctcactgcaa cctccacctc ccgggttcaa   34860
gcaattctcc tgcctcagcc tcccaagtag tttgtattac aggcgttagc cgccatgtct   34920
ggctaatttt tgtattttca gtagagatgg ggtttcacca tgtttgtcag gctggtctcg   34980
agctcctgac ctcaggtgat ccatctgcct cggcctccca agtgctggga ttacaggcg   35040
tgagcttctg caccgggcct agattatttt ataattcacc acagtaacaa aggagaaaga   35100
gccatatgat tatctcaata agtgtggaaa gattatttaa agtccttgct gaggattaaa   35160
aatgacacat agcaagctag aaatagaagg gaacttctaa gatttctaag agataactgc   35220
aacaacatca ctcataatga tgacatgatg aaagcattgt tttaaaaaaa tatgggaac   35280
aaggtaagtg tgttcattct taccacttat acttaacatt atacttctgt ctccctgacc   35340
ttatactcta ggtcctagtt agtacagtaa gcaagaatga gaataaaag ccataaggat   35400
tggaaagaaa taaattaact gtctttaat ctgtttatga ggccactata gaactttcat   35460
agccaaagca ggaaggttca gtaagaggaa taaaagtata aaagttttat ctgttgctat   35520
ataacaaacc accccaaaac agtggcttaa acaatagga gacattatt atgttcacaa   35580
atctaggggt tgactaaccc cacataggtg attcttgctc aaggtctttt gtgtaattgc   35640
atttcaaatg ggggctgggg ctggagtcac cttgaagaag caacttcttt actcttgttg   35700
actgtgacct caactgggct gtcaccagga cacctacac aaggcatctc tatgagacct   35760
ggactttatc acaaggcaac tgagtttcaa gagtgagcat tcttagagag caaggcagaa   35820
gcttcattgc cttttgtgac ctagcctttag aagtcacata caacttccac aacattccgt   35880
ttgagaagta actcactaag gccatgcatg ttcaaggaag ggtacttaa tactcttatt   35940
agtttgatgg aggaagtatc agtgaattgt ggacatattt taaaaccatc accactatag   36000
atgatacgaa ttgcttcgta gataacccct ctagaaatgt gcagacaagt caaagaatta   36060
ttaagaaaca ttttgatagt cttagaatta taagatgata gaccttcaaa tcattaaaaa   36120
gaaacttta aacttaccag aaagtgcttg tcatcttttct tagtaatagc agatttagat   36180
aaaaacttag ttctataata ataatccgaa taagtataga ttttaagttaa attttatgt   36240
aactattatg taaatatttg ctaacatttt ttcttatccc attaaagttt gaaaataaag   36300
accagatgtc agtgtagtgc tttaccttct caaaatccgt tgttgacagc ttttttacta   36360
aaagattttc tcactcactg ttagggtctt tagttctatc ttcaatttt ttttttttt   36420
tttaaatatt cagttttggc ctagtgcagt ggcttatgcc tgtaatccca gcactttagg   36480
aggcagaggt gggtggatca cctgagtca acatgggaag accccgcttc tactaaaaat   36540
acaaaattag ttgggcgtgg tggctggcat ctgtaatccc agctacttgg gaggctgagg   36600
caggagaatt gtttgaacct gggaggtgga ggtgacagtg agccgagatt cgcgcattgc   36660
attccagcct gggcaacaag agcgaaaaaa aactccctct caaaaaaaaa aaaaaaatc   36720
tttaattta atcaaagcca aatcaaagct atttatgatg ttaataattt attcctgcgg   36780
gctattgatg cactggagtg gttccaagga agaagaacta gaactcttag agaagaagct   36840
```

```
agcattgatt agacagggaa agagaaaacc taaacagagc agcatgatag ctgactttag   36900
ataccctgaac ttttacatgg aaaaaagagt tctttatcct gtgttaagcc caaaatatag  36960
aactaggggtt catgagcgaa taatagcact ggtgaatatc aggttagcat tagctcttaa  37020
gagctgtttt aaacctacaa acgaaccctc tgaactagta cacttgttat tggaggtatt  37080
cacgcagagg gtgatcttc tcactgtcag atcttctaga gaatatttgt gaatgaatta   37140
tagagggttg cattagatta ctttggtcta tttcttgtat gcttcatttc ttgcccctgt  37200
tcatctcttt ctcaccaatt tcccgcattc acctttctgt cctattacat tgtgaattcc  37260
ttaacagatg aaacttttt ttttttttgga ctgacaaaaa tcttgtacat agttttgtca  37320
tagggtagta aagagagtat taaagatatc attaagtttc tctttctctg tccctgaata  37380
attaaatcta taaagcactt ggggttgggc ccacatgtgg aaggcatgtg agtaaaggtg  37440
gtaatgtcct tgaaaaagaa gcctgtaata ttggttagc attgctgtat ccaggtatga   37500
atgcatggtt ttcagtgagt atagatacac agataaatat gaacataggg atgtgtatat  37560
acctatattt cttatccctg tccactggga aatcttgaga gcagcgatag ctgatgagcc  37620
attgggcatg cttagctttt gataccaaat tttattctcc actaggagga gaatagagct  37680
ttggagaaat ggctggttcc acgtctgcga cagggaaagt gtaagaatag cctggaatgt  37740
cttgtagtga cagaacataa agacatgccc aaaaaatgat gaagacatat cagaaggatg  37800
tagaagccaa gctgagtcca ctggccaaac ctgggataat ctgagcatga aaataaataa  37860
tggttacaac ctattgaata aaataggaat taatgtgtct atactgatgt aaagaaaacaa  37920
atgaatacat aaatgaggga tagggaaagt tctacctttg tataggttgc caactaataa  37980
atattgaaat ggatactaaa gttggtgggt gaaaatttgg tgaagaacaa ggtatttaca  38040
taatcttgaa gtatccctt acaaaatact tattaaatat aagaagagga atagtacctc   38100
tacactgagg aagtctggcc aacaccagcc ttaaatatgt ggtcatgacc agtcatgaga  38160
tataccatgt cagaatcctg aaccaccga taagatgcag tgaatactta gcatctttct   38220
gagatgaaca tgccaaaaat atacaaactg aactcatcta tagggaaata gatatctgac  38280
aactcaaatg gaggaacact ataaacaac tgacttacag tttcaaaagg ttaaaaaata   38340
ccgtgaaaga acagattgta tccttttgtt taaaggacat tatgggaca gttggtagaa   38400
cttgaatggt gtctgggtta gtaaagtatc actgttaatt ttataatttc gatggctata  38460
ctatgagtaa gtaggattat gtcattgtag aagataaaaa aatggaataa tcaggtatgt  38520
ttgcaacttg ctgtcatgac ttgggaagaa aattctttgt gcttgaatt tttctgtaag   38580
tttaaaatt atttaaacat acaaattaaa aatacatata aatttgaggt actgaatcct   38640
agccagtaca tgaagtcaag aaaaggaaat aaaaggcata caggttggaa gggaagaaat  38700
aaaaatgacc ttattagcag atgacatgta gaagattgca aagaatctac ccaacaatgt  38760
cctagaacta ataagtgagt taaacgaggt tgtgggatac aaggtcagca tacagaagcc  38820
aattgtattc ctgtatatta acaacaaaca cgtggaaacc aagattaaaa acacattgtt  38880
gtttacagtt gctctaagaa aatgaatat gttggaataa atctaacaaa atacacatatag  38940
gatctgtatg ttgaaagcac caaacacatg gataaaagaa atcaaagat gacctaaata   39000
aatgaaaaag gcctaccatg ttcatggatt ggaagactta gcatagtgaa tcagtcctcc  39060
ccaaattgtt ctatagatct atagtgactc atagtgtcaa attgttccta aagatctaac  39120
acaatttctg tcagaatttc aggaagttt tttgtagata aaaacaagct tattcttta   39180
tgtgaaagg caaaggaact aaaataaaat ggctaaaatg atcttggaaa ataaaaacta  39240
gaagaatcac tctacctagt tttaaaactt aatgcataac cacagtaatc aaaacagtgt  39300
ggtagtggca gagggataaa tacataagtc agtgaacat aatctagaaa tagacttgta   39360
aaaatatggt gaactgattt tttgacaaag gtgcaaagca atttaaaatg aaatctcaca  39420
ccttacacaa aagttaactg aagatagatc atagatggat cataatgtaa aagctttcat  39480
aagaaaatgg gagaaaattc aggatgtaag gctagatgaa gagttcttag ctatgacacc  39540
tagagcacaa ttcatttaaa atatcaataa tttatactaa atcgaaataa aaaacttctg  39600
ctcctcaaaa caccctgtta agaggacaaa aagtgagta cagacttgga gaaaatgtaa  39660
accacatatc tgacaaagaa cttagatctg gactatatat agaactctca aaatgtaaca  39720
gtaaaaagaa acaaaaccc cagttaggaa atgggcaaaa gatatgacac agatggcaga  39780
taagcctatg aacatataaa aaacttcatt agccattagg aaaatgcaaa ttaaaatcat  39840
ggtggtggga tgtcactaga cgcctactaa aacagctaaa gtaaagagat cacaataccc  39900
taaaaatgca gagaagctgg atctcatata tgggtggtgg gaatgtaaac tggtatagcc  39960
actctggaaa atagtttggc agtttcttaa aaagctgaac gtatacttag cttatatgac  40020
ccagcacttg cactcctggg catttatccc agagaaatgc agtcataatg tccacacaaa  40080
agtgtgtca tgaatattca cagcagcttt atctgtagta gccccagagt cgaaacaacc  40140
cacatgtcct tcagtgggta agtggttaac tatggtatat tcataacaca gaatactact  40200
cagcaataaa aaggaagaa cttgacgtaa caacatgggt agctctcaga ggacttacgc   40260
tgggtgaaaa caatccagtt tccaatgatg acatagtaca tgattccatt tatataacat  40320
tcttgaaatg atgagaattc tcgagaggga gagcagatcg gtggttaggg gtggaatggg  40380
gaagagtgtg cctgccaagg ggcacacaga acctttgtc tgatgaata ggtatgtgtt   40440
gttttggtca tgtgaatttg tttgtggtaa aatggcatag aactgagcac acacaaatga  40500
gtgcctgtag aactggagaa atcaaaataa ggtctgtgga ttgtagcagt gtcttttcat  40560
gcttctgagt ttgatggcct tctggaacta ggccctggac agcgcattgc taggagtggg  40620
gctctgtggt gagtctgaca gcgtccctgg ctgcaaagag cttaactgtg gcaagaaggc  40680
tgctactggg tgcctgggtg ctcctgctgc cctccaccag cggagctgat cagaatcttg  40740
ccctaagagg cccctcttaa aagccacagc accttgggtg ggctggtctg ccctagagca  40800
cttacgctgg gtgagggag ctgtggaagc gtgcagtggg ggagtgctgg agtccaggac   40860
agtcagctgt actcgggatt gggttgaggg tgtggttgtt tctagattaa aatacagata  40920
catgatcaag tagaattctg aaattccttt aaatgtttct ggtaaaatag gaattaccaa  40980
ggaattttgt actttaatac cctcttaggg tattaaggag ggtttgtcag tgaaaataat  41040
caagaaggac tggtccattc gagccactga ttttgacaga caagaaaaca gacccctgag  41100
tgcccccttat cataggactg tcggcgactg ggatgctgat agtgttttctc aagtagtagt  41160
cacccttttc tgggaaatca tgactacgtc tggaatcatg taggttggta gagccaaaag  41220
acagatcaga atccacatct ttagatccct caaactcccc tcacccatgt ttttcatctg  41280
cgtcgcaaaa ttccaggtac ctgtactaag aagtcctgaa ggtttctgcg cttttccttt  41340
ctgccgaatt agtttacgct taagaaagtc agttaacgtc atttcatttc ctgcttatgg  41400
ttcagaatgg gttgatagtg atttgtcatt ctaacaaaat tctagcaggt gtaggaattt  41460
gaatatgtga aaatcttctg gaattcatca tataaacaat gtttgaatac ttgctgactt  41520
aaattgttat gacactctac taggtaggcc cgctgagaaa atggaagtag cagtccttt   41580
```

-continued

```
tccctgacag tcaaatttag gagaaatgaa tcagtacagg atttcttgac tctccgaacc   41640
taaactgcag actgctcctc tccgctttgt ccccgtggct ccagccacat tcttcatgtc   41700
cctcagacat gttaggtatg taccaccta agtcattcgc cgttctctgt gcttggaaca    41760
ctgttaacta aaatatccgt gagactgacc ccttccacat ctgtgcttac atgtgaccca   41820
cctgggtggt cagccacaag gcccatcctg accaccctgt ttagaattgc aacctgcccc   41880
tctcccagc gctgtgagtc ccgttactct ttttttcttag catttattac tcatatactt    41940
tacttagtta tgcttattgc tatatcacca atatagatat ttggtccgca ttgtttgcat   42000
ggtgtctcat gggcctttgg atgtgatgaa agttaaatct tttccctaa gtccctccac    42060
cttcaatttg tttaggctct aactctccta gaagcggaga gtctgagttt caaagaaaat   42120
ggtgcaatac tgctgagcgc cgtggctcac tcctgtaatc ccaacacttt ggggaggcga    42180
ggcaggtgga tcacctgagg tcgagagttc aagaccagcc tgaccaacat ggagaaaccc   42240
cgtctctgct aaaaatacaa aattagctgg gcgtggtggc acatgcctgt aatcccagct   42300
actcaggagg ctgaggcagg agaattgctt gaacccagga ggtggaggtt gtggtgaact   42360
gagatcgcac cattgcactc cagcctgggc aacaagagcg aaactccatc tcaaaaaaa    42420
aaaaaaatgg tgagatactt actgattatt ttaaagtgaa gattagtatg tcttatttta   42480
tacaagctac caaagaggaa aaatgtctgt tttccaaact aatgaatttt acctatttg    42540
taaagacatt tctcaggtat tcttttcatt gcagactctt ggggacagat taaagaggac   42600
tttttcaatt aggagatttg tggaatcaga atttaattag tgacattgtc ctgtcaagtt   42660
taggatcttg aaatcatgat gggttgaaag acgctgatga tttcaaggac agtaaactat   42720
tgtttggaaa aggttgaact taccaaatgt ttcctaaaca atgtatactt tattagcaaa   42780
gctgtgatgg tgctaccttg gaaatactct ttacattccc accgccacta cttgattcag   42840
gcctcatcac cttttgatta cgcttttcagt gtattggtgt atgaagttgc cttcttcttg    42900
gttcagtcca tcttctatgc tgctgagagt tattttcatg aaaatcaaat gtgtttatac    42960
cagtccttta aagaacttca ctggggcct gtccagagcc tgtgcctgta gcacggccca    43020
cgtgcccttc agggtccgcc cttaatgtgt ctggggagcc ctctctagcc agctcgccag    43080
ccttttctgaa tctgccagtc ctgccgtac accattcctc ttcattcctc tttatgatgt    43140
gccctctgct ggaatttccc cttcctgctg atctcactag gccattcag gtagcaacta    43200
ctcaagctcc ttcccacaat attttatgca ataaagtatc agtactcaga gtcacggctt   43260
aatataattt ctttttctcct ttttaaaagc ttcaaacaaa taatgtctta cctttagatc    43320
cctataggtt aaaatatgtt tgttgactaa aaattgtgta ttgattgctga aagtattcaa    43380
tgcagggaac agaccagttc atcatggagg cattccatca gagcgtctag ttagagaaga   43440
tatgtcatgg actgcatcgg cacagaagtg gggtttatgt gagagaggag ttggaagtca   43500
cacctgagtg gagagcaacg tgaaaaggtg atgtcagcaa gaatttagga tgtatggaaa   43560
ggatggtaaa ggcaccaact ggatggatca gggagacatg gaatgcagaa tgcaggaaat   43620
aggtaatctc ttaaattgca caaatctagg tttcattttt gtgctctagt gtgttacact    43680
tgtgatgact tgacttccct gagtgacagt gcgatgggtg tgatccatat tcatatgcac    43740
ttcataggc tgtgaggact gagagaggtg acccagtgac gagtgtcaca caaacctgac    43800
atgtcgtagg caccaaatgg ttctagacag tggttctggt tggttttgtg gtcaattgga   43860
aaccttcat caagtagaat tttcttgca gagcaaacaa ttgaaatgtt aatattctat   43920
gtgtactaaa gtttgtattc tccattaata tgggggagta tatggtgacc tggtgtttag   43980
tgccagcttt gttttggtt cattgctcga tttatgagag agaatgcata atatttgttg   44040
ttcgactatt ttacttgcag gattgaagag agttgacaaa tctagaaaat gctttgagtt   44100
cttggacatc actgtttgaa aacgtactga ttacccttag ttgagaatgg gaaaatctaa   44160
agggggaaaag tcactggttc acgctgtact attagaattg gtcatcttct tgcctgactt    44220
gtaagttaag gatgctgat cttgtgctgtg atttaacctg ttcaggatga attgtaacca    44280
gttacaatga atacaaattc tccttctgt ttgacctgga aaacttttcca aaaggagatg   44340
tcttttacaat aatgatatat ttggtgaaag ctgtgggttg ttttttttt tttaaagctt    44400
atgatgacag tattgaaaga ggaaactaat ctgtattgtc agcacagcca cagctagcac   44460
tagtcatttc ttgagaggtg gagctgtttc tcagaaaaca tgctgtttga gggtaggagg   44520
tgaagggact ccttgtcaga aattggctta atttaatcc aagttataaa ccacagttct   44580
gtttgggtat tgcatttctt catttactca gtgacaagaa ttaaggcaga tgatgcctgt   44640
agaaaaaaaa gtgtatgttc ttgatagttc tgctactagt gctagtagag gttgagaaat   44700
aagatttcct gtgaagtgtg gtttggttgc ttttgtggta tcccatgcaa aagagtttga   44760
actatcttca ttttttctccc tttactggat cctttaaaag aggaagggg gagataacca   44820
gacttacaag gatggtaaag tatagtgggc tttggggctt actatacag cccaaaggtt    44880
atgggatgct gctgttatga taatctcatg tcagaggttc ctatggaaga ggagaaagga   44940
tgtaccttc tgtgtgttct cattcagaag tcaaaagttt gttttttaat gattagttta   45000
cagatttggg gctgactgat agtatctggg caggaaaag agacctgtga ctcaggttgc   45060
taagggaacc tgtgtatatg ctctcacaaa ctcgaaaccg tgtgttgtga tccttaattg   45120
gagaagaggt agtgccttc tttgttatca tcactaaaga gtataaatta taaagtcaca   45180
gtttctcata aagaggcttt gatagtttca cttcctgaaa tgtgtatatt cacaatcttt   45240
tgcaatagtt attttaaggt gatgtgtttt attttttct ctactgcctc ttcgaaatca    45300
aaaagttata tactttttt atttatatt aatcttttc aattttttgtt tttataattt     45360
taatgtattt taaatttatt ttaagttttt atttctcctt tttgctttaa tatttcttcc   45420
tttttaaatt gttttcatt tttccttgt atgtgttttt cttaaaagaa cagaagaatt    45480
aaaataatat ctagtgatgt aggtatttca gttttgtttt taatcagcct tgagaagaaa   45540
atacaggctc aaataacatt tgtagtcagt tctaaatagc tatagagttt tcccaaggat   45600
taccttttctt tttttagtatt atctgataac aaaataaaaa aaaattttcc tgagaaaatt   45660
caccgttcct ttgcttttgt tgactctgta tattaatgtt aaacaggaag cgaggccact   45720
gccaggggct gagccctgca gacccagtgc cctgcaggta gtgccctcct ccctactgcc   45780
tcccaggact ggatctgggc ttttctggtg tgtggttact gtgcttatag agcattgagg   45840
taacacctcg tgcatatttt acagataaa ggaaaatagc agtgaatttt agttcagagt    45900
cctgagggtg aggtatcaaa tactctggct gaaggtcttt ctctaggttt acttcctgca   45960
tagctgggca agggtgtggg gtggtgccat gtgggtaac cagattccca gcaccctgta   46020
aggtggacct tcccgggttt tatgattcc taccgcatgt tagctaaatg gctgttttca   46080
gttgtgcaat agatatgagt agcctttggt tagtgttctt tctgtgatta caacatgagg   46140
aaatacattc ctttggtgtg atatttagt ggaactttaa ttttaaaatc atgtagtttt    46200
ctaaaaccag gctttctttt tttggtatgt tgtctaggag atatgtggtc tttatttta    46260
ttaagttgct gaccttttta ctattttaca taatataaca gttaaagggt gattaaactg   46320
```

```
tttttttaaaa aagtgatttt taaaaaaaag tgcttgttga catcatcttt ctgagaacac   46380
tagtatatgt gatttactat aacaagatct tagttttttcc tgttggcaaa tgacatgtaa   46440
tatttacaga ggtcttgggt tcagtccagc agaaacatct cagataaatt gatgtgtgaa   46500
actaaagcca ttttacattt tctttcatat ggagataata taaacagttt tttcatttaa   46560
aagtaaggag agactggcta tttagtatgg atttcttttga gagggacaac ttgtaatagt   46620
atgcattctc tagagttaaa catcaaacac catgttttta gttttataat tcagtgatat   46680
gcatccggca gttgtgtgtt gaggattctg agttaattca tgggcttttt ctcctggtgt   46740
catgcttctc ttgctttccc atctaaatgt ataaggtcac attttgtatt tcacatattt   46800
aaattagcat aaattctcaa tctatgagat ttttactttt aaaaactaga aatatctcta   46860
aactgttaac agagtctaag tagtgaagta tcttcagtgg tcttttaaag aatacagttg   46920
gaatattcca actgtcttta aatattttca gcatttaacc taaacacagt tcagtgctaa   46980
aatttattta aatatagtgg aattcttatc tgttgagaaa tgaagaggtt gaaatatagt   47040
aacctcggaa atctagtctc atctatttga gaccagttat cgttttgtag gtagaccaat   47100
caattcttag gtaccaagaa tctgaatgat cctttctactt ttaggaaggt aagtacttta   47160
ttcatttaac tatgtttact cctggtcgat ttttcaagtc acaatggcta atgtgctaca   47220
aacagaagtg cttcctttcc agcactatag taataaacaa gattgcattt tatactcctt   47280
acaaaaaaag tagagaatag tttaggattt gtctcaactc tattatgatg ctaattcatt   47340
tttcttattt cttctgtctt tttataaata cctagaatat taatatgaag ataaaaacag   47400
taatttgaa atgacagttg tggtttatca ttctctattt tcagatgatc acagtcgtgt   47460
taaactgcaa aatgctgaga atgattatat taatgccagt ttagttgaca tagaagaggc   47520
acaaaggagt tacatcttaa cacaggcaag taatacgata ccacgcaaat gtctgaaaat   47580
gatgtgtttg tgcttgttct gcttaaatc ataggtaaaa tgtatatcttg acttcttttg   47640
gaaatgaaat ggtatttcag ttttttttctg acgatgtaat gaattatgga cattataagg   47700
ttttgaagct ttgagtattt aagataaaag gcaagttatt tttgatatta cacgttctgt   47760
gaaggaaaat tcttaggaaa tggcttaggc cagttctttg gcagattgtg ttccttacat   47820
tatatctgac acagagtgct gcttatgctt cttagtgtct tcttttctct tcccataccc   47880
tgtggcaaaa ccagaggccc tggacagctc ttctgtagct cccccctgcct cgcatatatc   47940
ttcagagagt acaccaagcc ctggatggtg tctggtcgtc ttcaaggacc tgagcgggtg   48000
ctgagaccag gtgctccaga ggcccagcca caaggccttg tgctccctgt ggccttctgc   48060
ccagtttgcct ctgagcgcat cagccacacc tgtgtgcaag catgattctt ccttccattc   48120
tgagatagta ggagagattt ttgtgtatcc acagctactc tttattcatc aagtaataaa   48180
gacttgatta tcaacagggc tgtctttccc cctaaagatt tttaaatatt caaaagatat   48240
accataaat ttgagatttt tgaaaacata acttaaatca gaatgactta tttgaaagag   48300
aaaaatattt gataagtaaa aagatatgca gattaatgta atatgagct attatactac   48360
gtcaattcac aggaaactaa aatgcatttt ttacttgagg tagtacagct cctgcaagtc   48420
aaaaagaaaa aaaacagccc atggaaaaaa ctggcaaagg acataaactc ctagttcaaa   48480
gaatcaaagg tggacacttt gcacatgaag aaatgctcca ttcagtaacc agggaatggg   48540
cctttcacct gtcagaaaag gagagatttc aaagtgtata atactcagtg ttcaaatact   48600
ctgaccgacc aagaaagtct acttagagaa atacagtcag acataaagat atatgtgatg   48660
ggccaggcgc ggaggctcac acctgtaatc ccagcacttt gggaggctga ggcagatgga   48720
tcacctgaga tcaggagttt gagaccagcc tggccaacac ggtgaaaccc catctctact   48780
aaaaatacaa aaattagctg ggcatggtgg cgggtaccta taatcccagc tacccaggag   48840
tctgaggcag gagaatcgct tgaacccggg aggtggaggt tgcagtgagg caagatagtg   48900
ccactgcact ccagcctgag cgaaagagca aaactgtcca aaaaaaaaaa aaagacatat   48960
gtgatcatgt tcattgcagt cttattttaa cgcatcagac tcaagcaatc tgtaagggac   49020
tggttaaata agttaatcat acatatacca ttagtaataa tttgtggagc ttgggaatag   49080
agactttaat tttccatttt attccttttct gtaatattgg aagttttttt tatgtgcatt   49140
tgtatttaa actactattt agagttaaaa attttatttt ctgtttgaaa tacctatagt   49200
tgaccttga accatccagg gttgaactgt actagtccac ttacaggcaa atttttttca   49260
accaaaaacg ggtcggaaat acggtattca tgggatgtga aatccatgca tacagagggc   49320
tgactcttg tatctgcagg ttctacaggg ccaccagtgg ggcttggaca tgtgtggatt   49380
ttggtatact gcagtgggtg ggggcaggt tgggtcctgg agccagtccc ttgtgtatat   49440
tgagggacaa ctaattacat taaaaaatag agaagaatta ccacccctaga tcccttatca   49500
caaccctttc tccctctgta ctgttcttct ccattatcac ttactggttt tttgttctct   49560
tcttagttct taaaaacata ggtcttaaga ttctaaatta gcttttttt ttctcctcca   49620
gtctgcacta cagcccttta agaccatggt tttcaaccct tgtaacctaa gataggtag   49680
actactgtca tggtacctgt gctggaatct tggtgccagc atttcactgg gtattcactc   49740
acccagcaaa gacttactga gacctactct gtggcaggca ttgtttaaat aaaacagact   49800
ttcataaaaa ccctattatg aattttatga attttacatt ataataggaa ataataacag   49860
ttaaaaattt tgtaatggtg tttttacatg ctttgtataa tttaaaccttt aggacaaccc   49920
tctgtggtaa atagtattac ctttattttta tacacgagga atctaaggag atccagagac   49980
attaaataac tttcttttt tttttttttg agatggagtc tcactctgtt gcccagcctg   50040
gagtgcagtg atgcaatctc agctcactac aacctcctcc tcccgggttc aagtgattct   50100
cgtgcttcag cctcccaagt agctgggatt acaggtgctc accaccactc ccagctaatt   50160
tctgtatttt tagtagagac aaggttttcac catgttgctc aggctggtct caaactcctg   50220
gcctcagatg atccacctgt cttggcctcc caaagtgctg ggattacagg ggtgagccac   50280
cgtgcccagc ctcctagtaa ttgtttttga acttcttgtc gctgtgtgtg tcctgaagga   50340
gccctgccca tttaatgcga gaactcagaa gcctgtgtct ggcttttcct tctctcctga   50400
attcctctct atgtttttca ggtctctatt ggatattttt actggattc aaagtctgca   50460
tgttctctgt ctttttttacc aaggtagctg ccttccatatt tttctcattg ggattgagac   50520
tgtcctcatt gtctgccaag ttcttttctga tcttctattg cccctcgctt ttttcagagc   50580
tctcttcaat tacacctgtc ctgttgcagc agctttttaa ggtctcccct tggcaccatc   50640
cctgtcactc tagtggtgta gtcaccaact acatccctcc acttctaccct cactgatcta   50700
tttgtcttttt cccaaatatg ccctaaactt tcatgcactt tgccttatgc ttgagggcca   50760
tggagtggac cctaactccc tcccattctt ctgcattccc tctctgtatt aggacctttt   50820
tcgaggctct tctgtagttt ccttcccagc ctttcctgct ccctaagacc tgatggttta   50880
atttgccat actcttgtac tacttaactg tgtccattag tcatacaagt acttctcctt   50940
ctacctttgc aagctcttaa agagccaaga ctgcatctca gtctagctct tggccttgca   51000
tctagcaggt tgtttggaat ggaggataca gaaaactaga gatgcagtaa cccagctctt   51060
```

```
ctgattgtcc tttgtagatt gttacttcag tcatctttt cttctgagtt ttatgaatta    51120
gtatttttt aaaagtcacc tccttggtgt attatgtctg ttttgcagat gaagaacatt    51180
ggtagcattg ctggtaaatg aagagctga gatgtgaatc tctgttcctc tgatttaaaa    51240
acctatggct gggcgtagtg gctcaacgcc tgtaatccca gcacttgggg aggctgaggc    51300
aggcagatca cctgaggtca ggagtttgag accagcctgg ccaacatggt aaaacccgt    51360
ctctactaaa aatacaaaaa tcagcctggc atggtggtgc acgcctgtaa tcccaactac    51420
tcaggaggct gagggaggga gaattgcttg aatccaggag gcagaggttg cagtgagccg    51480
aggtcgtgcc attgcactcc agcctgggca acagagcaag actccagctg tgttcctgtt    51540
tattatttag tcttttagaat caccagtgga atggcatggg ttgtgattgt gtgtatacac    51600
taaggagtaa cctcactggc aaattgctac atccattttt tttttcctaa ttaaagaaaa    51660
aggtattcat tttactgggg atttcctcat tgctgttttt acctttagac tgtgttttgt    51720
tttagaagta gatcaagtaa tagaaaaata agttgagtga ggaaaacgcc actctcaaat    51780
attaggttgt agtttgtcag gatcctcagt agacttctag cattttaca acttaacctt    51840
ggtttattca tttaagtaat atttattgag tatctgctac ataccaagga gtacaccagg    51900
cctaaagatg ctttagtca gctgggcacc atggctgata cctgtaatcc cagcactttg    51960
ggaggctgag gcaggtggat cacttgaggt caggagttcg agaccaacct ggccaacatg    52020
gtgaaaccct gtctctacta aaaatccaaa atttagccag gtgtggtggc gggtgcctat    52080
aattccagct ccgtgggagg cttaggcagg agaatctctt gaacctggga gtggaggtt    52140
gcagtgagct gagatcgtga cactgcactc tagcccgggt gacagagaca ccatctcaaa    52200
aaataaaaaa tgcttttagt ctagaaccac tttaaccccc ttgttgtatg tgggtctgaa    52260
gctctgggca gccctagccc ccactcctga ctctgcccct aactcatacc actctgctac    52320
attccatgtg agttgaatgc atgttcatag ttatttagg tgtagcaaaa ctacatctca    52380
tttttaacctt ctcatttaaa actcgttaaa atttgtacat aggcttttca tctcttatta    52440
gatcttcctt ttgccctatg ctatcattaa aatgtgaaag caattggaaa tacatgaaat    52500
attttgcttt tatccccatg gcattgttgt aacatggact gttgcccctt tttaactctg    52560
cccaatactc ttccattgag gccgtacata ctgtgcattt gtagattaac agtttcattg    52620
tggttcaggt actttaatga ttcctacttt ttctagaaat ctttttgtag ttgacttgag    52680
ttggttggct ggccagtgat ggtacagact tttttctcat ggattttcta tgatgtgtgg    52740
gaggcacatc ctcttggctg tagaagatga agaggacaga aatttccttg gtctaccttc    52800
tttgcagcta gaacatgatc agtcagatac tcctactcgt gattttgtct ctgatttgcc    52860
tatagattgt acatgaatac tatagccacc ttcatatggc agtgccagca aaagcaagga    52920
gatagtagtg acggtatcaa gagcagcatc ccaggttgac tttctttggg gcaggacctt    52980
gcttgtgtct taacccttgg ttcctaccca agtttgtctc tctagtcctc aactctgaaa    53040
gccacttgat atcttacaca attccttttt tgcctgagaa aataaaagtc agttttgatc    53100
atttacaacc aaaaatccta actaacacag acctgttttt gaaatcaggt agattggaag    53160
tcttggttta cttcttataa gcccgtccgc tgtctgtctt gtaacatccc aggagcagac    53220
ttaacaaggc cttcctggag ccttgctctt tctgtctgct tccctcatct gctctctctc    53280
ctctctcttc acagggtcca cttcctaaca catgctgcca tttctggctt atggtttggc    53340
agcagaagac caaagcagtt gtcatgctga accgcattgt ggagaaagaa tcggtgagta    53400
atatttaata tttacaactt agtatactgt atgtgatcat tagcatataa agattttcat    53460
tttgggggcca atattcattc cttagttttg gcctttaatt gctaaaggct agcggtcaaa    53520
gtgtttctgt ccggaaaaac tcatgtatcc tttttccttc ttaagtattt ttataacaat    53580
tgcagacctt tcatctccaa gatagaaata caatgaaata aatatggact agcagtgaca    53640
tatagatctt tggaatccct aggaatcctt attgacctat tgtcaataag tcctcttcca    53700
gctttaagat cttgtactgt tctacttcag atttcttact ttattctaca tttcataatt    53760
gctggttttt aatgatgatg aaaatttcct aatccacttc taattagatg tggcaatgac    53820
atgccagaat ttccagcagt atcagcatag tcatttacag gggttttttcc tgatcttcaa    53880
tatcatttaa aaattaagga ttaggccagg cacggtgcct caaacctgta atcccagcac    53940
tttgggaggc cgaggcaggc agatcacttg aggtcaggag tttgagacca gcctggccaa    54000
catggtgaaa ccccgtctct actaaaaata caaaattagc caggtgtaat gctagcact    54060
tgggaggctg aggcaggaga accgcttgaa cctaggaggc ggaggttgca gtgagccgag    54120
attgtgccac tgcacctcaa cctggatgat agaatgagac tccatctcaa aacccactgc    54180
actgcagcct gggcggtaga gtgagactcc atctcaaaaa agaaaaaaaa aaaaatcaag    54240
gattatgaca ttgtcagttt gagcaccatt gtagactaca tgatttgcaa attttatttc    54300
tctcattttg gagtataatt actgtattaa taagataaca ctgccaccag aatttagaaa    54360
tcatgtttat ggtggttgaa cctagatggt taacaagagt caggtttaat tattttgggg    54420
aagattactt cagaggtggt gggtaatgtg ttattcatca agagaccat aatgtctgat    54480
tattgttctt tttatttcat taatagccat tattggtcag tgttcagctt cttaattcat    54540
tatgggttac aaatgatgat aatccaattc tgtcattact tctcttaaaa gcagttttcc    54600
aaaaaaaagt tgattcccta ttgaggtcat ctgttctcaa cagatgacca attaggagtt    54660
tttctggtgg agagtggcag gagaggttga attattatgg gtttggacat actgattaa    54720
ttttactcct ttgcagttat ttccttatt tttgatcaaa ttaccctgtc attggctagc    54780
agcaatgtct ttaggttggg tcctgagtcc tctttttttt tttttttttt tggagacaga    54840
gtctcgcctg ttgccaggc tggagtgcag tggcatgatt tcagctcact gcagcctcca    54900
cttcccgggt tcaagagatt ctccgtctc agcctccga gcaactggga ttacaagcac    54960
ccaccaccat gcccagctag ttttttgtaga gatggtttta ccatgttggc caggctggtc    55020
tcaagttcct gacctcaagt gatacgccca cctcggcctc ccaaagtgct gggattacag    55080
gcgtgagcca cctcacccag ctctgagtcc tttttaacaa acctttaata gtttccttgg    55140
ctgggtgcag tggctcacac ctgtaatctc agcacttggg ggagctgagt tgggtggate    55200
gcttgagccc aggagtttga gaccagcctg ggcaacatgg tgaaactctg tctctacaaa    55260
aaatacaaaa attagctggg tgtggtggcg catgcctgta gtcccagcta cctgggtac    55320
tgaggcagga ggatcacttg aggccaggaa gtcaaggcta cagttagcta tggtcgtgcc    55380
actgcactcc agcctgggga cagagcgaga ccctgtctca aaaaaaaaa atttttttg    55440
ctgtctgtaa tgactgcatc tcaggctcat cctgaaactc tgctgcccag acctggaac    55500
agccattct ctaaggagtt ttggttctt ttaatgggca gcagtatttc aagatcacag    55560
caaaaataag gatatatatt gcaactggac tggtcattgt ttttagggct tttcagtgga    55620
caaaagctaa ggaacaatat gcatatgtta agataacata cttcaagagt tcataatgat    55680
attcccagtt caaatttgga actataagtg ttgcttagcc ccttccatct tacatctgct    55740
atttcctttt tcataccaag aatcctggtt ctcaaagata tgagagatgt aaactatctt    55800
```

```
gtaatgactc atttccttct tcccatatca tatacaatat ataaccataa tcatgatatc    55860
atctgctacc aaaataatta ctgaaaatgg tttacaattt ttaatatttt tttcattctc    55920
ttcctggtgt ttctgagttg tactttacaa actgtagtct ctcccttaca tctcttgtag    55980
actcttagtt ctacaagcaa gcattattta atattcatca acagtctttg ctgatgtctc    56040
tccagtcatt ctgactaaag ctcattctct agtggctccc aaggagggac ttgtgagcat    56100
tatagtctga ttttttttaca tgtcagtgat ggttcatctg ctgtcttaat atctgaaagt    56160
cagtttggcg ggatataaaa tccttggctc atgtgctatt ctttgaacaa ctttttttt    56220
ccatttcctt ctggtattcc accaaagtct aatggacatc ttatttcctt tataagtctc    56280
ttgttctttt tatctgcact acccaaagaa ttcttttttt cttttctttc agatattatt    56340
agttttacca aaaatatgtc ttagtaattg gccattctgg gtcagttttt acaggtacat    56400
gatgtgttct tgagagtttg acttcaagta cttttttaaaa tttttttaaat acttttttgtt    56460
aaagaaatat ttgttgaatt acagtcctta gtatttgttc tgctccctg cttgctttaa    56520
tgttcttctt tgggtcttcc tattatacgt atgtttggatt ttcttttgcct acctttttta    56580
tttgtcacgt tctctttaat cctgtttatc tcttttattc tattttactt aaaaaaaatt    56640
tttttttttc tggccaggtt ggagggctta cacctataat cccagcactt tgggaggctg    56700
aggcaggagg gtcacttgag cccaggaatt caaaaccagc ctcgacaaca aagtgagacc    56760
ctgcctctac aaaaaaataca aaaagtagcc aggtgtggtg gcacgcacct ggagtcccag    56820
ctgggggttgg gggattgctt gagcccagaa gattgaggct gaagtgagcc aagttcaccc    56880
cagtgcactc cagcctgggc tactacagag caagacactg tctcttaaaa aaaaaaaaaa    56940
ttatttattt tcctcttaag gcattattat tattattatt ttttttttttt tttgagacgg    57000
agtctcgctc tgtcgcccag gctggagtgc agtgctgcta tctcgactca ctgcaagctc    57060
cgcctcccag gttcacgcca ttcttctgcc tcagcctccc aaatagctga ggctacaggc    57120
gtccaccacc acaccggct aatttgttgt atttttagta gagacggggt ttcactgtgt    57180
tagccaggat ggtctcgatc tcctgacctc atgatccgcc tgcctcagcc tcccaaagtg    57240
ctgggattac aggcgtgagc caccgcgctt ggccagcaac atttattttg aagataaaat    57300
tccaaga gtttgataat tttagaaaca taaagtgaat gtcccatgac gttaaaatat    57360
aggtaatcat gctttaagaa tgataaattt atttttattt tatgaatatg atacctatgg    57420
cttttttagt ttataagtta caggaacact taaaaaatac cttataagac cggacatggt    57480
ggctcacgcc tgtaatccca gcactttggg aggctgaggt ggtggttca cttgaggtca    57540
ggagttcaag accagcctgg ccaacatggc aaaaccctgt ctctactaaa aatacaaaaa    57600
ttagctgggt gtggtggcag acgcctgtaa tcccagctgc tcagaaggct gaggcaggag    57660
aattgcttga acccaggagg cagaggttgc agtgagccaa catcacgcca ctgcattcca    57720
gcctgggcga cagagcaaga ctccagctca aagaaaaga aaagcctatg agacagaaa    57780
atggatcagt gcttgcctgt ggcttggagt gggaatagga cacaagggga tttctgagtc    57840
tgagagaaat gttctaaaac tggcttacag tgatgactgc acacacataa aaaatgctttt    57900
ataaaatttc aatctctacc cgccctgctc cccgagatgg agtcttgctc tgtcacccag    57960
actgagtgc agtggaatga tcttggctca ctgcaacctc cacctcctgg gttcaagcga    58020
ttctccttgcc tcactctcac aagtagctgg gattacaggc gcccgccatc gcgcctagct    58080
agttttgta tttttagtag agcagggtt tcaccatatt agccaggttg gtctcgaact    58140
cctgatctca ggtgatcctc ccgcctcagc ctcccaaatt gttgggatta caggcgtgag    58200
tcaccgcgcc cggctataaa atttcaatct tactaaaata cattaagcgt agaatatagt    58260
agtgacttct tagttttggg tacttgaaaa aatatagcat gtatatatct ggtttgttt    58320
cattttttaa ctttatggtt tcatgatgtc tataaactaa aaaaaaatca tatacatatt    58380
tctaaattta ggttaaatgt gcacagtact ggccaacaga tgaccaagag atgctgttta    58440
aagaaacagg attcagtgtg aagctcttgt cagaagatgt gaagtcgtat tatacagtac    58500
atctactaca attagaaaat atcaatgtaa gacctttctt gccgaaatt gtggacttta    58560
tatgatggtt taaagaatta ttcttttatta ttagattgtga agtttgataa gcacatgcat    58620
ttggataatt cctatagtat ctagccataa tcacgtgttt ttagattgtg tgtctgcatc    58680
tagtagcttt ctgaggactc tgaagaaaca gtagaaacta agaatttcaa agttcagttt    58740
gatattggg gattaaaaat taattaatag aaatacatga ggattaatag agagggcttt    58800
agaatcaggc aaacctggat tcagatccag ctctgctgct tagtagagct gtactttaga    58860
cttgttcccc acccttcactg atcccttcct catctgtaaa atggaggtta ccacgccttc    58920
cctccggggc tgtcctgaag gtcaaatgag gatgtgtatg cagagcacct gaccttagta    58980
aatgcccagc aagcaatagc tcccaggacc tgtgactgcc aagaatagca aaatagtcaa    59040
gaaaataact tacaaagcta ttgttaagtg attcacaaca caaaaatttg tccctattga    59100
gttgaaaaaa aaatggtgtt ttatatatat atgtaacacg cacacataca tacatacata    59160
cacacacatg tataaatgtg gcatgtggtc tcaagaacat ttacttgggt gtttgtttgg    59220
ttggttggtt ggttggttga ttggttttttt gagacagtct tgctttgcca cccaggctgg    59280
agtacagtgg cataatcaca gctctcaatg aggcctccaa ctcctggcct caagaaatcc    59340
tcccacttca gcctcctgag tatctgggat tacaggcatg agccaccata cctaattttc    59400
ttattttttt ttaatagaga tggggtcttg ccttgttatc caggctggtc tcaaactcct    59460
gagctcaagc gatcctccca ccttggcctc ccaaagtgtt gaggttacag tcatgagcca    59520
ccatgccagg ccttacttgc attttttctctc cccagaaaca tatgaactgt tccttgggcc    59580
ttggttgagg tacatacaca tagtgggtta tgaacctgcc aggtgatgattga    59640
ggcatttctc ccccttttcgc catttacctc ttttgccctc tttgtgttgt aatagaataa    59700
actagaaaat aatgaaatga gagtaattct gagatgctaa tagaaactgt gatagcttga    59760
aaataggaga atgtttagcc tcatatgact ttaggaatgt atgtagtcta taagtgaaat    59820
actgttttag ttaaccatta agtaaattaa gtgatcacta acaatacaaa aaaaccttaa    59880
agagaaggga gatatataca tgcttttttag atgtgtggca gtccctttta tggtggatcc    59940
cttgaaacac ttgtgttttt tgctgcattg agtaagcaca ggtgcatgct ctgtgcgtga    60000
ggctaggtt ctggttttcc ttctgtccag ctttccgtga catccgtact aagcttatta    60060
tacagtctct tgagtcacct aaaaaggctc aaaattacga atgataatgc ttagatttat    60120
ttatacattc ccattactat atttattttg tcccaactct ttcagctttac atgtgtctta    60180
aactgcattg agatacatca ataactcttt gatactggac tgagctgtac attgttcatt    60240
cccagaaaca gaactgtatt tccacaaggt tctgaaagtt ctctgaatca tcttctcttg    60300
gtatttatcc caggtaattg ctcatttgct tatggcatta aaattgattt agatgaaggg    60360
catagatgtg tttccctgtt tctgaaacag tccttattga gaattgatta taccttaagt    60420
aacaataaaa tagaatgatt tttgtgttttt gtttatcaga ttccaaaatg ctttcacata    60480
tatatcatct gaccagtagt cttcagttag tgtagatagt gtaaatattc ttattatccc    60540
```

```
cgtattttat attataaaaa ataatagtta aaatccatta ggttatagga atttttccat   60600
cgattactta gctaataagt gacagactga tctcattagt tctcctggtc ccctattttt   60660
taagacaaag tctcattctg ttgcccaggc tggagtgcag tggcatgatc ttggctcatt   60720
gcagcctcca cctcctggat tcaagtgatt ctcctgtcct agcctcccga gtagctggga   60780
atacaggtgt gcaccaccac gcctggctaa ttttttagtg dategatggggttt         60840
cgctgtgttg gccagactga tcttgaactc ctgacttcag gtgatctgcc cgcctcagcc   60900
tcccaaagtg ctgggattac aggtgtgagc caacacgccc ggccatctcc taactttttga  60960
catgggata agtcctttg aaaagatgct aattgttgta aagagagatt attgattctg    61020
aagcatcttt ctggagttga ggccatcatg tgagttggcc agccactctg ttttagttga   61080
tagcaactgt gtggtataat gacatgatca ctgattttt tattggcctg ggtttagaac    61140
ataccacaat ataatagcaa gaatttgttt gtgttctact ttataatttt taattagaac   61200
tagggattct ttattcttta gaaggataaa gtagcatttc agtatgagag gcagaattac   61260
atttgcctaa gtagataacc tctagaatca gatagcccaa gtttaaatcc tgactctgcc   61320
attcttgctg agtgacttgg gtcacattac tttactatag atgataaaca gtacctgttt   61380
tatcatctat aaaatgaggg tgataacgta cctacttcat aggattgctc taaggatcaa   61440
gtgagttaat atcatgatgg tgcgggagcc acaattaccc ttttagttga tcagtttcct   61500
ttttgtaaca gtaatgaatt ggaagggaca acaggaaccg ggagtagttg aaaaggatac    61560
tagcaagaaa gaaagaacca atgggagtga gaaaaagtga tgatggagta ggggctgat    61620
agccaatctc aacacgcaga tctctgtctt tattggagtc gctggggtgc agagatccag   61680
tttgcatcta agggagtctg acacgtatct attaacaagt ccaaaggtaa agctgttgtc   61740
taagcaagcc ctgcgcctcc tccagtctaa tggaacagca aaatgacata ccaggagccc   61800
tttagtgact tacttaaagc taaaagtttg aactcttgcc cctgaagaag agattgcatc   61860
tcggctttca gtgtggcctg tggcttaagc tatggagata attttgaggg attttaaaaa   61920
tataaggtca tctagagtac ttgtctttca gttttttctt tttagttgcc cttcactatt   61980
tctgtaatgt tggcccgctt tacgtttagt gagttccagg aatactgtta taatgctgac   62040
tgtcttctat ttccctgtcc ctaaagattt agcaagatga gagtcctcaa ttattatgat    62100
gcttagctgg gatttggttc aaaatagttt aaacagttta ttctacctag aatgtcctct   62160
ctcttctctg cacgtcctta gtaaccccctg tggcccactt cttacttagg tctctcctaa    62220
catgtatcta tgacacattg atccctaaca gctatgattc ttcttatact ttttcagtaa   62280
tttaaatttt atcattctac tgcttgttca atacatctct ctatgtaaat cttgactcca   62340
taatgaggtt tttaacttcg aagggggttgg aagttatctg ctgccttggt acccccccgc    62400
cattacacaa gagtacattt taagcacatt acacctgagt gattgttgta aaacacagat   62460
gcaatctttc caccatcctc taagaattct tctgtggctt ccattggtta ccaaaaaaag    62520
tctgtgtcca gtgcacaaga ccatgaccca gctcagcctg gtccttgcct ccttgtctaa   62580
ctccctctcc ttcgggtatc caggatttgt tcgtgctaac agacagactt ctctaatagg    62640
tgaattcctt ggtgggggtg ggtggcatgc ctttgcatat tgcttctct ctgctgagaa     62700
tgcaagcctg tccctagccg tttctgccac tcctcctgat ctggtgagtt tgatctgcct   62760
ttcacaatga atcccagtca gtaaatattt atcactgaca tgctgaccct ggcaaaaatt    62820
gatgagagac tcaactaagg cagtgatagt gaaggtacag atttgacatc tggttaggac   62880
atagggttga caaactttgt cactctttag gtgtagagga aatacccaat gaagaggttg   62940
aaaatgtgtt gagttttaca attgactgga gctttctagg ggccacaata aaggcaattg   63000
gtgagtatag ttgttttaaa aatatccagt atctgttaag catttaccat gtgcagggat   63060
atggcaggca cttcacatta attgttttat ttattcctta acaacagttt gtaaggtaa   63120
gtagtattat taaccctat tacagatgac agaactgggg cttagtgaaa gtcttttaga   63180
aacaaaatct tggtacccttc catatatacc taaagtgtga aagtaattgg gcctgggggtc    63240
atagagctgt atagatttt tatgataatt ggaaaatgta taatcttatt atatatttat    63300
gatgattatt aacttgcatt tgaaggctgt gaacagggca tatgcttaaa ttgctgtggc   63360
ctaacaattc ctgttgttac acttgctcaa ctcacaggtt atttttcctgg cttcatatat   63420
gcaagtttga cattgctgtt caaagactt aaatttagaa ttctctttta aaaatgtaaa   63480
tgggattttg ccttagaaca gcaagccact gacattttgt gcagaatgta gtatacataa    63540
tgcagagttt tacacagaaa acttggcagg catgtgtgga acggctgcag acagggacag   63600
cctataattg tgggtgcaac ccgcgtgtgt gtagggaggg gggtgaagca gcgagaaggc   63660
tggagggcag cagctgggga ccagaggaga agtagtgtga ctcggtgacc aaggagaaga    63720
aaagggtgct tccacagttt tgaaaataag gagtttgcca aaaattgtaa agtctaaatg    63780
cagaccttgt ttggaataaa gatgaatttc gttttagctc tgtatccttt ggcaaccctt    63840
ttttttcccct ctcatttttt ttcctgcgtg aaaaagaggg aaaggggtcc atccagtcat   63900
gcatatgaat gtttctatac cagagtagta aatatatgca tcttatgcct tcgtgtggtc   63960
ctttgtaact gtgaattatg attttggaaa gctgtgtttt tttaatcttg tttctgtaag    64020
gataaattaa tcaaagttaa cctctcaaaa aagtcctggt tctgtagggg ggaaaaaaaa    64080
caacaactga ttttcaaaaa tctattagtg gggaagacta tattatacaa atagtcatga    64140
gcatttctgg gaactggctt ccaatatccc agacagcgtg acctgaatgt gaaaaaagtt    64200
gagaccacta gttttgagcc aaaatcatac aagcaaagag aaagcaagct gttgcccaag   64260
attgtggggt aaccatatgt ttgagccagg acttgatgaa gtaattgtgc gcaggacccc   64320
gtaggggtac tgggccgtag cccacagagc actgcaggcc cctgctcaaa gcagaccaca   64380
tgaaggccca cacagactga gtctggtcct gctggtggcc gcagcaagta agaaacaaag    64440
tgggttatta acatccactg gaatcttaac ctcatttaaa ggaaaacttg actttgagtt   64500
aactgtatcc cccccacccc ccgctgtcaa gaacccacct ctctagctca ttcctgtgtc   64560
agtgttgccg tattaactgc ccacctgctg cttttgtaaaa ggagactaga gtttaccctt   64620
cttatttag aatgttttga attctctttt ttaatgcaat aaatttaatt tacctttttt     64680
ttttaaccta caataagatt gattcctttt ggtgtacagt cgtgttgtga cttttgacag   64740
tgcattcagt catgtaacca ctgcccataa cagaaacata gatcggttct gtcacctctc   64800
ccctgcccca gatgttcttg tgttgcttgt gtacagtcag tcctgtcctc tacccccagc   64860
cagaaaccag taatctggtt tctgtttctg tttttctgcc ttttcagaa tgtcataaaa   64920
atgaaatagt atagtatata gcctttagtc tggctttgct cacttaccat aattaattta   64980
aaaataaatg tcttaaagcg tagaaaccat gatcatttta atttgtaatg gagaaatttt   65040
ttattgcttt tagtatattg agaacttgtg gatcacactg tatttgaaat tattaatgct   65100
ggatgttaaa aggtcactaa aagtatgtac tttttagaaa atttatttca ctgtattta    65160
ttagtattat accttatata ctgagtctgg gacatagaag tcttaaattc tactgcaaaa   65220
tggatttttt tttttttttt tgagatggag tttcgctctc gttgtccagg ctggagtaca   65280
```

```
atggcacgat ctcggctcac cacaacctcc gcctcccggg ttcaagcgat tctcccacct   65340
cagcctccca agtagctggg attacaggca tgcacctcta tgcccagata aggtttgtat   65400
tttttagtaga gacggggttt ctctatgttg gtcaggttgg tctcgaactc ctgacctcag   65460
gtgatccacc cgcctcagcc tcccaaagtg ctgggattat aggtgtgagc cactgcgccc   65520
ggccgaaaat ttatatttt aaagcgaaag ctaacttctca attttgaaaa tttttattgg   65580
gagcaggata ttataataat aatctttagt tgttaaacca ttaaacatca aggtttttta   65640
cattgtttct atgcctcctc cctcaaaaaa aaaaaacctc ctacaataaa actgaaaaat   65700
tgcacaaaga catattagtg gaagaccact gcttcgttta cacaaatgaa gagtataaag   65760
cagagaagtg ctccttgggg caaaaggcaa ttggcaaaaa gctaaggaac attttcataa   65820
tgagttagaa atacagatca tcaggaatat ccaggaagcg atagtgaata ccaggcaggc   65880
ttaagagaca ggaaacattt agcatgttgg taaaccactt tagcacatca gcaaaagcat   65940
ataaacagct ttaggattgg aaattattgc catgggaaa gcaacaatt tagaggagca    66000
attccaatta aaaatataaa gatcgtttct ttagattaat tcttgagttg ctccccctatg   66060
cctgtgtagc agaatctaaa agataatcat gtgaacggga gattatattt aaaaaataaa   66120
ctttgaaatt cataaaaagg aaaatgttaa agaatgtaaa attatactgg tagaaaaaaa   66180
atttttttt ttgaagatgg agtttcactc ttgttgccca agctggcgtg caatggcacg    66240
atctctgctc actgcaacct ccacctccca ggttcaagca attctcctgc ctcagcctcc   66300
caagtagctg agattacagg cacgcgccac cacgcctgc taatttttg tatttttagt    66360
agaaacgggg tttcaccatg ttggccaggc tggtctcgaa ctcctgacct caagtgatct   66420
gcccacctcg gcctcccaaa gtgctgggat tacaggcatg agccattgca cccggcagaa   66480
attttttaaa atagaaaaaa atagcccatt catgatacat gaattaaaga aaatattggt   66540
aacatgtatg gtaacagatt agtagctgag aacccaaag ctgccccagg ttgcttcaaa    66600
tcctggttct gccatgttcc agctgtgtga ccttgggcaa actatcttac cctttgtttc   66660
agttttcctca tcaggaaaat gggctttaat aggattattg tgtggattga gttaataagt   66720
aaagtgctta gaacaggcct ccaaaatagt aagtgttgta tgcgttagct attattaata   66780
catcacaaat ttccactaaa gaaaatcttc cctagttttgt atatgggatt gtcagaaaac   66840
aaatgaaaa atcatagtat aaacagccta tatggcttta aagaattata taaaacacat    66900
gatcttttctg aagtagtttt ttaaagaaa aagttagaa ctaacttctc ccttgatttt     66960
cacttttag agtggtgaaa ccagaacaat atctcacttt cattatacta cctggccaga   67020
ttttggagtc cctgaatcac cagcttcatt tctcaatttc ttgtttaaag tgagagaatc   67080
tggctccttg aaccctgacc atgggcctgc ggtgatccac tgtagtgcag gcattgggcg   67140
ctctggcacc ttctctctgg tagacacttg tcttgttttg gtaagtgctt cttacgatct   67200
cattttaatc tcattgattt ttttttttaa attgcttcca ctggcagtga ataaactctg   67260
atgctgtatc ccagaactga ggttttttcaa cttaaacttc tacttttgga aaaacctaaa   67320
aatctccattt ccaccgttgc aactgcctct tattcatgac tggtaggaat gtatccatga   67380
tgattttaga gatccctaag aaggtgtttt tcttcctggt agcttatat tacagaaata     67440
ataggtctct cccccacatt ttttcaaata taaattcata tgtaatattg aattccttcc   67500
tcctcagaca gatactttat ctcatttttt aaatttaaaa actagggata atgatagaca   67560
tacttcacag ggttcctgtg agaattcaat gaattaatca attaaggaga ttagaagag     67620
tccctgatgt tttctgagca ttccataaat gtcagtatta ctgttactcc cctgaggttc   67680
ctgtctgtgc ccccaacggc taattctttc tccaccagtc attcccagtc ccagcctgta   67740
tacagcctag atcttttctt ctcttttttag gacctttatt ttttcgttac ttgggataca   67800
tgaaacttct gtttgcccttt atacttctcc taacttctgt ctttacttct cctcttatt    67860
ataggatcaa acccaacaat aatactgtct gctttgattt ccatgccatc tactccttca   67920
gtagtccctg cagcttagtt tctgcttctt gagcgtgttc taagattatc aataacctaa   67980
gcagtttagc ttgtcctggt attcagtctg gtggggattt tgttttttgtc tttgtttaga   68040
cagagtcttg ccctgtcacc caggctggag tacaatggtg caatcactgc tcactgcagc   68100
ctcaacctcc tggactcaag tgatcctccc acctcagcct cccaagtagc tgcctgcacc   68160
accacaccca actagttttt gcttttttat ttttagtaga gacaaggcct cactatcttg   68220
gccaggctag tctcaaattc ctgggctcaa gtgatcttct tgcctcagcc tgccaaaatg   68280
ctgggattac aggttgagc caccacgctt gacacaagac tggtgttctt aaccttgact    68340
ttaaggcccct gtattagtct cttcgatgtt tctgtaaaac gtagctatgc ttcattgcag   68400
ttatgtcagc attcttatgc tttccaccat gactgccagc acaaagtaga ttcccaggtg   68460
aattaatatg atgatgcttt tcattgtaaa cacacacaca aggagcttga tcaatggagt   68520
gatactcttg gaaggagtga tactcttgga agaacatttc agacgttgca tctctaatga   68580
aagctaggaa ttgggaacgg ttgagtctta actaaacatc tgtattactt taccactctg   68640
cgtatatata gtatacttca atcaaaatta gattgttaca tcaaagtttt aaaactctgg   68700
tgattatttt gttaatgaca cctgttccct gccaactata acttcaacaa ttttttttct   68760
tttatttttg gtgagcctgg gtgtggggat tctaacacta ggtcagtagt ccagagcagt   68820
gctgtagctc agcagttgta tcgtgggatc gggcttttgc tgtcttttcc accgtctttc   68880
ttcattttat tttattattc tatttattta tttattatt tatttgagac gaagtttcgc    68940
tctgttgcca gggtggagtg cagtggtgca atctcagctc actgcaacct ccgcctcccg   69000
ggttcaagag attctcctgc ctcagcctcc cgagtagctg ggactacaag tgcgtaccac   69060
catgcccagc taatttttgt attttagta gacgggggt ttaccatgt tgtccaggaa     69120
ggtctcaatc tcttgacctc ataatctgcc caccttggcc tcccaaagtg ctgggattac   69180
aggtgtgacc caccacattt ttattttatt tatttattat tttattttatt atttatttat   69240
ttatttattt ttgagatgga gtctcgctct gtcgcccagg ctggagtata gtggcactat   69300
ctgacctcac tgcaacctgcc gcctcctggg ttcaggcgat tctccagcct cagcctccaa   69360
tgtagctgga attacagaca tgcgccgcca cacccagcta attttttgtat ttttagtaga   69420
gatggcattt cgcgatgttg gccaggctgg tctctagctc ctggcctcaa gtgatttggc   69480
ctcccaaagt gttgggatta caggcatgag ccatcatgcc tggcctcttt tccaccattg   69540
ttagatgggg gctgtatatc cagacatcgt gtctgtagtg cagacatgaa ggaggcgaa    69600
ggggaatgag cagaaaggtt gactcctgcc atgacttta aaaaaaaaaa tagtcctat    69660
actagccaga actggttata aatccttcct ttaaccaatg actggccaga aggaatgaga   69720
ttactatgat tggtttggaa tcagttgtga atcagctaaa gaatcaaagt cctccaacta   69780
cttgaggggt tgagatgtgg ggagggatga gtaggctggg atagttgttg tgtacataac   69840
agttatagct ggagggttaa attatcgttg ttctttcaga ggagaaaatg catagcaaaa    69900
atcttagcaa tgatccttgca ttgattctgt ttcctgggtt ccaataacaa gacttgtctc   69960
attttttgcc tttcttgcag atggaaaaag gagatgatat taacataaaa caagtgttac   70020
```

```
tgaacatgag aaaataccga atgggtctta ttcagacccc agatcaactg agattctcat  70080
acatggctat aatagaagga gcaaaatgta taaagggaga ttctagtata caggtaaact  70140
tcatacaggt tttaaatcat atctatttgt taaatacaca tagcatcaaa taactgcact  70200
ccacttgagc ccttgtcttt gtttcaaaga gtgtatttga attttttgtgg taaatccagc  70260
tggctgtctt aaaattgtaa aatttagct agcttcctca tatatactca gcctcaggtt  70320
aaatcctgtg tgttacttaa aagcccttgt agaaacaaga tttcattaaa gaaactgaat  70380
ttttcatttt gggggtggtt aatctttttaa ttattaaagt aactggaaac ttgagatact  70440
tttgccttca ttaaacactg atacttggtt tatgtgatat ttgactttat aacaacaagc  70500
aacttgaata tttatggcag atataatgaa attccagcaa aatgttatat tcttctggtt  70560
ggtggcttta ttctcattaa gctatttta ctgcatattt gtagaaccta agttcaaaga  70620
ctgatcagaa acttgtgtta tgtactaagt taaaatgtaa aatagaaaca accacagact  70680
ccattttttg tctggtttaa tcacatagta ttggacataa gcagtactg taagttgatg  70740
cataatataa gaagatcgac tgtctttca ttatgtttct catgtgtgaa catatttact  70800
agcactttca tttctctgat tactagccaa tataagaatg taaattagat cggaccattg  70860
gtgtcagaat aaaggtttat ttaaaaagat ttttttccaaa tctttaaata gcattaaaat  70920
attcttaatg cacagaaaca ttagggcact cagagccaaa atacgcaatg tttgggaaac  70980
tcagcccatt agaacatgtc ctgcttcaga cgccagactt tgggaacact ggatttgcca  71040
gggtcacttt ggcagtgatc agtgatttag gtgaagtaaa agttatttca gatgtttaag  71100
attaggaaaa tttcccttttc taatcacagt gagctttcac caacttaaat ctggagttca  71160
aaaagaaaag tagttcaatc agatttcccc atgccttcac agcctgcatg ccgccttccc  71220
tgcctgcttc ctgctgtga tgagacgggg aactgggagg gaaatgtatt gtcctttgga  71280
ttgtgtcttt cctaccactg cttttttttt tttaagttt tgtgtcttta gttttagaat  71340
acatacttta tctgagggtg gatctttttt tatcacagag atgagttttt ctggacacac  71400
tttttttgtgg agtctttgac agtgcagttt gtggctagga aggatttttt ttctgttaat  71460
ttatctggtg tgatattgtc ctcaggctct caattctaag gcattttctg ccctattcc  71520
agataggata ttggaaacat cttttatcct caggtactca ggatcagaaa agcatgctgc  71580
ccattccaag gggttaattt ctgcagaaat ggtcttggca ttctgagaat cttttttaat  71640
tggtgcattt agaccatcgg catatgaagt gattactgat aaagtggat taataaatac  71700
ataccacaca tgctactggt tttttttttct tttttgaga cgcagttttg ctcttgttgc  71760
ccagactgga gtgcaatggc acaatctcgg ttcactgcag cctctgcctc ccaggttcaa  71820
gtggttctcc ccactcagcc ttccgagtag ttgggattac aggtgcctgc caccactcct  71880
ggctaatttt gcattttag tagagatggg gtttcacagt gttgaccagg ctggtctcga  71940
actcctgacc tcaagtgatc gcccacctcg gcgtcccaaa gtgctgagat tacaggcgtg  72000
agccaccgca cccagcccaa agtgattgta tcttaagtct gtaaatatgt gtaattataa  72060
tcttaaagca tgtattcatt tacagaaaac ttccaatgac tttgacattc ctatagacat  72120
ataggctatt tgcaattgcc tttcagcaca aggtcaggca taaatactta agctggttgc  72180
tggtattacc acatatttat tagcatattc ccagtattga tgatgacagt taaccccca  72240
gagtaaatat ctagttttggc aattcagaac taatgttgta agatctctag ctggtaattt  72300
gatattacta ataaagtatt aaatgtaaat gataaacttt taacaaatta cagaggattt  72360
gaagtttaat tgcattgctt aaagcttttct tcagtgagaa aaatgggtag agctagggtt  72420
ctaggcattg tgtgggggc atggctccta gtggcagtga ctcatgggtt ggtgcaacgt  72480
gagcacagaa ttagaaagaa agatgaaaca gtaccaggcc tcaaaatgag agctcctttg  72540
aggttatagt ttagtgaaat gtaattcctt ggcttcacca gtcagcatta atgacctgag  72600
gcaggtgact caggagtgct ggctcccttg tgtgtcacag ggaggacaga gacgagtgag  72660
tttgctgaac ctatataggc atgagtgagt ttgctgaaca taggcacgag tgagtctgct  72720
gatcatagcc atgaatgagt ctgtcgaaca tagccatgag tgagtttgct gaacatagcc  72780
atggcaaaat gacattgttg ggtttgtggg gttttttttaa ttcactagca ttaaatatct  72840
cttttatttc tctctctgcc gagtgctttc cttgttgacg tattctgaat ttgttgcata  72900
ttctgggaag tggtccagtg agacttgatt tttggtgtca tcttatttgt tgacattgtt  72960
gagtgttgtc cagctataag gccaagttac ataactaggt ctcagtcaag agtggaaact  73020
tcaaaaattg accagtgtaa atttctggaga caatttaaca tttttgtgag gtactttgtt  73080
gaacacacat ctttataagg ggtcacagca tagtcaaccc agacttgcct aggttaaaat  73140
tctgtctcta ctatttgtta ggtgcatatc cttgggcgag ttacctaatt attctccca  73200
catcttccgt aaaaagggtg taataatggt aatattagta ttagtgctta tctcctaagg  73260
ttattgtgag gattaagagc tagcacatt gaagtgttga aatatggcat ggagagtagc  73320
aagtactcca tgtcttcact ataaaagatt tggattgagt aacaaaacaa acaagggaac  73380
aaagaaaata gacagtcatc taagtgaaga catccttaat tactcctgtg ttccattata  73440
ttgtagtttc ttgattgttg gcacagtatt ctttcgggga catggtttgc gccctcttag  73500
ggctcaggat tttcagttct acccactac tcatgaagtc agagacctc ttcccggaa  73560
gtctatttcc tttccagcct catctctcct actcaagctt tgcgtgtttt ccatcctcta  73620
gacaaattgt accaaactgt actactaact gttctccaaa cacaacaaac tgtagaattt  73680
cacatttct aaatcttctg taaatcaact attataaaac aaaaaagcca gccgtggtag  73740
ttctctccta tagtcccagc tactcaggaa tctgagacag gaggactgct tgagcccagg  73800
agtttgaggc tacagtgagc tgtgatcaca ccattgcatt ctggcctggc caacagata  73860
agacccccatc tctaaaaaaa ttaaaacat aaaaagaggt acattgatta tgcagctaag  73920
taaaatagcc atatctggga acggtgaagt gtggaaaatg cttttttttt tgaaacagag  73980
tttcactgtt gttgcccagg ctggattgca gtggcgtgat ctcggctcac tgcaacctcc  74040
gcctcccaga ttcatgcaat tctcctgcct cagcctccca agtagctggg attacaggt  74100
tgcaccacca tgcctggcta atttttgtatt tttagtagag acagggtttc tccatgacac  74160
cgagtctcat ctttcaccca ggctagagta cagtggcaca atctcagctc actacaacct  74220
cggcctcccg ggttcaagca attcttctac ctcagcctcc caagtaactg ggattacagg  74280
catgtgccac cacacccagc taattttgt atttttggta gagatggggt ttcaccatgt  74340
tgcccaggct ggtctcaaac tcctgacctc aagtgatctg cccacctcag cctcccaaag  74400
tgctgagatt acaggcatga gccactgtgc caggcgtgc tttttcttttt taatacctct  74460
ggtacatgat gacaatgaga caaattagaa actagtttat ccattgtatg aatggatttc  74520
ccagagattt tttaaagatc tgaatacaag cattgctttt aacagtacca tattgcacaa  74580
gagtaactcc agggaatgaa tattccctaa gttctaaaaa actttaagtt gcaatgttac  74640
atctctgtcc aaaatcatta gactcctcgg gcaataagta gagtattcct tatttattag  74700
atccaagact cccttgcgtcc ttgataggat cttcaaagaa ggccatccct gtccatacca  74760
```

```
agtcatttgg gccagtgtca gtcataggta atcaaaacca ttggctccca ctgcttctgc   74820
ctctaccact tgccactggc agatacatag atggggatca tgtttcatcc tttcaaggac   74880
ttgagagact atagtcccag tgcataggtt atatatgcgt ttttcttctc tggcatgtac   74940
aattgtcact gctttcatct gcaggggccc agatacactc ttcttcctct accttttgtcc  75000
ctaggaatgg tgacaagtga gagcacagga aacatatttt ctagacatga tgctgggcgc   75060
ttcacatgcc atctcattaa tcacaactgt ctcccagggt agatgatgac atcctctttc   75120
atagaagaaa ctgaaatttg tcttcatctt ggtccgaatc ctggtttgtg ttgccatcta   75180
ctcctgaagg ccatgctaga ggcatgctgg agggtgtttc tctagcccag tggtgggcta   75240
gccagctgcc tggagctgct agcgtacctg atagacacaa ccaaattaaa gtccttttagc  75300
atcacaagga ccagcttgga gatctcaccg ttagttctcc cctagactga acagtggcaa   75360
ggagcaagaa ggttccagat cacattcaag caccactgtg gtgactactc cagtgttaca   75420
tacctctgga ttagaagtgg attaagattc aagcaaaatc taccttggct gaaatctttt   75480
taaaaatttt tgtgtttttt gtgcagtgct actttatttt ttattttgtt tttttgtctg   75540
ttggttggtt ggttcttttg agacggagtc tcgctcgtgt gcccaggagt gcagtggtgt   75600
gatctcagct cactgcaacc tccgcctcct ggggtcaagt gattctccta cctcagcctc   75660
ccgagtagct gggactatag gcgtgtgcca ccacacccag ctaattattt tgtattttta   75720
gtagagatgg ggtttcacca tgttagctag gatggtctcg atctcctgac ctcttgatcc   75780
acctgcctca gcctcccaaa gtgttgggat tacaggcgtg agccaccgca tgccccggcc   75840
tttgtttttta attgacactt agtaattgta catatttatg gggttcagtg tgatattttg   75900
atacatttat gtaatgacca aattagacta gcacgtctat cacctcatac atttatcttt   75960
tctttgtggt gaaaacgttc aaaatcctct cttccagcta ttttgaaatc tctatttaat   76020
tatatattat tatgtgctaa tatatttcat agtacttgaa atatatataa tgtatataaa   76080
gtatttcgaa atagccagaa gagaggattt tatgtgtata taaaatgtgt atgtatataa   76140
atttttttcg agatagggtc tcattctctt gttcatgctg gtgtacagtg gcacgatcat   76200
ggctcgctca ctgtagcctc cgcctcctgg gctcaagtga tcctcctgcc ctagtctctt   76260
aagtaattgg gactgcaggc gcgtgccacc acatatggat aatttttaaa tttttgtaga   76320
gactgggtct caccatgttg cccaggctga tctcaaactc ctgggctcaa gcgatctgcc   76380
cgccctagcc tcccaaactg ctagaattgc aggcatgagc caccacaccc tgtctgaaat   76440
attaaatatt attaaccata gtcattcgtg gcagtaaaac accagaactc atcccctgt    76500
tgaactgttg ttcagtttct cactatgccc cctcttccct actctgcgaa gcctccagta   76560
ggtactattc tactctctgc ttctatgaga ttaacatttt tagattccac atatgagtga   76620
gaacatacag tatttgtctt tgtgtacttg gcttaatgtc ctccagtttc atccatttg    76680
ccacaaaaga caggatttct tttttttta atggccaaat agtattatat tatatatata    76740
tatatatatt ttttttttt ttttttcca cattttcttt ctccctccat tcattgatgg     76800
acatttaggt tgattccgta tcttgactac tgtgaatagt gctgcaataa gcacaggagt   76860
gccgatatgc ctttgaaatc ctaatttcat ttcccttgga taaatacccca gtagtgggat  76920
tgctggatca tatgatagtt ctatttttaa tcttttaagg aaccttttatg ctgttttcca  76980
agatggctgt actaatttac attccaccag ccgtgtacaa gagttcccct ttctccacat   77040
tcatgccagc atttattttt tgtcttttg ataatagtca ttctaattgg ggtgtggtga    77100
tatctcagtg tggtattgat ttgcattatt ctgatgatta gtgatattga ccatttttctc  77160
atgtatctgt tggctctttg tatgtctttt aagaaatggc tattcaggtc ttttacctat   77220
ttttaattgg attacttgtg ttttctgcta ttgaattttg tttgagtttc ttatatattc   77280
tggatattaa tccctgtcaa atgtatagtt tgcagatatt ttcttccatt ctgtagattg   77340
tctcttcagt ctatcgattg cttccttttgc tatacagaag cttttttagt tgatgtaatc  77400
ccatttgtct gtttttgctt ttgaggtctt atacaaagaa ccctttccctt gcccagacca  77460
atgtcctgaa gtgtttccct atcttttctt ctagtatgta tatttgtttg gggtctcata   77520
tttaagtctt tagtccattt tgagttgatt tttttaatatg gtgagagata ggggtctagt  77580
ttcattcttg ggcatctaga tatccagtgt tcccaacacc atttatcaaa gagactgtcc   77640
ttcaccagtg tatattcttg gcatctttgt caaaaataaa ttggctgtaa atacgtagat   77700
ttatttccat gctctgtctt ctgttttatt ggtcttata cctgttctta tgatagtagc    77760
atgctattt ggttactata gcttttgtagt atatttgag gtcaggtagt gtgatgccc     77820
cagcttttg ctcaaaattg ctttggctttt tggggtcttt tatgatttca tacaaattt    77880
aggattattt attctgtttc tgtgaagaat atcattggta ttttcattga attgcattga   77940
atctgtagat cactttatgt agtatggaca ttttaacagt attaatttta atccatgaac   78000
ataggctatc tttccatttg tgtcctcttc aacttttttcc attaatgttt tataattttc   78060
attatagaga tctttcacct ccttggttaa atttattcct aggtaatttt tttgaaaatgt  78120
gaattgcttt cttgatttct tttttcgat agttgttag tgatgtataa aattctactg     78180
attttttattt gttgattttg tatctgcaa ctttactgat tttttttatt agttataaca    78240
gtttttttggt agagtctata gggttttcta tacataagat tatgtcttct gcaaacagag   78300
acaatttgac ttcctccttt ccaatttgaa tacccttct cttagctaat tgctctggct    78360
aggacttaca gtattatgct gaataaaagt gttgaaagtg ggcatcctag cccggtgcgg   78420
tggctcatgc ctgtaatccc agcacttggg ggggctgaga tggcagatc atgaggtcaa    78480
gagattgaga ccaccctggc caacatggtg aaactctgcc tctactaaaa atacaaaaat   78540
tagctgggcg tgctggcacg cgcctgtagt cccagctagt ggggagctg aggcaggaga    78600
atcgcttgaa cctgggaggc agaggttgca gatcatgcca ctgcactcca gcctggtgac   78660
agagcaagac tccatctcaa aaaaaaaaaa aaaagaaa ggaggcatct ttgtcttgtt     78720
ccagatctta agaggaaaag ctttcaactt tttcatgttc agtatgatat taactatggg   78780
tttgtcataa cgtggctttg tgttgaggca caatttcctc catacttaat ttgttgagag   78840
tttttatcat gaaggtatgt tgaattttt ttttttttg agacagagtc tgtctgtt     78900
gcccaggctg gagtgcagtg gtgcaatctc ggctcactgc tacctccgcc ttctgggttc   78960
aagcgattct catgcctcag ccacctgagt ggctgggatt acaggcatgc accaccacac   79020
ccagctattt tttgtattta tagtagagat ggggtttcac catgttggcc agaccagtcc   79080
caaacgcctg acctcaagtg attcacccac ctcagcctcc caaagtgctg ggattacagg   79140
catgaaccac cacgcccagc cgctatgttg aatttatca aaggtttt ctgcatctgt       79200
tgaaatgatc atatggttct tgtccttgat tctgttgatt tttgagagat catgtttatt   79260
gatttacata tgttgaacca tccttttcatc ccttggatga atcccactg gtcatggtaa    79320
atgatgtttt taatatactg ttgaattcaa tttgctatta tttcattcag gattttttgca  79380
tccatattca tcaaggatat tggcctgtag ttttcttttt tgttgtgtcc ttgtctggtt   79440
ttggtatcag ggtaatgctg gccttacaga atgatttgg aagatttccc tcttcagttt    79500
```

```
tttgaatagt gtgaaaggaa ttagtattat ttaaatgttt gttagaattc agccatgaag  79560
ccatcaagtc cgggcttttc tttgatggga gactttttat tactgattta atctcactct  79620
ttattggtca gttcaggttt tctatgtctt catggttccg ttttgatagt tcgtgtgtgt  79680
ctaagaattt agccatttcc tctaggcttt tcaatttgtt ggcatacagt tgtttataat  79740
agtctcttac aatactttgt ttatgtgtatt agttgtaata tctccttttt catctctgat  79800
ttgagtcttt tttttttctt agtctgctat aggtttgttg attttgtttg cctttttcaaa  79860
aaaatgatcc ttggttttgt tgatctttcg tttcttttttt ttggtcactt tatttccatt  79920
cttctggtct ttattatttt ctttgttctg ctaatttttgg gtttagttta ttattttcta  79980
gttccttgag gtacatcagg ttgtttattt gagaactttc ttttttcttttt tttttttttt  80040
tttttttgaga cagtttcact ctgaccccta gactggagtg cagtggcatg attttggctc  80100
agtgcaacct ccgcctcccg ggttcaagtg attcttatgc ctcagcttcc caaatacttg  80160
gaattacagg tgcccaccac cactcctggc taatttatgg tagagatggc atttccaccat  80220
gttggccagg ctggtctcaa actcctcacc tcaggtgatc ctccagcctc tacctcccaa  80280
agttcttggg tgtgagccac ccacctggcc tgattgtgat ttttttcttt ttttaatttg  80340
ttgagacttg ttttttgtggc ctaacatatg gtccatcatg gagaatgttc catgtgctga  80400
tgagaaaaat gtgtattctg tggctgttgg agggaatgtt ctgtaaatgt gtgttaggtc  80460
catttggcct agagtgcagt ttaaatccaa tgttttttttg ttgattttat gtctggatga  80520
tctgtccatt gctgaaagtg ggatgtagcg ttctcctgct attattgtat tgcagtcgtat  80580
gtctccctttt agatgtaata atacttgctt tatatatttg tgtgcaccag tgttgtgtgc  80640
atagatattt aaaatcatta catcctcctg ctgaactgac ccctttgacc tttgtttctt  80700
tttacaattt ttgacctaaa gtctatttta tcaaaatata gctactcctc ttctctttttt  80760
ggttttaatt tgcatggagt atcatttctc atcccttcac ttcagtctt agtgtgtcct  80820
tacaggtgaa gtgagtgtct tgtaggcaac atagagttgg attttgtttt ttgttttttttc  80880
atccattcag ccactgtatc tttttcattga agtatttaat ctatttacat tcaagggtat  80940
tattgataga taaggactta cacctgccat tttgttaatt gttttctgtt tgcttttcat  81000
attctttatt cctttctttc tctcttattg tttaccttttc tggtttggtg attttctata  81060
gtgataagct ttgattttatt tctctttctc atttgtgtgt ctgctgtagt tactttttttt  81120
ctttgtggtt actctggggc ttacattaaa catcttagag tgttttaagc tgataataac  81180
ttaaccttgg tctcataaaa tattttttggc ttttacccctc cccccacaac ttataattttt  81240
gttgcttaat ttacatcttt ttatattgtg tggtccttaa caacttgtag ctgtagttac  81300
cattaaccat tttttacttt taaccttcat aatggagatt tgaaagatta tattccacag  81360
ttacagcaat ggagttttct gaatttggta attaattttac ctctgtcagt gagattatat  81420
tttcatatat tttcatgata gtaattatac ttttgcttcc agtcaaagca gctcccttaa  81480
gcatttcttg taaggctagt ctagtggtaa taaattcttg cagcttttgc ttgtctggga  81540
aagactccat ttttctttca tttctgaaag atagctttgc tagtagttgt tatcttttcag  81600
cactttgaat atattatccc attctctaca gtctgttctt tcttggcgtg tacaggtttt  81660
ctgagaaatc tgttaatagc aacctgccag gttcccttac atgtgacttg atccttttct  81720
cttgctgctt ttagaattct ctatgtctga cttttgatgg ctttattata atgtaccttg  81780
gagagaggac ctctttgcat tgaatgtgtt cagtgtgctg tcgagtttca tggatctgat  81840
taccaatatt aaaattatat tactgtgact aatagttgag tgtggtccca gtataagtttg  81900
tctcaaaatag gtaaaagtcc acaagattttt attaagatta ttatattcaa ctatatactc  81960
atgtacataa atactaaatg ctttattata aaattttgaa attaaaataa gcatagttgt  82020
tacaagctac agtatggcaa aatgcctttt tcttttttcac tcatctttta gcatcattgg  82080
gttttcttaa cttgaatata ggattttaat tcataaattt ttttatttaa ggaaaataaa  82140
ttttttaatgt ttgcatttgt ttttcatttc tcttccctac ctagaaacga tggaaagaac  82200
tttctaagga agacttatct cctgcctttg atcattcacc aaacaaaata atgactgaaa  82260
aatacaatgg gaacagaata ggtctagaag aagaaaaact gacaggtgac cgatgtacag  82320
gactttcctc taaaatgcaa gatacaatgg aggagaacag tgagaggtaa gctttctata  82380
actacaggct gaaagatgag gcttttttat tttaaaaata aatttatgg gaccaggtgc  82440
cataggattt caggtatgta atttttatat taggaaaata caatcacgcc tgtaatctca  82500
acactttggg aggccaagga gggaagatca cttgagtcga ggagtttgaa accagcctgg  82560
gcaacatagt gagaccttat ctctacagaa aataaacaaa attagccagg tgtggtgatg  82620
cgagcctgtg gtcccagcca ctcgggagac tgaagtggga ggatcacttg agctgggagg  82680
gtcgaggttg cagtgagctg acataccacc actgcactcc cacctgggtg acaaagcaag  82740
accctgtctc ataaataata aataaaataa ataattatg tggatatgat atatgaaata  82800
atataggccc tttttttttat tgaattaata taaccttttt ttttctctgt cacccaggct  82860
agagtgcggt ggcacaacct tagctgctcc acctcctggg ttcaagcaat tctcctgcct  82920
cagccctccc atgtagctgg gattacaggc gcccaccacc atgtccagct aattttttgta  82980
ttttagtag agagaggggtt tcaccatgtt aacaaggctg gtcttgaact cctgacctca  83040
ggtcatccac ccgcctcagc ctcccaaagt gctgggatta caggcgtgag ccaccgtgcc  83100
cagccaaatt aatataaacct ttatttctta cctgagggta tttagtatat gatgacaaag  83160
gtgttcttaa ggagctttca gccaatactt agaaccagt tcaaaaatcc tttaaaacaa  83220
taatgattga gtgtaaaagt taataaattt gggtgctaaa atatatggta tggtacagaa  83280
aataagtagt atgaataacct gccatttgta ctataattat aatgtaactg ataatatgcc  83340
tttaataaaa catttaaaca tgtaagctta attgcattac tggagaaaga aaaggcgtt  83400
ttttaaaaat ccatatgaat gtggcatcta ttcagaatttt taaattacaa ttacatttct  83460
aagactgtct ctcacagatt aggaagctga taacctggta taagtcacat agcaaagtga  83520
atgaggtttt tctttcctct ctcctgcatc tctgaataac ttttcttctt ctcttttgtg  83580
caaatatact tcttatcatg gggaatttta tcttgtggtt atatttgtta gattggaatg  83640
aaaatagtcg aagtctgcca tacattatag ctttactgct gtattttcct aatataaaaa  83700
ttaaatacct gaaattttat aaatgctaac atattccaat atataataca tgtattatta  83760
tatattatag tggaagagtt tattatgatt tagtaatgtt attcccaatt tttgacttca  83820
gtagttttag actgcaagag aaagcataat tttttggtt cctttttttca tcttaaaatag  83880
aatatcttta aatcaggaaa taatagtttt aagttacctt agctttttttca ataataaggc  83940
tttcagattc ctagtgttac tgcttttttcc ccccttttat ctagtactat ctgcagaatt  84000
aaatgaaaaa caggctgat gactgaaatg gcattcttag tatttcagaa gtgttgagtt  84060
ttaatctaca aagattcaga acaaccatgt taatcctagt gagttaaatc actcatacaa  84120
gcttgcaaat acagaggaga ctactaaaac cactctagag tctataactc taaggagtta  84180
tagagtgatt gcagaagact gttttatggg gtctgtgtgt gtgtttatgt gcctgtacat  84240
```

```
gttttcgcat gtggtggcgg tgttttcttc tttcccttt ttccttcct gtctgataaa   84300
tgagactggt gcatgtttga aagcagagag tcccaacaga aaagtcagaa ttctaagcgg   84360
agaagtctga ttacaaaaac aaggttacag aaatgaaaaa gaggaggccg ggcgtggtgg   84420
ctcacgcttg taatctcagt gctgtgggag gtcaaggcag gtggatcact tgaggtcagg   84480
agtttgagac cagcctggcc aacatggtga accccgtct ctgctgaaaa tacaaaaatt   84540
aaccaggcac tgagagtgag aaacaacttg gacatacgaa ttttaaaata caaaaattaa   84600
agaggcatta acgcctgttg tcccagcttc ttgggaggct gaggtgggag aattgcttga   84660
acccaggagg ttgcagtgag ccgagatcat aacactgcac tccagactgg gcaacagagc   84720
aagactctta tctcaaaaaa aaaaaaatgt aaaagaagag cataggatca gggtgtgaag   84780
taaaggttac tctgaacagt ttattttt aatcagtccc agtaattttt aatacctata   84840
gatagctttg cattaaagat cctcataaaa gtcttatcaa aagaaattca agtttctttt   84900
ttttcttttt tttttcctg agacgggagtc ttgctctgtc acccaggctg aagtgcagtg   84960
gcgcagtctt ggctcactgc aacctccacc tcccgggttc aagcaattct cctgccttag   85020
cctcccaagt agctgggatt acaggccccc gccactacac ccagctaatt tttgtattt   85080
tagtagaggc agggtttcac catgttggcc aggctggtct cgaactcctg accttgtgat   85140
cctcccgcct cagcctccca aagtgctggg attacagaca tgagccacca cacctggcca   85200
gaatttcaac tttcaaaaga aatagaacac agtactttct tgtattcatt ttcattgtat   85260
tcatttggag gatattcatc ctccaaagca gtgtttttca aattgaaggt caaatcacat   85320
agtcgtgaag tttattggat tataaacatt ttttaaagaa gaaaatagaa taaaatagaa   85380
attatcagca tatcacaaat aataacatga atttaacaga tgctggcgag ttgtgggaga   85440
aaaaggaatg cttaaacact gttggtggga gtataaatta gttcaactat tgtggaagac   85500
agtgtggtga ttcctcaaag acctaaaaac agaaatacca ttcaacccag caatcccatt   85560
actgggtata caccccaaaag aatataaatc attgtactgt aaagatgtaa acacacgcgt   85620
atgttgattg cagcactatt caccatgaaa aagacatgga atcaatctaa atgcctatca   85680
atgatagact gcataaagaa aatgtacata tacagcatgg aatactatgc atccataata   85740
aagaatgaga tcatgtcctt tgtaggggct tggatggage tggaggccat tatccttagc   85800
aaaactaatg gaggaacaga aaccaaata cccatgttc ttactaacaa ttgagagcta   85860
aatgatgaga acacatggac acatagaggg gaacaacact gggggcctgt cggaggatgg   85920
agggtgggag gagggggaca atcaggaaaa ataactaatg ggtactaggc ttaatacctg   85980
ggtgatgaaa taatctgtac aacaaaactt gttgtacatg tcacggagat gacacaagtt   86040
tcaagcttat gtaacaagcc tgcacatgga cgtaccctg aacttgaatt ttaacctgtt   86100
tttatatg tatgtgtgat gtataaattc catatattta catatacatt gtgtacctat   86160
gtaagtgtgt gtgtgaggtt actctgttgt gatgctattt cttactgtag gttgcagtct   86220
gaatttgaaa ggcagtattc tcaattacag ttcaacccag aaaccagat cactgagagt   86280
gagaaacaac ttggacatac gaaaagtctg gagcaggcag agtggctcat gcctgtaatc   86340
ccaacactcg gggaggctga ggcgggtgga tcacttgagc ctagcagttc aagaccagcc   86400
tgcgcaacat ggcaaaccct gtctctacaa aaaatacaaa aatccgccaa atgtggtggg   86460
acctgcctgt agtcttaagg gaggctgagg tgggaggatt gcttgagccc aagaggttga   86520
ggctacaggg agctatgatc acgccacatg atcttccctg ggcaagggtc cacaggaggc   86580
attcccattg gttaatatcc taaattgcat aaatatacgg gaaaacctgg gcaggtccca   86640
tttggcaagt cattacacag acataatttc tttaggcccc actaaggaag aaaagatttt   86700
atcacaaatc gagagtagtc ttgtcattct ctggaattgt gttcttaaat tagatacagg   86760
catgctctgg tatttgtctc tagtccattc ctgaattata tagtgcactt ttggaaagca   86820
aaaacctctg ttccattctt ttaaatgaga aaaatagtgt gttgtcagcc caaccagaaa   86880
gcataaccag ttcccccaaa tatagtacaa aaccttttaa actcctatgt agcatttaaa   86940
gcactaatta tgtaatcata taacacttaa gggactcatt attgggcttg tatggtaaat   87000
gacaaaatac tagatacaaa ttataattgc cttctatacc gcaatgaaaa taaaaaatga   87060
aataatacgt taaagattat atctaaattg gaaccttgtt aacgataccc ccaggctcct   87120
ggcaaaagct aataaagggc ccatgggagg ctaaccccct ctctgttttt atacatatt   87180
tgcctacact tgaacacaaa tgttttcact aacaggtaca tgcatatttg tgatagtgaa   87240
ttttcaattc agagagtgaa ttctgagtaa gaatttttgc aagtcattat agcagatatt   87300
cagatggagt tcagacagcc agggatacct gtatatatga taacaaaaag tgaaaaagac   87360
atgagaaagc accataagat gaacaaagat agcaaaccc agtctgtcct caagttgcag   87420
aatatgtgat gaagataaaa caagtaccca agttagcaca ttattagtaa attataaatt   87480
acttcaaatt aaatgccgta agaatagaag ggctagaggg ggtggagcaa gataattgaa   87540
gagtagaact gaaatgagag gacaggagag aagggaaggt ttctatttta gtggggaaca   87600
aatttggaga acagcaaaaa aacggcaaga acaaagttct gcatagcagg agaatattgg   87660
caagcgtttg catggacatg tgttctcagt tctcttgggt acatatctag gagtggaatt   87720
gctaggtcat atggtaactc tatgtttaac tttttgagga gctgtcaaac tgtttttcgt   87780
ggcagctgaa ccattttaca ttcccactaa caatctcttg gggagagaag gttccagtac   87840
accaaagaag tgtaacattg attaaaaatat tctaatacat agttcaattc agatttctct   87900
tgtctgaaag attcaccata tagctttttt aataaagttt tatggaaata taatttatt   87960
agcataaagt ttactcattt aaagtataca attcagtgac ttttaatata tttaccaaat   88020
tgtgtagctg gcaccacgat ctaattttag aacatttttcc tgatcccaac ttctgtagct   88080
gtttaaaaaa tatttcaaga ttaatcaaag attgatacta tatttagttg atgtgattct   88140
ttggtctcct ttaatctgga actgttccct gccttttttct tccttgcttg acatttgtat   88200
ttttgaagct tctaggccag atatcttta gaatgcccca tacaatgcat ttctttaatc   88260
attatttatc atagttaaat tcaggttaaa cgtcttggcc aggaaaaagg tagtctcaat   88320
gtaggagaca ttgaagaggc atttgagatt tttaagcacc atcgtgcact aggccccggta   88380
acgaaaaaaa aaaaaaaaga ttttaaatca agctacgtgt ccaggggtat gctctagaaa   88440
aattaccatg gcaataatat ttaatttgag ggcaggaag ctggttaggc ctttgctgta   88500
atacagaaaa gtgaaaagag ggaatggaag aaatagtaac ctatatgttg ccattggccg   88560
ttttttttgtt tttgtgggtg tgcttttata gagaggcaag acttgctata ttgcacaagc   88620
tggactttgaa ttcctgggct taagccgtcc tcctgagtag ctggatggca ttattatta   88680
tatagaacca gaactaagta tcttgagagt cagagaccttt ccactgaaac aaaattctg   88740
agaccggaca cagtggctca tgcctgtaat cccagcactt gggaggctg aggtgggcgg   88800
atcacttgag atcaggagtt caagaccagc ctggctaaca tggtgaaaca tcatctcact   88860
aaaaatacaa aaaattagc caggcgtggt ggtgcacgtc tgtaatccca gctacttggg   88920
aggctgaggc agaagaattg cttgaacccg gaaggcgggg gttgcagtga gccaagatcg   88980
```

```
tgccactgca ctcccgcctg ggcaacagaa caagactcca tccacccgc ctccccacc    89040
acccaaaaa aatttctgta ttgactatga aaatgggagg tagaaatgtg tatggtcaaa    89100
taaaagaata agtgctccca caacagaata ttcatggaaa tattaaatag ctagctttta   89160
taagagcctt aaccatcaaa cgtgaccagg aaatgggatc agatgcaagt ggtaccccct   89220
tgtcttccca ctcctgctcc tgctgactag ttaacaagga aggaaagaaa actaacagtc   89280
atcaattcac gtgtcaagaa agtaccttgc ttattttcag gtcccactaa aagcagttat   89340
caatataaaa ctgtaccagg aatggttgtc aaggtacatc tctgaatcat taaagaatat   89400
tgaggctttt cttggccggg cgccgtggct cacacctgta atctcaggac tttgggaggc   89460
caaggcgggt gaattgcttg aggtcaggag ttcaagacca gcctggccaa catggcaaaa   89520
ccctgtctct actaaaaata caaaaaatta gctgggcata gtggtgcacg cctgcagtct   89580
cagttacttg ggaggctgag gcacgagaat cacttgagcg tgggaggcag aggttgcagt   89640
gaaccaagat tgtaccactg cactccaggc tgggtgacag agcaagacgc tgtctcaaaa   89700
gaatattgag gcttttcccc tcattattcc agtgttcaaa tagggtgaaa actatgtgga   89760
tggttttatt tgcgcctagg tcctctgtgt tagagtactc aagtcctgct ctgtgtgcac   89820
ttcctttcac ttgtttttat ttcctcatag tgctctacgg aaacgtattc gagaggacag   89880
aaaggccacc acagctcaga aggtgcagca gatgaaacag aggctaaatg agaatgaacg   89940
aaaaagaaaa aggtggttat attggcaacc tattctcact aagatggggt ttatgtcagt   90000
cattttggtt ggcgcttttg ttggctggac actgtttttt cagcaaaatg ccctataaac   90060
aattaatttt gcccagcaag cttctgcact agtaactgac agtgctacat taatcatagg   90120
ggtttgtctg cagcaaacgc ctcatatccc aaaaacggtg cagtagaata gacatcaacc   90180
agataagtga tatttacagt cacaagccca acatctcagg actcttgact gcaggttcct   90240
ctgaaccccca aactgtaaat ggctgtctaa aataaagaca ttcatgtttg ttaaaaactg   90300
gtaaattttg caactgtatt catacatgtc aaacacagta tttcacctga ccaacattga   90360
gatatccttt atcacaggat ttgttttggg aggctatctg gatttaaacc tgcacttgat   90420
ataagcaata aatattgtgg ttttatctac gttattggaa agaaaatgac atttaaataa   90480
tgtgtgtaat gtataatgta ctattgacat gggcatcaac acttttattc ttaagcattt   90540
cagggtaaat atattttata agtatctatt taatctttg tagttaactg tactttttaa    90600
gagctcaatt tgaaaaatct gttactaaaa aaataaattg tatgtcgatt gaattgtact   90660
ggatacattt tccattttc taaagagaag tttgatatga gcagttagaa gttggaataa    90720
gcaattcta ctatatattg catttctttt atgtttttaca gttttcccca ttttaaaaag    90780
aaaagcaaac aaagaaacaa aagttttttcc taaaaaatatc tttgaaggaa aattctcctt   90840
actgggatag tcaggtaaac agttggtcaa gactttgtaa agaaattggt ttctgtaaat    90900
cccattattg atatgtttat ttttcatgaa aatttcaatg tagttggggt agattatgat    90960
ttaggaagca aaagtaagaa gcagcatttt atgattcata atttcagttt actagactga    91020
agttttgaag taaacacttt tcagttttctt tctacttcaa taaatagtat gattatatgc    91080
aaaccttaca ttgtcatttt aacttaatga atatttttta aagcaaactg tttaatgaat    91140
ttaactgctc atttgaatgc tagctttcct cagatttcaa cattccattc agtgtttaat    91200
ttgtcttact taaaacttgaa attgttgtta caaattttaat tgctaggagg catggatagc    91260
atacattatt atggatagca taccttattt cagtggtttt caaactatgc tcattggatg    91320
tccaggtggg tcaagaggtt actttcaacc acagcatctc tgccttgtct ctttatatgc    91380
cacataagat ttctgcataa ggcttaagta ttttaaaggg ggcagttatc atttaaaaac    91440
agtttggtcg ggcgcggtgg ctcatgcctg taatcccagc actttgggag gctgaagtgg    91500
gcagatcacc tgaggtcagg agttcaagac cagcctggcc aacatggtga aaccaccatct   91560
ctactaaaaa tgcaaaaatt agctgggcat ggtggagggc acctgtaatc tcagctactc    91620
aggaggctga ggtaggagaa ttgcttgaac ccaggagatg gaggttgcag tgagctgaga    91680
tcacgtcact gcactccagc cagggcgaca gagcgagact ccatctcaaa agaaacaaac    91740
aaaaaaaaca gtttgggccg ggtgtggtgg ctcacgcttg taatcccagc acttcggaag    91800
gccaaggcgg gcggatcacg aggtcaagag atggagactg tcctggccaa catggtgaaa    91860
tccccttcttt actaaaaata caaaaattat ctgggcgtgg tggtgcatgc ctgtagtccc    91920
agctccttgg gaggctaagg caggagaatc acttgaaccc gggaggcaga ggttgcagtg    91980
agccgagatt gcaccactgc actccagcct ggcaacagag caagacttcg tctcaaaaaa    92040
aaaaaaaaaa aagtttgaa aaccattggt atagatagat attttgaatt gatttgcata    92100
gtctccttga atgtgttaaa ttatgttgaa agtatgaaag caggatgtag gtggtactac    92160
atattaaata agatttatat aacatgtgcc tgtgtcctga ttcagtatta ctgtgtcctg    92220
taaccttgaa gttggagagga ggtaagaggg acattttttt atgtctgtct gcattaaacc    92280
tgtgttgagg catccaagac cttacatttt caggttgtta ttggtttaaa acctcttttcc   92340
agtttgcatt ggtttgtctt tgctaaatgc agtatgttta tgttactctg caagtcacat    92400
acaggtagac cttatgacat ttccagttga aactaggctt gctttcggta cacaggtgaa    92460
gacttgagga agccagtgcc agagaggacg tgcctcaccc ctcagctggc tgaatgcagt    92520
tcattggctt acgctttgct ttctgtatgc tttctgtcct tctgggtggt gtcgcatata    92580
tttttaaaac cacattcagt gtgatgaaca cttgttggta cacttctaag gttagtcatc    92640
tttccttctc tgagcagatc cttgagaagg gcattgacag tggatgcttt aaatagtgtt    92700
cagtttttac cagtaataat attttttggt ggatgtcatg aaaacacatg acatcgtgtt    92760
gtgcccatga taaaaagtcc tgacttttta ttgaatgagg tgtgctggtc aaagagacag    92820
acgtggctgc cttctctggt aacagccaga ggaaaagtt agcaattcta gatgggttct    92880
acagctttaa aaaactgtt gtatccttag gtcctcataa tattaaatat tttctaatt    92940
taacagattt taagagtcag atatatactt tgacttgaat gatgtagtgt tgcttaagga    93000
agaaaaatt ataaaaaaaa tgtttcttttt attttcagga gttttttaatt catatctagt   93060
tcatttccac tcatatctat ttctgctaat agattgacag caaccttttgg tttaatgctg    93120
tgttctctag ctacaccaac aagttatata ttccttttcca atattaacca agtatttatt   93180
ttatgttagc ctatgactga gttttatcta tgcttgcaca tatatagaat gtaaaaatat    93240
aattctccat gtttaatgta tccatataaa aatgaaaata cccatttct gcattcttaa    93300
agggttaaga aaagtaacat gtaataagca catggaggac tttagaccat ttcttgtgtt    93360
agaggagact ttatacattt gtgaggtttt ctgtcttttg gtccttttat gttccttagtc   93420
catttcatta ttgtttttaat atttctacca aggaatgacc aagaaaagag aaggaagaa    93480
aaaaaatgtg ttaatcattt tcttttaatg gtatgtcagc agaagggggt ctgactgtaa    93540
gctaatgtgc acttgtgcct gtcctctttg tcttaaacta agttggtgg tatgaatcga    93600
aaaatgtgta ttggttaaa aagcagttta tgatatgaaa cagtcttcca gttttttatat   93660
caactccttt gctttcaaca gtcagttcaa agcaccattt attgatggtt tactgtatgc    93720
```

```
cagacactgt attttttctt tacgtattac cctacttaat cctcaacaca attttatgaa   93780
gtagttattg ttagcctgaa actggcattt ctccatcctt ttatggtgct gtctttgaaa   93840
agtctcagat gtgtaacatg tcctagaagt agataattat caaaggaaga ctgcaactgc   93900
aactcacttc cctctgagaa aaaatatccc tgactagatt acatatctag ttccagacca   93960
gaacctggtg gtattaaaag tgttttggtt gactattgta taccataatg agtacctaca   94020
ttcccaaatt gcctgcctgg ttgttgtaca gacttaaaaa tctagcctgc cttgattttt   94080
acttttcaga tacacatgtt taaagagatc tttgctggtc acagtagctc acacctgtat   94140
tcccagaact ttgggaggcc aaggtgggag gattgcttga gcccaggagt ttgttcaaga   94200
tcagcctggg tctctactta aaaaaaaaag aaaaatttag ctgggtatgt tggcacgtga   94260
ctgtagtccc agctactcaa gaggctgagg caggaggatc acataagcac agaagtttga   94320
ggctgcagtg aactatgatg gagccattgc actccagcct gggcagtaga ggagacttgt   94380
ctctctctgt atatttgtct ctctctccct ctctctctct gtctctcata atacatatat   94440
acatacatat atatatacac acacacacac acacatacag agagatatat aaaatagata   94500
taaaaataaa gatatttttaa agattattta taaatatatg tttttttaaaa atgtagtcta   94560
ttataagcca aatgtcatta ggcatgtagt ccatttcttt ctgtgttcag gcaggagttc   94620
cagttctata aacattggtt tatctgtttt tctagcaggt gcacacatgg gttctcagtg   94680
atgtgtagcc ggggcataga ttgctctcag tctgttgcac cctgcagggg agatgtctga   94740
ggtcctccct cgcctggctg tgctggacgc acagtgcata gcagaactaa ctgcacagca   94800
gaaatgcctg ttctgcgttc ccattgatac accaacagct aatgaagtct cttttacttt   94860
taagaaaccc ttatttggct ttggcatatt tacatggtag aggcctagaa ttttataaat   94920
aaaattttga agaatagaaa tgtatttttt cacgatttaa aaaccacctg tatggtttac   94980
tctggagttg acctgttcca ctcatccttc tccccagttc atttgtttcg tttcaattcc   95040
actttcccctt atagctatct tcaaagcagt gtctatggga cagcattgcc aagagccctg   95100
actgggcctg gctggtaac tcactcctgt aatcccacct gccccctagaa gtgcagatat   95160
actagaaaat acagctgtct ttgttccagt gaatatgtat aaggggtgac atgccttggt   95220
ggaaagcagc tcagattgtg tggactcctc aatccctgct ctaccaagag ctctccagtt   95280
ccaaaactgt acactcagtg gctatgttct gtgtgcctgc tcccaataca gccattatgt   95340
tgttcatcca gatttgagaa tttaagcttt tcactcctct ttgggtagta ttatttaagt   95400
aagaacttct aggaaaatag tatgagtttg gttattttttc cctcggcagc aggaattttc   95460
tgaatattta gcacattcag attgctccaa gaacagcatt gagcaatgct gtacatgtgc   95520
tttctcctaa ggctgtctcc cctgtctact gggttctgga aagactcatt gtccttcagg   95580
gaagggagca ttttttcctca ctgccattgc tgagccttt ctcctgttgt atactattta   95640
gcccagcatg aagccatcgc cgactgtaag gagtgatgga tagaagtgtt tacttggttt   95700
gtgaggcctt gtctctaaag ggtaacagtc tgacaaggaa aacatttcaa agagccctga   95760
ccaggcctgg cttggtaact cactcctgta atcccagtac tttgggaggc cgaggctgga   95820
gaatcatttg agcccagggg ttcgagacca gcctgggcaa cacggtgaaa ccccactcta   95880
tttaaaaaaa aaaaaaaaaa aaagccctga tcccctctc tgggcgatcc attgggagaa   95940
tttgaaaagt tcaacttttt gaactcttcc tactttattt ttttaaattt agaatggaag   96000
gtgggaatta tgcaattgg tgaagatgtt acagaaactg cttcacgact ttctggtttt   96060
acgttataca gtatgttttg aggagctcca agaattgcac aggaattttt ttctttatac   96120
agaccatttt ttaaagacgc atcaagttat tctttattgt ggctctaatt tggcatattt   96180
ttcagacaca ggttgctctt gatacatcaa atttctgctg ttaaaaactt cagttatttt   96240
gagtttagtt aattcaggag cgggaaccta ggtaagtcat ctgtagagca tctttgcacc   96300
ttaagagaag tttctgatta gcctcaattc agtttagtag aatattagtg tggatatctg   96360
gtggcaaaac ctattcttgg tgcaatttgg cttttcgtgg cctcaggcat agagctgact   96420
tggtagtgga ccctctgtcc acacccaccc ggcccttgcg ccttttctagc ataaagtggt   96480
gtgtcagagc cactgtctcc acagaaagca ccacgttttgt ttcattttgac ttatttgaac   96540
ccgtttctcc tgcctttgcc tttttaaata aaaatagcaa aaattgattc aagtgaatct   96600
attagaattt tctaaaatgg agcccatttg tcttttcagt cttgcaagta aagtctttaa   96660
aacaattaag cctcccaatg atttaaccgt attttcttac ccccccaccc tgaataatat   96720
ttacaaagaa ataataacgt gaatttttaa aaacccccgtc cttcagttgt tataaatgat   96780
agttcattct tggtaagtat atctgtaaca aaatactggg gaaggacatg aggtatggtg   96840
aacacttaaa attctgccag ccagcttaaa tacataatct aaatttaacc cacgtaacac   96900
ctcttctagg taaacagcat tctccctata ttcagatgag aaaactgagt caaagaataa   96960
gtaacttgcc caagattgca cagctagtac atgacagaac tgagattcac tctgcagtct   97020
gtagacttcc agtaactcca aacctcatac ttttttcttt atgttacacg gactctgttt   97080
ttaatggaat atttaaatga gatatttaag tgggaaagta atagacaacc actcttacct   97140
gttaaaatcc aaagtaattc tctagtttttt aaatggagca catttaaaaa actttgtgca   97200
ccagtttgaa ctaccactgc aacagagaaa tactagaaca tcagtatt ctctaaacca   97260
gatcattact tcattcacttt tgattgaatt gagttgctta ttttaaaaag acttctggat   97320
gcatggaaaa catatatatt ttgcagcact cagaatcaat acaaagtacc ttcagccact   97380
ttggttcaca ttctgaagat tcatgtaata aacacccata gtagttgtgg gctcacatta   97440
tctaatgaga atgttttctt gatgacttga catttctccg tcactgttgg ataatcagag   97500
aaaaaaagga cgttcagaac accaaggtgc ttggtacaag tatgccaagt gccctgtctt   97560
taaagggagt agcctaattc tcagcatttg ggagtttttg actaaatgtg tggatatgat   97620
ttgtatttcc tatttcttaa tatatatgtg aagatacaat actgacaagt acttagattt   97680
ggaggttttg cggtactgag gggagttggg ggaagaatgg aaataccatt gacctcctaa   97740
aaagttgtta cttgcaaagt ttgggaggtg acatcaaaga ctcaactgcc cttacaaatag   97800
tcattccatc catctgttgc ttatttgaat tctcatttat ttttacttta tggcattaaa   97860
atacaataaa tctgtcaatt atgtattttta tattagtagt agcttaagat tgggtcactt   97920
catttcggta gatataattg ttagtattat ccttcaggac aaaaagcatc tgctaacaac   97980
ctgtggttta aaaatatagg ccaacttat gttcaaacat tatgttgata atattttag   98040
cagtattaca cagtggaggt ccaaattgga ttagacttttt gcattgaatt ccaaagtatt   98100
ggtaagtcta gcacatagta taagtcttg ctaaattcgt gttgggtacat tattttaaa   98160
acctgtctgt ctgtcggtat cacacagagg tcacttcttg agtaaaataa gatgacctta   98220
agaattcaca taattcttga agaagaatat aagtcacgat gcttccacat gaggccgcgt   98280
cacaccacca tcgtttggaa atccagcacc ccagccgttt tacccctaaga taacagtgca   98340
gcacttagtg tggttgaatg tgtcatgtgg gaatgatttt tggtcacctt ttcagttcat   98400
tgttagtcct tttatgtttg tgtgcatcta tgttcgtctg tgtgtttggt aaatatgaat   98460
```

```
tgaatagatg acttcttatt ttatgttttta ggccaagatt gacagacacc taatattcat   98520
gacttgagaa tattctgcag ctataaattt tgaaccattg atgtgcaaag caagacctga   98580
agcccactcc ggaaactaaa gtgaggctcg ctaaccctct agattgcctc acagttgttt   98640
gtttacaaag taaactttac atccaggggga tgaagagcac ccaccagcag aagactttgc   98700
agaaccttta attggatgtg ttaagtgttt ttaatgagtga tatgaaatgt agaaagatgt   98760
acaagaaata aattagggga gattactttg tattgtactg ccattcctac tgtattttta   98820
tactttttgg cagcattaaa tatttttgtt aaatagtc                           98858

SEQ ID NO: 315        moltype = DNA   length = 59258
FEATURE               Location/Qualifiers
source                1..59258
                      mol_type = genomic DNA
                      organism = Mus musculus
SEQUENCE: 315
acctgggcag tctctggacc acgccccgc ctgccccgcc tcctccacga cgtccgaccc    60
acgcggcgcc caggcagcgc gctgacgtcc gacgttccag gtactttccc caaggccggc   120
ttggctcaac gtgggggggc ggggcggggc gcggagcgcg catgcgccac agtgccagcg   180
ctctcccccgg atagagcggg gcccgagcct gtccgctgtg gtagttccgc tcgcgctgcc   240
ccgccgccat gtcggcaacc atcgagcggg agttcgagga actgatgct cagtgtcgct   300
ggcagccgtt atacttggtg agtcttaggc ccgcgcggcg tcccgggggct tccgagggtc   360
ggagctcgcg cctgccggct ccgtgtcacc tcccccgtct cccgctcggg cggaagtggc   420
gagcgcgggc cgcgtcaggg gcgcgcctgc gcggacagtc ctcaccgctg tgaggcttag   480
acctgaagca ccgaggtgcc ggtcgcctgt tggttctgaa ggcggcgcca cagcggcgcc   540
tgctggcgg ccggccggcc tcggcgtgtg gtgcgccggg cggagggtcg aggggcaccc    600
ggcgcggggt gggacgggct ccggcttcct cgctgaccgt gttcttgtcg gccgaatgtt   660
cggtgccgga gcgcgctggt agcgggagca gcgagaaggg cgagagagcc ctctaggatc   720
ggggccagcg aaggcaaagc ggggtcccac ggagtctcgg tcatttgcgg gtgtcccggg   780
ggcctgtggc cggagctcta taccagagcc ggagctgaag cggcggccta agctcctgag   840
ggatcgggga tcgccagtct tttcattggc cactttctct gggagagcgg gtcatcttct   900
gcttagagct ccccggaaca acaggggctt tggttgtatt accattgatt aaagtagcgt   960
cctctttaga atttccttttg cttaggcata ctttatagat gtatatatag tacaccacag   1020
gaattttatat gagccttgca gttggttgca tttcccaaat gagtgcactg gtcgtcgtag   1080
cactcaaaag taacccaaca atctttcggt ccaaaagagg ccacatgtct ataggccgcc   1140
gctgtgctct gtcaccagag aataaccttta cctattcagc tcattctaaa gtattctttc   1200
ctatgaacgc ttgtgactac cttttttacag cgtgtgggct accttttaat ccaggcaaaa   1260
cttttctccc cttaaaaatg attcattgct aatcattaac gtctatccca gatcagattt   1320
agtgattggt gtctccttat gttttggctt gttactacag tacagaaaga agctagaaag   1380
cttttctttta gctctggatg actctgggtt ttcaccattt catttaatta gatgcagta   1440
aaaattcgct ttgtttagga cttatttctc ccatcctcct ttgagataag gtctcacagt   1500
ctataaccttt tgctggctca gaacttgctt tgtagacctg cctgaccttg aactcctagg   1560
ctggctttga agtcctagtc ttctaactac cagtgtcaaa gttctggaaa gaagttgtag   1620
aaaatcttaa atgcaaattc tagtggattt gtgtgtgtga acttgcaggt ctgtgggtac   1680
attagattta gcagagtgcc gcctcaaaaa tgccaatgac aaaagggggta ctaaatcaag   1740
gaagattgct gggtggtaca tgcctataac cccaaagttt aagaggcaga gggaggtctg   1800
tgaagtgatt ttattttatt tatgtagcct tggctgacct tgaactcaga ttgtcctgcc   1860
tccccagtgc tgggactaaa gccgtgcacc tccatgtcca gcacagctct gagtttaggc   1920
tagcctggtc tgcatagttc cagaccagcc agggctacat agtaagatca agtatgcatg   1980
atcttatata catacataca tacatacata catacataca tacatagagg tgggaggggg   2040
actagagaga tggctttcat ttaagagaac ttgttcttcc aggttgattc ctagcaccca   2100
caagcagctc acaactgttt ctagctcctg ttattgggaa tccgaagcac tcctctggcc   2160
ttcagggatg ccagttatgc acatggtgcc taggcagaca aaatgccata cactcagaat   2220
caagggggaa aagtaaaata ataataataa ttactattgt tactactact attatttttaa   2280
aaacaagggt tcatactagc aacttaattt agcctaattt attttctgag accaggtctt   2340
gcttagtatc acaaactggc ctataattta ccactaggtt tggatttgtg acagtccttt   2400
tgccttagtc ccccaattgc taggattata gggaagagcc accacatgg gcttaattgg   2460
gtacatacat gtaagtcatt aatgtctgag aagtaagtga aagttgtgat cccacttaac   2520
agggaaaaaa agcactatg ctggatggtg gctcagcctg taacctgtca attaggctga   2580
agcaggagga ttgttgtgag tttaagacta gcctgcagct gggctttggt ggccaagcct   2640
ttaatcccag cagagtcagg ttgatcttca gtgttcagcc agcctaggct gcatggtgag   2700
ttctatgcta cccaggacta aggaatacat tcttgtgttg gaataaaaaa tttctaaaca   2760
aaagccagtc atagtggcat ggttttttg ggaggggggc atgtttcgag acagggtttt   2820
tctgtgtagc cctggctgtc ctagaactca ctctgtagac caggctggcc ttgaactcag   2880
aaattaaagg tgtgtgccac tacagcctgg ggtggcatgt ttttttaatcc tagcaccgag   2940
gaagtgctcc cagaaagtat ctggagtttt aaaggtcatc tccagctatc cgtggagtta   3000
tgggtcagcc tgggataatc gagactcggt ttaaaagtaa aaatcttgct ggcaaggttg   3060
ctctgtgggt taacagttgc ccagcctgaa aacttgagtt cagtcctgtg attcacaagg   3120
agggagagaa ccacctttct ttcacagatc ttcgtatata cctgccttttt tgtgtgcagc   3180
cacaatagcg aagttaaaat gtaattgtaa acaattggat gttcagggag atggcttatt   3240
tgtttagtgt ttgctgtgaa agcatgaaga cctgcttttc gatcttccca atttccataa   3300
aaagccaggt gtagctctaa tcttttgtgc tggggaggtg aagacctgca aatctctgga   3360
gctcactggt cagcgggcct ccctgaagca gtgagctcca ggtttaatga gagcccagt   3420
ttcaaaagat aagggtttgg gggctgcaga gatggctcag ggttaggag cccttgctac   3480
tcttgcagag gacactagtt cagttcccag tgtccacatc aggtatctca gaactgcctg   3540
taagttcagt gccagaggat ctgacatctt ctgtcctcta ttgggagtgc aatcctgtgc   3600
acaaacacat gtttacacat aactaagagt aaagataaaa acttttttta aaaaaggta   3660
tagaactgtc aatggcaaga agattcagag catatgtgtc acctcccaag cctgacagtt   3720
tgtttgatcc ttggtaccca catgatgaa gaagataact gattcctaca agttgtttcc   3780
tgatctccac atgcatgcat agcctttata agtaaatgtc agaaaaata aatacaggca   3840
aatacactta acttgtgttc actgaaaatt tcttttttcag aaacccttca tagacaagtg   3900
```

```
cacaagatct ttaagcaaaa tagtagttct gtgctggcac ttttttttc aagcccaaga   3960
gcattaaaac catgctatgt acattggtgt tacagtaaaa gcaagccagg agccactgaa   4020
gctaataatg acaagcaagt ccggaagagt ttggacttaa tgctttctta gtatcctgga   4080
gcatccatct cacattccac agagatggct gctaccaaca tctgtgctgt caaggctcta   4140
attctgtgag tcttgaggac ctctttggaa ggtcatactt tgctttctct cttttttttt   4200
ttgagacagg gtttctctgt atagccctgg ctgtcctgga actcactttg aagaccaggc   4260
tggcctagaa ctcagaaatc cacctgcctc tgcctcccga gtactgggat taaaggcatg   4320
cgccaccaca cccggctaat tgagttactt ttaagatatt agaataactg gccaggcgga   4380
gaagtagctc aagcgaagca gttatttctc tccttcagct ctgtactcac tgttttccca   4440
gtgcccacat gtaaaattca gctcttctgc ctcaatacca ctggggctgc ctctgtgtgg   4500
ctttatttcc tatgtcattt ttctcccccct cctgcactat tgtggtctgt tcttggaaat   4560
gtgtgtatcc acttatcccc gtgagcctct agaatgaaat ttcctttgca caactgctct   4620
cctgttgctt ctttcccctg ttgcttaaca cctttgctca tgtctgacgc tggactaatt   4680
tgggaagctt cctaacctac cagtccatgc tggatatgtg caaatctttg acagtagggt   4740
tgaagaaatg cagaggttct gtgtgtgttc ccagcaccca catggcagct cacaaatgtt   4800
tgtaactcct gtttaagtga gcattcttcc ttattacaag taagtgacgc tagtaataat   4860
gttttatgag ttctgctttt tctgaaatgc taaaggagct aggagaagaa aggattgctc   4920
tcaagggtaa atcaagatcc tcagcttttta gctgcttgat ggacatgaga atgtttactt   4980
cgtattttat ttcagttttt gtacttacga ataaattgag tatttttggt tgaggttctg   5040
gcctcctcgt cttttttatt ccctatagac agttgcttta gagcatcact tttggaaata   5100
ggtgtcgtag ctcatactga tactagcact tgagatactt cagggtggag gatcttagag   5160
gtcagtctga gcagcgtatc taatttcaag ttaattcatg taatttagca tcatcctatt   5220
tttaaataaa agaaaacaaa cctaaaaagc catgatttag taataggaag agtttcttgg   5280
ttggttggtt ggtggtagg tttttttttt tttgagacaa aaaactcact ctagccttgt   5340
ctgacttaga attcacaatg taacccggtt gggctccaac tagcaatcca tcttcttctg   5400
cttcttcagt gctaggataa agtcaagcac caccatgcc tactttttgtt tttttgttgt   5460
ttttgttttt ttgttttttt gagatagagt ttcaatctat atagctctgt tactttggaa   5520
ctcactgttt agccttgaac caatgctgat cctcctgcat cagttctga gtactgggat    5580
tagagacatg ggtcatcacg cctggtgaat gttgctggat ttgtgttttt gttttctggg   5640
ggataccagt catcaagtct gtggtttcac aatgccaatc agatgctcta ccactgagcc   5700
agagccacag ttacctctct tctctcccca cacaatttct gagctaggtc tctgtaattt   5760
gctagccttg aacatgatat ctttctcctt tagcctacaa gttgttgggt acaggcctgg   5820
gccaccagga tgggcaaggc gaaagttctc gatttataga aagaaagaaa aacaaaatgc   5880
tgcagttgct aaaatctata ttaaggccaa atcttcagtc tgaggaattg gaaggataaa   5940
gaaatttgct ggttttgctg ctgtggtgtg tgtaagtgtg ctaatatgga aaaggactta   6000
aattgcagag ctgagtatta ttatctggtg ttctacattc actgggagct aggaatgaac   6060
tcccacagat aagtctcttg gactattta catatttata cacatctgta gatttttttt   6120
cttttttttt tcttagatat ttccttcatt tagattcaa atgctatccc caaaacctct   6180
tatcccccc cccccccccc ccccgttcc ccaacacacc caactcccgc ttcctggccc   6240
tggcattccc ctgtactggg gcatatgatc ttcaaaatac caagggcctc tcctctaatt   6300
gatggccgac taggctgtcc tttgctatgc atgcaactag agacacagct acacagctct   6360
ggggggtggg ggtggggtac tagttagttc atatcgttgt tccttcaata gggttgcaga   6420
ccccctttag ctccttggta cttttctag ctccttcatt agggcccat cccaatagat   6480
gactgtgagc atccacttct gtatttgcca ggcattggca tagactcaca agagagctat   6540
gtcagggtcc tgtcagcaaa atcttcctgg catatgcaat agtgtctggg tttggtggtt   6600
atatatggga tggattcctg ggtggggcag tctctggatg atctttcctt ccatcttagc   6660
tcagaacttt gtctctgtaa ctcttttctt tcttttttt ttttttttaa acctttaact   6720
tattttcttt tttttttaa attaggtatt ttcctcgatt acatttccaa tgctatccca   6780
aaagtccccc ataccccccc ccatcccta cccatccact cccccttttt ggccctggtg   6840
tttccctgta ctgggcata taagtttgc aagtccaaag ggcctctctt tccagcgatg   6900
gctgactagg ccatcttttg atacatatgt agctagagac aagagctctg gggtactggt   6960
tagttcatat tgttgttcca catatagggt tgcagttccc tttagctcct tgggtacttt   7020
cttgggggcc gtgtgatctg taactctttc catgggtatt ttgtccccca ttgtagagtt   7080
attttttaaa ttatctttgt gatgtatagt gtgatgacat actattaatt tttacttttg   7140
ctgatgtata gagtcctaaa ttcttgtaat gaatatgtat taatttatta aaggtgcaaa   7200
tttcttttc tctccaataa aatcacagat aaaaacccaa agtaaggcta ggtatagtgt   7260
ggtgcatgcc tctaatccca gcccttagga ggcagaggct attagatttc tcagtttcat   7320
aggaggcaga gcaacataaa tgagacccta tctcaaaaaa caagagtaag attctttggc   7380
cacttggtag cctggttctc ctgagattac tggtacaccc tcatattgga acagggtctc   7440
aagtagccca aactgacttc taactactta actgagactg gctttgaata tataatcctg   7500
ttgcctctac tccaaagtgt tgcaaccaca aacttattac caccatgctc agaatatttt   7560
gtatttaaa ggtaagcatt ggttattaaa acaaaacact agtaagctag gtatggtgtg   7620
tatgcatgta atcccagaat ttagaagact gagattaggt ttgccatgaa tttgaggcca   7680
gcaaggcta caaagtaaga ccctatttaa aaacaaacaa acaaacaaaa aaaaaacaaa   7740
atccaaacaa agtaaaaccc tgcaggagat cttagaattt attttttctac attgtatcaa   7800
cacagtaagg tttttttgtta tgtgtgtagt aagtacagcc tgttcatgcc atacgtgtat   7860
agagggtcac ctaaaacttc tgggagtagt tttctcctcc tcagcaagct cctgcgatca   7920
aactgaggtc atcaattgt gtggtgctag cccttttatc tgctgagcca tctcaacagc   7980
ctgagactta agattttttt atacatacat acttttaaaa ttaaaaggtt gtttcaatat   8040
gtaacccaac agaaagattt taactaaaaa catttgctta tctcaattcc aataactgca   8100
ctgaaataaa ttccttcctc cctcaaattt gtatttagac caggtatcac ttacttcaag   8160
ttaattataa aagctatctc cagaatatat gtacaggtac acacacacac cacttacttc   8220
aaagtaattt tgaattatcc ccaaaacata catgtacaca ccattaacat ctgtctgtct   8280
atctatccat tcatccatcc atccatcccc ccacccatcc atcacacac gtaaaaatag   8340
tgcttggtct tgtattcaga tctccacctac caccaccatc tagttttttt ttttttttt   8400
tgagataagc tcttttttgt ttgtttgttt gttttttgtt tttcgagaca gggtttattt   8460
gtatagccct ggctatcctg gaactcactt tgtagaccag gctagcctcg aactcagaaa   8520
tccacctgcc tctgtctccc tagtgctggg attaaaggtg tgtcccagca cgcctggctt   8580
gtggctgttt cttttaatgat cgtcttataa caaattgttt taaggatttt ataaatatct   8640
```

```
acttaggagg atcttctcaa ttctgtgatc tgtgtaaaag aattattta tggtctggtt    8700
tgttgcagtt aaaaaaaccc tgaaaatatg gtagtgactg taatgtagac ttcagtgatt   8760
tcttcagcat aagtgtgcca tcgggtacca ttcttcacct agtaatgtag aagcatagtt   8820
atggcttctt tctgctgcag acggggaaac ttttagcacc agaatgcaca tcagttgttt   8880
ttgcaacatg gccttggtgg tagctcagct gttggccttc cttgtctctt tttgagaaac   8940
actttgtatt tcattaacta tactaaaaga tcggatacat gcagggaagt ggggtatctg   9000
ggggcctgcc aggctgtgcc gttaaaaatt acgccatgta acaggtttat tgggagagta   9060
gggagactga aatgcctccc tagactggga cattagagag agatagacag acagacagac   9120
acacacacac acacacacac acacacaaag atagataatg aaggagagag aggagtaatt   9180
gaagagagaa acaagagagt gatctggggt ggggtggagt taggaggggg ttacacactg   9240
tgtgcacctg ccacacctgt cccctgttg gctggggtgg aaggtgacat aagccacctt    9300
tatattcctg agggctaaca ctaaatgctc ataaaagtta catcttgggt attgctcccc   9360
cccccccca aaaaaaaaa gaaaagaaaa gaaagctgta cagtgtcaga tggtagtttg    9420
tgatgagttt tggttataca ctgtcttagg gtttttgtta ctgtgatgaa acaccatgac   9480
caaaaccaag ttagggagga aagagtttat ttgccttaca cttcctgttt gaaggaagtc   9540
aaaccggtca ggaaactgga ggcaggagct gatgtagagg ccatggaggg gtgctactta   9600
ttggcttgct ccttaaggct gctcaggacc accaatccag gggcaacacc acccaccatg   9660
agctggaccc tctccctattg atcactcatt aagaaaatgt ttacagttga atcttatgga   9720
acacttgggg ttccttccta tcagctaact gtagcttgtg tcaagttgtc ataaaactag   9780
ccagcacatt ctcattattt agacatctga tttagctgca taggaaggaa aataaagcag   9840
taattgacaa taggtttgtg gttttgtttt ggtgagagtt ctgaagctag gctgctgtt    9900
gtgactccct agtgccactg atggtagcct ttaatttctg tgtagctttt ttttttttt    9960
tttttttta agcctagtga tcacaggagg ttcctgccta ctcccatccc ttactcctgg   10020
tggtcaaaac agaagagagg gcaagagttt gctgaggcag tttttctta ttattgaggt   10080
ttcatttttg aggcaggatc tcgtcttaag tgttgccctt ggccaagcat ggtggcacac   10140
gcctttaatc ccagtactcg ggaggcagag gcaggaggat ttctgagttc gaggccagcc   10200
tggtctacaa agtgagttcc aggacagcca gggctataca gaggaaccct gtctcaaaaa   10260
acaaaaaaac aaaacaaaac aaaacaaaaa aaaaaaagtg ttgctcttga tcactattct   10320
tgggttcagg tggtcttccc acctcagccg aggagctgct actgcccagc agcttatcca   10380
gtgtgtgcag gccactcagc tggcacagat agcaggataa acctttctct acaaccaagc   10440
ccagtgctgc tgcttattcc attggccacc ttttgtcaca agccttttaa aatttgagac   10500
agggtcttat tccctatgta ggtgaggctg ctttcataga gatccacctg gctgtgcctc   10560
cctagtgctg ggattgaaga ctgtgcacca cccatgcctg gctcatagac atcaagctct   10620
tgtaaactag aaaatcaaat tagaaaacctt cagttaggaa gaagggaaag tgggattggc   10680
tgttggtgtg tgtgtctctg gaactggtct ttataaagca ttgggatttc ttatcttaca   10740
ctggccagag ttaaaaacag aaaacaagtg gaagattgaa ggtctgaaag aataaattca   10800
ctaagggttt ttttgtattc ttagctaaca aaagaaagta agtatggctc tattttttta   10860
gggctgaata tttggattgg ggtgtatata tggcattgtt ttgtaactct taagtcctta   10920
ttgctgtact agctcctgcc atctttatt tatctaataa tgcatcttaa ttaattcttt   10980
gagaacttgt atcttgatca tattaatatg cccctcccct gctttttccc tgaaactctt   11040
gccaggtcca tccacttctt atctccccat cacattatgc ctttttatt taaccttttt   11100
atggatttat tacttttaat tttatgtgtg ttttgccttc atgtatattt gtgtcatgtg   11160
agtttagtgc ctacagcggt aagaagaggg ggtcagatcc cctggaactg aaattataca   11220
tgttagccac catgtgggtg ctgggaattg aatctgtgta ctctgaaaga caatcagtg    11280
ttcttgactg ctgagccatc tctctggccc ctatgtttag tatttaaaga gatgcctgga   11340
gagatggctt agctcttaag agcactggct gcggagctgg agagatggct cagtggttaa   11400
gagcaccaac tgctcttccg aaggtcctga gttcaaatcc cagcaaccac atgttggctc   11460
acaaccatct atagtgtggt ctgatgccct cttctgggat gcagatgcac atgcaaatag   11520
agcacttgta tacataaaat aaataaatct tgggggaaa tccttaagaa gagaccgtct    11580
agctgggtgg tggtggtgca ggtggtgcat taattcaatg agaggcagag acaggtgagt   11640
ctctgagttg gaagttagcc tggtctgcag attgttgcag tatcctgtct tctgactcaa   11700
tctttgttct ttcttcgtag atttttccct aaacccctag gtatgtagga agtatgttgt   11760
ggatttagtg gctggctaac ccctggttag ctccctgcat tttgacaagt tgtgaatggt   11820
ttctgtgtta catgaagttt ctttaataag cagcctgtcc tacacttatc tatggatata   11880
agataaatag taggagtggg attgagagct atactttgtt ggttttttgtt tgtttttgttt   11940
ctctgtataa cagaggccta gctgtccttgt agaccatact ggccttgaat tcaaagaaat   12000
acacctgcct ctgactccca agcactgggg ttaaaggtgt gtgccaccag gcctagccct   12060
ttttttcccac caacatcagt aattattata gtgtatacat agaattttgt ctagactgaa   12120
aaataagaac tagcaactaa tagacaatca ctgaggaaga taggattata caacagaaca   12180
gttgaagatt cttgtacagg tttcatggag ggaacctctg ctgaccagta aatttccttt   12240
ccttgtctgt ctgtccgcct gttcgttcgt ctgttcatcc atccagctat ccatccatcc   12300
atctattgag tctggcctag aactctacct ctagctcttg agtgttgaga ttaaagacat   12360
gtgccaccac acccagccac cagtagtttt ttaaaaatct catttataat tgcattagag   12420
ttaataagat tactcagatg aaactgttag catattattt ttgaagaaaa ataaattaaa   12480
atatgagctg taacacaaaa gaggtgaata aatagaaaca aagcaacttt tatttccata   12540
tatttagact ttactattta gcattagtaa ctaaaattta attatcttga tgataaatga   12600
aattttgaaa tagaattaca ctttgaaaga acaagtgtaa ctggtgaatg taaaaattaa   12660
taaatggcat ggatcatttc tgttagcatt gtgaggtttg atatgatata aacatttctt   12720
tgtagagtac ttaaagtaag tgcttaatgt tgtcctatat tgcctgggag aatatatgtt   12780
gctgtataaa atttaagagg gatattaaat atatatttt gttatttaa ggaaattcga    12840
aatgaatccc atgactatcc tcatagagtg gccaagtttc cagaaaacag aaaccgaaac   12900
agatacagag atgtaagccc atgtaagtac tgtaagatac agagatgtaa gcccatgtaa   12960
gtactgtgag atacagagat gtaagccat gtaagtactg tgggtttatg tgcatgtgtg    13020
tgttcttcag cttgtttcag gagacccgat gcagtgacag tctttgggta aagattgatt   13080
agtatagcaa ttttttaaact tttatatact tttgtttga cacaggcttt cactctgtag   13140
tcccactgtt ctgaaattaa ccatgtgca caggctgacc tcaaatttgc agcagtcgtc   13200
ttgtctcagc ctccagaata ttgggattat aagtgtcag ccaccacacg aggtttaatg    13260
tatacatttt ctcatgtgtt tgtacacacg catgtggaag gttgaggttg atggtcagat   13320
gtcttcctga attgctcttt accctagaga tctgttccag ctagtctggc tggccatctt   13380
```

```
gttctgttag aacttgtcct gggattacag tcaggctgcc acacccacct ggccttccat   13440
gcgggttcta gggatccagt ctccacccct tacatttact tagtcatctc cccatccctc   13500
tggtttgagg aacatctgat tagctcttct aagctctggt agaattcagc acttaattgt   13560
ctgttgcact caggtggagg atgttcctat aacagctcag catttcctat cctcatccag   13620
ggttctgcag tctgccagtg aactgaccct cacaaaggct ctccttcctc gttgtacagc   13680
tttttctcc aggtgtcaga gccacttact gtgtgtcgtg tcatcccct cttcagcaca     13740
ttcatcctgg tgtcctgata tctgagtaaa cactatgaaa caccagcctt agagtaccta   13800
ggcctttca gcactctttg atcttgtgcc cacaaagaaa gcagggaggg attttttaaa    13860
attttgtggc agggctccct gcatctgcta tactgtcttc caactgtgac ttcctgatca   13920
gtctcctaag tgctggaatt acaggcctgt gcaccacacc cagctttcac cctgcacctt   13980
gaaggtcact ttctgtgtgt cactactgct tttgttgttt attttttgt tttgctttgt    14040
tttattttg tttgtttttg aatatttcac ttagaatgta tatggttttt cctggcattg    14100
ggttcttaa tactttgagt tttagattac tcaagtgttg ctatatcctt cagtttgttt    14160
gttcgttgag acagggtttt tctatatagc cctggttgtc ctggaactca ctctgtagac   14220
caggctggcc tcacactcag aaatccacct tcctctgcct ccaagtgctg ggattaaaag   14280
cgtgcaccac cactgcccag ctgctatatc cttccttaac cagtctgttt ctcatatcta   14340
tttagctgtt ttattttaaa atatctttga ccttaattct ccaatttatg aagccccatt   14400
tggaagact ttattcttta ttcccttaga gagtttaaaa actcaagaac ttagagtcaa    14460
gaaacaacac ttaagctgta atgtgacacc ggggaagtgc ctcagcttat gcacatccct   14520
gaagtcccag ggcttctgtt tctctattcc ttttgtacata catcccttcc ttcttttcctc 14580
ctcctggtct gccttgctat cttcagcctc tttgtccctg cttttccttc ttattacata   14640
aataggatgt agaatgcttt tcccttttccc tcccacccc aagttattc ctaggtagat    14700
ctatgcatct acacaacagg ggttttttgtt ttttgttttg ttttttgttt tgagacagg    14760
atttctttgt gtagccttga ctatcctgga actcactctg tagactagac tggcctcaag   14820
ctcacagata tccacctgcc tctgcctcca agtgctggga ttaaaggcat ataccaccat   14880
cgctgctatc atcactgccc tgctgaacat aacagtttaa aaagaatata ttctgggact   14940
ggagaaatgg cttagaggtt aggagcactg gctactcttt tagaggacac gggtttaatt   15000
cctagcaccc aaatgcatct gtaactatag ttctagggaa tctgatgtcc tctcctagct   15060
agcctctgta ggcactgggc acacaagtgt aggtacatag gtatacatgt aggcaaaaca   15120
cccatataca taaaatttaa aaaaaaaaac aaacccaaaa caaacaaaaa ggccaggtgg   15180
tggtggcata cacacaatct tgactggggg tgggggggg tgggaagaaa gaaacaaaaa    15240
gatcagttag ttctccttc tgtctgtcct gatcacctgt gctctcttca tgaaccccca   15300
tgcagctacc acaccctcct cactggaact tagttacctt gctagctttc agatgcaatc   15360
aatgacttc ccttggttc cctcttatc cttctgtgtc ttgtgagatt gccgactctg     15420
tcttccttct caaggactta tttacttttt ctgtctgctc tcccattttt agagccgtcc   15480
atcctcaatt tatctttatt ttttcaagg gtcttttcct ctcctcacta tttttttctta  15540
atctatgagt gatctcattt tcttggggggc caattgccat gcttatttc atgacttcac   15600
atttgatctg cagtcttggt cttaactcca aacagatgtt tgcaagttgt catgtgccaa   15660
cctgacatga agttagtcaa agaaccatag aaccatagaa agcttataga accaatggtt   15720
gggtattccc tacattgctt tattccttct atttgtaact ggtaccacca tttacatatt   15780
gactaatact ggaaacagac tccttattca tctgccacat ctaattagta actaaatagt   15840
ttactgtgag tgtgatctat ttaaaatgtt ttcttatgta catactagct tttttgtgat   15900
ttattatagt aactttctaaa cttttgggac tatatagatg gctcaggagt taagggccaa  15960
atactgcttt tgtagaggac ttgggttcgt ttcttagtat ccatcggtgg gctcacaaaa   16020
cacctgtaac ttcaacacat ccaacaggca tgcagccccc cttctctctc tctctctctc   16080
tctctctctc tctctttctc tctctctctc tctctctcac acacacacac acacacacac   16140
acacactaaa ataacctcta tagctccatt ctattactgc tttcttcctt tctcttacta   16200
tccaagttgt tttcccgccc cattaaggca gaaatttaag tttgtcatca ttatcattct   16260
agactttta tatacctttta tgacccttta tacacatcta gattttactt atagctattt   16320
tcctacaaat tattcatttg agtaagagtg gattacttag cattctccca ttatgactag   16380
tttctaacat actgtgttct caaatatgtt gctcactcat ttcttttcttc tcttttaatga 16440
cagtgacggt cttctccctg cagtgccaaa tcagccgcgc cttccgccgg ctggtctttt   16500
caccatggag aggatattat ggaagcaggg ttttgtgtgt gagcatgcat tttaatgttt   16560
tttgagacag ggtcttctgt ctattatgta gctctggctg tcctggaact tactcttat   16620
acctggctgg cctctaactc acagagatct gcctgtatct gctgtcagga gatagagaca   16680
gtggagtcac tgtgagtgtg aggccaacct gatctacata gtgagttcca aactgctaa    16740
gaccatatac aaaagaccctg cttcataaaa acaaataaat aaaagctgca cagatttatg   16800
attctattag tatggcttac ctataatcat agtccattgt agctacagaa caagaatatt   16860
ctcagtaaat atgtgtataa atgagttgat acatggagag aaaataacaa aaagttagag   16920
acttatcttc ctcctccagt gaaatgacat tgtgctcttt tggagagagg gtctcagtat   16980
gtagccttgg ctggcctgaa gttttacata catcaggctg gctttgaatt catagacatc   17040
aaccttcccg gcctcccctt tgctaggatt aaaggtatat attaccacat ctggggacaa   17100
gtctgtgctc ataggctttt aaaatttatt tatttttgta ttttatgtat atgaaggttt   17160
cttctgcatg taattctgta ccacatgtgt atgtggtaac tgagaggct aggagaatgt    17220
ggatccctgg gacttgttat ccaagtaaca gatggctgtg agctgccatg tgggttctgg   17280
aaattaaaac tagtcttccg gaagatcagg aaataattct ttttgttttt gttttgtttt   17340
gttttgtttt gttttgtttt tttcaagaca gggtttctct atgtagtctt ggctgccatg   17400
gaactcactt tgtagaccag gctggcctca aaactcagaa atccacctgc ctctgcctcc   17460
aagtgctggg attaaaggtg tgcgccacca ccgcccatca gcagataatt cttaactgca   17520
taagcatgat gtctccagca atggaccttt tttttctttt cctccaattt tttattaga    17580
tatttcttc atttatattt caaatgctat ctggaaagta tcccataccc ctccccac      17640
tccctaccc acccactccc acttcttggc gctggaattc ccctgtactg aggcacataa    17700
agtttgcagg accaaggggc ctctcttccc aatgatggcc gactaggcca tcttctgata   17760
catatgcaac tagagacacg agctctgggg tactggttag ttcataatgt tgttccacct   17820
acagggttgc agaccccttc agctcctggg gtactttctc taactcctcc attgggggct   17880
ctgtgttcca tccaatagtt gactgtgagc atccacttct gtatttgcca ggcattggca   17940
tagcctcaca cgagacagct atgtcagggt cctgtcaaca aaggactttt tttgtgataa   18000
atttcatact gtaccctaag ctgacctcag ttgtggcaac tcttcctgcc tcagcttccc   18060
aaatgctggg gttacagttg taagccacca cagctagcct tattttggc ttttttgagaa  18120
```

```
aagggtctcc ccaagttggc cttgatcctc ctccttctgc ctccaaagtg ctaagaccct   18180
gtgtgctcat ggtggacaca gtattataaa gaagttgatt tatctcttgc ctatcactga   18240
atctcatgag gagcagaagt gtgaatttat tcaagataag gcttcttact taaccctcct   18300
atgaaggtat tgctgctgga agtgtactaa acattaattc tgcattgcca gaggtgctga   18360
agattgccct tatcctagca aaatggattg acacagtagt agcatgccta tcctttatgt   18420
tgactcatcc acctgtgatg tgtgtcaggt ttgctgagca cagaatgagc ctcattaggg   18480
gtgatgatta gaagctaggg aagtgagtaa gcctctgcag gaccaaccaa aagggaaaaa   18540
cttggctaag tgctaacttg tactcgtgtc atgattaagg atgataccaa agaattctca   18600
gattagcgat gtcattgatg aacacttcaa atgcaagaaa tgaaaaatag aagcttttgg   18660
gggagagatg gctcagtgtg taagagtgtg tgctcttgca gaggacctgg gctcaattcc   18720
cagcatttac aggttgctca taaactgtct cttaactcta gttccagggg atctgatgcc   18780
ctcttctgat atccattggt accagacaca cacatggcat acataacata catgcagtca   18840
aaatagtcat acacctaaaa ataagatcca tatgttttata aaaagttttt tattttcctt   18900
atcaaaatga aactttaaaa atactgatga aattttagtt tagtgttttta agttctcaag   18960
tcattgtttg ttttgttttg ttttaaagac agggtttctc tgtatagtcc tggctgtctt   19020
agaactatct ctgtagacta ggctggcctc gaactcagaa atccgcctgc ctctgcctcc   19080
cgagtgctgg gattaaaggt gtgtgccacc acgcccagct tggattctag ttttatagac   19140
agtgaactgt tcccactacg ttctttactg tgtttattca tgcagagtgc agattccttg   19200
caggtacttt ctagagaaca tttctaagta catggaaagc ttcaacagag acctggaaac   19260
agctggttta tgcttttttg ttttggggga ttgaagcaaa gactaggtgc atgttagaca   19320
aatgctaacc atgctcttac acctctatcc ctctgtacta tttctctttt gagacagcgt   19380
actgctcagt tgcataggct ggctcttgag ccagcatgta ggctaggtca agaaacaggt   19440
cttaaccttt agataatctt gcctcaacct cctaagtgac tgggaagtac aggtctacct   19500
cattgtatct caccgttatt tgcctccatt tgtttcaaaa accctctcc cgtgccccct   19560
ttatctcttg attctttatc aagtgcagcc ttcctcctca cccttcccag actgaagttt   19620
ccattcccca gtaaggagct gtttgggttc tgttttgttt gtttgggtgc caggtgtcaa   19680
atactgggct gatgacttct aagttggttt catttcctag ctgttgtgaa tagttcatag   19740
tagtatacat ggatgtgcaa ctgtctgtgg catgttggca tagatttctt tgcccacgct   19800
tttgaaagt tgtgggaatc ttttcttgtt cttttgtgtat ttgttaacta tttcattaaa   19860
aatttataca ttagcttcca tttttttttca ttcatagcta gggtattcca attttcttt   19920
gctatttatg gatagtagaa taaaaaaggg agtaattgcc gggcgcagtg gcgcacacct   19980
ttaataccat cactcgggag gcagaggcag gcggatttct gagtttgtgg ccagcctggt   20040
ctacaaagtg agttccagga cagccagggc tccacagaga aaccctgtct cgaaaaacca   20100
aaaaaaaaaa aaaaggggggg ggggagtaat tgaaaacact attacactgc catgatatta   20160
tgcctttaat cccagtactc aggaggaaga ggcaggtaga tcttttgagt tcagggctct   20220
gtgagttcaa agctagcctg gtctacagca ggttccagga cagccagaga tagacacaaa   20280
gagaccttgt ctcaaaaacc aaccaagcaa aaaaacccctt actatactta cacttctcac   20340
tcactgaata attcaatctg acagcccttg gggtgggggt gatggtctta aaagtcatgt   20400
aaaggtgata atgtcctaaa aggaaagacc ttgtgtgcca attgagctaa gagtgagccc   20460
tgtattgtta gattaggatt gctgtgttct tgtatgttag gacctggttt tcagtgagta   20520
ctgatatgta gaaaaggctg ggaatgtata gttcagaggt tgagtgcttt cccagttata   20580
aagacatgtt tgaatttttgg cagccatatt catatgttta ttagccttttt ttattgagac   20640
tttattttt taacattttt acttttatat atatgtgcat catttgtgt tgggatgcct   20700
gggcatgtgt acatatgggt aagcatcttt ggagccagag ggttgatgca tctgaggcta   20760
gagttatagg ctgtggtaag ctgcccaatg tggatactgg gaatcaaatt catgttccct   20820
gcaagaggac atgttcttaa ccactgagcc atgtctccaa cataattgag aagtcttaag   20880
agcaattgtt ttctctttgtc accgggcata cttagctttta gttgttcaag ttcattcttt   20940
acaacaagga aacatggttc cttggatgag tggctgatct ctgggaatgg aacaatatgt   21000
aatccccttag gtagatgtag tgacaaaagc ttgtgttccc agcactcagg agtcaaaagc   21060
agaattgtga gctgaacagc agcttgaaca acactgccag attctggctc atagaaaagg   21120
ggctggatat gatggcacat gcctttaatc acagctctaa gggagacagac gggcagattg   21180
caaaggctag ccagagctac agagtaagac cctgtctcca aaacaaaaca aataaaagga   21240
agaaagaagg gggagtttag aatgtctcaa atttctagaa agtacagatt ttattaccga   21300
ttgaataaat aaatacttaa atacaaaggg gagatagtaa ttgtccagaa gaaatgaaca   21360
ggaaaaaatt tagtattgaa ggctgttgaa gatgtcttgg gaagacacca aaagcataag   21420
ttatatacag tttctaaaat tagtgaattg taatagatgt ttgtgtgtgt ctcctactta   21480
taattctagt acttgggaga ccagggcagg agaaggctgt gagtcctaga ttcatctggg   21540
cttcagagag aaagactttg ttcagaaaaa taaagctgag ttactgaatg gtaatgtgtg   21600
ctttcaattc aactcttggg cagctagggc aggggaatgc tatgagttcg cagccagcct   21660
gattacacag ggagttccag acaagctgca aatacatagt gagacctcct cttaaaataa   21720
aaggcataaa tgaacatttt aaagttttgg agaataagat caacagattg actagggaat   21780
atatatttga aataggcaga ctagaaaatg gacagaaggt atgaatacaa aaggcagata   21840
aatgtgaacg tgaaaaacat cattagctat tagaaatatt agtatgtact tactaaacag   21900
agggcatact acctcagggc tgcagaggag cttgataggag gctaatcaag ctgatagcaa   21960
tggtgtagct gtatccccaa aatctcccaa gtcagggggtt ctctttgtag gctaagctgg   22020
ccttgaactc agaggtttgc ctgcctctgc ctcccaatag ctgggattaa aagcatatgg   22080
caccatacg tgatacgact attttttcaca aacctgaatt tacacttctg tgacctagca   22140
aaatagattt tttagctatct tagagaaatg aaaatcctat tcttacacag ctgtgtaagt   22200
gaatgttcat aacagcttta tttggaattt aagctcaagt gatcttaaat tgggaacaac   22260
ccaaatgcct ttcagtaata ggtgattagt aaattttatt tgttggatat tgctaaacaa   22320
accattgatg cacacacaca caaacacaca cacttgggta gatctcaaag aatttagatt   22380
gagagtatca ggagattaca taactatatt tttatatata atttaaaagc ttttattatt   22440
gcctgtggat ttatatatgt catggcacaa caatggaagt caaaggacaa attttgggac   22500
ttgtgtctgt aaactcaggc tgtcaggctt ccatggtgaa cactttaaat agtagctatt   22560
taccagcctc tatttaactt tttttttttt tttttttttt tttttttttt ttaaagattt   22620
atttattttat tatatgtaag tacactgtag ctgtcctcag acactccaga agagggcgtc   22680
agatcttgtt acagatggtt gtgagccacc atgtggttgc tgggatttga actctggacc   22740
ttcggaagag cagtcgggtg ctcttaccca ctgagccatc tcaccagccc aacttttttt   22800
tcaaggcagg gtttctctgt gtagccctaa aactcactct gtagacctga ctggcatcaa   22860
```

```
actcggagat ccacctgtct gtgcctctgc agtgctggga ttaaaggcct gtgtccagct   22920
gactttttttt tttcttcttc tagatggttg gttgtcctag aacttgctgt gtgatcacca   22980
gcctggctca tagagattga cctgactctg tccttcaagt gctaggacta taggtgtgtg   23040
ctactgcgcc cagcctatgc cattcctgaa gtaatacagt gtcagtagtg gagactgtgt   23100
ttagtgatgc agttagaggt aggggtgaga ggaatgggac tcagtgtgaa atagcacaca   23160
gtacctttgg tgatgtaata gttctatact acaccatagt tacatacata tataaagaat   23220
acacagaaat gaatgcctgt aaaaatggga gaattccagt aaggtgtgaa ttggaccaat   23280
atctttccat ggttttttaa tttaatagcc cgttgaagtt ggtcctgggt agcataatcc   23340
aggcgaggtg ggagtcagtg aggaacataa tggttctgat taccaagagc ttcatcttaa   23400
aaggcaaatc ataatgagtt cagggcctga gggaatgttc cttccttgct aagtgactga   23460
gaatcttgtc ctacggtagc attttgagca ggcccgtgta gaagccgcag ttcattgtct   23520
ggaagctctg ctggagaacg tgtactggat ggtgcagcca cagtgcacgt ggagagaact   23580
ctgagtgggg atgcatgggg tgccctccag aactacctgt atttagaact gggggaaga   23640
tgaatgaagc agaagtttca aactactaaa atcttttaga taaaatagga atgtcagaga   23700
atttgtagtt gtcattggaa tgtttaaggc tgagtctttc tgagtagtca agccgctcca   23760
tctgtcgttt ccttcatatg ctgttttctt ttgcaacact ctgcttaaca tggggtgtga   23820
ttgcaagtat gtggcctcta agagaggaac ctagtattac attgaaccta gtattaaatt   23880
aattggacat gattttgttt aatacaaaca catgagactgc aacaattgtg ggtttaagac   23940
agagtctcac attggttagg agttgctgag gctgggatga ttttgaactt gtggtatttt   24000
tgctgggatg acaggcctat ctgttaccat cctggttagg agggactagg aagttaaagc   24060
tctggtgttc taggccagca ctctatcttt tgagctacat cctaagcact aggactctag   24120
ctcagaataa tggaattgcc ttatttatag gccctagtga ggtcaaagtc ctccttagtc   24180
aatacatgga attagggtgc taatgattga acatgacctt atggaaactc ttatctagaa   24240
cttccttatt cctcttctaa gtctgatcac acagtgtgat tggggttgtt cagtagtctg   24300
tagctgtgaa ctgttctgtg tgattgaaat ccttcagttt aagtccctct agtctgaaaa   24360
gaatgatgac tttctacctg atggcagcaa aaagggcatg atagtttacc atctgcttta   24420
taaggttatg aggattgagg cggtgaccgc ctagtaagat gcgtctggca tatcataatc   24480
actaaacagt gctttctgct agttcaagtt gattgtatgg tcagtgagaa gctatttata   24540
ggtttgtttg tttttttttt aaattgtaag taagcaggtg aagtgttcag acttccatat   24600
gtgctaagat ttatatttct tcattaaaat gatagtgctt atgggactta gtttagttc   24660
tgtcttttgtg taggactcct tgctcagttt atgaaaaaaa ttatatttat tttatcagtt   24720
tttggagttg aacagtgttg acatagttat aagatgtgct gagttcttat caggaaagta   24780
ccccaagtag agattaggaa aatgtaagga ggaaaaataa ccagtaatgc tatcttaata   24840
gaattgtcct gtatttgctc aacttgtgag ttcataattg gcttctgcca tgatgaacat   24900
gaaccttgcc ctctgtttga catgtgacac tctgcagtga cagagcgtt tacgacagtg   24960
atcaatgggg gaatatcctc tgctcttgtt cttttcagtt tattgtgaat gttgaaagag   25020
gaagcttctg tgtgcgttag ccacaggctg agcaagtcat ttcttgagag ctgagacaat   25080
ttcccagaag acactgagag tgggaggcag agagacttcg tcagaagtgg gtgggactaa   25140
ttttttaatcc aatgttttag ttacagtatt gttagatatt aaatttcata attcactaat   25200
tcactcaatg ataacaatta agaacaaata atatcctaca gaataataaa ctgtgttcct   25260
tacagtgctg ctgctgctgg tactgttaga agtggagaag tgtgattcct gtgaaaaagt   25320
ggtttcttac cttcccctttc ctttacctttt taaaagatgg gtgggcaggg gctcaggaag   25380
gtgcgggaga atatgaatga gccacagaag gctgagcaag tactgtgagc tcaggtgcct   25440
ttggtgatct cactttagag aggctggagg gaaaaggtgg aagagcacaa agcatgtgat   25500
tttctgacct ttttaaattg taactgtgga gtcaaatgtt tccttgttag aaataaacaa   25560
gtcagggctc caaagagcag gaagggaaag gactcaagtt cctggcatct acatctgtca   25620
gcttacaggg aagcccttt tggccttttaa aagcacccac acactcatgg ctcacacacc   25680
cacatacata tatgtagtga aaaaaataaa tcttttaaaag aaaattcaag ccgggcgtgg   25740
tggcgcacgc ctttaatccc agcactcggg aggcagaggc aggaggattt ctgagttcga   25800
ggccagcctg gtctacaaag tgagttccag gacagccagg gctacacaga gaaccctgt   25860
ctcgaaaaac caaaaaaaaa aataataatt caaacagttc acagatttgg gatcagctaa   25920
cactactgga ccagggaaag gaagcagtta actcccgggt tgggagggaa cctgcatgtt   25980
tattcagact gagcatgtgt aagtgattcc tgcctgctta gtgaatgcca gggtcctttg   26040
ttttttgttga gaattggaag ttgtgaagtc acagttcgc aaggttttgg tgggaatttc   26100
acttcctgaa atgtatatat gtgtgctctt tgttagatat ttcagggtgg tgtatattaa   26160
ttaacaccaa aaactgtcta tggttttctt tttagaatct cttttgaata aagtttgtg   26220
tgtgtgtgtt gatacagggt cttatgtatc aaaggcctgg aattcactat ttagaccagg   26280
ctggcctaga catagacact gacagtgtta acagtgtgtg caccatgctc tgttctcaca   26340
gtcttttttca tagaactaaa taatgacatt gctgtgtatc tgagagtttg atttcctgat   26400
aagaacatat aaattggggc tggtgagatg gctcagtggg taagagcacc cgactgctct   26460
tccgaaggtc aggagttcaa atcccagcaa ccacatggtg gctcacaacc atccgtaaca   26520
agatctgact ccctcttctg gagtgtctga agacagctac agtgtactta catataatca   26580
ataaataaat ctttttaaaaa aaaaaaaaga acatataaat ttagtcacca gctgtgctta   26640
attctaaaaa cctattatgt tttctaaag attacttact gttttctatt ttcgtctgcc   26700
aacaaaactt taaacttgt tttctaaacc ccatagaatg cagttttcct ttgctgactt   26760
gataacttgt taggaagtga tgcaaagccc tgtagttgca caggaccttg ggtgactttc   26820
acgtagtagc cagtgcactg cactgtgctt ttagtcattg ggtatgatta ctgcaaagtt   26880
ttgggttaaa gactgaaaga acatatctga attccaggaa cagagaccac tgcttaagct   26940
gctagctttt ttctagtctt agcgtctaaa ccctgccttg gtctgggaag gcattatgta   27000
ggcaaactga attcctagca ccctgtgtgg ggccttaaca tcttgaggtg tgttggtcaa   27060
aagactgtat gatttgtgtg tgttttgtt tgtattcttc ctgtgattgc aacatgaggg   27120
aatgcatccc tttgcaggat actgttgtgg aatttacatt tttgtggttg tattgctttc   27180
tctaagagct tacattcttc tgttggtgtg ctatccagga aactaatgg tctttattct   27240
gttaagtagg aagctgtcca gtatcttgta cagtgtgtca attataagat gactaagctg   27300
ttaagaaaac aacaattaaa aaaaaacttt ttaaaaagtg cttgctgaca tcatcttttcc   27360
ccaaagacta attaatatat gtgtttacta tagcaagatc atagttgttc tgttgtcaag   27420
tgacatgtag tatttacaga ggccttctgt tcagtccaac aggagcagct gagatagatt   27480
catacgaaa ctaaagatat ttaacatttt tattcatatg aagaatagtg tctttgggtc   27540
ttattgctgt ggagacacat catgaccatg gcaaggcaac tcttataatg gaaaatgttg   27600
```

```
aattggggca gccttacagt ttcagaggct tagtctgtta tcatcatggt gggaaagaaa     27660
catggtggca tgcaggcaga cttggtgctg gtgaagaagc tgagagttct acatcttgat     27720
ccatagcagc agaaggtgac tgtatgccat actgattgtc accttcctcc aacaaggcca     27780
cacctactgc agccttctaa tagggccaat ccctgtgggc ctaggggac cagttacctt      27840
cagactatca taaatagttt agacagtttg gggttttgtt ttgttatgt tgtctggatt      27900
ttggtttaaa agtggttgct caaaagctag ttaaaatagc acacaccttt aatcccagca     27960
ttccaggagg cagagtcagg cagacctatg agtttgaggc cagcttggtc taccacaaaa     28020
aggtgtgggg aagagggaga aagaaaaaaa aaagggagtg agtggtgagg ttaggagtag     28080
cctaaactgg ggagaggtag tggtaagaag attaggattt taagatcatt ctttgctgtg     28140
tattcagttg tgggccagcc tgggctacat gaggccctag cttaaaaaag aaaaagccaa     28200
gagacagtgt aaagagagtg actatttagt atagatttct ttgaaaggag tagtttatca     28260
caaactatat tctctgaagt tgaacattat acattctgtt agtaacttag tttatgcttg     28320
tgtcttttt tttttatgtt tacgattctt aattaaagtt catcttgggg ataagtgctt      28380
acatgctcct catcttttt tttttctcat ctaaatgata caagatgttg tatttagat      28440
gttgaaatta gcataaattc taaatccgaa aatttatttt ttaaaatgta gaaatgtgtc     28500
taacctgtta acataatcgt aagtaatgaa gtgtttccag tactcttgta aagaatacag     28560
tttgggtgat ccagttattt tagcttttcc gtgttaagaa ttatttaaat atacttgtat     28620
gcatgctacc gggaaatgat aagtctgttc tcagtttgag cccagttatg gtttttgcagt    28680
tatggttttc ctcagtccct gggcactgag acttgagatg gcgtttcact tctgggaagg    28740
taagtgtctt cttcactttta ctgcactttta ctgctgggca gtgtctcagg ttactgtaga   28800
tagagtgcaa acagaagcac tttttttcca acacccagta acaggattat agtctcactt     28860
cctattcta aaaatagaaa taggtaattt aggacatgtc tcaactctcc tttggtatta     28920
atttatgttt tctttatttc tcctatcatc tataactacc ttaaaatatt aaaatcaaat     28980
aaaaagtatg aaaagttgaa atgacagtta tgattttatca ttctctactt tcagatgatc    29040
acagtcgtgt taaactgcaa agtactgaaa atgattatat taatgccagc ttagttgaca    29100
tagaagaggc acaaagaagt tacatcttaa cacaggcaag tggtatggtg ctgagcagag    29160
gtggagggc tgctgtgttt cagacacggc taaacatggg tctggacatc tgcaaatgac    29220
atgctatctt ttagttttct gattctgaaa tcagttttgc aaatgccata gttttcagat     29280
ttcgaatata ttgataaaaa gtaaaattgt tcctaatgtt actattttca atggagggaa    29340
gtttttttgaa atgtcttggt gcagttctct tcaggtaaat tgactgtatc taacatggct    29400
tggagttctt gtcccctaac ttgtgatgaa gaactagaga ggccctggaa gcccttttct    29460
atccttctct cccctatgaa tatactttca gagagtatag tcatggatgc tgaggatagg    29520
gtctgaccat ctgcagagcc tagacatttg tacactgctg ctctgctgcc ttttctcctc    29580
cccagtggct cctcacagca acctccacag tgcaggaact aggaacttct gagatcatag    29640
cttactcttt atccagtaag aggctaaaca gcaaccagca ctgtcacatt tcccagtcaa    29700
agatgttcag aaatgtaact taaaatattt gagagtttta aattgtattt gattattatg    29760
tgtctctgtg tgtatattta tatatacatg tgcacagggt gtccacagag acaaaaaga     29820
agtggcccct agcactgaaa ttacaggctg ttgtgagctg tacaacatgg gtgctaggaa     29880
tcgaactctg gacctctgga agagaagaaa ttgtccttaa ctctatctat agtaccatgt    29940
ttgaggtttt taaaaagcca agaggttaat gcaacctgct atttgaagga ctgagaaaag    30000
tgtgaagtaa ttgttttttt aagttcagcc taatgtaccct gtgagccatt agaattttct    30060
ctgctacaga aacattgttt cacttgaagt ttcctatgac taaaaggaag gagaaacagt     30120
caggtgtaaa ccttgttaag gatattaatt cacaattcat aggacaaaag aaagctagag    30180
aatagggctg gagagatggc tcaaggttta agagcactga ttgctcttcc agaggtcctg    30240
agttcaattc ccaggaacca catggtgact cataaccatc tgtaatgaga tctggtgccc    30300
tcttctggtg tgtctgaaga cagctatagt gtactcatat aaataaaaat aaataaaaaa    30360
tttttaaaag aaagctagag aatatacatt tgcaaagatg ctatgtttgt acatagcata    30420
aagtgggccc agtcactgag cctccaccaa ggactcagct gctttcccct caggccgcct    30480
ctctttcctc tcctcagatc ttgtcctgcc cttcccccct aaccttcctt ctatagtcac    30540
tttctgaagg tagtttacac ctaggagaag gagtgtttgt gagtccttg agaactttta     30600
ctctgttgac tcctttgctc atccaaataa gagtgatgag ttgcttcctg ctaggcacac    30660
acttgagatc aacagaatta gcaggaatat cccaaccgcc actctgggat tgctagtgtc    30720
catgcagcta ggtgtagcat tatgaaatag atttgcctgc agtggtaatt cagctatact    30780
gagactaatt cctgaagaga caatagtagt tcattgcagg gagagtatat aatactcagt    30840
ggtcacaatg tgcttgaaa actgacctga gaaattctac atgtgtttat tccaacctca    30900
gtttcacaag agggctgcca tgggttgaat gatgaatcat acacatacct tttagtagcc    30960
gtctttaatg cgaatgggga gcataaactt taatttgctg ttttatagtg agtgaaattt    31020
atcttatgta tagtcataat catttaggat ttcaaaaaaa ttcaagaaat ctatattcag    31080
aactgaaaat ggactttgta ctgagaatga gtgtgggcat gtggaaaagc atgtgtgaag    31140
ttaggctctc gttgctatga caaatacgga aaggaaaact gaaaaggaaa aatcatttat    31200
ttggcctcaa atttccagag atatgactca aggtcagctt taaggctaag gtgaggcaga    31260
atattgtggc agtgtggacg aagagagaaa gagctacatg acaagggcat tcctgtgacc    31320
tgcttccccc tctaggtac cacctcctag tcctggtaca ctaatctacc aacagattaa    31380
cctttgatta ggccagagcc ctcccaagca tccatgagat gacatcaggc ctgcagcact    31440
cgagccccag gtgagcctt tcccacctaa accgtaatac agctattcct tctcctgccc    31500
tttccctcca gatcattgtt cttctttttc cttttactca gttcctacag acaggtctgt    31560
ctgtcttttt tttttctttt tttttttcct ctttttttggt tctccaagac agggtttctc    31620
tgtgtaactc tagctgtctt gaacttgtt ctgtagatca gaccggcctc caactcagag    31680
atctgcctgc ctctgtttct ctgagtccag agattaaagt cataggccgc cacctgggct    31740
aatgattgtt ttataagcat ctatatctca tatgaaaaaa ttcctgatga acaattccat    31800
ggttttaac tcagttatcc ctgttggact gttctcatga atcctgatag acaggactct    31860
acacactagg agtgtgagaa tatagcagct tgtctctaga tttttttgtt tatttgtttg    31920
tttgttttt tgttgttgtt gctttggttt ttgttttttt cctgatttcc tttctgtatt    31980
ctggtgtact tttcccagtt ttctaccctg gccttatgag ttgctcagtt ccacacacat    32040
cagtgcagca ttctaagatg tttccttgca accagctctt cagacatggt tcgctactgt    32100
gatactccca catctaccat gtgccctggt tctttgtgtg cctcaccttc tgcttaggac    32160
atgcagagtg accataacta cccatgtcct gcctatcacc tctctgccag acttgccttc    32220
cttttggctag actgtaaatc ctcaggtttt cttacaacat aaggcctgag gattgagcat    32280
ttggtggtag tgatgctcct ctgtgcacct tgtagggctg agactacatc tcagttgtac    32340
```

```
ttgtgcatag catgttactt ggtcacagag aaaacctgca acatttagtg tttgttaact   32400
acagtggtag tccttgttgc ttattaatta gattagcttt cttcccctg agttttagga    32460
tttcttttcc taaccaaccc cttggtatat catgtccatt gtacagttta aaaaattggt   32520
agcattgcta gttttgaaa gaactgatac acgaaaaaat tcttgtcttc ttaaaatcct    32580
ttattcttta tactgtaaca gctgttgcat gtttattggt tagtctttaa aagcagtatt   32640
agaaatgatg tattcatgtg cacacagagg acttcactcc tgagttgctt catgattttt   32700
tttaaagttt tatttattta ttttaataca gatggttgtg agccttcatg tggttgttgg   32760
gaattgtttt taggacctct gctcgctccg gtcaactctg ctcaactctg cttgctcagt   32820
ccctgctcac tctggcccaa agatttacta cactgtgtac acagtacact gtagctgtct   32880
tcagatgcac aagaagaggg catcagatcc cattacggat ggttgtgagc caccatgtgg   32940
ttgctgggat ttgaactcag gacctttgga agaggagtca gtgctctttt ccactgagcc   33000
atctcgtcag ccctcatgat tttttttaa agtgtactt attttcatat ctgtatataa     33060
attcccaatg aggccagaag agagagatct ggagctagag atatgagtaa ctgtgagcca   33120
caccgtggtg tcctttgaaa gagcagcaag tgccctaac aaccaagcca tcttttctagt   33180
cctgcttcat gattgttgtt tttgagacaa gatctcactg tgtagcccta agtggcctag   33240
aactcactga gtagacaggc tggccttgag ctacagagat cctcactctt ctgggattaa   33300
aagagctcaa ctgggcccat cgccaggcg tggtggtgca cgcctttaat tccagcactc    33360
gggaggcaga ggcaggcaga tttctgagtt caagaccagc ctggtctaca aagtgagttc   33420
caggacagcc agggctacac agagaaaccc tgtctcggga aaaaacaaa aaacaaaac     33480
aaaacaaaaa agcctaaaaa acccaactgg gcccatgatt tttttttaa ttttttttct    33540
taaaagaac taattatttt attcaatacg agtacactgt agctgtcttc agacacaccg    33600
gaagagggca tcagatctca ttacagatgg ttgtgatcca ccatgtggct gtgggattt    33660
gaactcagga tctctggaag agcagtcagt gctcttaacc acagagccat ctctccagcc   33720
tccccataat ttttttttaa gatgaaagaa aaaggcattt atgttactgg gggtttctc    33780
agtgttcttt ttggtagaga agatgatgtt ggttcacctc actgtatgct ttatattgta   33840
agtagatagt gtacattgga tggagagaat agtatcctt aatgtaaggg ggtcgtttct    33900
cagattacta gctttttaca ggtcaacccg agagtttatc catctaagtg attggctaga   33960
caccaagaaa taatctgccc taagatgat ttaccttcta attggggtgg ggtgtagctc    34020
tggtattgta ttctctgcca catgacactg gtagttggtt acatgttaca gttactttag   34080
gcacagtgga acttagttct atttcagcct tcactcagaa ttattaagga ttctgtctta   34140
gtcagggttt ctattcctgc acagacatca tgaccaagaa gcaagttggg gaggaaaggg   34200
tttattcagc ttacacttcc acattgctgt tcatcaccaa aggaaatcag gactggaact   34260
cacacaggca ggaacctggg ggcaggagct gatgcagagg ccatgaagt gagctgctta    34320
ctgccttgct cagcttgctt tcttagaaac ccaggaccac cagctcaggg atgacaccac   34380
ccacaatggg ccctcccaac cttgatcact aattgagaaa atgccttaca gctggatctc   34440
atggaggctc ctttctctgt gataacttca gctgtgtcaa gttaacaaac aaaaccagcc   34500
agtgcagatg aaggtcggtt gttagagtat ctacctagct tgtgtgaggc cctccgttac   34560
atctccagcc ccacatataaag gaggaaagga agtgacggtt ggacattctt tttcatctca  34620
tggcttggtt tttttgtttt tgtttttgtt tttttttgg ggggggtggt ggaggttgtt    34680
tttgtttttg gagacagggt ttctctgtgt agccctggct gccctggaac tcactcgta    34740
gtccaggctg gcctcgaact cagaaatcca cctgccctg cttcccaagt gctgggatt     34800
aaaggcgtgc gccaccatgc ccggttcatc tcatgttttt tatttttgt ttttatttt    34860
tttttgtttt ttcgagacag ggttttttctg tagccctggc tgtcctggaa ctcactctgt   34920
agaccaggct ggcctcgaac tcagaaatcc gcctgcctct gcctcccaag tgctgggatt   34980
aaaggcgtgc gccaccacgc ccggctctct catgttttt aaaaaacccc tatgctatca    35040
ttaatcgaaa tgtaaaagta attggaagta atatatttga tttttctcc tccattgcat    35100
tttgtaatat gaactattat tcacttttaa ttctgccaga tgatactagg cataacaaac   35160
caatatgcag gtactttcat ggttattttt tttttcctg caaattcttt tgtattgact    35220
tggggttgtt ggttggttag taatgaaata aacttccta ttttccacag ttccctgatg    35280
tttgtgtgag atatcacctg cctgttacag aaactgaaag acagatttt ccttttctaa    35340
cagccttttt agctagaata cgaacagcca ggtggtgtta tactgtaggc acctttggta   35400
ataacagcaa agccatatgt aataagacag tgaactgtgt aataataact atataataag   35460
actaatgaac aaggctggct ctgtttcgga cagaaatctt agctgtattt tatagttgtt   35520
atttgaacct agttatccag ctcttcccat aagccctata tggttctttt cctgccaagg   35580
taaagaaaat gtctttacat ggaggtaaag ttttattgaa tgcacactat attttggatt   35640
taagtgcatt tgaagtctta atttactcat caggccccaa tgcactggtt ataacagtgt   35700
gttccagtag catccttgca gccttgtcct tccccagccc ctctctcatg tggtcttctg   35760
tcgttacagg gcccacttcc gaacacatgc tgccatttct ggctcatggt gtggcagcaa   35820
aagaccaaag cagttgtcat gctaaaccga actgtagaaa aagaatcggt gagtattctt   35880
ctcttctctt ctcttctctt ctctcctctc ctctcctctc ctctcctctc ctctcctctc   35940
ctctcctctt tctcttcttct atcttgtttg tgtgtttgtt ttgttttgtt tttttggaga  36000
cagggtttct cagtataacc agccctggct gtcttcactc actgtgtaga ccaggctggc   36060
ctcaaagtca cagagctctg cttgtctctg cctccttagt gctaggatcc aaggcgtgct   36120
ccaccatgcc tggctggtga gtcatattca acattagtgg ttgaatatgc cgcgtgttgg   36180
atgtgtgatc gttatcttac acatttcttt tatttgtgg aatgcttgtg gtggctaaca    36240
gctagtggcc aggttatttc tttctttttt ttttttggt ttttcgagac agggtttctc    36300
tttttatagcc ctggctgtcc tggaactcac tttgtagacc aggctggcct cgaactcaga   36360
aatccacctg cctctgcctc ccgagtgctg gattaaagg cgtgcaccac caccgcccgg    36420
cagccaggtt atttctgacc aggactaatg gatactttgc tttccttca tttctttaca    36480
gttttttaaa aatgcatttt atagatttat agtaatacat atcttattct gctacataag   36540
cacattttt ataagtatag gtgatatgtt gggagtattc cctactttca gccctccttt    36600
ctcccactct cctattatct ttttttgtact ccccgacagt tctactactg cttttgtgtc   36660
tgtctcctag attttgtata ggtaggtacc ttaaagcaca cacacacaca cacacacaca   36720
cacacacaca acttctcttt gtgagattgc catatttcat tggtactatt tatcttagtt   36780
gcatctatag ttctgcaaat gacataactt tgctgttttt ggttaaaagt tttcattctg   36840
taaatatacc acatttcttt catttttctg ctgttaggca agtgtattgg attctcaatt   36900
taggttttgt gagtagtgcc ttggtaaatg tcaataaagt ataaatctct ctgtgataga   36960
cctaccttgg acttggagtc ctgtggttag atactcagaa gtgatatagc tgggtcatat   37020
tgtaggtcta tttcactttt gtgtagaacc tctgtacaga tttccatagc tgctggacca   37080
```

```
gtttacattt tgaatagcag tgtgtagcgg ctcccttttg gtcacatctt tgccagtgtt   37140
ttggggtttgg ttttggtttg tttagtggta gtggtgtcac tgttgaggtt ttcctttatt  37200
ttgtgtagcc ctggctgtcc tggaactccc tgtgtaggcc agactggcat cacagaaacc   37260
tacctccttc tgcctcctga gtgcccgaat taaaggtgtg gattgctgtg tccaacagtt   37320
cttttctttc tacagtcatc ctgactagag ggagatgtaa atgtctgtgc ggtttcaatt   37380
tgcatttctc tgatagccag ctagactgaa aactttttat gtatgtaatg acatttgtgt   37440
ctcattttgt ctgttcatta gcccatttac tgattgggtt gtttgtcttt ttgtttaatt   37500
ttttcagttt tttatatatt ctagctatta actgtctgtc agataaatta ggtagcaaag   37560
atttttctcc tatttggtag attctgttca tttaactact tgcttttcta tgcagaaact   37620
tcttaatttc atgaggtttc ttttgtcatc tgtttgcata tttttcttaa gtgagtagag   37680
tcctgttaaa agtcattgcc tgggctgggg agatggctca gcagttatga gcactgactg   37740
ctctccagaa ggtcctgagt tcaattccca gcaaccacat ggtggctcac aaccatctgt   37800
aatgagatca gacgccctct tctcgtgtgt ctgaagacat ctacagtgta cttagatata   37860
taataaacaa atcttaaaaa aaaaagaaaa agtcattgcc tagggtgtct gtctgtatgc   37920
gtgtgcccac gctagggga gcagagttta ttcttcagtg cttttctgctt tatatttga   37980
gaccttcttg ggtcctgttt tgactggact ggttgtgagc cctcaggatc tgcttttatg   38040
aacccaccca ctcctcccca gtgacatctg catcagaaac cacatggatg aagctgcctt   38100
ggcttctctc tgggttctct ttctcttggg ttggtttgtg gacctgctgc ttttgttact   38160
atgactgtgt ggtatgcctt gaaatcatgt ctgattagac ctcagtctct tatgtttgtt   38220
ttcttttctc aggcttgcat tgcccttccc ccaggccttt tagagcttt gtaagagcag    38280
tgctgggatc aaaggtgtgt accaccactg ccaggctaag cgctttaaga ttttttctgag  38340
atgtacttc aaatatgcatt ggaatttga tggggattgc actgaatctg tagattgctt    38400
tggatagtat agccggtttt acaatattaa ccagtctaca tactttctctt cctttcttct  38460
ttctgtttgt caatattggg gactggaccc cagcctttat gcctgctaag caagaatttt   38520
cccagctaag ccatagttcc tgtgggcaga gaaagtcttc agggtttgtt ctccccccc    38580
ccctattgtt gtagcttttg tagagatttt tcttaccta ggtttattac atggtattcc    38640
ttaatgcagt tagaatgagc ttctatcctt catgcgttgt gagcatgttt gttattgaga   38700
taatagaaag acttctgatt ttatatatta tatattaatt tctatcttga tgcaaagact   38760
tctcattaat cctgaatttt cttttgcagt ctttaggatc ttttaaaatg gaatgatttt   38820
atctgtaaag aaggatacat aggcgtcttc cttcctgtt tgtacctcac tcattttctt    38880
ctcttgcttt acttatgatt gagacttcaa gtgtcatgtt gaataagggt agagaaagat   38940
gagaactttt gtctttctcc tgatttagcc aacatgttc agattttct ttggtgtgat     39000
gctggctttt gggttgtcat ttatagcctt tattgtgttg aaatatgttc ttcctattcc   39060
tagcctcctt aggactttta ttatgaaggg atgttgtttt aaatatcacg tatgcaattt   39120
ctccttgagt cattttacgt agtgaattat gattggtgat ttgcatatgt tgaaccaccc   39180
ttgtatctct gggatgaagc caacttgatc atgatgaatg atctcttatg tcttgaattc   39240
cattactgat acttattata gtgagaactt tgcagttttg ttatttgtgt gttggtcttt   39300
gtccgacatt attattagag tgatgctggc ttcataaagt gaatttgcta gcatttgttt   39360
tgctgattct tagtattgtt tctttagttt ccatttcatt cacttctgcg caggtgttaa   39420
ttcttaccat ccccctacttt gggatgtgcg cgcatgtcca gtttccatag ctagcctatc   39480
tgagatctct ctgatttatt tacttacttg acacttagag ctataaacat tcttttgaga   39540
actgcttgt atccagagag tttggaatgt tgtgcaattc tatatatttt tctgtttcca    39600
gcggctcata tttctttcag tggtgtgttt tcttttttgt ttccttttg cttggtgtgt    39660
tgttttcagt ctgtaaatct gcatggtttc tgtagtttct cctgttgttt tgtagttttg   39720
ttcctttgat tttctataag attgtgtgtg aatgtttcct gaggcacaca tctgctagct   39780
ccaggtaggg catcagtgat agaaacaaag tgtagtttgg caagctaatg aatggatagg   39840
tgtgagatta tttttagaaa cattggagaat taagtggctc tactactacc aaagaaaaac   39900
aactctctgt gagactagta attttttggag gcattgtacg gccttggctt tttatatttc   39960
ctttgttttct cttttgtata tatgtatctg aggttaggct gttttttgtt ttttttgttt   40020
gtttgtttgc ttgtttttcga aataagtttg tagtgttcag taagatctgg gttgtagtag   40080
tgttgaagtg tttttatctg ttgggctctt tttcagaaca ccagactcaa tatccgtaa    40140
ctcttgacag aagtattaca cctttataaa caatcactaa ttaagagtaa acccattata   40200
aatatataga aataatcaag tagcactcag tcgccactta cacccaagc atttcagaaa    40260
gtaaaggaag ccttatagaa tcaagccttg tttactgagc tgctagttac tgtgagtgtg   40320
actacaagaa aaataccaca gtgcctcaca gttggtatta ggtaataga gaaaatctcg    40380
aggatgagat tagatgagag tcagcaaggc caagtagaag ggtgagtcag ttttgcctaa   40440
aggtaggatg gaaagggaga gctaaagaaa tggtttcagg ggttaagagc aaacactgct   40500
cttgcaggag cccctagttc agttcccaca cctatgtggt agctcacaac catgttattt   40560
cagcttcagg gggactcagt gtcctttctg agttcaccag acactgtatt cacatgcaca   40620
ccccctgcac cacacacaca aacacacaca cacacacaca cacacacaca cacacacaca   40680
cacacgcttt aaagtatgtt tttaaaagaa aaagggcca ggtgcagtgg tgcatgtttt     40740
ttatctcttc attcaggaaa cagaagcagg aagatccctg tgagtccag gccagataag    40800
taagaccatg tcttaaaaga aaggaggagg gctggagaga tggctcagtg gttaagagtt   40860
ccgacagctc ttccagaga cctgagttca aatcccaaac aaccacatg tggctcacaa     40920
ccattaaatc agacgccctc ttctggggtg tctgaagata gctacagtgt acttacatat   40980
attaaattaa taaaagaaa gaagaaggga agaggagtgg aggatgttat cagaaaaccc    41040
aatatctata atattttgcc agttcaaatt taaactaaga tttatgtgtc tttagactct   41100
ttctgtca aaattagaaa gtcttgactc ttaagattat ttccagttta aatataccac     41160
acacacacac actcacatgc tttaaagtat gtttttaaat ctgttctatg acagatttct   41220
ggttcttaat tcttcctaaa ttaatagtta ctgggttttg atgataatgt gtatcatgac   41280
attggcctaa cagaatttcc aataattgcc atctgtagtt gttttccgtc ctctcccact   41340
aatctagaga ttcaggggtg gggcatagtt ttgtttgttt aatgtgttg caaactagat    41400
gatttgtaaa tttcatccct ctcacgtcaa agtagattca ctttttttaa gattcatttc   41460
tttatgtgt attattttgc ctgaatgtat atatgtcac cacataagta cctggtactc     41520
ccagaggcta aaggaagaca tcagatcctc tggaactggg ttaaggcata gtgtaagaca   41580
ccatgtaggt tctgagacct gtgtaggagg aacaagtact cttaactgct gagccattcc   41640
tttagtccct tgtgggcatt ttaatctctg gttcctttt tttttttttt tttttttttt   41700
gttgttgttg ttggtggggg tggttttttg agacagggt tctctgtata ctcctggctg    41760
ttctagaact cactctgtag accaggctgg ccttgaactc agaaatccgc ctgcctctgc   41820
```

```
ctcccgagtg ctgggattaa aggtgtgcgc caccatgcct ggcccttaat ctctggtttc   41880
ttaagtgtca gtgaaagtgc atctgctctt ttagtactta aacgtcattt tggcagggta   41940
taaaaaactt agctcttgct tttacttgaa tttaaataca ttcttttcat tttagtgttt   42000
tagattactg tccaagtcaa atggatgtca tttttttttc ttgtacctat attacgctgg   42060
ggttttctcc cttttttattt attttttttaa attttatgtt tatgaatggt ttgattgcat   42120
atatatatgc taccatgtgt gtgcctgttg gatccctag aacaaggttt atgggtggt    42180
ttgtcccatc atatgggtgc tgggactcaa acccaggtct tttgcaagaa caagaagtac   42240
tcttaacaac taagccgtct ccctacctag ccaggctctc tttctcttta acattaactt   42300
ttgaaactgt atcttaccac ttgattggct ttttgcaagt aaatagtttt gtccttaaa    42360
tagttgcaaa tgcttttttt tgtgtgtgaa aaataaaaag attattaaat tatatttggg   42420
atttgttctg ttcctgtttg tcattgctgg tgttttgag gggtgtgtgt gtgtatttc    42480
tttgtatttg tcctgctctt gttaatcctg tttctatttc tctctattta ctgtaaaatg   42540
tccttcttgt cctcttaagc tttatccatt acacttatcc tgcactacag ttctaggtgt   42600
caaaacaaac caaaaggctt attcttctga ttggctgtcc tggaactcgc tctgtagacc   42660
aggctagctt tgaacctaga ggaaagccgc ctgcctctgc caaacaagtg ctgggattaa   42720
aggtgtgcgc caccaccgtt cagggtgaca gaaagcctct ttagtgctct ctgaaataac   42780
attcttgcaa gagcttgata cttctagaaa ctcaaactga atatgttaaa gtgtaattat   42840
gctttaagaa cagcacactt ttgggttggg catggtaaca catgcctta aatccagcat    42900
gtggggctg aagccagctt gatgttcata ctgaattcca ggacagccaa ggctatataa   42960
agagattctg tctcaaaata aagaagagca tattttaatg aatatttat gtttatggct    43020
ttttaaatgg aaaggaaaca ttttatggag ctactttaca gaatattctc attaaaatac   43080
ttaagatatt cttaggtttc agtacttgga gaagtatagt atgtatgtgt gagatttgtt   43140
tttatggttt tataatatgt ctaaactatt cttaaattta ggttaaatgt gcacagtact   43200
ggccaacgga tgcagagaa atggtgttta aggaaacggg attcagtgtg aagctcttat    43260
ctgaagatgt aaaatcatat tatacagtac atctactaca gttagaaaat atcaatgtaa   43320
ggcttttctt gtttcaaagt ttcagttta tctgatgtc ttaagaattc ttggggggttg    43380
atactatact tacttgcctt tggatatttg taataaatatc taggtataag catgtttta    43440
gagtatttct atataaagta actctttatg cattctgaag aattctaaaa acaacaaaga   43500
attacaatgt tcaggttaat attaatatt aagaattgaa aattaactat tggagctgga    43560
aggctggctg tagtgttctt gtagaaggcc caggttcagt tcccagtacc catgtcacga   43620
ggcttaccac tgcctgtaac tcctgctctg ggaaatcctt gtataagaaa aatgctagaa   43680
ctaacttctc cttgattttt acatttcaga ctggtgaaac cagaaccata tctcacttcc   43740
attataccac ctggccagat tttggggttc cagagtcacc agcttcattt ctaaacttct   43800
tgtttaaagt tagagaatct ggttgtttga cccctgaccc tggacctgca gtgatccatt   43860
gcagtgcggg catcgggcgc tctctcttgt agatacctgt cttgttctgg              43920
taagtgtcat gcgatctcat tggtgttttg tgcttctctg ttttgttta tcattttata    43980
atgttgatga taaaaagata aataattttg catgactggt gcctgaggag ttagaagaa    44040
agcattgagt ccctgaaact ggagttgcag atagtaagac cctataactc gtgggtggga   44100
accaaaccct gatcccttt aagagcagcc agtgctctta accatctgc ctgtttaattt    44160
gttttaact gtttctatag gcagcagtaa attttgaagt aatatcccaa aactctaggg    44220
tttttttttt ttaaacactt tacttctata gtttaaattg actctagctc ctgcaggtac   44280
atgtgtgtcc atgacaatta taaagattcc ctagaaagtc tcaaccaggc ttggctcgta   44340
cctttcatcc caacactaag taagttgggg cagaaaattt gctccaagtt tgaggttagc   44400
ctgggctacg gagttagacc ctatccaaaa taaaaaggga agaaatgaag aatacagta    44460
agtctccctc ctaaaaggga gaaatgacaa aggaaagcaa tcctgaaaga gtgactcatg   44520
cctgttgtct gcacgtctga gccagccggg gttacctagt gagattcacc tcaaaaaga    44580
agagaatgcc aacgaactgg ggccatggca agcatgacca ctgactccta gtgcatgggt   44640
aaaagatgag cagagtagca catgtctgtg accccagaac gtggtgaagg gcagttaggt   44700
gggtttaata tagtttactg accaccagct tatccaagtc attagctcca ggtccagtaa   44760
aaaacactgt ctcaaaatg gcttgaattc taccctagac cctactgggt aggagaaaac    44820
tacctccaat aagttgttga cttttaaagat ttttaagcca ctgtgctggt acctgtctgt   44880
aacccccttgc ttgatagagg caagagaagc aagtccatag agagtttgag caagtctgag   44940
caacatgaga atttgtttca ataccccctt tcttctggt actttgtata cagaattaaa    45000
agcttctacc ttcagcaata aatttttaaa tttaaaatg tgatttttttt tccttcttgg    45060
ataagtacat catctcttat ttataaacca aggctaaaa gtacttccca gggttactgt    45120
gataattctg tatattaatg atattttctg tcctggttaa cgtcagctaa caacttgaca   45180
cagcccagag tcatctgaga ggagtgcctc aattaaagaa agacttttta agatcagatt    45240
ggtgttattt gtagggaact aattgataca ggacagccca gcccactgtg agattatctg   45300
tagagagaat gtcttgtata tttttatggat acaccaccca tcaattaaaa agcctatgg    45360
ttaggcagga agtaggaggt gggacatcgg ggaggcagaa agagtctgg gatagagcca    45420
ggcacgggag gatttgccca ggaagatgtg aagagatgga tgtggggtac ctgaacacag   45480
gtaaccagcc gcgtgtcaga atgtaaatta aaataaatgg gttatgggct ggagaggtgg   45540
ctcagcgggt aagagcactg actgctcttt cgaaggtcct gagtttaaat cccagaaacc   45600
acatggctgg tcacaaccag ccataatgag atctgatgcc ctcttctggt gtatctgaag   45660
acagctactt tattgttatt attattgttg ttgttgttgt tattagatat aataaaaaat   45720
aaatctttgg gacggagcga gcagaggttc tgaattcaat tcccagcaac cacatgatgt   45780
ttcataacca tctgtacagc tacagtgtgc tcacatacat taaataaata atttttttt    45840
ttttttttt tttttttttg gttttttcgag acagagtttc tctgtgtagc cctggctatc   45900
ctggaactca cttttgtagac caggctgtcc ttgaactcag aaatctgcct gcctctgccc   45960
cctaagtgct gggattaaag gcatgtgcca ccatgcctgg caataaataa atctttaaaa   46020
aaataaataa attattatgc ttaaacaaac cctaatgggc tactttaaca ttttgcctag   46080
acaagttata gtttcaatca aaacttgaat tgttagagct gagaggtggc tcagtgatga   46140
aggacagttg ctgctctttta gaaattaat gttcggttct agcacccaca gtgggtgact   46200
cacagcccctc tccagctcca gggatcacat gctgtctctc ggccgctgtg tgcatctcta   46260
cacacttggc atgcacacat acacatgcac tcacaaatct ttaaaaaaaca aaaaactcat   46320
ttactaataa aattaacctt ttgctcaaag gcagtagatt ctgttaatga tcaatattaa   46380
aactgggtta tgagaaccgg cggtcttggg cagagtgttt gcctagcatt taagggttca   46440
tgagtttcaa actgcattgg atgttcatac ctgctctcta ccaactgtgc cttgctcatc   46500
cttccttctc ttcagtttat ggtttgtttc taaaaccaga tcagtagtcc agagctcaga   46560
```

```
ggtaattttg taggtcaagg cttccctatt tcctgccatc tttaagtgt ctgctgtaca  46620
tccacaaagc atgtctttgt ccagatttga gatggggaag ggcactgagc agcaaacttt  46680
atctctgaca aaaccatttt ttaaaactat ataaataatc ctaatcatat ctgggtgtct  46740
gtgtgcatat ttctcacccc ccccccatg tgtgtgtgtt aaattatcct tcttttaaga  46800
aggaacctgt tcacagctaa ggtctgagca gtgagtggcc ttatattgct ttttttttt  46860
ttcaactcaa acaacttggt tttaccttc ttgcagatgg aaaaaggaga ggatgttaat  46920
gtgaaacaat tattactgaa tatgagaaag tatcgaatgg gacttattca gacaccggac  46980
caactcagat tctcctacat ggccataata gaaggagcaa agtacacaaa aggagattca  47040
aatatacagg taaactcagt atcattagtg tcaaataacc atgttccatc taaatcctca  47100
gccttccct acttcatttg gtagatccag ctgactgtct agaattcata aaactttcca  47160
cagttcaaga ggcaaagatg aaagctagtc accaagagtt caagaccagc ctggtctata  47220
cagtgagatc ctgacttaat tttttttttt cttcaagatt tatttattat tatatctaag  47280
tacactgtag ttgtcttcag atgcaccaga agagggcgtc agatctcatt actaatggtt  47340
gtgagccacc atgtggttgc tgggatttga actcaggacc tttggaagag cagtcggtgc  47400
tcttaaccac tgagccatct ctccagcccc caatttttt ttttatatgt atataagaca  47460
catatataca tatatacttg tttcctcagt ggaaacaaga ttcaattaaa ataatttttt  47520
tcatatgaga agatttcagc atttaattat tgaaagaaaa aaaaacccag aaaacataag  47580
tactttttatc ttagtaaaaa cttactgtag aggcctgagg agatggctaa gtggtcacag  47640
gttacaagca cttactgctc ttccagagca cccaagtgtg tttttaagaa ctcatgtcgg  47700
gcagctccag gggatccagc atctctggcc tctcatggca cttacagtca tatgcacata  47760
cctaaatgca cacacacaga actaaaaatg aaggaaatag ccgggtgtgg tggtgcacgc  47820
ctttaatccc agcacttggg aggcagaggc aggcggattt ctgagttcga ggccagcctg  47880
gtctacaaag tgagttccag gacaaccaag gctatacaga gaaaccctgt ctcggggggg  47940
aaaaaaaagg tggaaataaa aatttttaaac ccttcatgtg ggagtaaaga ctatttctat  48000
ataggtactt tatagctgaa taacttcagt tcttactaca gacataaagt gctaggagta  48060
aactttacaa acttttacatg tctgatgtg acattctgca gtggtgtctt ttttttttt  48120
ttggtttttt gagacagggt ttctctgtgt agccctggct gacctggaac tcactctgta  48180
gaccaggctg gcctgaactc agaaattcac ctgcctctgc ctcccagtg ctgggattaa  48240
aggcgtgcgc caccacaccc agctctcagg tggttttat tgtatatta tagaccgtaa  48300
gctcaaagag tatcagaact tagtttcatg tgataaggaa aagtgtaagg tagaaagaga  48360
aataacagta tatccttccc tgcatcgtct gcataataaa gacatacctac gatcgaaacc  48420
aacaatctta atccactact ctttgactat ctatttataa atatctgctt taaaatagaa  48480
tatatctttt aggggctag agagatggct cagcagttaa gagcattgac tgctcttcct  48540
aaggtcttga gttcaaatca cagtaatcac attgtggctc acaaccatcc gtaatgagat  48600
ctgatggcct ctctgatgt gtctgaggac agctacagtg tacttaaata taataaataa  48660
atttaaataa atagaataca tcttttaaat caattctatg tgattattt aaatgtctat  48720
gaatgtgttt gtgtttgtgg gcaagtgctg ggataaaagt taatgtcaag tttacctgtc  48780
tgttccctgc ctcatattga gtaattgcaa tttgtagatt gtgatttaaa gaaaacaaat  48840
tttattgtt tttatttctg ttctatacct agaaaccggtg gaaagaactt tctaaagaag  48900
atttatctcc tatttgtgat cattcacaga acagagtgat ggttgagaag tacaatggga  48960
agagaatagg ttcagaagat gaaaagttaa cagggcttcc ttctaaggtg caggatactg  49020
tggaggagag cagtgagagg tatgtgccat atatgtgcta gcctaccgag atatgcgggt  49080
agtcactaca ctcagggagt ctgcgacagg accaccctgt gttcagacag ttaatgctcc  49140
ttttacttgt gtcagagtgt ttaggtggta tgtgatgaca taaatatctt cagagagttt  49200
tccgtcatca taagaaagcc ggtacagggc ggggcagtgg tggtgcatgc ctttaatccc  49260
agttggtggc ttactaccaa cttaactcca gcttttttgg gatccaaggt ccttatggtg  49320
gtttgagtgt gcttagttcca tgggaagtgg cactattatt ggccttgagg tggctttttt  49380
ttttttttta agtttattta ttgtatgtat gtgagtacac tgtagctgca cagatagttg  49440
ttgggaattg aacaagggct cactctggtc agccctgctc cctctggtca actctgcacg  49500
cttgctcagt ccctgcttgc acctctaatg gcacatacct aaatgggacac acatagaact  49560
aaaaatgttg gaaataaaat gttaaaaccc ttcacgtggg agtaaagact attttacagtg  49620
tacataagta cactgtagct gacttcagac acgccagaaa aggtcatcag atctcattac  49680
aggtggttgt gagccaccat gttgttgctg ggatttgaac tcaggggcctt ctgaagagca  49740
gtcagtgctc ttcccgctga gccatctcgc cagcccgga gtggctttgt tggaggaaat  49800
caatcattgt ggggatgggc tttttgcggt ctttgtgctg agcccccacc atggttgaag  49860
agattaggct ccaggctgcc tggagaagac agtcttctgg tggcctttgg ttcaagatgt  49920
agagctctca gctcctccag caccatgtct gcctgcccac tgccatgctt cccatcatga  49980
ggagaatgga ctgaacctct gaaactgtga gccagcccca gttacatgtt ttgttttat  50040
aagagttgcc atgatcatgg tgtctcctca caacaataga aaccctaaga caagcctcct  50100
taggcttttg gttttttatt tttatttaga tttatttaat ttacatgtat gagttttttg  50160
ctgcatgtac accacatgtg tgcctgatac acacagaggc cagaagaggg tgtcaggtcc  50220
tttaaactga tcattcagac agtgaactat caagtgaata ctgggaattt tccctggctc  50280
atttgcaaga acaagtgttc ttaaccactg atccatttct ccagcccaag aaatcaaaat  50340
ttgaaaacat agtaatgata aatttaaaag ctattgttta gagacaacaa aaacctccaat  50400
actgctcata tacagaagtt agtgtaatta ggtgataaaa ataaatagta taatacagaa  50460
gatgagttgt ataaaaatac ctaattggcc gggcagtggt ggtgcatgcc tttaatccca  50520
gcacatggga ggcagagaca ggtggatatc tgagtttgag gccagcctgg tttacagagt  50580
gagttccagg acagccaggg ccacacagaa aaaccctgtc tcaaaaaaac aaaacaaaac  50640
aaaaatgccg gccagcaaat agaagcctaa tgacctaagt ttgttcactg agtcccactg  50700
tagaaggaag atacccaact tctcacagtg tcctctgacc tctacaggtt tatacctctc  50760
tttctcctcc tccctctccc tcctcccca cctctcatgc actcaagcag agtaattaaa  50820
taaaagagaa aattcagagc tgtatgccta tccccatgca cttaggaggc agaagcagga  50880
gaatctcaag ttcaaggata gcttacatac tgcgatcctg tctcaagca aatcattaat  50940
cctatctata tctagtcaag gctcatgctt ggatctgaat gagacctgat gccttggtgt  51000
tcttagtcag aacagatccc ccacttttt ctcctctgtt tgaaaatgaa tcttttagca  51060
tgccttatag tttggatttc tctaataatt gttcttcttg gttagaatca agttaaatgt  51120
tttgactaga aaaggtcttg tgatctagta gacattgaag agccagtcaa gatttttttt  51180
ttaaatcaag ctgcatgttc aaagctgtga cttaaaaaat gactgccaag ccgggcatag  51240
tggcgcacgc ctttaatccc agcacttggg aggcagaggc aggtggattt ctgagtttga  51300
```

```
ggctagcctg gtctacagag tgagttccag gacagctagg gctacacaga gaaaccctgt   51360
ctggaaaaac caaaaaaaaa aaaaaaaaaa aagccaagac tgaagcactc acagtgagtg   51420
aaaagagatg ggttttgtga gattttttt  tttctagagg aagagagtaa atggctgaca   51480
tgttgacatt ggccattttt caatggatgt cagagaactt tcattgaaac aaaattctat   51540
gttgacagg  aaaatgggtg ctagatgtac ggatggtcaa atagaagact gggtaacctc   51600
caaacacagc attcatagaa attgtcaaca gtatttgtca aaggacattg aattttcata   51660
tgctgtcacg caacaggacc agatgctgag aatctccagt ctgtctcctt cgtggtagag   51720
aggaaagcag agtgtgcaga aaacatgtct gtcttagctt caggtcctgt aaaagcgtta   51780
cttactgtag gcacagcaga cgtgaccctg aactgtggag cacaccactg gcctgtggga   51840
ccgcttgtcc ttcccttttgt tactgcagta cactgaatga gatggaaagc atacaaatga   51900
gtgtccatgg tttgatggtg gcctgggccc cactgtcagt gtgatgaagg cctgcagtgc   51960
agacactcac ttgtttctgt ctattcacag cattctacgg aaacgtattc gagaggatag   52020
aaaggctacg acggctcaga aggtgcagca gatgaaacag aggtaaatg  aaactgaacg   52080
aaaaagaaaa aggtggttat attggcaacc tattctcact aagatggggt ttgtgtcagt   52140
cattttggtt ggcgctttgg ttggctggac actgcttttt cactaaatgt tctataaatt   52200
aatagtttta cccagcacct ttctgcacta gtagctgacc gtggtgcatt aatctcaagg   52260
gtttgttagc aatgcctcat acccagaaac actgcgctag agtagacatc agccagataa   52320
gggatattac agtcacaagc ccagcatctc aggactcatc actgcaggtt cctctgagac   52380
ccagactgtc aatggctcac aataaagaca agcatgcttg ttggatactg ttacttctta   52440
cagctgcgtt cacaccagtg tattgagaaa tcctttatcc caaggattgg ctttttggagg   52500
ccttctggat tttaacctgc acttgatata agcaataaac attgtggttt ttttctacat   52560
tattaatgga aagaaaatat cctttaaaca atgtatgtaa tatgtaatgt actgttgaaa   52620
tgggcattac aactttatat aaccatttta gggtaaaatat attttataag tacctattta   52680
atcttacttt tgtagttaaa tgtacttttt aaaggttcaa tctgaaagtc tgttatcata   52740
gaaaaataaa ttgtatgttg actcagttgt atactgaata cattttccct ttcctaagca   52800
gacgtttgat agaggcagtt gaaactataa gcaagctaag actactacac attcttattt   52860
cctttctatt tatgctttat cttatttaaa aaagaaaaac aaaaattttc taaacatgtc   52920
attgaaggaa attgttttttt tctgcgatag ttaagaagtg acagttggtc aaaatatagt   52980
tgaaaacaaa caaaaacttg gtttctgcag gatgtggtag cacacacagt gctcaggaag   53040
ctaaaacagg aggctcaatg gtttgaagcc agccaaaact acatagcaag gtcctatctt   53100
taagataag  agaaaatag  aggtggtgga ggagagatca gacaacacca agaataagaa   53160
atcgattctt agccatattt aatggacaaa cctgtcatct cagcttttgg gagatagagg   53220
cagaaggctc acaagttcaa ggccagcttc aactacatag ctagcccag  agtttggggc   53280
cagtcaggac tgcaagaaac actgtctcag aaactgaagt ggtttaaaaa cattttgatt   53340
tctgtaaagt aaagcccatg catgactaca ctgttaattt tttgtgaaaa tgtaaatgta   53400
attacccaga cgggataaat tatggttagt aagttaaagg aaccagtgtt ttatactttt   53460
gatttcagtt cactagactg aaattttgaa gtaaaaaaaa atttaatttc tttacaagtt   53520
caataaatag tacaatggtg tacaaacttca cattgtccct taccttttgta atgagtattt   53580
ttaaagcata accactaatt gggttttggt ggtttcaaac cctgcttggt ggaaaggttc   53640
caaaccatta ggacagcatt gctgcttcat ctcttttata tatcacgtaa aagtgcgtgg   53700
taaatcttaa ttagttttaaa tgagacagtt aatttcttaa tgcagttttga accccatagg   53760
tgtagttaga aattgtgaat ggccttgaaa agcatctcac aaagcgtatg atgtatgtgt   53820
gtgtcctgac tcagcatagc tgtcctaagg cttttgaaatg gcagcaggt aagaaggatg   53880
tttcctcttg tctgtttaat ctctgtttaa gcggaggcct tagaattaga tggctatggg   53940
ttttgagctt tctaacactt actggtttgt ttttccaaaa tgtagtatgt tatcctacta   54000
gaccttatta aaacttacag tccaagccaa taaggtggcg tacaccttta atctcaacac   54060
taagaacacc aagacagaca gatccctgtg agttcaaggc tagtctggtc cacataataa   54120
gttcccaggc agccagaaat agacattgag atcctgtctt gaaagaaagc aaaccaactg   54180
aagatagcct gagcttaaac aacttccac  aagaaaaact gataaggctg agaccagtcc   54240
ttccttggac gatatgcttt ctagagatag cattgagcac cactctttct gcctcttggt   54300
gtgtatttta tgttttgtgag gattccttttg gcataccgga ccctcagtgc tcctccccgg   54360
agcccgtctt tctcccctga acacatcttt aaggatgagt tttaacagga gaacctttaa   54420
gtcacactgt catgttgctt actaaaggta catggcctgt ggtgacagtg tcactggcat   54480
catcctgagc ctgtatgaga tgtgctgtgc tgatgagaga agggtgctgg gcagagaagg   54540
atactagca gttctgatg ggtcacggc tttaaacaca gtgtgcgtca gtctcggtag   54600
cagcttattt taactaattt aggaataata gtttgtcttg atcaaattc  tgttttttgt   54660
ttgtttgttt gttttttgtt tttggtgttt ggttttttt  taatttgggg aaaaaatagg   54720
cttttttaaag gggattattg tttactgaa  agaatcctca cttcctgttt cctcccaccct   54780
tgctgtaatg tcagtggtca caagattcac caggtactgt gttatctcag cctcctgatt   54840
tctatccatg ctcaaaccta aagtgtaaaa gtacacattc ctttttaaaa atacgctatat  54900
gcatcatttc tacgttcagc agaatctaca catttgtcaa gttttccaca gttctcagtt   54960
cttttttatcc attccgttat gtgtcacctc atgtatcaaa cagtgaacat aaaaagatat   55020
gaagacctgt attaattagt tttgtccaa  acagctgtgc tctgaagctg cgtcagagga   55080
aaggtcctaa tttctgagct cagcttccat gcactcggct cggcccttttg tcttaaagta   55140
aagctagtgc tgtgagttta gaactgtggc ccacgtttca agttatgaca cagaacagcc   55200
ctctctggtt gtcatttcat ttccttgttt gcttttagca ccagtcccag ggtgctggct   55260
cccatttttct gccaggcaca gaaaggctac agctgactgc tttaaaaata gctctgcgta   55320
gattctgcag agaagctgga acctaatggt agtaaaagta ctttttttg  gccattgtat   55380
acaatctact taacaagttt acatttctgt caagcactta cagactgaga atctacattg   55440
ccttaatttg ttacttactg atacaaatct ttatttgtag ttgttgtttt ggataggttt   55500
gtatattctt tttttttttt ttttttttt  ttgtatgtgt gttgagatag taccttgcca   55560
ttgcccaagc ctggccttaa actcagctca acgactttc  ctacctcagc ctgttgagta   55620
actaacacca caggtacaca ctgtgcacac agctttcaag tataaatctt aaagagatta   55680
tttaaaact tgtagataaga tttcaggccc ttagtcaagc ggtgtcagca ccttctctga   55740
gtagggccat ctctgggtcc tggtgagtag tgtctatgtc tgtgggaagg aagggctgct   55800
cggggccttc atctggctga gctcgattca tctgttcata gcatgggaca aaataccaac   55860
agaaatgtcc attctattta catgccaaca cctaacaaag tctcttatttt ttaaaactcc   55920
tttatatggc tttgccatag aatcctgtat atactttttt tttttttca aaatagaaat   55980
gatttttttt ctcattaaat ttgtcatctt attacttgaa acgtgggcct ttgttattgg   56040
```

```
cagtggcttg ctcccgagga ggcctgttct gtccaccctg tcccagaacg cactcatttg    56100
agtcagatgc cacagttctt cctcacactg gtctttggtt tataccatgc agcaccatac    56160
ctagagtcac agctgtctct aattgtcccc tgaatatgga atgagagact caggctgtgc    56220
cctcattcac tgctgctctg cactggagcc tgtcccccaat cagagaactt gcctcgtggc   56280
cagcagtctt ccttcctggg tcctgagcag cttcaagcct tctgcattag tgctttctct    56340
tagccgtggc tgttgggaag aagacccact gttctccaca ggttgggttg ttttttttt     56400
ttttcctggc tgtccttgtc ccagcacagt gccatcagcc attgtgagca gtgcttaaag    56460
tggaaagcta caccagccta agaggctttg tgtaagctga cgtttaggat ttaaagagcc    56520
tggaccatct gagttctgac tctgaagctc tgcttggttg taaagttcca gttgattctg    56580
agcagtgagg tgtgaggcca ctgtcaccgg tagggtctgc ttggatgccg cctgctttac    56640
ttggatctgt tttgttgggg actgctgcaa ggagaattgc atgggaattt tcttcttttt    56700
ctttacagag acttataagc atcgagttat tctttgtagt cactcattag gcatagtttt    56760
ttttttttaa gacccatgat gctgttgcta ttccccccc cctttttttt ttggttttt     56820
gagacagggt ttctctgtat aactctggct gtcctggaac tcactttgta gacctcaaac    56880
tcagaaatcc ccctgccttt gcctcctgag tgctgggatt aaaggcatgc gccaccacgg    56940
cccggctgct gttgatattt taaatgacta ttttaaaag tcgttcagtg tggaaagttg     57000
aggagaggaa gcctaggtaa gttccttaa agcatgcttg gctcacctcg gttagtcctg     57060
atcaatctca gtcggatgct aatgtaaatg tcgtgtggca aaacaacttt taatgcagtc    57120
tgactttccc tctaacacgg gcaaggaaga agacaccagc atttgcctct gcagcacaga    57180
ggcagccccc aggataccca cgtagctcat tgcttggttt gctcgcccat tttacttttg    57240
ccttattaaa aataaaatgg tgaagatcca ttcaagtgaa tataatagaa ttatctcaaa    57300
agccatttat cttaatagtc ttacaaataa agtcatttct tagaagctat tccattgatt    57360
tcctcttatt ttgctacccc taaacactat ttgaaaagaa gtaatgagtt tcaaaaacca    57420
cagcgtgtct gttaaatggc aaatttatta ttcttggtaa atgtgtattt aacaaacact    57480
aggaaaggat atctcgtgtg tatgtgagag agaaagagag agtgcttcac aacactttaa    57540
ataatgccag ccatattttc agataagaaa cccagtggag gtgtgactca cgccttattt    57600
tccagcctgt gcagatagag ctgagatgca gactccaggc tgtggtttca gtccctccaa    57660
ggctcaggct cattgtgcta ctccactgtg tatttactta aaccagatgt ttaagcgggg    57720
aaatagtaga caccccacta gtggagggt ggaatccctt ttacaatgct tcactgacta    57780
tggcggacca gaacgtttct gtgccaaagc cccacttcat tccttctgt tctgttccac    57840
attctgccag agtcagaacc agccgttttgg tcccaggtcc tgcgacccat tgctatctaa    57900
agagtatggt tccctaatga gaacactgca gagaatcact gttgggaaat caaacaagac    57960
tttgtagacc accacagggg cttggtagat ctgcctgcct atggagaaag aagccagtag    58020
acaggaagaa gcttcattct catggttggg gaggagccta agtggtggag atctagtgta    58080
ttgcctgttt atacagtgat aaagtcaagt attttcatgg gtagagagcg agggtggagg    58140
aagggaggg ctgcgatcgg tgcaaaaatg gaaatacctt taatctccca aaagctttga    58200
ccactggcaa acaattgaaa tatcagcaaa gactactgct cttaatggtc acaccctctt    58260
gtttaaatgg cgtcccctc ccaagcatta aattgcgctg aactatcaca gttttactta    58320
gttctagtag ttataatcat tagcattctc cttcaggaga aaatctaaat gctggaaatc    58380
taattcagag ataacaagcc aactttatgt gcaaacttta tatttaaact gtttctagca    58440
gtgttacagt gattgtccaa actggattag acttttgcgt tgaaatcaaa gtatgggtaa    58500
gtctagcaca tgtaataaaa ccttgctgtt tcttgtggct acatttttt ttttaacttg     58560
tctgtctctt agcctaccat gtagaggtca tttcttgagt taagatggga tggcctaaaa    58620
gattcagtgt gtagttactg aagaagtaag tcccggcgcc tcagagcagt ctgtctcaca    58680
gccccgcttc catttggaaa cctgccattc tggaaggaag cacttggtgt tcttggaatg    58740
ttcatgttgt aatgattttt gttgttgttg ttgttgttga cttttagtt cagtcttagt     58800
tcttttgtgt ttgtatctat ctatgtacat ctgtgtgtgt ggtggccatg gattgaatag    58860
atgacttctt atttttatgtt ttaggccaag attgacagac acctaaatgt tcatgacttg    58920
agactattct gcagctataa aatttgaacc tttgatgtgc aaagcaagac ctgaagccca    58980
ctccggaaac taaagtgagg cttgctaacc ctgtagattg cctcacaagt tgtctgttta    59040
caaagtaagc tttccatcca ggggatgaag aacgccaacca gcagaagact tgcaaaccct    59100
ttaatttgat gtattgtttt ttaacatgtg tatgaaatgt agaaagatgt aaaggaaata    59160
aattaggagc gactactttg tatttgtactg ccattcctaa tgtatttta tacttttttgg   59220
cagcattaaa tatttttatt aaatagacta tgttggtt                            59258
```